(12) United States Patent
Palová Jelínková et al.

(10) Patent No.: US 9,987,307 B2
(45) Date of Patent: Jun. 5, 2018

(54) TOLEROGENIC DENDRITIC CELLS, METHODS OF PRODUCING THE SAME, AND USES THEREOF

(71) Applicant: SOTIO A.S., Prague (CZ)

(72) Inventors: Lenka Palová Jelínková, Klecany (CZ); Klára Dáňová, Prague (CZ); Radek Špíšek, Prague (CZ)

(73) Assignee: SOTIO A.S., Prague (CZ)

( * ) Notice: Subject to any disclaimer, the term of this patent is extended or adjusted under 35 U.S.C. 154(b) by 0 days. days.

(21) Appl. No.: 15/521,053

(22) PCT Filed: Oct. 22, 2015

(86) PCT No.: PCT/EP2015/074536
§ 371 (c)(1),
(2) Date: Apr. 21, 2017

(87) PCT Pub. No.: WO2016/062827
PCT Pub. Date: Apr. 28, 2016

(65) Prior Publication Data
US 2017/0340669 A1    Nov. 30, 2017

Related U.S. Application Data

(60) Provisional application No. 62/066,994, filed on Oct. 22, 2014.

(51) Int. Cl.
| | |
|---|---|
| *C12N 5/071* | (2010.01) |
| *C12N 5/00* | (2006.01) |
| *C12N 5/02* | (2006.01) |
| *A61K 35/15* | (2015.01) |
| *A61K 39/00* | (2006.01) |
| *C12N 5/0784* | (2010.01) |

(52) U.S. Cl.
CPC .......... *A61K 35/15* (2013.01); *A61K 39/0008* (2013.01); *C12N 5/064* (2013.01); *A61K 2039/5154* (2013.01); *C12N 2501/051* (2013.01); *C12N 2501/22* (2013.01); *C12N 2501/2304* (2013.01); *C12N 2501/39* (2013.01)

(58) Field of Classification Search
None
See application file for complete search history.

(56) References Cited

PUBLICATIONS

Paulina García-González et al: A short protocol using dexamethasone and monophosphoryl lipid A generates tolerogenic dendritic cells that display a potent migratory capacity to lymphoid chemokines 11, Journal of Translational Medicine, vol. 11, No. I, Jan. 1, 2013 (Jan. 1, 2013). p. 128.
Tatjana Nikolic et al: 11 Regulatory Multitasking of Tolerogenic Dendritic Cells—Lessons Taken from Vitamin D3-Treated Tolerogenic Dendritic Cells 11, Frontiers in Immunology, vol. 4, Jan. 1, 2013 (Jan. 1, 2013), pp. 1-13.
Manfred B. Lutz: 11 Therapeutic potential of semi-mature dendritic cells for tolerance induction 11, Frontiers in Immunology, vol. 3, Jan. 1, 2012 (Jan. 1, 2012), pp. 1-9.
Sochorova K et al: 11 Paricalcitol (19-nor-1,25-dihydroxyvitamin D2) and calcitriol (1,25-dihydroxyvitamin D3) exert potent immunomodulatory effects on dendritic cells and inhibit induction of antigen-specific T cells 11, Clinical Immunology, Academic Press, US, vol. 133, No. I, Oct. 1, 2009 (Oct. 1, 2009), pp. 69-77.
Brusko Todd M et al: 11 Human regulatory T cells: role in autoimmune disease and therapeutic opportunities 11, Immunological Reviews, Wiley-Blackwell Publishing, Inc, US, vol. 223, Jun. 1, 2008 (Jun. 1, 2008), pp. 371-390.
M Naranjo-Gómez, et al., Comparative study of clinical grade human tolerogenic dendritic cells, Journal of Translational Medicine, 2011, 9:89, pp. 1-14.
Gabriela Bomfim Ferreira, et al. Vitamin D3 Induces Tolerance in Harm Dendritic Cells by Activation of Intracellular Metabolic Pathways, Cell Reports, Feb. 10, 2015, vol. 10, pp. 711-725.
Rachel A Harry, et al., Generation and characterisation of therapeutic tolegrogenic dendritic cells for rheumatoid arthritis, Ann Rheum Dis., 2010,69, pp. 2042-2050.
Wendy W.J. Unger, et al, Induction of Treg by monocyte-derived DC modulated by vitamin $D_3$ or dexamethasone: Differential role for PD-L1, Eur. J. Immunol. 2009, 39, pp. 3147-3159.
Sonia Chamorro, et al., TLR Triggering on Tolerogenic Dendritic Cells Results in TLR2 Up-Regulation and a Reduced Proinflammatory Immune Program, The Journal of Immunology, 2009, 183, pp. 2984-2994.
Fleur S. Kleijwegt, et al., Critical Role for TNF in the Induction of Human Antigen-Specific Regulatory T Cells by Tolerogenic Dendritic Cells, J. Immunol, 2010, 185, pp. 1412-1418.

*Primary Examiner* — Amy E Juedes
(74) *Attorney, Agent, or Firm* — Leason Ellis LLP

(57) ABSTRACT

Described herein are methods for the preparation of stable semi-mature tolerogenic dendritic cells and compositions comprising such stable semi-mature tolerogenic dendritic cells. The stable semi-mature tolerogenic dendritic cells described herein and compositions thereof can be used for the establishment of immune tolerance when treating an autoimmune disease, graft rejection and/or graft-versus-host disease.

25 Claims, 93 Drawing Sheets

Table: IL-10 tDCs 1

Figure 1A:
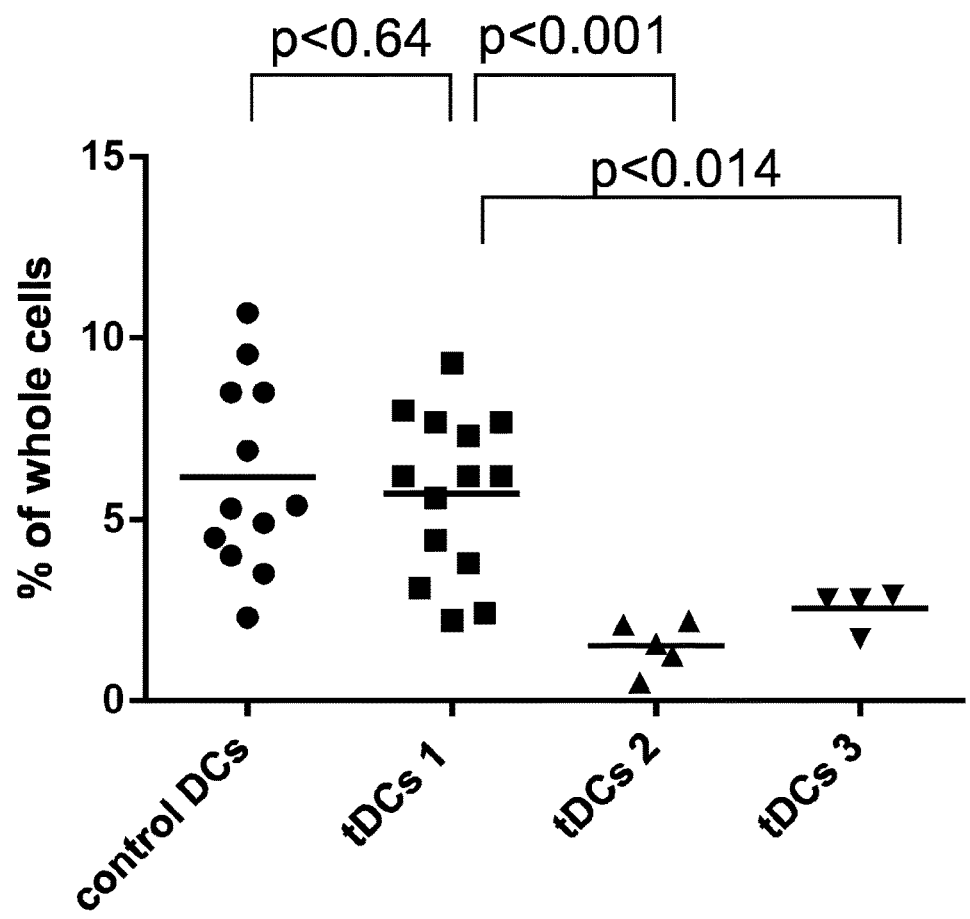

|  | RPMI |  |  |  |  |  |
|---|---|---|---|---|---|---|
| tDCs 1 | 187 | 360,9 | 261,7 | 226,4 | 224,4 |  |
| tDCs 1 SB | 140 | 157,3 | 140 | 20,7 | 0 |  |
| tDCs 1 SP | 89,2 | 70 | 89,2 | 0 | 53,6 | 0 |
| tDCs 1 PD | 72,5 | 73,6 | 72,5 | 0 | 0 | 0 |
| tDCs 1 Bay | 67,5 | 60 | 67,5 | 0 |  |  |
|  | RPMI-CC |  |  |  |  |  |
| tDCs 1 | 790 | 619,2 | 950 | 1266,7 | 177 |  |
| tDCs 1 SB | 199,2 | 253,6 | 199,2 | 134,3 | 171,1 | 159,15 |
| tDCs 1 SP | 87,5 | 155,5 | 87,5 | 0 | 115 | 0 |
| tDCs 1 PD | 120,8 | 108,2 | 120,8 | 0 | 0 | 0 |
| tDCs 1 Bay | 56,7 | 59,1 | 56,7 | 0 |  |  |
|  | RPMI-LPS |  |  |  |  |  |
| tDCs 1 | 1748 | 2379,1 | 627,5 | 2203,6 | 3726,7 | 718 |
| tDCs 1 SB | 582,5 | 614,5 | 582,5 | 316,4 | 895,6 | 209 |
| tDCs 1 SP | 242,5 | 353,6 | 242,5 | 153,6 | 616,4 | 566,7 |
| tDCs 1 PD | 197,5 | 414,5 | 197,5 | 232,1 | 393,3 | 117,8 |
| tDCs 1 Bay | 62,5 | 65,5 | 62,5 | 0 |  |  |
|  | RPMI-pIC |  |  |  |  |  |
| tDCs 1 | 171 | 355,5 | 321,7 | 350 | 388,9 | 450 |
| tDCs 1 SB | 214,2 | 223,6 | 214,2 | 6,4 | 83,3 | 245 |
| tDCs 1 SP | 86,7 | 69,1 | 86,7 | 0 | 55,9 | 0 |
| tDCs 1 PD | 96,7 | 74,5 | 96,7 | 3,6 | 0 | 0 |
| tDCs 1 Bay | 65,8 | 57,3 | 65,8 | 0 |  |  |
|  | RPMI-CD40L |  |  |  |  |  |
| tDCs 1 | 700 | 427,3 | 814,2 | 1384,3 | 888,9 |  |
| tDCs 1 SB | 265,8 | 147,3 | 265,8 | 35,7 | 44,4 |  |
| tDCs 1 SP | 134,2 | 73,6 | 134,2 | 0 | 0 | 0 |
| tDCs 1 PD | 120,8 | 93,6 | 120,8 | 0 | 0 | 0 |
| tDCs 1 Bay | 65 | 55,5 | 65 | 0 |  |  |

Figure 11C - 2

Table: IL-10 cDCs

|          | RPMI     |      |       |        |     |     |      |      |      |
|----------|----------|------|-------|--------|-----|-----|------|------|------|
| cDCs     |          | 0    | 32    | 151,8  | 158,3 |   |     | 217  | 190  |      |
| cDCs SB  |          | 0    | 0     | 99,1   | 83,3  |   |     | 212  | 166  |      |
| cDCs SP  |          | 0    | 0     | 66,4   | 61,7  |   |     | 210  |      |      |
| cDCs PD  |          | 0    | 0     | 65,5   | 65    |   |     | 62   |      |      |
| cDCs Bay |          |      | 0     | 58,2   | 53,3  |   |     |      |      |      |
|          | RPMI-CC  |      |       |        |     |     |      |      |      |
| cDCs     |          | 302,2 | 124  |        | 313,3 | 102 | 172 | 357  | 353  |      |
| cDCs SB  |          | 0    | 66    | 245,5  | 90,8  | 68  | 65  | 340  | 253  |      |
| cDCs SP  |          | 0    | 0     | 68,2   | 71,7  | 18  | 22  | 400  |      |      |
| cDCs PD  |          | 0    | 8     | 67,3   | 82,5  | 27  | 0   | 140  |      |      |
| cDCs Bay |          | 0    | 0     | 63,6   | 59,2  |     |     |      |      |      |
|          | RPMI-LPS |      |       |        |     |     |      |      |      |
| cDCs     |          | 1180 | 442   |        | 1943,3 | 54  | 575 | 1115 | 1115 | 1076 |
| cDCs SB  |          | 65,6 | 93    |        | 221,7 | 52  | 213 | 157  | 93   | 470  |
| cDCs SP  |          | 66,7 | 72    |        | 192,5 | 40  | 43  | 647  | 720  |      |
| cDCs PD  |          | 0    | 81    |        | 107,5 | 18  | 131 | 107  |      |      |
| cDCs Bay |          | 0    | 0     | 60,9   | 68,3  |     |     |      |      |      |
|          | RPMI-pIC |      |       |        |     |     |      |      |      |
| cDCs     |          | 0    | 34    | 51,8   | 60,8  | 115 | 92  | 182  | 331  |      |
| cDCs SB  |          | 0    | 55    | 52,7   | 55,8  | 61  | 106 | 0    | 385  |      |
| cDCs SP  |          | 0    | 53    | 49,1   | 49,2  | 75  | 781 | 197  |      |      |
| cDCs PD  |          | 0    | 28    | 53,6   | 54,2  | 163 | 111 | 45   |      |      |
| cDCs Bay |          | 0    | 8     | 69,1   | 55,8  |     |     |      |      |      |
|          | RPMI-CD40L |    |       |        |     |     |      |      |      |
| cDCs     |          | 222,9 | 0    | 52,7   | 100   |     |     |      |      |      |
| cDCs SB  |          | 0    | 0     | 53,6   | 52,5  |     |     |      |      |      |
| cDCs SP  |          | 0    | 0     | 52,7   | 63,3  |     |     |      |      |      |
| cDCs PD  |          | 0    | 0     | 54,5   | 64,2  |     |     |      |      |      |
| cDCs Bay |          |      | 0     | 54,5   | 61,7  |     |     |      |      |      |

Figure 11C - 4

| | RPMI | | | | |
|---|---|---|---|---|---|
| tDCs 1 | 0 | 0 | 0 | 14,5 | 3,3 |
| tDCs 1 SB | 0 | 0 | 0 | 0 | 35 |
| tDCs 1 Bay | 0 | 0 | 0 | 0 | 43,3 |
| | RPMI-CC | | | | |
| tDCs 1 | 0 | 0 | 0 | 0 | 6,7 |
| tDCs 1 SB | 0 | 0 | 0 | 0 | 51,7 |
| tDCs 1 Bay | 0 | 0 | 0 | 0 | 0 |
| | RPMI-LPS | | | | |
| tDCs 1 | 0 | 0 | 0 | 9,1 | 10 |
| tDCs 1 SB | 0 | 0 | 0 | 0 | 65 |
| tDCs 1 Bay | 0 | 0 | 0 | 0 | 81,7 |
| | RPMI-pIC | | | | |
| tDCs 1 | 0 | 0 | 0 | 4,5 | 0 |
| tDCs 1 SB | 0 | 0 | 0 | 0 | 48,3 |
| tDCs 1 Bay | 0 | 0 | 0 | 0 | 13,3 |
| | RPMI-CD40L | | | | |
| tDCs 1 | 14 | 4,2 | 0 | 0 | 0 |
| tDCs 1 SB | 0 | 0 | 0 | 0 | 30 |
| tDCs 1 Bay | 0 | 85 | 0 | 0 | 85 |

ILT-3

| | RPMI | | | | | | | |
|---|---|---|---|---|---|---|---|---|
| tDCs 1 | 7387 | 8072 | 8072 | 6724 | 2867 | 4294 | 6525 | |
| tDCs 1 SB | 6299 | 6299 | 3452 | 5334 | 1138 | 2112 | 4699 | |
| cDCs | 2995 | 3403 | 2435 | 3430 | 2023 | 3178 | | |
| cDCs SB | 2051 | 2674 | 2710 | 3333 | 2399 | 3019 | | |
| | RPMI-CC | | | | | | | |
| tDCs 1 | 6921 | 6546 | 7164 | 7648 | 4294 | 6525 | 6525 | |
| tDCs 1 SB | 6567 | 5018 | 5261 | 6133 | 2112 | 3699 | 3699 | |
| cDCs | 3273 | 3900 | 4342 | 2641 | 1827 | 2041 | | |
| cDCs SB | 2877 | 3756 | 2218 | 2377 | 1978 | 2064 | | |
| | RPMI-LPS | | | | | | | |
| tDCs 1 | 8073 | 8273 | 6691 | 8976 | 5260 | 3951 | | |
| tDCs 1 SB | 5813 | 5994 | 4971 | 6456 | 4263 | 2838 | | |
| cDCs | 2454 | 3345 | 3345 | 2641 | 1827 | 2041 | | |
| cDCs SB | 2248 | 2129 | 2633 | 2377 | 1978 | 2064 | | |
| | RPMI-pIC | | | | | | | |
| tDCs 1 | 11109 | 10564 | 8405 | 9516 | 8405 | 9516 | | |
| tDCs 1 SB | 10094 | 9215 | 5465 | 8152 | 5465 | 8152 | | |
| cDCs | 3057 | 3194 | 4184 | 2113 | 1402 | 1862 | | |
| cDCs Rap | 4361 | 3099 | 3567 | 1877 | 1319 | 1961 | | |
| | RPMI-CD40L | | | | | | | |
| tDCs 1 | 9459 | 9064 | 6346 | 9775 | 9530 | 8657 | 10638 | 12128 |
| tDCs 1 SB | 5966 | 6259 | 3753 | 5710 | 6726 | 6394 | 7292 | 7500 |
| cDCs | 2632 | 3209 | 3163 | | 5195 | 5412 | 4195 | 4510 |
| cDCs SB | 1957 | 2406 | 2445 | | 4593 | 5486 | 3886 | 4446 |

PDL-1

| | RPMI | | | | | | | |
|---|---|---|---|---|---|---|---|---|
| tDCs 1 | 855 | 405 | 855 | 443 | | | | |
| tDCs 1 SB | 709 | 363 | 709 | 461 | | | | |
| tDCs 1 PD | 807 | 318 | 807 | 490 | | | | |
| cDCs | 651 | 648 | 661 | | | | | |
| cDCs SB | 638 | 506 | 673 | | | | | |
| cDCs PD | 655 | 578 | 911 | | | | | |
| | RPMI-CC | | | | | | | |
| tDCs 1 | 1433 | 1600 | 894 | 902 | 902 | 894 | | |
| tDCs 1 SB | 1082 | 1027 | 590 | 595 | 595 | 590 | | |
| tDCs 1 PD | 1094 | 1416 | 758 | 608 | 608 | 758 | | |
| cDCs | 745 | 1278 | 810 | 997 | 880 | | | |
| cDCs SB | 569 | 1008 | 699 | 746 | 748 | | | |
| cDCs PD | 726 | 1182 | 862 | 815 | 847 | | | |
| | RPMI-LPS | | | | | | | |
| tDCs 1 | 960 | 1478 | 363 | 531 | 1478 | 1478 | 1479 | 1082 |
| tDCs 1 SB | 799 | 851 | 245 | 389 | 851 | 851 | 679 | 874 |
| tDCs 1 PD | 571 | 945 | 278 | 342 | 945 | 945 | 924 | |
| cDCs | 576 | 1137 | 566 | 965 | 633 | | 1298 | 1253 |
| cDCs SB | 370 | 642 | 490 | 681 | 588 | | 1269 | |
| cDCs PD | 473 | 774 | 536 | 756 | 762 | | 1247 | 1331 |
| | RPMI-pIC | | | | | | | |
| tDCs 1 | 735 | 986 | 314 | 385 | 986 | 986 | | |
| tDCs 1 SB | 671 | 707 | 256 | 265 | 707 | 707 | | |
| tDCs 1 PD | 465 | 730 | 249 | 355 | 730 | 730 | | |
| cDCs | 431 | 661 | 541 | 759 | 553 | | | |
| cDCs SB | 337 | 694 | 291 | 571 | 550 | | | |
| cDCs PD | 382 | 688 | 297 | 608 | 597 | | | |
| | RPMI-CD40L | | | | | | | |
| tDCs 1 | 919 | 1068 | 853 | 837 | 1064 | 994 | | |
| tDCs 1 SB | 526 | 695 | 420 | 655 | 510 | 854 | | |
| tDCs 1 PD | 1113 | 1491 | 857 | | 1126 | | | |
| cDCs | 873 | 1159 | 1300 | | 1368 | | | |
| cDCs SB | 1460 | 1270 | 517 | | 856 | | | |
| cDCs PD | 1176 | 938 | 1148 | | 1358 | | | |

Figure 11D - 3

|  | RPMI |  |  |  |  |  |  |  |
|---|---|---|---|---|---|---|---|---|
| tDCs 1 |  | 489 | 405 | 443 | 501 | 538 | 446 | 422 |
| tDCs 1 Rap |  | 492 | 342 | 397 | 463 | 455 | 453 | 472 |
| cDC |  | 757 | 997 | 880 | 663 | 463 | 835 | 945 |
| cDCs Rap |  | 805 | 751 | 953 | 773 | 612 | 841 | 756 |
|  | RPMI-CC |  |  |  |  |  |  |  |
| tDCs 1 |  | 674 | 902 | 844 | 1575 | 1586 | 1416 | 1534 |
| tDCs 1 Rap |  | 548 | 508 | 563 | 1201 | 1132 | 798 | 820 |
| cDC |  | 757 | 997 | 880 | 1035 | 957 | 1178 | 1331 |
| cDCs Rap |  | 805 | 751 | 953 | 1162 | 900 | 1209 | 1199 |
|  | RPMI-LPS |  |  |  |  |  |  |  |
| tDCs 1 |  | 690 | 431 | 646 | 833 | 840 | 732 | 732 | 690 |
| tDCs 1 Rap |  | 416 | 198 | 533 | 703 | 723 | 496 | 429 | 416 |
| cDC |  | 607 | 965 | 633 | 1149 | 1166 | 1203 | 1271 | 607 |
| cDCs Rap |  | 688 | 728 | 635 | 987 | 1017 | 1073 | 1015 | 688 |
|  | RPMI-pIC |  |  |  |  |  |  |  |
| tDCs 1 |  | 587 | 385 | 509 | 712 | 760 | 537 | 703 | 712 |
| tDCs 1 Rap |  | 368 | 135 | 301 | 460 | 506 | 432 | 428 | 460 |
| cDC |  | 460 | 759 | 553 | 804 | 836 | 850 | 819 | 804 |
| cDCs Rap |  | 559 | 615 | 559 | 632 | 629 | 845 | 895 | 632 |
|  | RPMI-CD40L |  |  |  |  |  |  |  |
| tDCs 1 |  | 1085 | 1398 | 559 | 750 |  |  |  |
| tDCs 1 Rap |  | 767 | 780 | 456 | 388 |  |  |  |
| cDC |  | 997 | 1255 | 528 | 1331 |  |  |  |
| cDCs Rap |  | 1156 | 1024 | 1020 | 1012 |  |  |  |

| | RPMI | | | | | | | | | | | |
|---|---|---|---|---|---|---|---|---|---|---|---|---|
| tDCs 1 | | | 7387 | | 6765 | 6765 | 6724 | | | | | |
| tDCs 1 Rap | | | 6627 | | 5131 | 4593 | 5974 | | | | | |
| cDC | 1704 | 2110 | 2995 | 2995 | 3403 | 1704 | 2435 | 2110 | | | | |
| cDCs Rap | 1945 | 2160 | 2332 | 2574 | 3018 | 1945 | 2877 | 2160 | | | | |
| | RPMI-CC | | | | | | | | | | | |
| tDCs 1 | 6921 | 6546 | 7164 | 7164 | 7648 | 7164 | | 4294 | 6525 | 6525 | 4999 | 5556 |
| tDCs 1 Rap | 6134 | 4954 | 5406 | 5784 | 6803 | 5784 | | 2214 | 4018 | 4018 | 2406 | 2576 |
| cDC | 3273 | 3900 | 4342 | 3273 | 3430 | 2023 | 3178 | | | | | |
| cDCs Rap | 3172 | 3555 | 3179 | 3172 | 2707 | 2742 | 2752 | | | | | |
| | RPMI-LPS | | | | | | | | | | | |
| tDCs 1 | 8073 | 8073 | 8273 | 8273 | 6691 | 6691 | 8976 | 8974 | | 3951 | 5260 | 4865 |
| tDCs 1 Rap | 5277 | 5151 | 5201 | 5655 | 4870 | 5869 | 6745 | 6794 | | 1870 | 2692 | 2899 |
| cDC | 2454 | | 3345 | | 4165 | 2454 | | | 1872 | 2041 | | |
| cDCs Rap | 2169 | | 2938 | | 3539 | 2169 | | | 1512 | 2212 | | |
| | RPMI-pIC | | | | | | | | | | | |
| tDCs 1 | 4360 | 4283 | 5828 | | 11109 | 11109 | 10564 | 10564 | 8405 | 8405 | 9516 | 9516 |
| tDCs 1 Rap | 3222 | 3179 | 4463 | | 4667 | 8718 | 9578 | 10028 | 6529 | 5845 | 8095 | 8692 |
| cDC | 1862 | | | | 3057 | | 3194 | | 4184 | 2113 | | |
| cDCs Rap | 1823 | | | | 2145 | | 2798 | | 2703 | 1795 | | |
| | RPMI-CD40L | | | | | | | | | | | |
| tDCs 1 | 9459 | 9459 | 9064 | 9064 | 6346 | 6346 | 9775 | 9775 | | | | |
| tDCs 1 Rap | 6737 | 5281 | 5355 | 5455 | 4414 | 4337 | 5394 | 7307 | | | | |
| cDC | 2632 | 2623 | 3209 | | 3163 | | | | | | | |
| cDCs Rap | 2588 | 2567 | 2793 | | 3140 | | | | | | | |

|  | RPMI |  |  |  |  |  |  |  |  |  |  |  |
|---|---|---|---|---|---|---|---|---|---|---|---|---|
| tDCs 1 | 921 | 921 | 489 | 405 | 443 | 422 | 647 | 810 |  |  |  |  |
| tDCs 1 Stattic | 855 | 855 | 279 | 225 | 282 |  | 780 | 590 |  |  |  |  |
| cDC | 651 | 651 | 436 | 648 | 661 | 945 | 1045 |  |  |  |  |  |
| cDCs Stattic | 772 | 772 | 520 | 737 | 380 |  | 349 |  |  |  |  |  |
|  | RPMI-CC |  |  |  |  |  |  |  |  |  |  |  |
| tDCs 1 | 894 | 1600 | 1433 | 1433 | 674 | 902 | 844 | 844 | 1586 | 1416 | 1543 | 2254 |
| tDCs 1 Stattic | 628 | 1120 | 1100 | 1100 | 282 | 276 | 297 | 297 |  |  |  | 425 |
| cDC | 810 | 1278 | 774 | 774 | 757 | 997 | 880 | 880 | 957 | 1178 | 1331 | 1704 |
| cDCs Stattic | 942 | 1444 | 845 | 845 | 296 | 334 | 291 | 291 |  |  |  | 477 |
|  | RPMI-LPS |  |  |  |  |  |  |  |  |  |  |  |
| tDCs 1 | 1478 | 960 | 960 | 690 | 431 | 644 | 732 | 690 | 840 | 1298 | 1357 | 1082 |
| tDCs 1 Stattic | 1111 | 744 | 744 | 287 | 280 | 312 | 510 | 287 | 644 | 461 | 544 | 931 |
| cDC | 1133 | 1176 | 576 | 1107 | 965 | 1635 | 1607 | 1271 | 965 | 1479 |  |  |
| cDCs Stattic | 901 | 1223 | 623 | 1102 | 879 | 1285 | 1607 |  | 869 | 751 |  |  |
|  | RPMI-pIC |  |  |  |  |  |  |  |  |  |  |  |
| tDCs 1 | 987 | 735 | 735 | 587 | 350 | 509 | 537 | 703 | 1112 | 641 |  |  |
| tDCs 1 Stattic | 876 | 573 | 573 | 285 | 169 | 267 | 285 |  | 490 | 516 |  |  |
| cDC | 661 | 431 | 431 | 460 | 759 | 445 | 850 | 819 | 869 | 1461 |  |  |
| cDCs Stattic | 778 | 369 | 369 | 328 | 721 | 272 |  |  | 420 | 725 |  |  |
|  | RPMI-CD40L |  |  |  |  |  |  |  |  |  |  |  |
| tDCs 1 | 1085 | 1398 | 559 | 780 | 1294 | 1146 | 1019 |  |  |  |  |  |
| tDCs 1 Stattic |  |  |  | 562 | 674 | 571 | 369 |  |  |  |  |  |
| cDC | 997 | 1255 | 528 | 1331 | 1468 | 1952 | 959 | 952 | 959 | 1765 |  |  |
| cDCs Stattic |  | 322 |  | 1200 | 950 | 846 | 705 | 599 | 705 | 595 |  |  |

| ILT-3 Stattic | RPMI | | | | |
|---|---|---|---|---|---|
| tDCs 1 | 2602 | 2216 | 2404 | 2404 | 5000 |
| tDCs 1- Stattic | 832 | 1125 | 1105 | 1105 | |
| cDCs | 2723 | 1704 | 2110 | 2110 | |
| cDCs Stattic | 1880 | 1230 | 2222 | 2222 | |
| | RPMI-CC | | | | |
| tDCs 1 | 2867 | 4294 | 6252 | 6252 | |
| tDCs 1- Stattic | 766 | 913 | 1068 | 1068 | |
| cDCs | 3430 | 2023 | 3178 | 3178 | |
| cDCs Stattic | 962 | 744 | 2247 | 2247 | |
| | RPMI-LPS | | | | |
| tDCs 1 | 2822 | 3951 | 5260 | 5260 | |
| tDCs 1- Stattic | 1025 | 860 | 997 | 997 | |
| cDCs | 2641 | 1827 | 2041 | 2041 | |
| cDCs Stattic | 1726 | 947 | 1865 | 1865 | |
| | RPMI-pIC | | | | |
| tDCs 1 | 2741 | 4360 | 4283 | 4283 | |
| tDCs 1- Stattic | 721 | 446 | 1016 | 1016 | |
| cDCs | 2113 | 1402 | 1862 | 1862 | |
| cDCs Stattic | 912 | 687 | 1846 | 1846 | |
| | RPMI-CD40L | | | | |
| tDCs 1 | 6638 | 7179 | 5057 | | |
| tDCs 1- Stattic | 4326 | 695 | 2330 | | |
| cDCs | 2613 | 1725 | 1848 | | |
| cDCs Stattic | 865 | 618 | 1558 | | |

TOLEROGENIC DENDRITIC CELLS, METHODS OF PRODUCING THE SAME, AND USES THEREOF

CROSS-REFERENCE TO RELATED PATENT APPLICATIONS

This is a U.S. National Phase Application under 35 U.S.C. § 371 of International Patent Application No. PCT/EP2015/074536, filed Oct. 22, 2015, and priority of U.S. Application Ser. No. 62/066,994, filed Oct. 22, 2014, which is incorporated by reference in its entirety. The International Application was published on Apr. 28, 2016, as International Publication No. WO 2016/062827 A1.

1. FIELD

Described herein are methods for the preparation of stable semi-mature tolerogenic dendritic cells and compositions comprising such stable semi-mature tolerogenic dendritic cells. The stable semi-mature tolerogenic dendritic cells described herein and compositions thereof can be used for the establishment of immune tolerance when treating an autoimmune disease, graft rejection and/or graft-versus-host disease.

2. BACKGROUND

Lymphocytes can be activated by antigens, leading to immune responses, or inactivated or eliminated, leading to tolerance toward the antigen. Tolerance to self-antigens is a fundamental property of the immune system. Failure to establish tolerance by the immune system leads to autoimmune diseases.

New therapies for the treatment of autoimmune diseases include generating or giving a specific type of lymphocytes, regulatory T cells (Tregs), to patients. Tregs suppress the activation and effector functions of other, self-reactive and potentially pathogenic lymphocytes, which results in suppressed immune responses and maintenance of self-tolerance. Tregs are a subset of $CD4^+$ T cells. The best characterized Tregs are $CD4^+$ CD25+FoxP3$^+$ T cells. Tregs can be generated by self antigen recognition in the thymus and by antigen recognition in peripheral lymphoid organs. Dendritic cells (DCs) are the most potent antigen presenting cells. DCs participate in the innate immunity and the acquired immune response. DCs perform many functions for the immune system such as: 1) uptake, processing, and presentation of antigens, 2) activation of effector cells such as T-cells, B-cells and NK-cells, and 3) secretion of cytokines and other immune-modulating molecules to direct the immune response. DCs recognize specific pathogens and various danger signals. Recognition of pathogen-derived products and danger signals mediated by specific receptors on DCs initiates the process of maturation, which can be further modified by inflammatory stimuli or T cell-derived signals. Maturation is a process when activated DCs undergo morphological, phenotypic, and functional changes that culminate in complete transition from antigen-capturing cells to fully mature antigen presenting cells (APC). Maturation is characterized by increased expression of costimulatory molecules such as CD40, CD80, and CD86, MHC-upregulation, the loss of the capacity to take up and process antigens and the production of wide spectrum of inflammatory cytokines and chemokines (IL-1β, IL-6, IL-8, and IL-12). Once activated, DCs migrate to the lymph nodes where they interact with T cells and B cells to initiate and shape the adaptive immune response.

DCs derive from the myeloid lineage of hematopoietic cells. Myeloid progenitors in bone marrow give rise to macrophage-DC progenitors, which further differentiate into common/myeloid DCs and plasmacytoid DCs. Monocytes can also differentiate into DCs. Differentiation gives rise to immature dendritic cells (iDCs). The primary function of iDCs is to capture and process antigens. Immature DCs can mature as they contact and process antigens in an inflammatory environment. A variety of factors can induce maturation following antigen uptake and processing within DCs, including: whole bacteria or bacterial-derived antigens (e.g. lipopolysaccharide, LPS), inflammatory cytokines, ligation of select cell surface receptors (e.g. CD40) and viral products (e.g. double-stranded RNA). Bacterial-derived antigens and viral products can be recognized via Toll-like receptor (TLR). TLRs recognize various components of invading pathogens. Ligand binding to the TLRs on DCs induces proinflammatory cytokine production and enhanced antigen presentation to naive T cells, and thus activates antigen-specific adaptive immune responses. Distinct TLR ligands provide distinct activation status and cytokine production patterns for antigen presenting cells, resulting in the induction of differential immune responses. Thus, TLRs are critical molecules to fine-tuned adaptive immune responses depending on invading pathogens. Given that stimulation by TLR ligands can fine-tune the immune response toward specific pathogens, it is important for therapeutic vaccination that the DC properties are maintained once the cells are administrated to the patient.

DCs can also be partially maturated resulting in upregulation of MHC and costimulatory molecules and lymph node homing capacity, but lacking proinflammatory cytokine production. Such DCs have been termed semi-mature DCs (Lutz et al. 2002. Trends Immunol 23:445-449).

Tolerogenic DCs (tolDCs) are antigen presenting cells with immunosuppressive properties. They can induce tolerance through the presentation of antigen with inadequate co-stimulation and cytokine production for effector cell activation. TolDCs are commonly defined by low or intermediate levels of MHCII, costimulatory molecules CD80, CD86 and CD40, and chemokine receptor CCR7, in addition to a remarkably increased antigen uptake capacity. TolDCs express high levels of inhibitory molecules such as Ig-like transcripts (ILT) molecules (ILT3/ILT4) and/or PD-L-molecules (PD-L1, PD-L2). Additionally, tolDCs secrete low amounts of proinflammatory cytokines (IL-12p70) and high quantities of anti-inflammatory cytokines, such as IL-10. TolDCs induce T cell anergy, T cell suppression and the generation of regulatory T cells by several mechanisms, including conversion of naïve T cells into Tregs, release of immunosuppressive cytokines, and expression of functional indoleamine-2,3 dioxygenase (IDO). TolDCs are generally considered as semi-mature DCs. Several signaling pathways involved in the induction and maintenance of immunosuppressive role of tolDCs have been identified. The proinflammatory DC maturation is normally associated with the activation of numerous signaling pathways including transcription factors NF-κB and p38 MAPK (Nakahara et al. 2006, J Derm Science 42: 1-11; Katholnig et al. 2013, J Immunol 190: 1519-1527). The pattern of activated signaling events triggered in tDCs is profoundly different and involves the activation of ERK1/2, non-canonical NF-κB pathway, STAT3 and IDO (Qian et al. 2006, Blood 108: 2307-2315; Harden et al. 2012, Immunol Invest 41: 738-

764; Manches et al. 2012, PNAS 109: 14122-14127; Farias et al. 2013, CNS 19: 269-277).

Expression of the indoleamine 2,3-dioxygenase in tolDCs and the ensuing production of tryptophan metabolites has been shown to induce direct suppression of effector T-cell activity and concurrent expansion of Tregs (Harden et al. 2013. Immunol Invest 41:738-764). TolDCs can be generated from precursor cells in vitro and represent potentially promising tool for a specific form of cell-based therapy for induction or restoring immune tolerance in the context of transplantation and autoimmune diseases (Fischbach et al. 2013. Sci Transl Med 5:179ps7). Different approaches that target DC differentiation and function by various mechanisms have been shown to establish a tolDC phenotype (Naranjo-Gomez et al. 2011. J Transl Med 9:89; Li et al. 2007. J Immunol 178:5480-7; Torres-Aguilar et al. 2010. J Immunol 184:1765-75). Notably, Dexamethasone and/or vitamin D3 receptor agonists (VDR; 1,25(OH)2D 3 and its analogues) have been described to generate tolDCs through the suppression of NF-κB-dependent DC maturation (Adorin et al. 2009. Handb Exp Pharmacol 251-73; van Hooten et al. 2009. Handb Exp Pharmacol 233-49). Such Dex/VitD3 conditioned tolDCs have been shown to acquire a robust immunoregulatory phenotype and are currently tested in early clinical trial in patients with rheumatoid arthritis (Stoop et al. 2010. Arthritis Rheum 62:3656-65). TolDCs can also be generated from DCs conditioned with 19-nor-1,25-dihydroxyvitamin D2 (paricalcitol), the analogue of the active form of vitamin D2 (Sochorova et al. 2009. Clin Immunol 133:69-77). Other approaches to establish a tolDCs phenotype have also involved the use of neuropeptides (vasoactive intestinal peptide or pituitary adenylate cyclase-activating polypeptide) (Chorny et al. 2005. Proc Nat Acad Sci 102:13562-7; Chorny et al. 2006. Blood 107:3787-84; Gonzalez-Rey et al. 2006. Gastroenterology 131:1799-811) or the mTOR inhibitor rapamycin (Haidinger et al. 2010. J Immunol 185:3919-31). None of cells produced by these methods have been demonstrated to have the characteristics of the Dex/vitamin D2 tolDCs described herein.

One of the major concerns associated with therapeutic vaccination with in vitro established tolDCs is their functional stability. Once injected into patients, tolDCs must retain highly stable tolerogenic properties in the absence of tolerogenic agents. A potential risk of ex-vivo prepared tolDCs is that their application to an organism with chronic inflammation, such as autoimmune disease, may switch them to an activated phenotype when encountering proinflammatory signals in vivo. This might than contribute to the further expansion of the autoimmune reaction and would be detrimental for the outcome of the treatment.

3. SUMMARY

In one aspect, described herein is a method for generating stable semi-mature tolDCs. In one embodiment, a method for generating stable semi-mature tolerogenic dendritic cells comprises: (a) isolating monocytes from patient blood; (b) culturing monocytes in culture medium (e.g., cGMP medium) comprising one or more factors that induce the differentiation of monocytes into dendritic cells; and (c) generating tolerogenic dendritic cells utilizing Dexamethasone and vitamin D2; and (d) culturing the tolerogenic dendritic cells in culture medium (e.g., cGMP medium) comprising MPLA or MPLA and an antigen(s) associated with an autoimmune disease, graft-versus-host disease or graft rejection. In certain embodiments, the culture medium comprises one or more factors that induce the differentiation of monocytes into dendritic cells throughout the method for generating stable semi-mature tolDCs. Examples of factors that induce differentiation of monocytes into dendritic cells include the combination of GM-CSF and IL-4, IL-13, IL-15 or IFN-alpha, or Flt3L. In a specific embodiment, the culture medium comprises GM-CSF and IL-4 throughout the method for generating stable semi-mature tolDCs. The monocytes can be isolated from a subject's blood by any technique known to one of skill in the art or described herein. For example, the monocytes can be isolated from a subject's blood by leukapheresis. In specific embodiments, the tolerogenic dendritic cells are generated utilizing Dexamethasone in culture medium on the $3^{rd}$ day of culture and Dexamethasone and vitamin D2 in culture medium on the $6^{th}$ day of culture. In some embodiments, the tolerogenic dendritic cells are generated utilizing Dexamethasone and one or more factors that induce the differentiation of monocytes into dendritic cells in culture medium on the $3^{rd}$ day of culture, and Dexamethasone, vitamin D2 and one or more factors that induce the differentiation of monocytes into dendritic cells in culture medium on the $6^{th}$ day of culture. In specific embodiments, the tolerogenic dendritic cells are generated utilizing Dexamethasone, GM-CSF and IL-4 in culture medium on the $3^{rd}$ day of culture, and Dexamethasone, vitamin D2, GM-CSF and IL-4 in culture medium on the $6^{th}$ day of culture. In certain embodiments, the Dexamethasone is present in the culture medium at a final concentration between 0.5 and 3 micromole per liter. In some embodiments, the vitamin D2 is present in the culture medium at a final concentration between 0.1 and 10 nanomole per liter. In specific embodiments, the tolerogenic dendritic cells are cultured in culture medium comprising MPLA or MPLA and the antigen on the $7^{th}$ day of culture. In some embodiments, the tolerogenic dendritic cells are cultured in culture medium comprising MPLA and one or more factors that induce the differentiation of monocytes into dendritic cells, or MPLA, one or more factors that induce the differentiation of monocytes into dendritic cells, and the antigen on the $7^{th}$ day of culture. In a specific embodiment, the tolerogenic dendritic cells are cultured in culture medium comprising MPLA, GM-CSF and IL-4, or MPLA, GM-CSF, IL-4, and the antigen on the $7^{th}$ day of culture. In certain embodiments, the MPLA is present in the culture medium at a final concentration of between 1 and 3 µg per ml. In certain embodiments, the tolerogenic dendritic cells are cultured in culture medium comprising MPLA or MPLA and the antigen for a certain period of time (e.g., 24 hours) before the cells are harvested. In some embodiments, the tolerogenic dendritic cells are cultured in culture medium comprising MPLA and one or more factors that induce the differentiation of monocytes into dendritic cells, or MPLA, one or more factors that induce the differentiation of monocytes into dendritic cells, and the antigen for a certain period of time (e.g., 24 hours) before the cell are harvested. In specific embodiments, the tolerogenic dendritic cells are cultured in culture medium comprising MPLA, GM-CSF and IL-4, or MPLA, GM-CSF, IL-4, and the antigen for a certain period of time (e.g. 24 hours) before the cell are harvested. In certain embodiments, the method for generating stable semi-mature tolDCs takes approximately 8 days of cell culture.

In another embodiment, a method for generating stable semi-mature tolerogenic dendritic cells comprises (a) culturing monocytes isolated from a subject's blood in culture medium (e.g., cGMP medium) comprising GM-CSF and IL-4 for a certain period of time; (b) generating tolerogenic dendritic cells utilizing Dexamethasone and vitamin D2 in culture; and (c) culturing the tolerogenic dendritic cells culture medium (e.g., cGMP medium) comprising MPLA or MPLA and an antigen of associated with an autoimmune disease, graft-versus-host disease or graft rejection. In certain embodiments, the culture medium comprises one or more factors that induce the differentiation of monocytes into dendritic cells throughout the method for generating stable semi-mature tolDCs. Examples of factors that induce differentiation of monocytes into dendritic cells include the combination of GM-CSF and IL-4, IL-13, IL-15 or IFN-alpha, or Flt3L. In a specific embodiment, the culture medium comprises GM-CSF and IL-4 throughout the method for generating stable semi-mature tolDCs. The monocytes can be isolated from a subject's blood by any technique known to one of skill in the art or described herein. For example, the monocytes can be isolated from a subject's blood by leukapheresis. In specific embodiments, the tolerogenic dendritic cells are generated utilizing Dexamethasone in culture medium on the $3^{rd}$ day of culture and Dexamethasone and vitamin D2 in culture medium on the $6^{th}$ day of culture. In some embodiments, the tolerogenic dendritic cells are generated utilizing Dexamethasone and one or more factors that induce the differentiation of monocytes into dendritic cells in culture medium on the $3^{rd}$ day of culture, and Dexamethasone, vitamin D2 and one or more factors that induce the differentiation of monocytes into dendritic cells in culture medium on the $6^{th}$ day of culture. In specific embodiments, the tolerogenic dendritic cells are generated utilizing Dexamethasone, GM-CSF and IL-4 in culture medium on the $3^{rd}$ day of culture, and Dexamethasone, vitamin D2, GM-CSF and IL-4 in culture medium on the $6^{th}$ day of culture. In certain embodiments, the Dexamethasone is present in the culture medium at a final concentration between 0.5 and 3 micromole per liter. In some embodiments, the vitamin D2 is present in the culture medium at a final concentration between 0.1 and 10 nanomole per liter. In specific embodiments, the tolerogenic dendritic cells are cultured in culture medium comprising MPLA or MPLA and the antigen on the $7^{th}$ day of culture. In some embodiments, the tolerogenic dendritic cells are cultured in culture medium comprising MPLA and one or more factors that induce the differentiation of monocytes into dendritic cells, or MPLA, one or more factors that induce the differentiation of monocytes into dendritic cells, and the antigen on the $7^{th}$ day of culture. In a specific embodiment, the tolerogenic dendritic cells are cultured in culture medium comprising MPLA, GM-CSF and IL-4, or MPLA, GM-CSF, IL-4, and the antigen on the $7^{th}$ day of culture. In certain embodiments, the MPLA is present in the culture medium at a final concentration of between 1 and 3 µg per ml. In certain embodiments, the tolerogenic dendritic cells are cultured in culture medium comprising MPLA or MPLA and the antigen for a certain period of time (e.g., 24 hours) before the cells are harvested. In some embodiments, the tolerogenic dendritic cells are cultured in culture medium comprising MPLA and one or more factors that induce the differentiation of monocytes into dendritic cells, or MPLA, one or more factors that induce the differentiation of monocytes into dendritic cells, and the antigen for a certain period of time (e.g. 24 hours) before the cell are harvested. In specific embodiments, the tolerogenic dendritic cells are cultured in culture medium comprising MPLA, GM-CSF and IL-4, or MPLA, GM-CSF, IL-4, and the antigen for a certain period of time (e.g. 24 hours) before the cell are harvested. In certain embodiments, the method for generating stable semi-mature tolDCs takes approximately 8 days of cell culture.

In another embodiment, a method for generating tolerogenic dendritic cells able to maintain a stable semi-mature tolerogenic phenotype comprises: (a) isolating monocytes from a subject's blood; (b) culturing the monocytes in culture medium (e.g., cGMP medium) comprising one or more factors that induce the differentiation of monocytes into dendritic cells (e.g., GM-CSF and IL-4); (c) after a first period of time in culture, culturing the cells from step (b) in culture medium (e.g., cGMP medium) comprising Dexamethasone; (d) after a second period of time in culture, culturing the cells from step (c) in culture medium (e.g., cGMP medium) comprising Dexamethasone and vitamin D2 for a third period of time to generate tolerogenic dendritic cells; and (e) after a third period of time, culturing the tolerogenic dendritic cells in culture medium (e.g., cGMP medium) comprising MPLA or MPLA and an antigen of associated with an autoimmune disease, graft rejection, or graft-versus-host disease. In certain embodiments, the culture medium comprises one or more factors that induce the differentiation of monocytes into dendritic cells throughout the method for generating stable semi-mature tolDCs. Examples of factors that induce differentiation of monocytes into dendritic cells include the combination of GM-CSF and IL-4, IL-13, IL-15 or IFN-alpha, or Flt3L. In a specific embodiment, the culture medium comprises GM-CSF and IL-4 throughout the method for generating stable semi-mature tolDCs. The monocytes can be isolated from a subject's blood by any technique known to one of skill in the art or described herein. For example, the monocytes can be isolated from a subject's blood by leukapheresis. In certain embodiments, the cells from step (b) are cultured in culture medium comprising Dexamethasone on the $3^{rd}$ day in culture. In some embodiments, the cells from step (b) are cultured in culture medium comprising Dexamethasone and one or more factors that induce the differentiation of monocytes into dendritic cells (e.g., GM-CSF and IL-4) on the $3^{rd}$ day in culture. In some embodiments, the cells from step (c) are cultured in culture medium comprising Dexamethasone and vitamin D2 on the $6^{th}$ day in culture. In some embodiments, the cells from step (c) are cultured in culture medium comprising Dexamethasone, vitamin D2 and one or more factors that induce the differentiation of monocytes into dendritic cells (e.g., GM-CSF and IL-4) on the $6^{th}$ day in culture. In specific embodiment, the cells from step (b) are cultured in culture medium comprising Dexamethasone on the $3^{rd}$ day in culture, and the cells from step (c) are cultured in culture medium comprising Dexamethasone and vitamin D2 on the $6^{th}$ day in culture. In some embodiments, the cells from step (b) are cultured in culture medium comprising Dexamethasone and one or more factors that induce the differentiation of monocytes into dendritic cells (e.g., GM-CSF and IL-4) on the $3^{rd}$ day in culture, and the cells from step (c) are cultured in culture medium comprising Dexamethasone, vitamin D2 and one or more factors that induce the differentiation of monocytes into dendritic cells (e.g., GM-CSF and IL-4) on the $6^{th}$ day in culture. In certain embodiments, the Dexamethasone is present in the culture medium at a final concentration between 0.5 and 3 micromole per liter. In some embodiments, the vitamin D2 is present in the culture medium at a final concentration between 0.1 and 10 nanomole per liter. In specific embodiments, the tolerogenic dendritic cells are cultured in culture medium comprising MPLA or MPLA and the antigen on the $7^{th}$ day of culture. In some embodiments, the tolerogenic dendritic cells are cultured in culture medium comprising MPLA and one or more factors that induce the differentiation of monocytes into dendritic cells (e.g., GM-CSF and IL-4), or MPLA, one or more factors that induce the differentiation of monocytes into dendritic cells (e.g., GM-CSF and IL-4), and the antigen on the $7^{th}$ day of culture. In certain embodiments, the MPLA is present in the culture medium at a final concentration of between 1 and 3 μg per ml. In specific embodiments, the tolerogenic dendritic cells are cultured in culture medium comprising MPLA or MPLA and the antigen for a certain period of time (e.g., 24 hours) before the cells are harvested. In some embodiments, the tolerogenic dendritic cells are cultured in culture medium comprising MPLA and one or more factors that induce the differentiation of monocytes into dendritic cells (e.g., GM-CSF and IL-4), or MPLA, one or more factors that induce the differentiation of monocytes into dendritic cells (e.g., GM-CSF and IL-4), and the antigen for a certain period of time (e.g., 24 hours) before the cells are harvested. In certain embodiments, the method for generating stable semi-mature tolDCs takes approximately 8 days of cell culture.

In another embodiment, a method for generating tolerogenic dendritic cells able to maintain a stable semi-mature tolerogenic phenotype comprises: (a) culturing monocytes isolated from a subject's blood in culture medium comprising one or more factors that induce the differentiation of monocytes into dendritic cells (e.g., GM-CSF and IL-4); (b) after a first period of time in culture, culturing the cells from step (a) in culture medium (e.g., cGMP medium) comprising Dexamethasone; (c) after a second period of time in culture, culturing the cells from step (b) in culture medium (e.g., cGMP medium) comprising Dexamethasone and vitamin D2 for a third period of time to generate tolerogenic dendritic cells; and (d) after a third period of time, culturing the tolerogenic dendritic cells culture medium (e.g., cGMP medium) comprising MPLA or MPLA and an antigen of associated with an autoimmune disease, graft rejection or graft-versus-host disease. In certain embodiments, the culture medium comprises one or more factors that induce the differentiation of monocytes into dendritic cells throughout the method for generating stable semi-mature tolDCs. Examples of factors that induce differentiation of monocytes into dendritic cells include the combination of GM-CSF and IL-4, IL-13, IL-15 or IFN-alpha, or Flt3L. In a specific embodiment, the culture medium comprises GM-CSF and IL-4 throughout the method for generating stable semi-mature tolDCs. The monocytes can be isolated from a subject's blood by any technique known to one of skill in the art or described herein. For example, the monocytes can be isolated from a subject's blood by leukapheresis. In certain embodiments, the cells from step (b) are cultured in culture medium comprising Dexamethasone on the $3^{rd}$ day in culture. In some embodiments, the cells from step (b) are cultured in culture medium comprising Dexamethasone and one or more factors that induce the differentiation of monocytes into dendritic cells (e.g., GM-CSF and IL-4) on the $3^{rd}$ day in culture. In some embodiments, the cells from step (c) are cultured in culture medium comprising Dexamethasone and vitamin D2 on the $6^{th}$ day in culture. In some embodiments, the cells from step (c) are cultured in culture medium comprising Dexamethasone, vitamin D2 and one or more factors that induce the differentiation of monocytes into dendritic cells (e.g., GM-CSF and IL-4) on the $6^{th}$ day in culture. In specific embodiment, the cells from step (b) are cultured in culture medium comprising Dexamethasone on the $3^{rd}$ day in culture, and the cells from step (c) are cultured in culture medium comprising Dexamethasone and vitamin D2 on the $6^{th}$ day in culture. In some embodiments, the cells from step (b) are cultured in culture medium comprising Dexamethasone and one or more factors that induce the differentiation of monocytes into dendritic cells (e.g., GM-CSF and IL-4) on the $3^{rd}$ day in culture, and the cells from step (c) are cultured in culture medium comprising Dexamethasone, vitamin D2 and one or more factors that induce the differentiation of monocytes into dendritic cells (e.g., GM-CSF and IL-4) on the $6^{th}$ day in culture. In certain embodiments, the Dexamethasone is present in the culture medium at a final concentration between 0.5 and 3 micromole per liter. In some embodiments, the vitamin D2 is present in the culture medium at a final concentration between 0.1 and 10 nanomole per liter. In specific embodiments, the tolerogenic dendritic cells are cultured in culture medium comprising MPLA or MPLA and the antigen on the $7^{th}$ day of culture. In some embodiments, the tolerogenic dendritic cells are cultured in culture medium comprising MPLA and one or more factors that induce the differentiation of monocytes into dendritic cells (e.g., GM-CSF and IL-4), or MPLA, one or more factors that induce the differentiation of monocytes into dendritic cells (e.g., GM-CSF and IL-4), and the antigen on the $7^{th}$ day of culture. In certain embodiments, the MPLA is present in the culture medium at a final concentration of between 1 and 3 μg per ml. In specific embodiments, the tolerogenic dendritic cells are cultured in culture medium comprising MPLA or MPLA and the antigen for a certain period of time (e.g., 24 hours) before the cells are harvested. In some embodiments, the tolerogenic dendritic cells are cultured in culture medium comprising MPLA one or more factors that induce the differentiation of monocytes into dendritic cells (e.g., GM-CSF and IL-4), or MPLA, one or more factors that induce the differentiation of monocytes into dendritic cells (e.g., GM-CSF and IL-4), and the antigen for a certain period of time (e.g., 24 hours) before the cells are harvested. In certain embodiments, the method for generating stable semi-mature tolDCs takes approximately 8 days of cell culture.

In certain embodiments, a method described herein for generating stable semi-mature tolDCs result in a yield of dendritic cells in culture at the time the cells are harvested is similar to the yield of dendritic cells obtained by culturing the monocytes in culture medium comprising GM-CSF and IL-4 without tolerising agents, such as Dexamethasone and vitamin D2. In some embodiments, the method described herein for generating tolDCs result in a yield of dendritic cells in culture at the time the cells are harvested is similar to the yield of non-adherent dendritic cells obtained by culturing the monocytes in culture medium comprising GM-CSF and IL-4 without tolerising agents, such as Dexamethasone and vitamin D2. In specific embodiments, the term "similar" in this paragraph means that there is less than a 50%, 45%, 40%, 35%, 30%, 25%, 20%, 15%, or 10% difference in the yield of dendritic cells.

In some embodiments, a method described herein for generating stable semi-mature tolDCs results in a percentage of $CD11c^+$ dendritic cells in culture at the time the tolDCs are harvested that is equivalent or superior to the percentage of $CD11c^+$ dendritic cells obtained by culturing monocytes in culture medium comprising GM-CSF and IL-4 without tolerising agents, such as Dexamethasone and vitamin D2. In specific embodiments, the percentage of $CD11c^+$ dendritic cells in culture at the time the tolDCs are harvested is at least 20 percent. In accordance with these embodiments, in specific embodiments, the percentage of $CD11c^+$ dendritic cells culture is assessed after same length of time in culture.

In certain embodiments, a method described herein for generating stable semi-mature tolDCs results in PD-L1 expression on the population of tolerogenic dendritic cells in culture at the time the cells are harvested that is lower than the PD-L1 expression on the population of dendritic cells obtained by culturing monocytes in culture medium comprising GM-CSF and IL-4 without tolerising agents, such as Dexamethasone and vitamin D2. In some embodiments, the PD-L1 expression on the population of tolDCs is 70%, 65%, 60%, 55%, 50%, 45%, 40%, 35%, 30%, 25%, 20%, 15%, 10% or 5% lower than the PD-L1 expression on the population of dendritic cells obtained by culturing monocytes in culture medium comprising GM-CSF and IL-4. In accordance with these embodiments, in specific embodiments, the PD-L1 expression on the population of tolDCs and the population of dendritic cells obtained by culturing monocytes in culture medium comprising GM-CSF and IL-4 without tolerising agents, such as Dexamethasone and vitamin D2, are assessed after same length of time for cell culture.

In certain embodiments, a method described herein for generating stable semi-mature tolDCs results in CD14 expression on the population of tolerogenic dendritic cells in culture at the time the cells are harvested that is at least 3 times higher than the CD14 expression on the population of dendritic cells obtained by culturing monocytes in culture medium comprising GM-CSF and IL-4 without tolerising agents, such as Dexamethasone and vitamin D2. In some embodiments, the CD14 expression is approximately 3.5 times, 4 times, 4.5 times, 5 times, 5.5 times, 6 times, 6.5 times, 7 times, 7.5 times, 8 times, 8.5 times, 9 times, 9.5 times, 10 times, 10.5 times, 11 times, 11.5 times, 12 times, 12.5 times or 13 times higher than the CD14 expression on the population of dendritic cells obtained by culturing monocytes in culture medium comprising GM-CSF and IL-4. In certain embodiments, the CD14 expression is between 3 to 4 times, 3 to 5 times, 3 to 6 times, 3 to 10 times, 3 to 15 times, 4 to 6 times, 5 to 10 times, 10 to 15 times, 5 to 12 times, 10 to 13 times, or 5 to 15 times higher than the CD14 expression on the population of dendritic cells obtained by culturing monocytes in culture medium comprising GM-CSF and IL-4. In accordance with these embodiments, in specific embodiments, the CD14 expression on the population of tolDCs and the population of dendritic cells obtained by culturing monocytes in culture medium comprising GM-CSF and IL-4 without tolerising agents, such as Dexamethasone and vitamin D2, are assessed after same length of time for cell culture.

In certain embodiments, a method described herein for generating stable semi-mature tolDCs results in CD86 expression on the population of tolerogenic dendritic cells in culture at the time the cells are harvested that is lower than the CD86 expression on the population of dendritic cells obtained by culturing monocytes in culture medium comprising GM-CSF and IL-4 without tolerising agents, such as Dexamethasone and vitamin D2. In some embodiments, the CD86 expression on the population of tolDCs is 70%, 65%, 60%, 55%, 50%, 45%, 40%, 35%, 30%, 25%, 20%, 15%, or 10% lower than the CD86 expression on the population of dendritic cells obtained by culturing monocytes in culture medium comprising GM-CSF and IL-4. In accordance with these embodiments, in specific embodiments, the CD86 expression on the population of tolDCs and the population of dendritic cells obtained by culturing monocytes in culture medium comprising GM-CSF and IL-4 without tolerising agents, such as Dexamethasone and vitamin D2, are assessed after same length of time for cell culture.

In certain embodiments, a method described herein for generating stable semi-mature tolDCs results in CXCR3 expression on the population of tolerogenic dendritic cells in culture at the time the cells are harvested that is higher than the CXCR3 expression on the population of dendritic cells obtained by culturing monocytes in culture medium comprising GM-CSF and IL-4 without tolerising agents, such as Dexamethasone and vitamin D2. In some embodiments, the CXCR3 expression on the population of tolDCs is 200%, 150%, 100%, 90%, 80%, 70%, 60%, 50%, 45%, 40%, 35%, 30%, 25%, 20%, 15%, or 10% higher than the CXCR3 expression on the population of dendritic cells obtained by culturing monocytes in culture medium comprising GM-CSF and IL-4. In accordance with these embodiments, in specific embodiments, the CXCR3 expression on the population of tolDCs and the population of dendritic cells obtained by culturing monocytes in culture medium comprising GM-CSF and IL-4 without tolerising agents, such as Dexamethasone and vitamin D2, are assessed after same length of time for cell culture.

In certain embodiments, a method described herein for generating stable semi-mature tolDCs results in tolDCs that induce a higher number of $CD4^+CD25^+FoxP3^+$ regulatory T cells than dendritic cells obtained by culturing monocytes in culture medium comprising GM-CSF and IL-4 without tolerising agents, such as Dexamethasone and vitamin D2. In certain embodiments, a method described herein for generating stable semi-mature tolDCs results in tolDCs that induce a 250%, 200%, 150%, 100%, 75%, 50%, 45%, 40%, 35%, 30%, 25%, 20%, 15%, or 10% higher number of $CD4^+CD25^+FoxP3^+$ regulatory T cells than dendritic cells obtained by culturing monocytes in culture medium comprising GM-CSF and IL-4 without tolerising agents, such as Dexamethasone and vitamin D2. In a specific embodiment, the Tregs were induced as described in Section 6, 7 and/or 8 infra.

In a specific embodiment, a method for generating stable semi-mature tolDCs described herein results in tolDCs with one, two, three or more of the functional properties of the Dex/Vitamin D2 tolDCs described in Section 6, 7 and/or 8, infra. In another specific embodiment, a method for generating stable semi-mature tolDCs described herein results in tolDCs with all of the functional properties of the Dex/Vitamin D2 tolDCs described in Section 6, 7 and/or 8, infra.

In certain embodiments, in accordance with the methods described herein, the antigen of interest can be any antigen associated with an autoimmune disease. See, e.g., Table 1, infra, for a list of autoimmune diseases and antigens associated with those autoimmune diseases. In a specific embodiment, the antigen is a GAD65 polypeptide. In another specific embodiment, the antigen is an insulin polypeptide. In some embodiments, the step of culturing the tolDCs with antigen involves culturing with one, two, three or more antigens associated with an autoimmune disease, such as GAD65 and insulin.

In some embodiments, in accordance with the methods described herein, the antigen of interest can be any antigen associated with graft rejection or graft-versus-host disease. In some embodiments, the step of culturing the tolDCs with antigen involves culturing with one, two, three or more antigens associated with graft rejection or graft-versus-host disease. In certain embodiments, a cell lysate(s) or MHC-peptide(s) obtained or derived from the donor of a graft (e.g., tissue or cell sample) is used as antigens.

In another aspect, provided herein are stable semi-mature tolDCs. In a specific embodiment, provided herein is a population of stable semi-mature tolerogenic dendritic cells produced by a method described herein. In specific embodiments, stable semi-mature tolDCs induce a cytokine profile and generate Tregs which are favorable for the treatment of autoimmune diseases. In specific embodiments, stable semi-mature tolDCs induce a cytokine profile and generate Tregs which are favorable for the treatment of graft rejection or graft-versus-host disease. In certain embodiments, the stable semi-mature tolerogenic dendritic cells are cryopreserved.

In another aspect, provided herein is a method for treating an autoimmune disease in a subject, comprising administering to the subject the stable semi-mature tolDCs described herein which were cultured in culture medium comprising MPLA and an antigen associated with the autoimmune disease. In a specific embodiment, provided herein is a method for treating type 1 diabetes in a subject, comprising administering to the subject stable semi-mature tolerogenic dendritic cells which were cultured in culture medium comprising MPLA and an antigen associated with type 1 diabetes, such as a GAD65 polypeptide or an insulin polypeptide. In certain embodiments, the tolerogenic dendritic cells are derived from monocytes from a subject with a hemoglobin ("Hb") A1c ("HbA1c") level of equal to or less than 60 mmol/mol Hb. In other embodiments, the tolerogenic dendritic cells are derived from monocytes from a subject with well compensated blood sugar levels. In specific embodiments, the tolerogenic dendritic cells are derived from monocytes that are autologous to the subject being treated. In specific embodiments, the subject is a human subject.

In another aspect, provided herein is a method for treating graft rejection or graft-versus-host disease, comprising administering to the subject the stable semi-mature tolDCs described herein which were cultured in culture medium comprising MPLA and an antigen associated with the graft rejection or graft-versus-host disease. In specific embodiments, the tolerogenic dendritic cells are derived from monocytes that are autologous to the subject being treated. In specific embodiments, the subject is a human subject.

In another aspect, provided herein is a method for treating an autoimmune disease in a subject, comprising: (a) culturing stable semi-mature tolerogenic dendritic cells, which were cultured in culture medium comprising MPLA and an antigen associated with the autoimmune disease, in culture medium with T cells to induce Tregs; (b) isolating the Tregs; and (c) administering the Tregs to the subject. In certain embodiments, the isolated Tregs are expanded in culture before being administered to the subject. In specific embodiments, the tolerogenic dendritic cells are derived from monocytes that are autologous to the subject being treated. In specific embodiments, the Tregs are derived from T cells that are autologous to the subject being treated. In specific embodiments, the subject is a human subject.

In a specific embodiment, provided herein is a method for treating type 1 diabetes in a subject, comprising: (a) culturing stable semi-mature tolerogenic dendritic cells, which were cultured in culture medium comprising MPLA and an antigen associated with type 1 diabetes, such as a GAD65 polypeptide or an insulin polypeptide, in culture medium with T cells to induce Tregs; (b) isolating the Tregs; and (c) administering the Tregs to the subject. In certain embodiments, the isolated Tregs are expanded in culture before being administered to the subject. In certain embodiments, the tolerogenic dendritic cells are derived from monocytes from a subject with a hemoglobin ("Hb") A1c ("HbA1c") level of equal to or less than 60 mmol/mol Hb. In specific embodiments, the tolerogenic dendritic cells are derived from monocytes that are autologous to the subject being treated. In certain embodiments, the T cells are isolated from a subject with a hemoglobin ("Hb") A1c ("HbA1c") level of equal to or less than 60 mmol/mol Hb. In specific embodiments, the Tregs are derived from T cells that are autologous to the subject being treated. In specific embodiments, the subject is a human subject.

In another aspect, provided herein is a method for treating graft rejection or graft-versus-host disease in a subject, comprising: (a) culturing stable semi-mature tolerogenic dendritic cells, which were cultured in culture medium comprising MPLA and an antigen associated with the graft rejection or graft-versus-host disease, in culture medium with T cells to induce Tregs; (b) isolating the Tregs; and (c) administering the Tregs to the subject. In certain embodiments, the isolated Tregs are expanded in culture before being administered to the subject. In specific embodiments, the tolerogenic dendritic cells are derived from monocytes that are autologous to the subject being treated. In specific embodiments, the Tregs are derived from T cells that are autologous to the subject being treated. In specific embodiments, the subject is a human subject.

4. DESCRIPTION OF THE DRAWINGS

Figures 1, 7A:
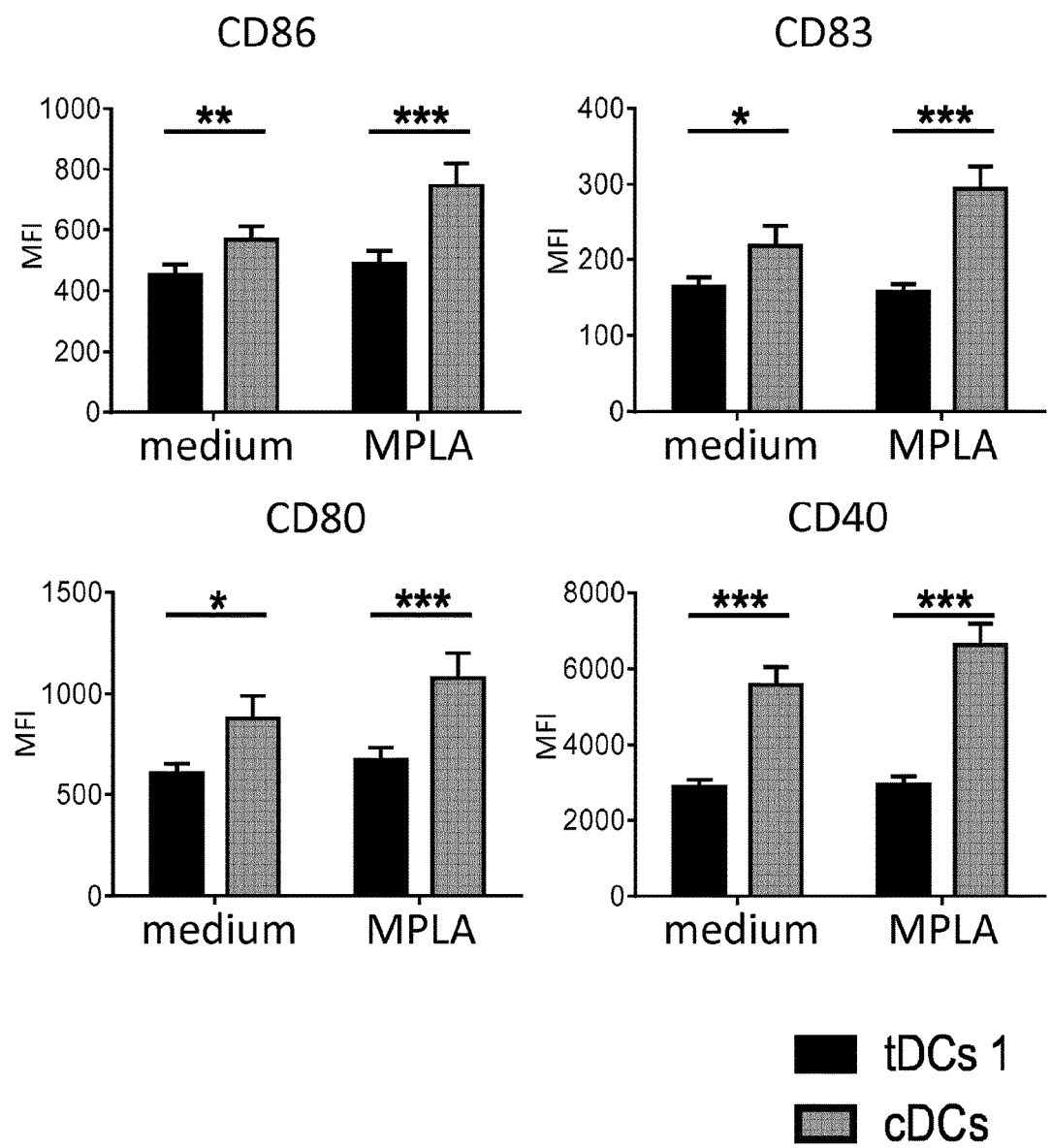

FIG. 1: tolDCs generated by the tolDC protocol 1 have the highest yield of cells in final culture (A) and the highest percentage of CD11c+ DCs in final culture (B) when compared with other tolDCs established by other methods. DCs were cultivated for 8 days in Cell Gro media without tolerogenic factors (control DCs), with Dex (day 3+6) and VitD2 (day 6)-tolDCs1, with Dex (day 3+6) and Vit D2 (day 0, 3, 6)-tolDCs 2, with VitD2 only (day 0, 3, 6)-tolDCs 3. Percentage of CD11c+ DCs in final culture was estimated by FACs analysis.

Figures 2, 7A:
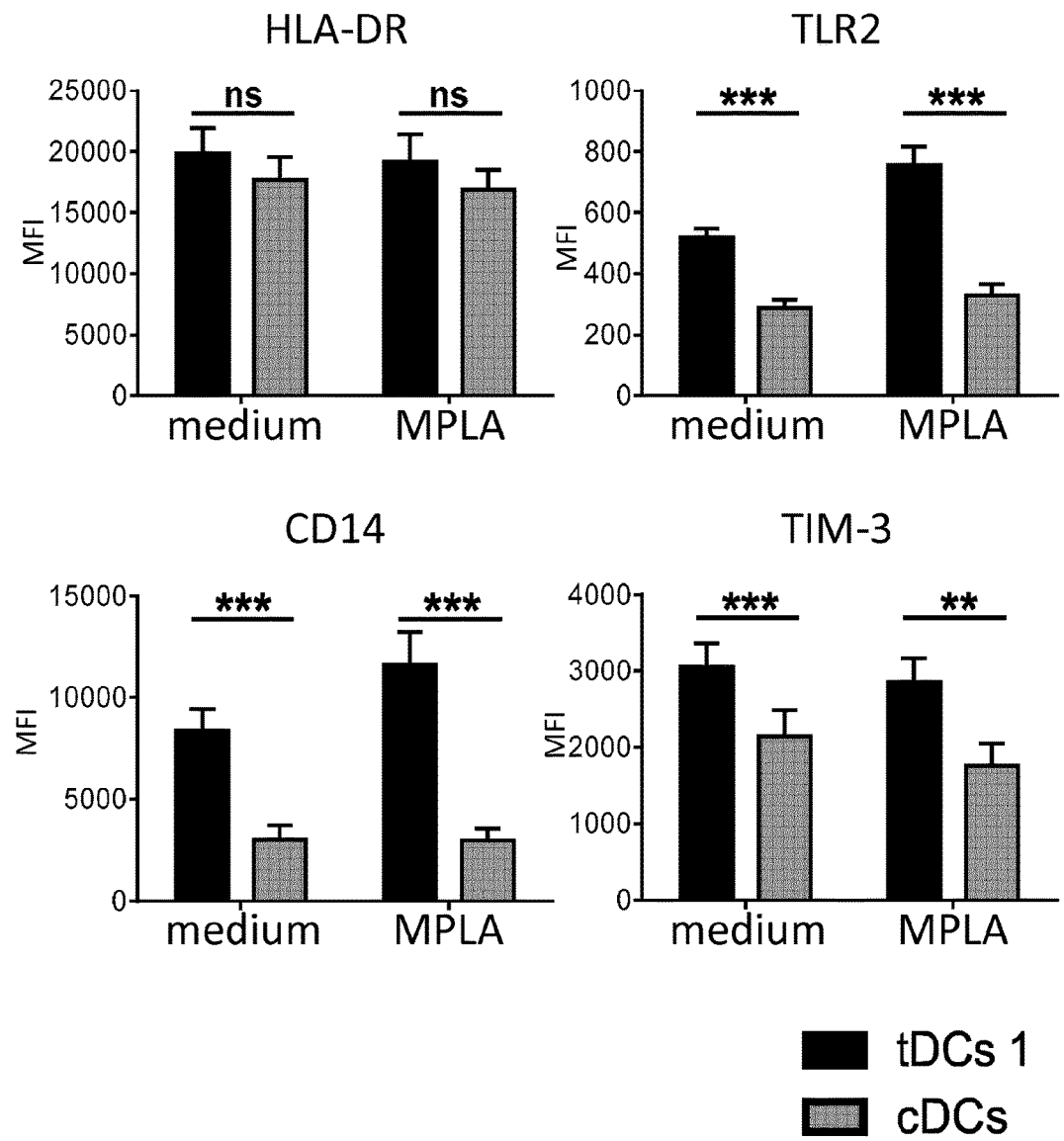

FIG. 2: tolDCs generated by tolDC protocol 1 express significantly lower level of tolerogenic molecule PD-L1 (A) but significantly higher levels of CD14 (B) in comparison with tolDCs generated by other methods. DCs were cultivated for 8 days in Cell Gro media without tolerogenic factors (control DCs), with Dex (day 3+6) and VitD2 (day 6)-tolDCs1, with Dex (day 3+6) and VitD2 (day 0, 3, 6)-tolDCs 2, with VitD2 only (day 0, 3, 6)-tolDCs 3. PD-L1 and CD14 expression on DCs was estimated by FACS analysis.

Figures 3, 7A:
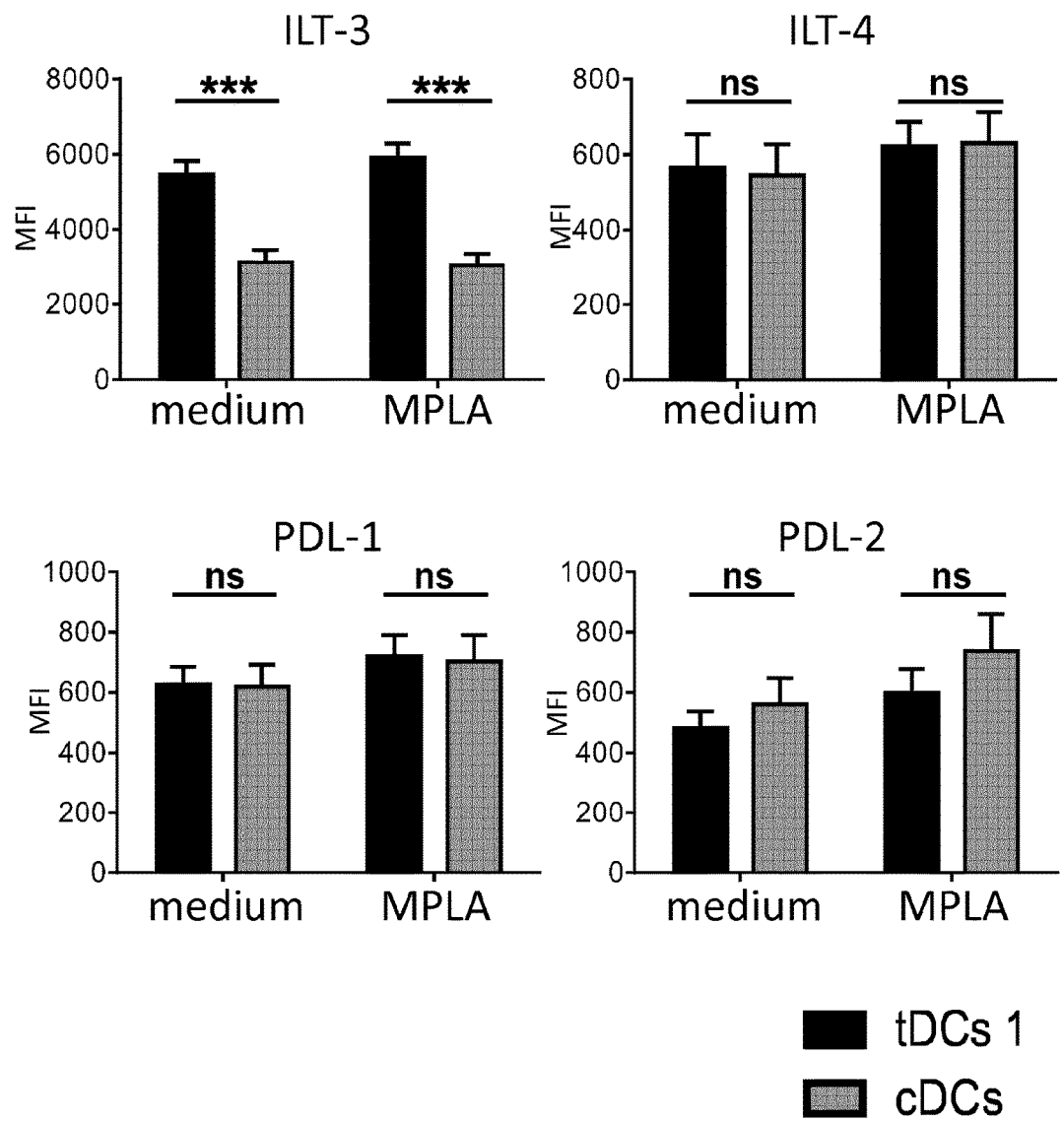
Figures 4, 7A:
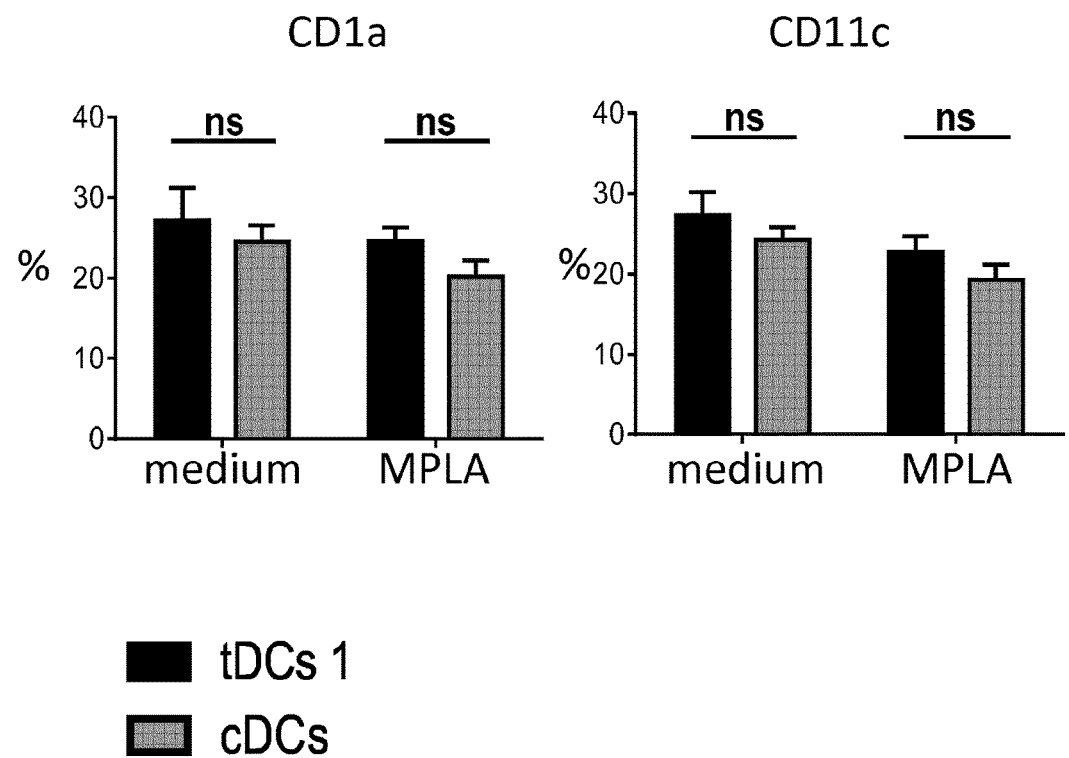
Figures 1, 7B:
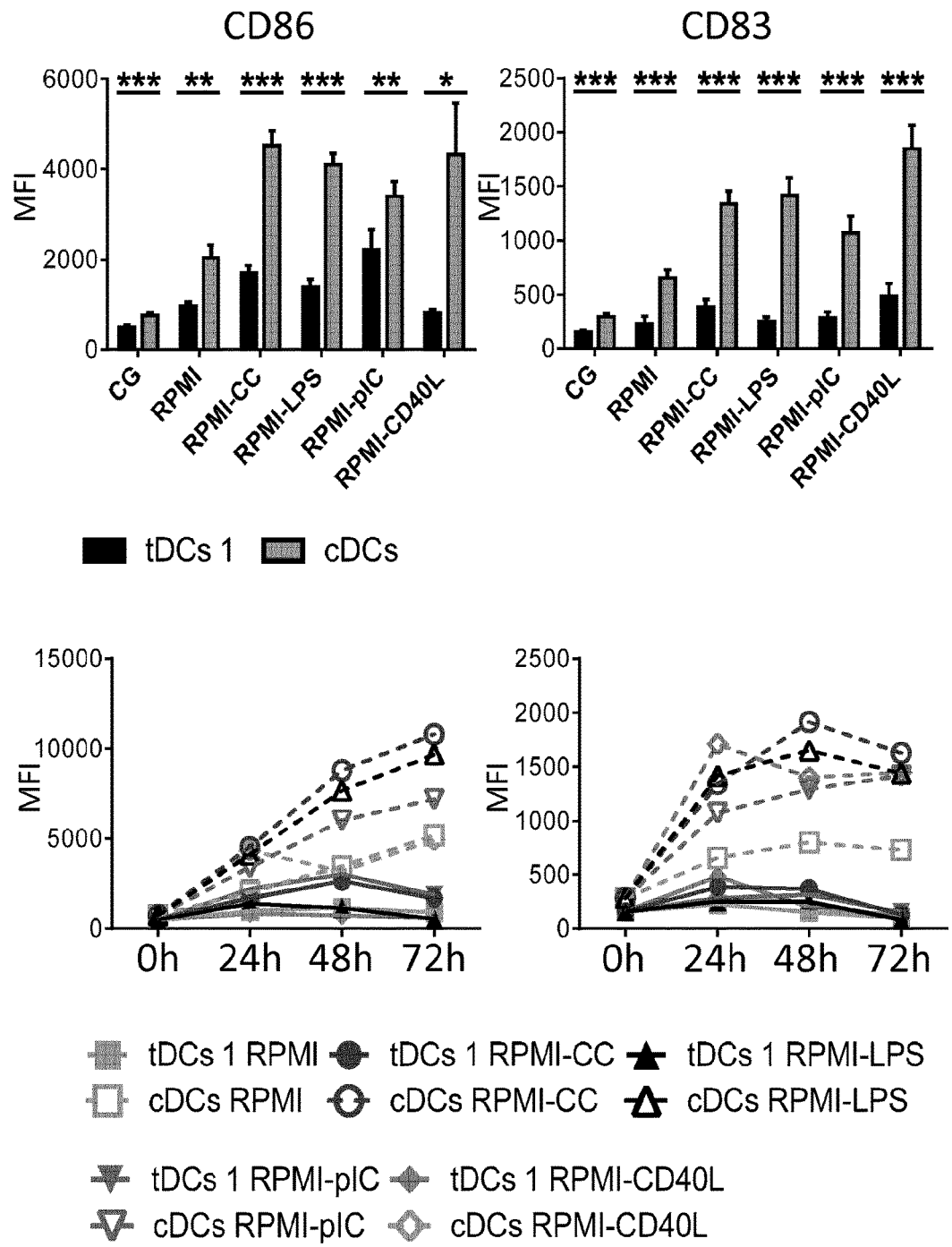
Figures 2, 7B:
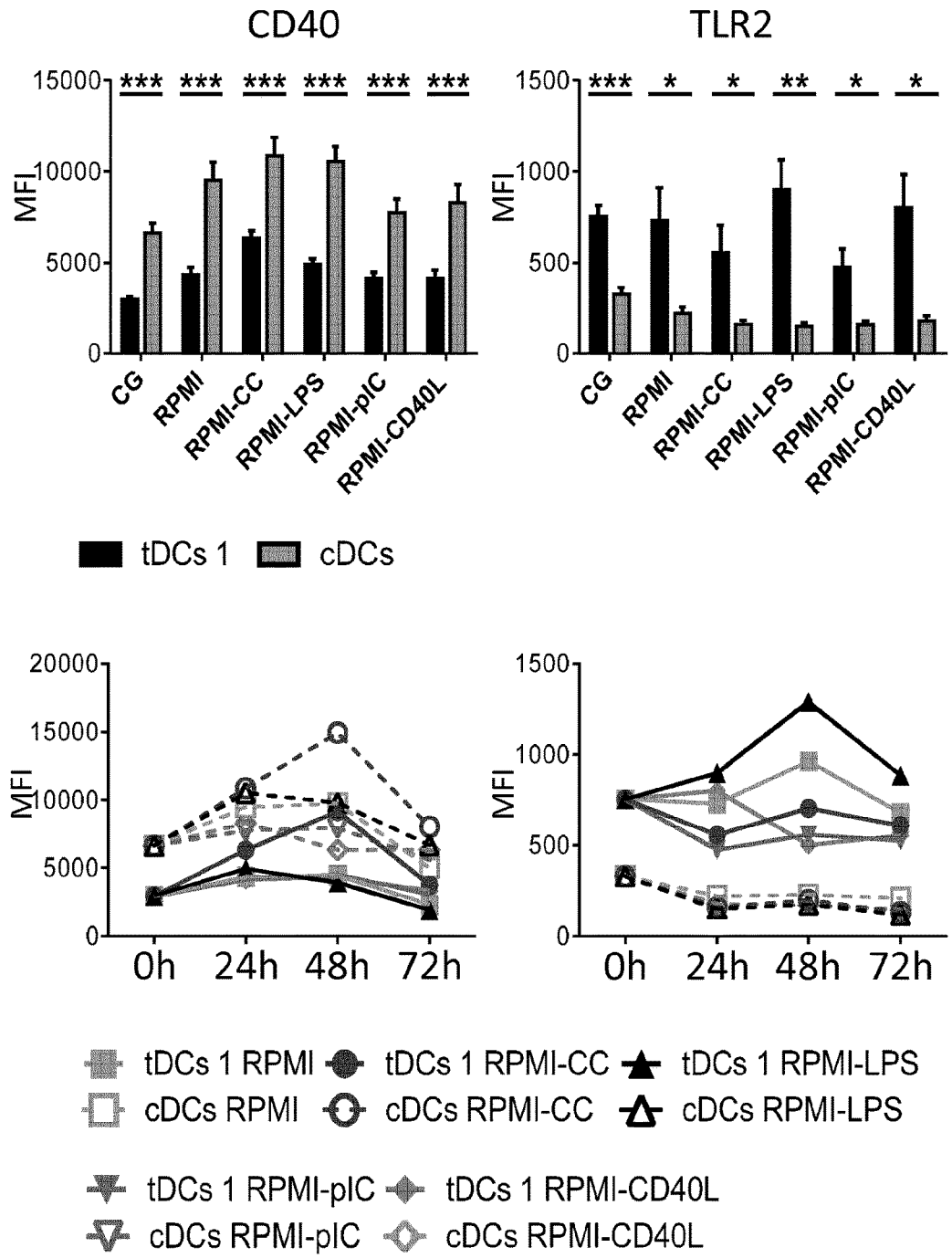
Figures 3, 7B:
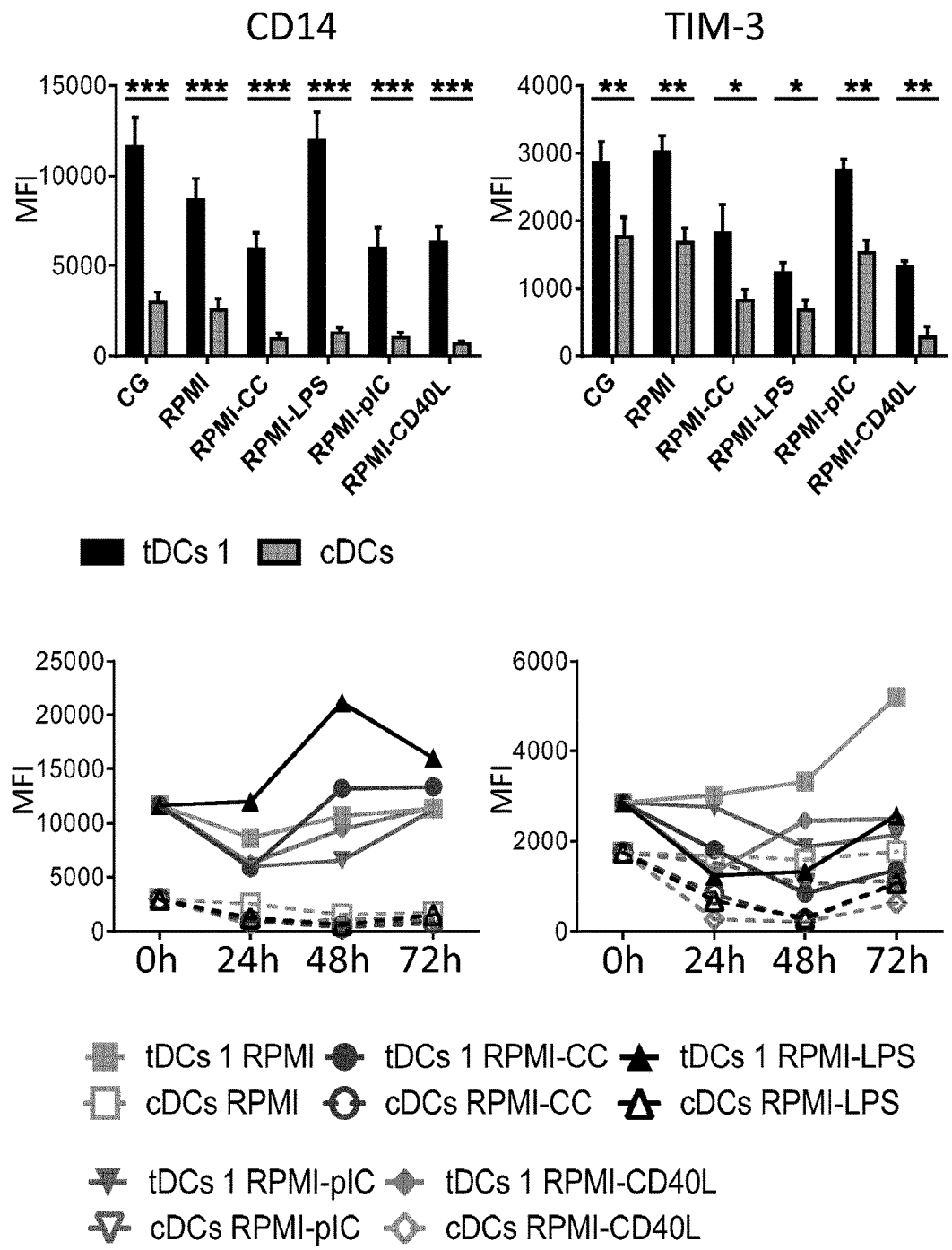
Figures 4, 7B:
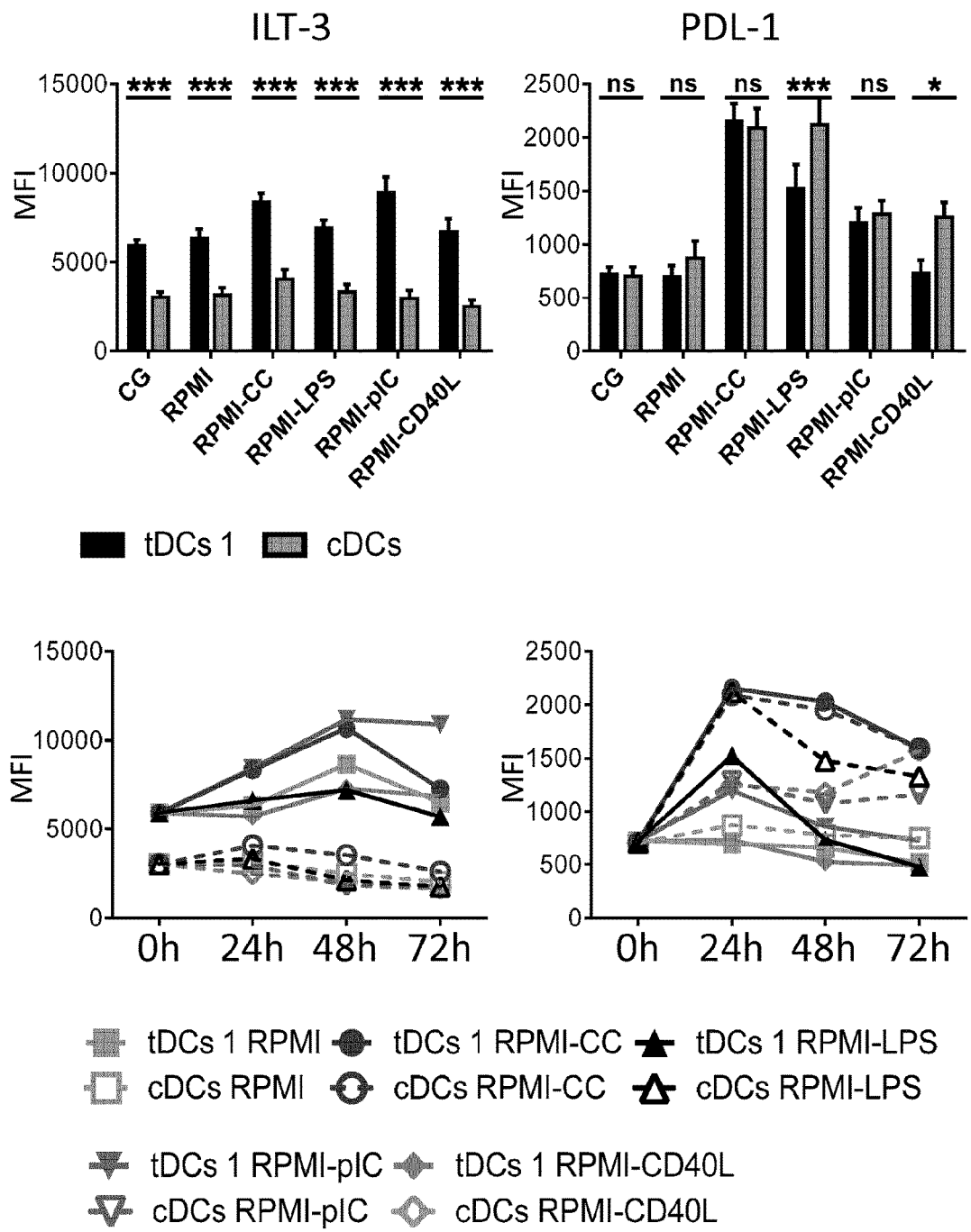

FIG. 3: tolDCs generated by tolDC protocol 1 express significantly lower level of maturation marker CD86 (A) but significantly higher levels of chemokine receptor CXCR3 (B) in comparison with tolDCs generated by other methods. DCs were cultivated for 8 days in Cell Gro media without tolerogenic factors (control DCs), with Dex (day 3+6) and VitD2 (day 6)-tolDCs1, with Dex (day 3+6) and VitD2 (day 0, 3, 6)—tolDCs 2, with VitD2 only (day 0, 3, 6)-tolDCs 3. CD86 and CXCR3 expression on DCs was estimated by FACS analysis.

Figure 4:
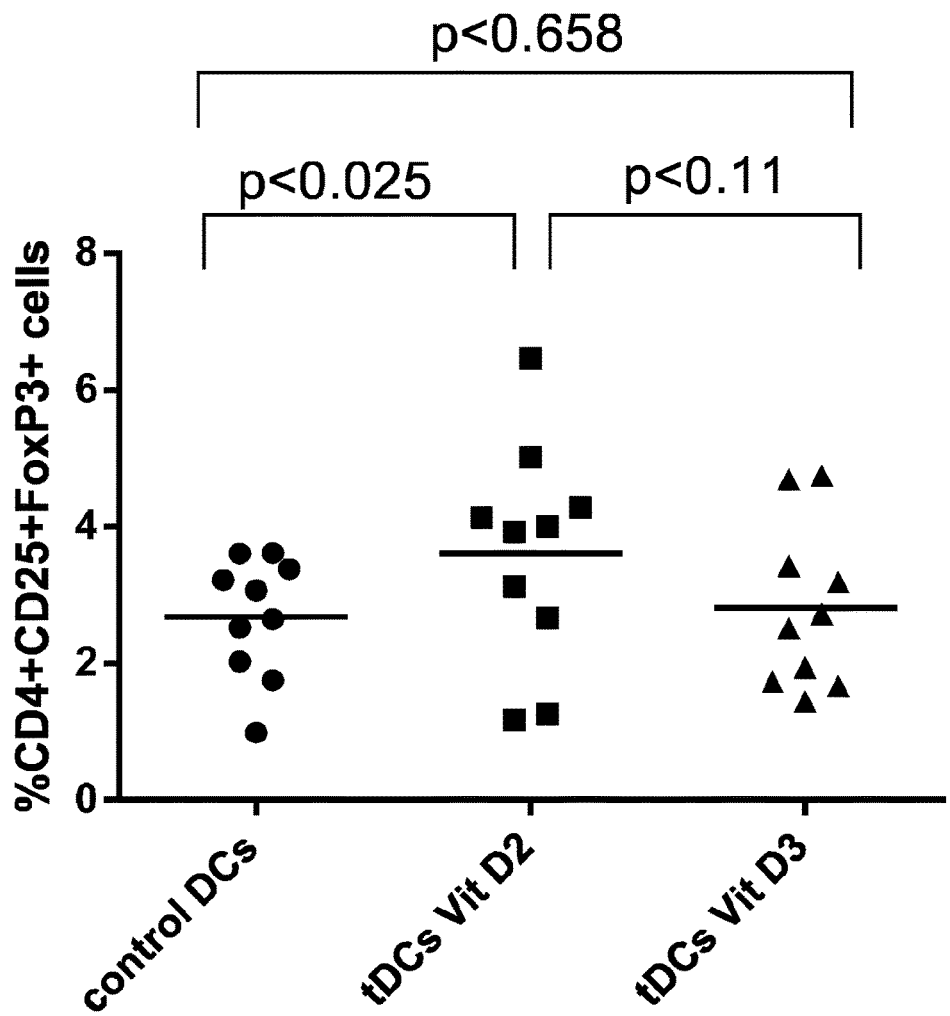

FIG. 4: tolDCs generated by using tolDCs protocol 1 (VitD2), but not tolDCs generated by using tolDCs protocol 4 (VitD3), induce higher levels of CD4+CD25+FoxP3+ T regulatory cells in comparison with control DCs. DCs were generated for 8 days in Cell Gro media with Dex and vitamin D2 (tolDCs VitD2), Dex and vitamin D3 (tolDCs VitD3) or without Dex and vitamin D (control DCs). DCs were cultivated with naïve allogeneic T cells in ratio of 1:10 (DCs: T cells) for 9 days. Percentage of $CD4^+CD25^+FoxP3^+$ T regulatory cells was analyzed by FACS analysis.

Figure 5:
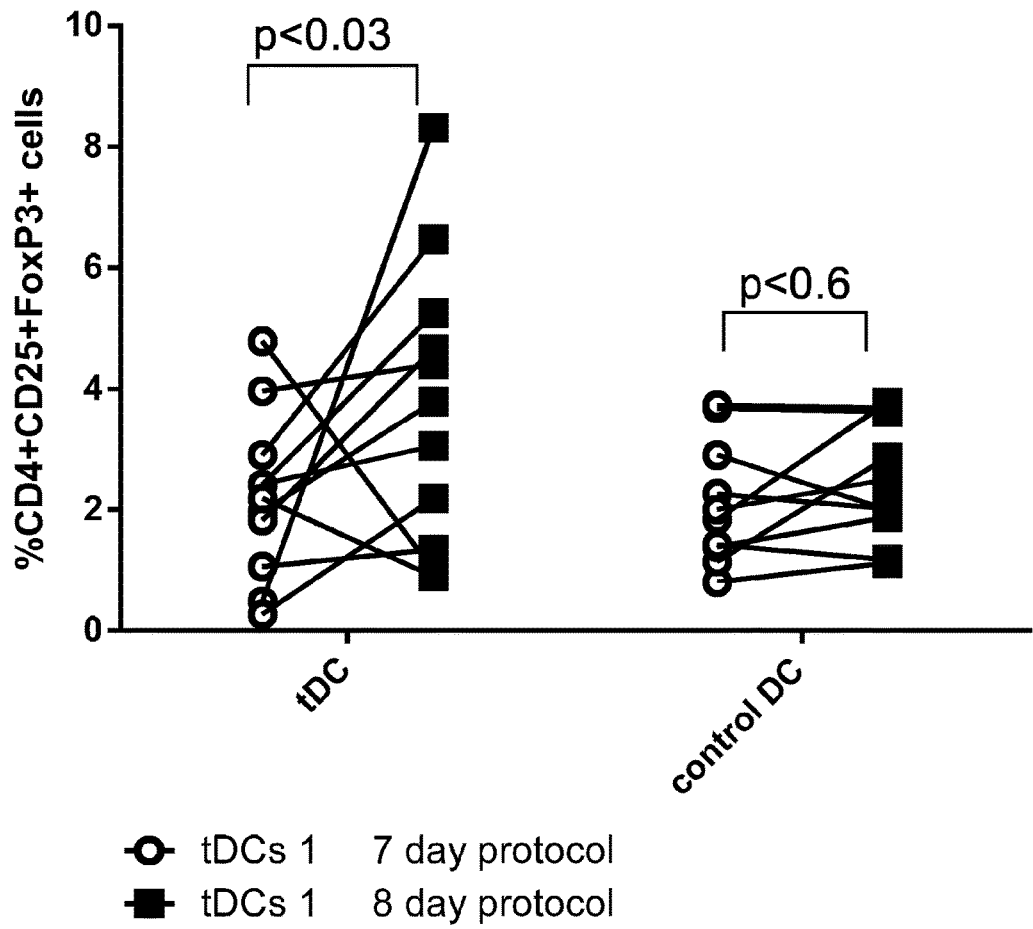

FIG. 5: tolDCs generated by tolDCs1 8 days protocol induce higher levels of CD4+CD25+FoxP3+T regulatory cells when compared to tolDCs generated by tolDCs1 protocol for 7 days. TolDCs were generated for 7 days (open circles) or 8 days (black squares) in Cell Gro media with Dex and vitamin D2. TolDCs were cultivated with naïve allogeneic T cells in ratio of 1:10 (tolDCs: T cells) for 9 days. Percentage of CD4+CD25+FoxP3+ T regulatory cells was analyzed by FACS analysis.

Figure 6:
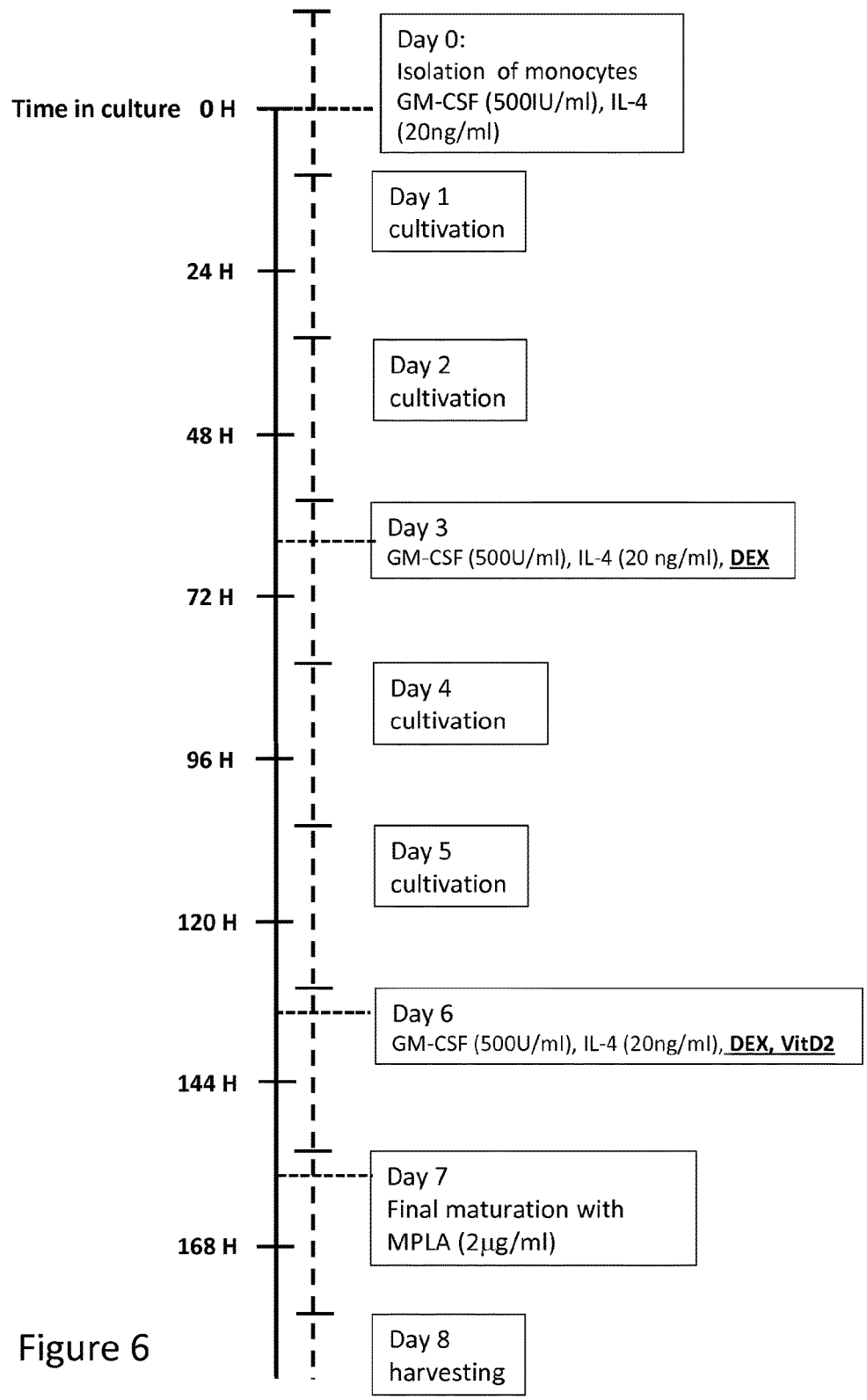

FIG. 6: Schematic drawing showing the timeline of the culture protocol tolDC 1.

FIG. 7: Dex/VitD2 tolDC generated by tolDCs 1 protocol display tolerogenic features and exhibit a stable semi-mature phenotype. DC were differentiated in Cell Gro in presence (tolDC) or absence of Dex and VitD2 (cDC) and then activated with MPLA. A (1-4) Surface marker expression on tolDC and cDC after maturation was evaluated by flow cytometry. B (1-4) tolDC and cDC were cultured in CG (CG), than washed and recultured in complete RPMI without tolerising factors and treated with following stimuli: cytokine cocktail (CC) containing IL-1β (10 ng/ml), TNF-α (10 ng/ml), IL-6 (10 ng/ml) and IFN-γ (100 ng/ml) or LPS (1 µg/ml) or poly(I:C) (25 µg/ml) or CD40L (1000 ng/ml) or they were left unstimulated in RPMI. Expression of surface markers was analyzed by flow cytometry. Bar graphs represent expression of surface markers after 24 h of restimulation, continuous lines represent expression level after 24-72 h of restimulation Data are expressed as mean fluorescence intensity (MFI)±SEM or percentages of positive cells (CD1a and CD11c expression) from minimal 10 donors.

FIG. 8: tolDCs generated by tolDCs 1 protocol exhibit an anti-inflammatory cytokine secretion profile. (A) DC were differentiated in Cell Gro in presence (tolDC) or absence of Dex and VitD2 (cDC) and then activated with MPLA. Concentration of IL-6, TNF-α, IL-10 and IL-12p70 (in pg/ml) in cell culture supernatants were analyzed by Luminex. (B) tolDC and cDC were washed, recultured in complete RPMI without tolerising factors and treated with following stimuli: cytokine cocktail (CC) containing IL-1β (10 ng/ml), TNFα (10 ng/ml), IL-6 (10 ng/ml) and IFNγ (100 ng/ml) or LPS (1 µg/ml) or poly(I:C) (25 µg/ml) or CD40L (1000 ng/ml) or they were left unstimulated in RPMI. After 24 h, cell culture supernatants were collected and concentration of cytokines was analyzed by Luminex and ELISA. Data are expressed as mean±SEM for at least 5 donors. *p≤0.05, p≤0.01, *p≤0.001 (paired t-test).

FIG. 9: tolDCs generated by tDCs 1 protocol show a reduced stimulatory potential in allogeneic stimulatory assay even after restimulation. DC were differentiated in Cell Gro in presence (tolDC) or absence of Dex and VitD2 (cDC) and activated with MPLA. Then, tolDC and cDC were washed, recultured in complete RPMI without tolerising factors and treated with following stimuli: cytokine cocktail (CC) containing IL-1β (10 ng/ml), TNFα (10 ng/ml), IL-6 (10 ng/ml) and IFNγ (100 ng/ml) or LPS (1 µg/ml) or poly(I:C) (25 µg/ml) or CD40L (1000 ng/ml) or they were left unstimulated in RPMI. After 24 h of restimulation, tolDC and DC were harvested, washed and incubated with allogeneic T cells at 1:10 ratio (DC/T cells). A (1-2) Proliferation of T cells induced by tolDC and DC after their reculturing into RPMI and following restimulation in comparison to proliferation of T cells induced by tolDC and DC from Cell Gro (CG) was assessed on day 6 by CFSE dilution method. Percentages of proliferating T cells and representative histograms are shown. (B) T cell production of IFN-γ induced by tolDC and cDC after their reculturing into RPMI and following restimulation in comparison to T cell production of IFNγ induced by tolDC and cDC from Cell Gro (CG). The number of IFNγ producing T cells was assessed on day 6 by IFNγ intracellular staining. Percentages of IFNγ positive T cells and representative dot plots are shown. (C) T cell production of IL-10 induced by tolDC and cDC after their reculturing into RPMI and following restimulation in comparison to T cell production of IL-10 induced by tolDC and cDC from Cell Gro (CG). The number of IL-10 producing T cells was assessed on day 9 by IL-10 intracellular staining. Percentages of IL-10 positive T cells and representative dot plots are shown. Data are expressed as mean±SEM for at least 10 donors. *p≤0.05, p≤0.01, *p≤0.001 (paired t-test).

Figure 10:
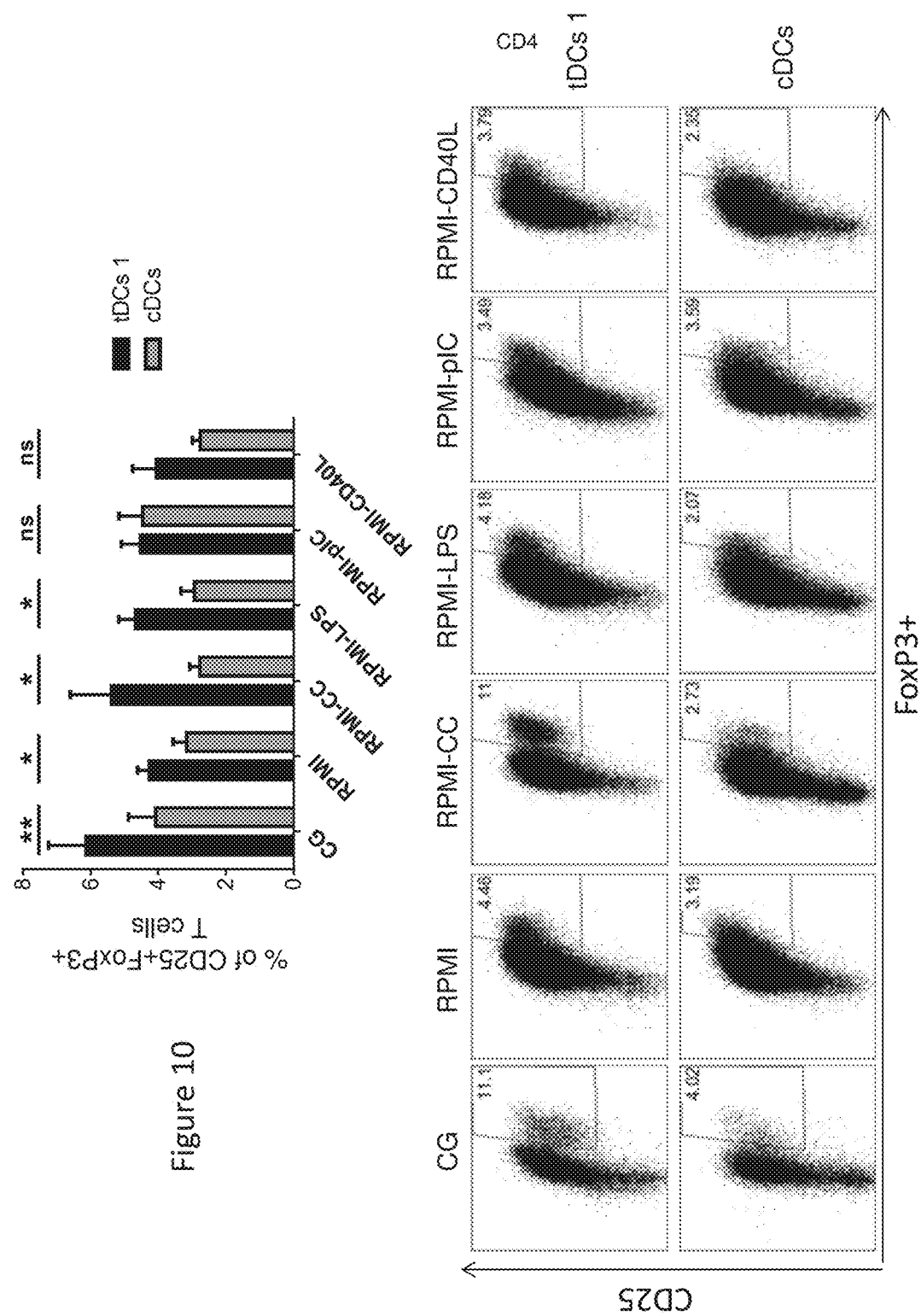

FIG. 10: tolDCs generated by tolDCs 1 protocol induce de novo CD4+CD25+FoxP3+ regulatory T cell differentiation from naïve CD4+ T cells. DC were differentiated in Cell Gro in presence (tolDC) or absence of Dex and VitD2 (cDC) and activated with MPLA. Then, tolDC and cDC were washed, recultured in complete RPMI without tolerising factors and treated with following stimuli: cytokine cocktail (CC) containing IL-1β (10 ng/ml), TNFα (10 ng/ml), IL-6 (10 ng/ml) and IFNγ (100 ng/ml) or LPS (1 µg/ml) or poly(I:C) (25 µg/ml) or CD40L (1000 ng/ml) or they were left unstimulated in RPMI. After 24 h of restimulation, tolDC and cDC were harvested, washed and incubated with allogeneic T cells at 1:10 ratio (DC/T cells). Differentiation of CD4+CD25+FoxP3+ T cells from naïve CD4+ T cells was assessed on day 9 by FoxP3 intracellular staining. Percentages of CD4+CD25+FoxP3+ T cells and representative dot plots are shown. Data are expressed as mean±SEM for at least 10 donors. *p≤0.05, p≤0.01, *p≤0.001 (paired t-test).

FIG. 11: Different intracellular signaling pathways are triggered in tolDC1 and cDC after mimicking in vivo DC activation. DC were differentiated in Cell Gro in presence (tolDC) or absence of Dex and VitD2 (cDC) and activated with MPLA. Then, tolDC and cDC were washed, recultured in complete RPMI without tolerising factors and treated for 60 min with following stimuli: cytokine cocktail (CC) containing IL-1β (10 ng/ml), TNFα (10 ng/ml), IL-6 (10 ng/ml) and IFNγ (100 ng/ml) or LPS (1 µg/ml) or poly(I:C) (25 µg/ml) or CD40L (1000 ng/ml) or they were left unstimulated in RPMI. (A) After 60 min of stimulation, cell lysates were prepared and western blot analysis for phosphorylated p38 MAPK, JNK/SAPK, ERK1/2, IkB-α were performed using specific mAbs. The level of IDO was also analyzed using specific mAb. Total p38 MAPK, JNK/SAPK, ERK1/2, IkB-α or β-actin in each sample were used as the equal loading control. One of three experiments performed is shown. (B) Analysis of DNA-binding activity of NF-κB subunits p50, p65/RelA, RelB and c-Rel. DC were left untreated (CG) or restimulated for 90 min in RPMI alone or in combination with CC, LPS, poly(I:C) and CD40L. DNA-binding activity of NF-κB subunits was analyzed by colorimetric assay. C (1-6) Production of IL-10 and IL-12 after restimulation of tolDC and cDC with RPMI, CC, LPS, poly(I:C) and CD40L in the presence of p38 MAPK inhibitor SB203580 (SB), JNK/SAPK inhibitor SP600125 (SP), ERK1/2 inhibitor PD98059 (PD), NF-κB inhibitor Bay 11-0782 (Bay) was evaluated by ELISA. D (1-3) Expression of PD-L1 and ILT-3 on tolDC and cDC after restimulation with RPMI, CC, LPS, poly(I:C) and CD40L for 24 h in the presence of p38 MAPK inhibitor SB203580 (SB) and ERK1/2 inhibitor PD98059 (PD) was evaluated by flow cytometry. Data are expressed as mean±SEM for at least 10 donors. *p≤0.05, p≤0.01, *p≤0.001 (paired t-test).

FIG. 12: tolDC generated by tDCs 1 protocol exhibit activation of mTOR and STAT3 after restimulation with CC, LPS, poly(I:C) and CD40L. DC were differentiated in Cell Gro in presence (tolDC) or absence of Dex and VitD2 (cDC) and activated with MPLA. Then, tolDC and cDC were washed, recultured in complete RPMI without tolerising factors and treated for 60 min with following stimuli: cytokine cocktail (CC) containing IL-1β (10 ng/ml), TNFα (10 ng/ml), IL-6 (10 ng/ml) and IFNγ (100 ng/ml) or LPS (1 μg/ml) or poly(I:C) (25 μg/ml) or CD40L (1000 ng/ml) or they were left unstimulated in RPMI. When indicated, cells were pretreated with mTOR inhibitor rapamycin or STAT3 inhibitor Stattic for 30 min before restimulation. (A) After 60 min of stimulation, cell lysates were prepared and western blot analysis for phosphorylated mTOR, p70S6K and STAT3 were performed using specific mAbs. β-actin was used as the equal loading control. One of three experiments performed is shown. (B) The levels of IL-10 and IL-12 secreted by DC after 24 h of stimulation were measured by ELISA. C (1-4) Expression of PD-L1 and ILT-3 molecules after restimulation with RPMI, CC, LPS, poly(I:C) and CD40L for 24 h in the presence of mTOR inhibitor rapamycin or STAT3 inhibitor Stattic was evaluated by FACS analysis. Data are expressed as mean±SEM for at least 4 independent experiments. *p≤0.05, p≤0.01, *p≤0.001 (paired t-test).

FIG. 13: tolDCs established from T1D patients using the tDCs 1 protocol, exhibit a stable semi-mature phenotype. A (1-3) Surface marker expression on tolDCs and cDC after maturation. DC from T1D patients were differentiated in Cell Gro in presence (tolDCs) or absence of Dex and VitD2 (cDC), loaded with insulin (1 μg/ml) or GAD-65 (5 μg/ml) and then activated with MPLA. B (1-2) Surface marker expression on tolDCs and cDC after their reculturing into RPMI and following restimulation in comparison to basal expression determined on tolDCs and DC from Cell Gro (CG). tolDCs and cDC were washed, recultured in complete RPMI without tolerising factors and treated with following stimuli: cytokine cocktail (CC) containing IL-1β (10 ng/ml), TNFα (10 ng/ml), IL-6 (10 ng/ml) and IFNγ (100 ng/ml) or LPS (1 μg/ml) or poly(I:C) (25 μg/ml) or they were left unstimulated in RPMI for 24 h. Cell surface marker expression was evaluated by flow cytometry. Data are expressed as mean fluorescence intensity (MFI)±SEM for at least 3 donors. *p≤0.05, p≤0.01, *p≤0.001 (paired t-test).

Figure 14:
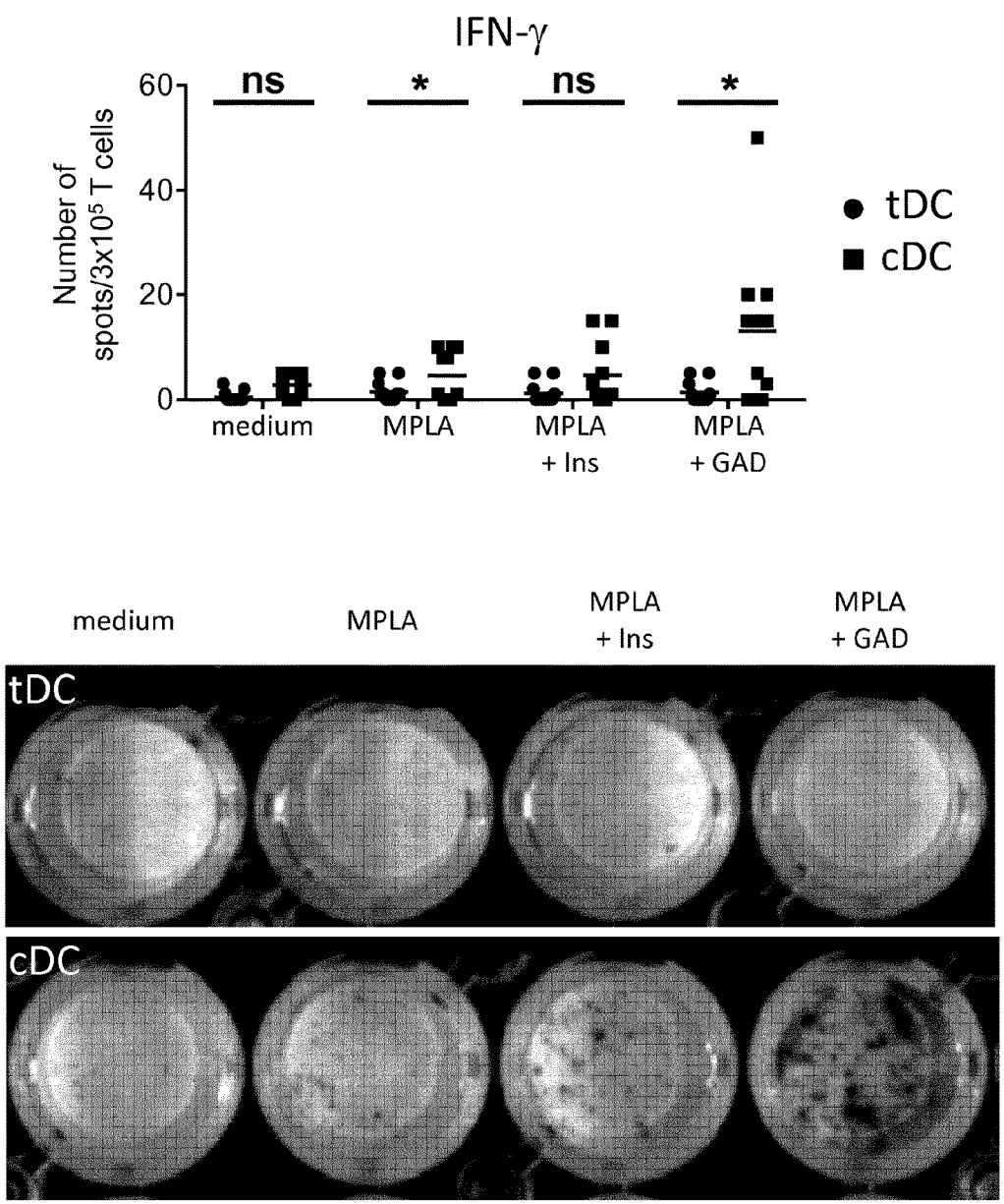

FIG. 14: tolDCs established from T1D patients using the tDCs 1 protocol reduce IFN-γ secretion from autologous T cells. Cytokine responses to insulin or GAD65 by T1D patients' T cells incubated with autologous tolDC or cDC evaluated by ELISPOT. 3×10⁴ tolDCs or cDC loaded either with insulin (1 μg/ml) or GAD65 (5 μg/ml) were seeded together with 3×10⁵ autologous T cells per well in 96-well anti-IFN-γ mAb-coated ELISPOT assay plate and incubated at 37° C. for 48 hours. Spots representing IFN-γ producing cells were developed using a biotinylated anti-IFN-γ secondary antibody and streptavidin—alkaline phosphatase conjugated with BCIP/NBT buffer and quantified using the Series-1 Immunospot Analyzer. Data from 11 T1D patients are shown. *p≤0.05, p≤0.01, *p≤0.001 (paired t-test).

FIG. 15: Dex/VitD2 tDCs exhibit a stable semimature phenotype and anti-inflammatory cytokine secretion profile. DCs were differentiated from monocytes in Cell Gro supplemented with GM-CSF and IL-4 in presence (tDCs, black bars) or absence of Dex and VitD2 (cDCs, grey bars) to obtain immature tDCs or immature cDCs (MEDIUM). Cells were finally activated with MPLA for 24 h (MPLA). A (1-4) Surface marker expression was analyzed by flow cytometry and (C) cytokines released by DCs were analyzed from supernatants by Luminex (tDCs black squares, cDCs grey squares). After activation with MPLA for 24 h in Cell Gro (CG), cells were washed and recultured in complete RPMI without tolerising factors and treated with cytokine cocktail (CC) described in FIG. 7B or LPS (1 μg/ml) or polyI:C (25 μg/ml) or CD40L (1000 ng/ml) or they were left unstimulated (RPMI). B (1-2) Bar graphs represent surface marker expression analyzed by flow cytometry and (D) cytokines released by DCs analyzed by Luminex or ELISA after 24 h of restimulation. Data represent MFI±SEM or percentages of positive cells (CD1a and CD11c expression) from at least 3 independent experiment and minimal 10 donors. *p≤0.05, p≤0.01, *p≤0.001 (paired t-test), nt-not tested.

FIG. 16: Dex/VitD tDCs maintain reduced T cell stimulatory capacity after restimulation. DCs were differentiated in Cell Gro in presence (tDCs) or absence of Dex and VitD2 (cDCs) and activated with MPLA (CG). Then, DCs were washed, recultured in complete RPMI without tolerising factors and treated with cytokine cocktail (CC) described in FIG. 7B or LPS (1 μg/ml) or polyI:C (25 μg/ml) or CD40L (1000 ng/ml) or they were left unstimulated (RPMI). After 24 h, tDCs and cDCs were washed and incubated with allogeneic T cells at 1:10 ratio (DCs/T cells). (A) Proliferation of T cells was assessed on day 6 by CFSE dilution method. Percentages of proliferating T cells are shown (B) Production of IL-17A in DCs/T cell co-cultures was analyzed by ELISA on day 6. (C) Percentages of IFN-γ producing T and (D) IL-10 producing T cells was assessed on day 6 or day 9, respectively. Data represent mean±SEM for at least 3 independent experiments and at least 10 donors. *p≤0.05, p≤0.01, *p≤0.001 (paired t-test).

FIG. 17: Dex/VitD2 tDCs induce IL-10 producing Tregs that are able to suppress proliferation of responder T cells. DCs (donor B) were differentiated in Cell Gro in presence (tDCs) or absence (cDCs) of Dex and VitD2 and activated with MPLA. Dex/VitD2 tDCs were incubated with allogeneic T cells (donor A) at 1:10 ratio (DCs/T cells) in RPMI (5% human AB serum) for two rounds of priming. Then, the cytokine production and suppressive capacity of induced Tregs was evaluated. (A) Tregs (donor A) were co-cultured with specific cDCs (donor B) at 1:10 ratio (DCs/T cells). Representative dot plots from 3 independent donors show percentages of IL-10, IFN-γ and IL-17 producing T cells assessed on day 6. Production of IL-10, IFN-γ and IL-17 was analyzed in cell supernatants by ELISA on day 6. (B) CD4+ Tregs were tested for suppressive capacity in MLR assay. CD4+ Tregs (donor A) were plated with responder T cells (donor A) and cDCs (donor B). cDCs were from the same donor as the Dex/VitD2 tDCs used to induce Tregs. Cells were plated in a Treg/Tresp/DCs ratio of 10:10:1 or 5:10:1. As additional controls, Tresp were cultured alone or with cDCs. After 6 d, cells were recovered and proliferation of responder cells was analyzed by measuring KI-67 by flow cytometry. The percent inhibition of responder T cell proliferation (black bars, mean±SEM for 3 independent donors, each performed in triplicate) and one representative dot plot showing proliferation of responder T cells are depicted. (C) Cell culture supernatants were recovered for IL-10, IFN-γ and IL-17A analysis. Data represent mean±SEM for 3 independent donors (each performed in triplicate). *p≤0.05, **p≤0.01 (paired t-test).

FIG. 18: Different intracellular signaling pathways are triggered in tDCs and cDCs after mimicking in vivo DC activation. DCs were differentiated in Cell Gro in presence (tDCs) or absence of Dex and VitD2 (cDCs) and activated with MPLA (CG). Then, tDCs and cDCs were washed, recultured in complete RPMI without tolerising factors and treated with following stimuli: cytokine cocktail (CC) described in the legend in FIG. 7B or LPS (1 μg/ml) or polyI:C (25 µg/ml) or CD40L (1000 ng/ml) or they were left unstimulated (RPMI). (A) After 60 min of restimulation, the phosphorylation of p38 MAPK, JNK/SAPK, ERK1/2, IκB-α and the level of IDO was analyzed by western blot analysis. Total p38 MAPK, JNK/SAPK, ERK1/2, IκB-α or β-actin in each sample were used as the equal loading control. One of three experiments performed is shown. (B) After 90 min of restimulation, DNA-binding activity of NF-κB subunits was analyzed by colorimetric assay. (C) Production of IL-10 and IL-12 after restimulation of tDCs and cDCs with CC, LPS, polyI:C and CD40L for 24 h in the presence of p38 MAPK inhibitor SB203580 (SB), JNK/SAPK inhibitor SP600125 (SP), ERK1/2 inhibitor PD98059 (PD), NF-κB inhibitor Bay 11-7082 (Bay) was evaluated by ELISA. (D) ILT-3, PD-L1 and CD86 expression on tDCs and cDCs after restimulation with CC, LPS, polyI:C and CD40L for 24 h in the presence of p38 MAPK inhibitor SB203580 (SB) and ERK1/2 inhibitor PD98059 (PD) was evaluated by flow cytometry. (E) Before restimulation, tDCs were pretreated with p38 MAPK inhibitor SB203580 (SB) and ERK1/2 inhibitor PD98059 (PD) and stimulated for 24 h. tDCs were then cocultered with allogeneic T cells. Proliferation was measured on day 6. Data represent mean±SEM from at least three independent experiments. *p≤0.05, p≤0.01, *p≤0.001 (paired t-test).

FIG. 19: mTOR and STAT3 regulates tolerogenic properties of tDCs after restimulation. DCs were differentiated in Cell Gro in presence (tDCs) or absence of Dex and VitD2 (cDCs) and activated with MPLA (CG). Then, tDCs and cDCs were washed, recultured in complete RPMI without tolerising factors and treated with cytokine cocktail (CC) described in the legend of FIG. 7B or LPS (1 µg/ml) or polyI:C (25 µg/ml) or CD40L (1000 ng/ml) or they were left unstimulated (RPMI). When indicated, cells were pretreated with mTOR inhibitor rapamycin or STAT3 inhibitor Stattic for 30 min before restimulation. (A) After 60 min of restimulation western blot analysis for phosphorylated mTOR, p70S6K and STAT3 were performed using specific mAbs. β-actin was used as the equal loading control. One of three experiments performed is shown. (B) IL-10 and IL-12 production by DCs after 24 h of restimulation was measured by ELISA. (C) Expression of CD86, PD-L1 and ILT-3 after restimulation with CC, LPS, polyI:C and CD40L in the presence of mTOR inhibitor rapamycin or STAT3 inhibitor Stattic for 24 h was evaluated by FACS analysis. (D) Before restimulation, tDCs were pretreated with mTOR inhibitor rapamycin or STAT3 inhibitor Stattic and stimulated for 24 h. tDCs were then cocultered with allogeneic T cells. Proliferation was measured on day 6. Data represent mean±SEM from at least 4 independent experiments. *p≤0.05, p≤0.01, *p≤0.001 (paired t-test).

FIG. 20: Enhanced glycolysis regulates tolerogenic phenotype and function of Dex/VitD tDCs. DCs were differentiated in Cell Gro in presence (tDCs) or absence of Dex and VitD2 (cDCs) and activated with MPLA (CG). Then, tDCs and cDCs were washed, recultured in complete RPMI without tolerising factors and treated with following stimuli: cytokine cocktail (CC) described in FIG. 1B or LPS (1 µg/ml) or polyI:C (25 µg/ml) or CD40L (1000 ng/ml) or they were left unstimulated (RPMI). When indicated, cells were pretreated with rapamycin or 10 mM 2-deoxyglucose (2-DG) for 30 min before restimulation. (A) 24 h later, supernatants were analyzed for the concentration of glucose and lactate as indicator of glycolytic activity. The activity of lactate dehydrogenase (LDH) was analyzed in cell lysates. (B) 24 h later, suppression of glycolysis by treatment of DCs with rapamycin or 10 mM 2-deoxyglucose 30 min before restimulation was analyzed by evaluating the concentration of lactate in DC supernatants. (C) ILT-3, PD-L1 and CD86 expression on DCs after 24 h of restimulation in the presence of glycolysis inhibitor 2-deoxyglucose was evaluated by FACS analysis. (D) IL-10 and IL-12 production by DCs after 24 h of restimulation was measured by ELISA. (E) Before restimulation, tDCs were pretreated with 2-DG and stimulated for 24 h. tDCs were then cocultered with allogeneic T cells. Proliferation was measured on day 6. Data represent mean±SEM from at least 4 independent experiments. *p≤0.05, p≤0.01, *p≤0.001 (paired t-test).

FIG. 21: tDCs prepared from monocytes of T1D patients exhibited stable semimature phenotype. A (1-2) The expression of surface markers on immature tDCs or cDCs and on MPLA-matured tDCs or cDCs. B (1-2) The expression of surface markers on frozen/thawed and restimulated MPLA-matured tDCs or cDCs. MPLA-matured tDCs or cDCs from CellGro (CG), were frozen and stored for at least 1 month in liquid nitrogen, then were thawed, washed and recultured in RPMI with 5% HS without tolerising factors and they were left unstimulated (5% HS) or they were restimulated with LPS (1 µg/ml) or CD40L (1 µg/ml) for 24 h. Graphs represent expression of surface markers analyzed by flow cytometry. Data are expressed as mean fluorescence intensity (MFI)±SEM from at least 5 independent experiments of minimal 15 donors. *p≤0.05, p≤0.01, *p≤0.001 (paired t-test). ns, not significant.

Figure 22A:
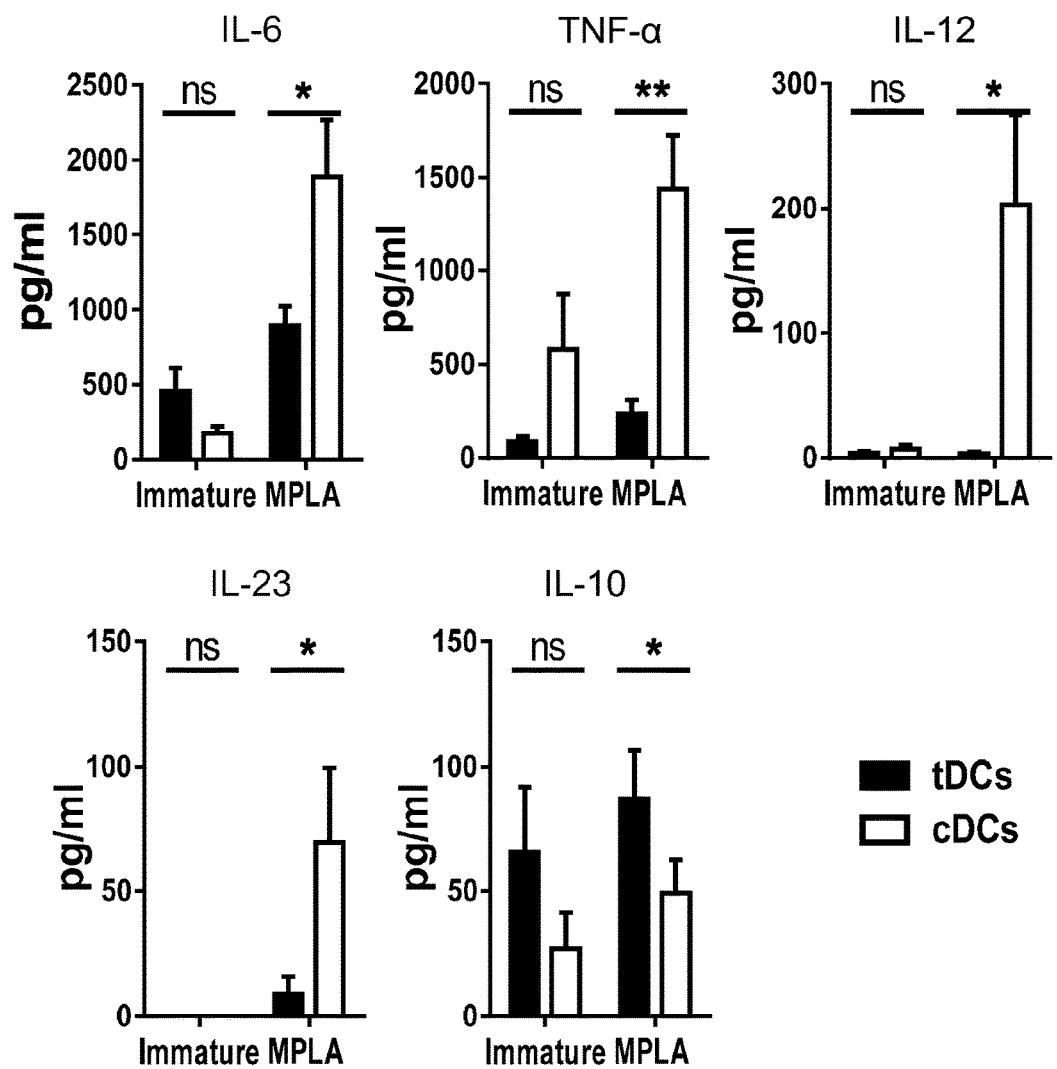
Figures 1, 22B:
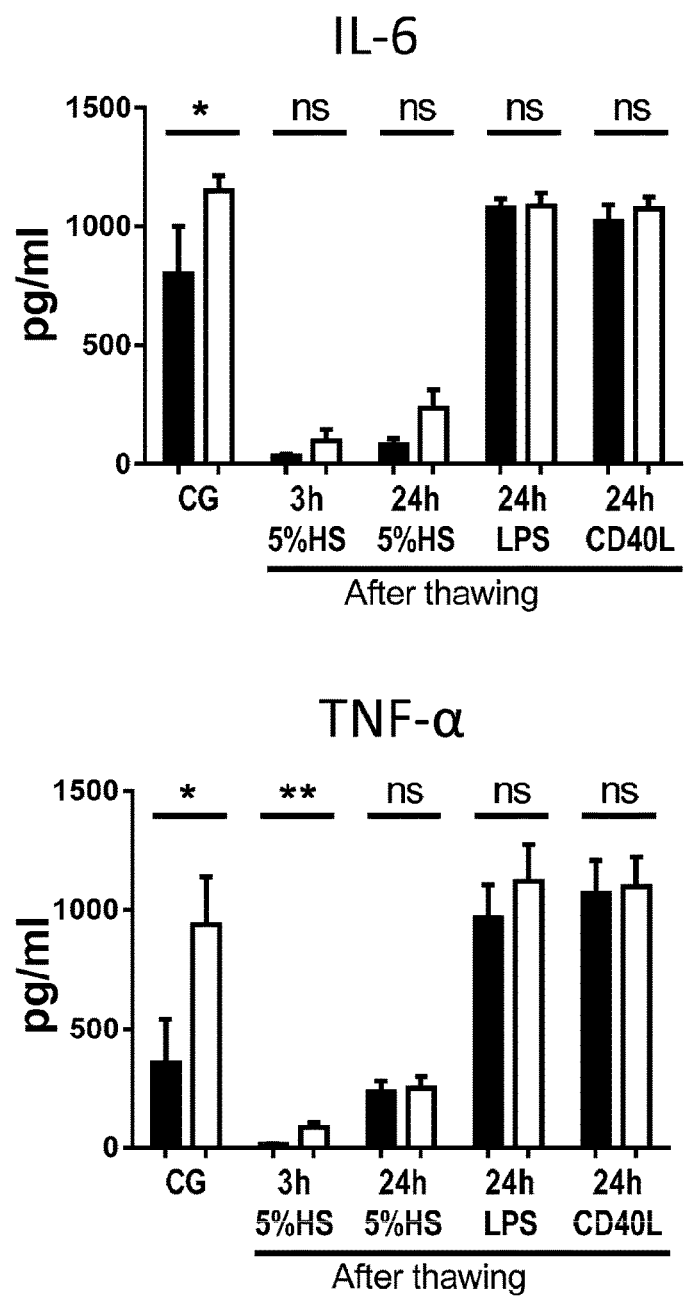
Figures 2, 22B:
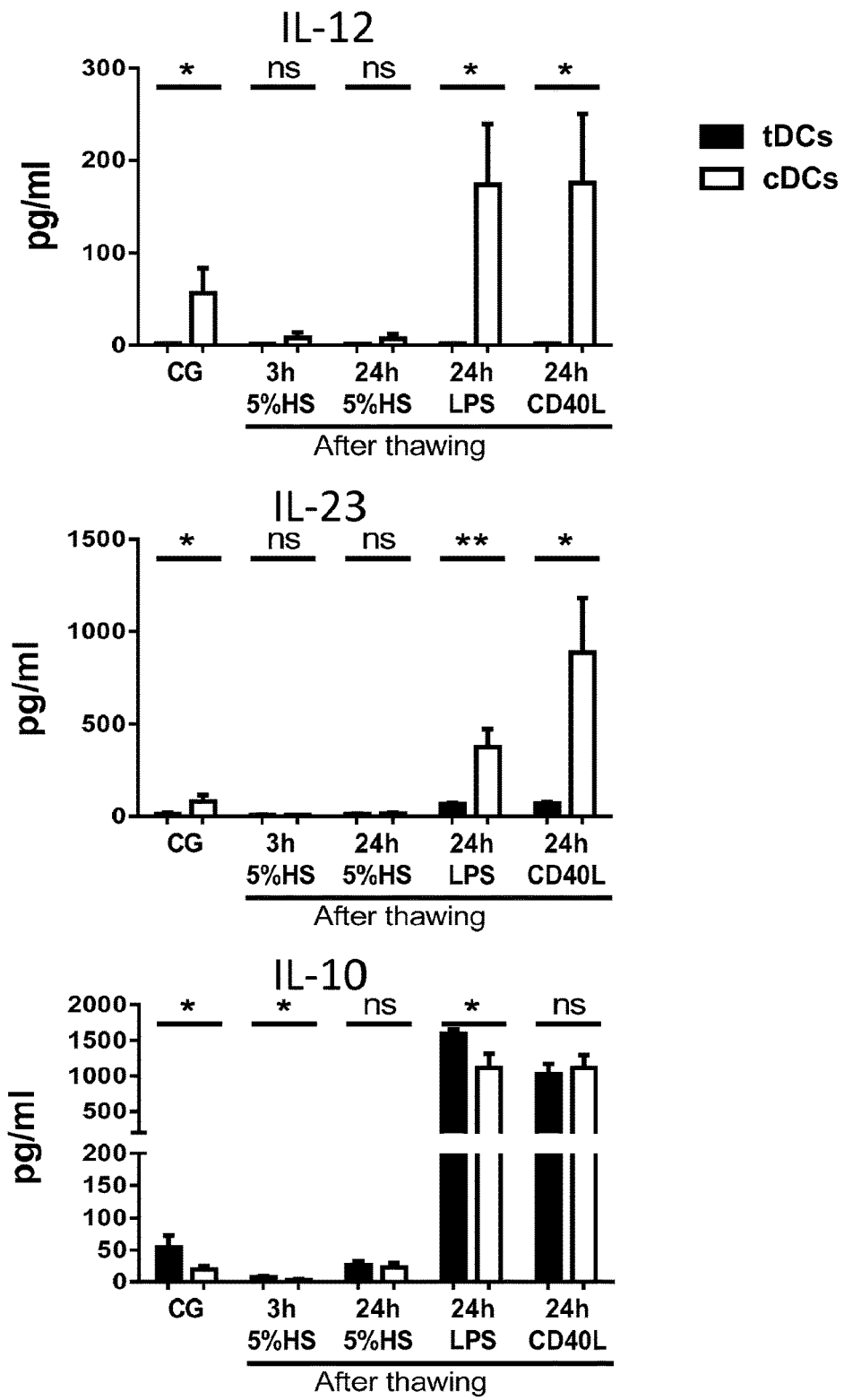

FIG. 22: tDCs prepared from monocytes of T1D patients exhibited anti-inflammatory cytokine secretion profile. (A) Production of cytokines by immature tDCs or cDCs and MPLA-matured tDCs or DCs. B (1-2) Cytokine production of frozen/thawed and restimulated MPLA-matured tDCs or cDCs. MPLA-matured tDCs or cDCs from CellGro (CG), were frozen and stored for at least 1 month in liquid nitrogen, then were thawed, washed and recultured in RPMI with 5% HS without tolerising factors and they were left unstimulated (5% HS) or they were restimulated with LPS (1 µg/ml) or CD40L (1 µg/ml) for 24 h. Graphs represent the secretion of cytokines detected in cell culture supernatants after 3 h or 24 h of cultivation or after 24 h of restimulation using multiplex cytokine assay. Data are expressed as mean±SEM from at least 3 independent experiments of minimal 10 donors. *p≤0.05, p≤0.01, *p≤0.001 (paired t-test). ns, not significant.

FIG. 23: tDCs induce lower proliferation of autoreactive T cells. (A) The proliferation of CD4+ and CD8+ T cells of patients with HbA1c≤60 mmol/mol Hb (group 1, G1) or HbA1c>60 mmol/mol Hb (group 2, G2). (B) The correlation analysis of the HbA1c level with GAD-specific response of CD4+ or CD8+ T cells (give as % proliferating T cells induced by GAD-loaded cDCs—% proliferating T cells induced by unpulsed cDCs) and the correlation analysis of the HbA1c level with % proliferating CD4+ or CD8+ T cells induced by unpulsed cDCs. The percentage of proliferating T cells was detected by intracellular staining of KI-67 and analyzed by flow cytometry at day 6. Each point represents the value from an individual patient from at least 10 independent experiments. (C) The correlation analysis of the HbA1c level with PPD-specific response of CD4+ T cells. r=correlation index according to Pearson's analysis, *p≤0.05, p≤0.01, *p≤0.001 (paired t-test). ns, not significant.

FIG. 24: tDCs induce lower activation of autoreactive T cells. (A) The percentage of IFN-γ+KI-67+ T cells from CD4+ or CD8+ T cells of patients with HbA1c≤60 mmol (group 1, G1) or HbA1c>60 mmol (group 2, G2). (B) The percentage of KI-67+IL-17A+ T cells from CD4+ or CD8+

T cells of patients with HbA1c≤60 mmol (G1) or HbA1c>60 mmol (G2). (C) The correlation analysis of the HbA1c level with GAD-specific response of CD4+ or CD8+ T cells (give as % IFN-γ+KI-67+ T cells induced by GAD-loaded cDCs—% IFN-γ+KI-67+ T cells induced by unpulsed cDCs) and the correlation analysis of the HbA1c level with % IFN-γ+KI-67+ T cells induced by unpulsed cDCs. (D) The correlation analysis of the HbA1c level with GAD-specific response of CD4+ or CD8+ T cells (give as % IL-17A+KI-67+ T cells induced by GAD-loaded cDCs—% IL-17A+KI-67+ T cells induced by unpulsed cDCs) and the correlation analysis of the HbA1c level with % IL-17A+KI-67+ T cells induced by unpulsed cDCs. The percentage of cytokine producing KI-67+ T cells was detected by intracellular staining and analyzed by flow cytometry at day 6. Each point represents the value from an individual patient from at least 10 independent experiments. r=correlation index according to Pearson's analysis, *p≤0.05, p≤0.01, *p≤0.001 (paired t-test). ns, not significant.

Figure 25A:
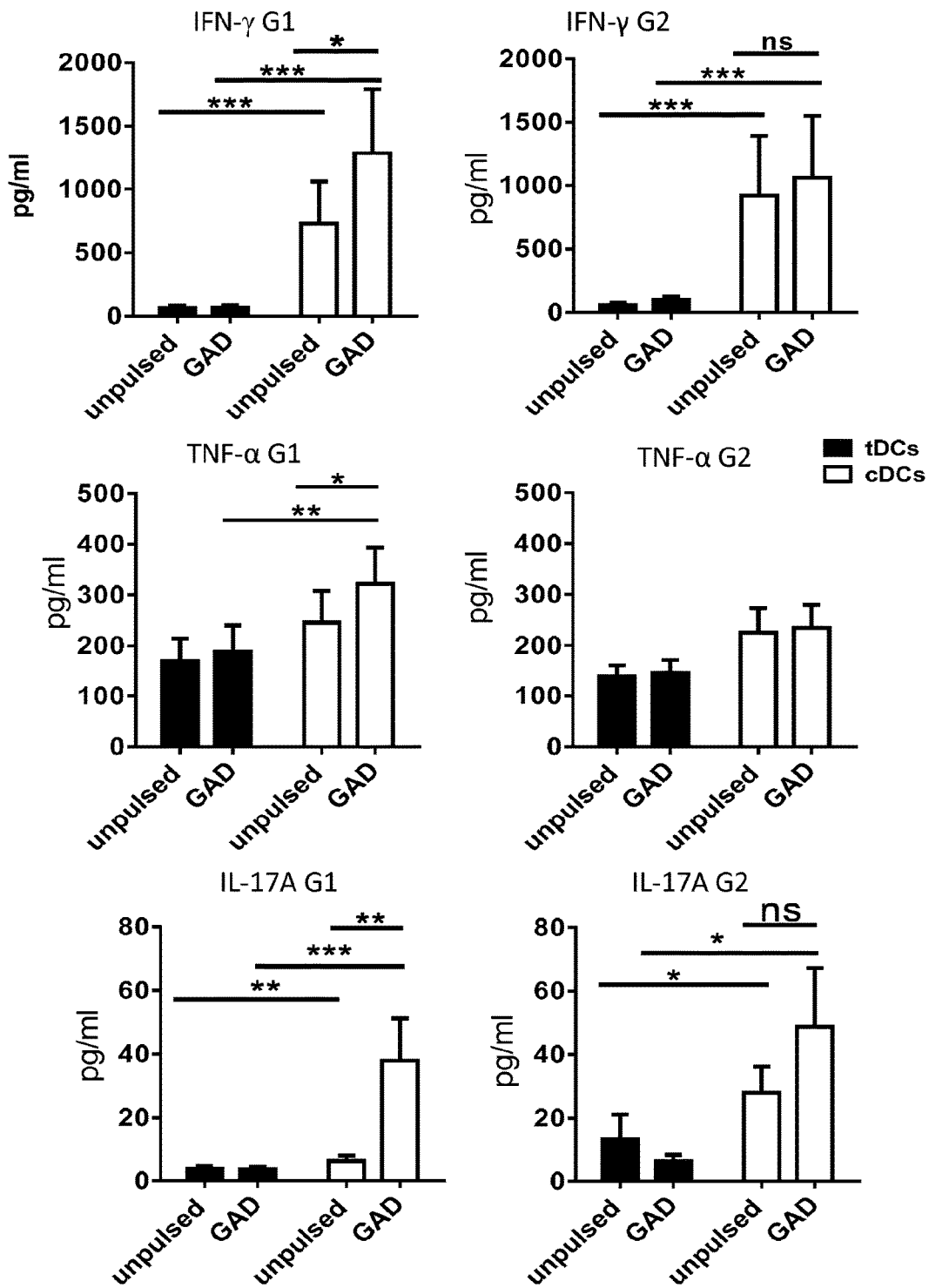
Figure 25B:
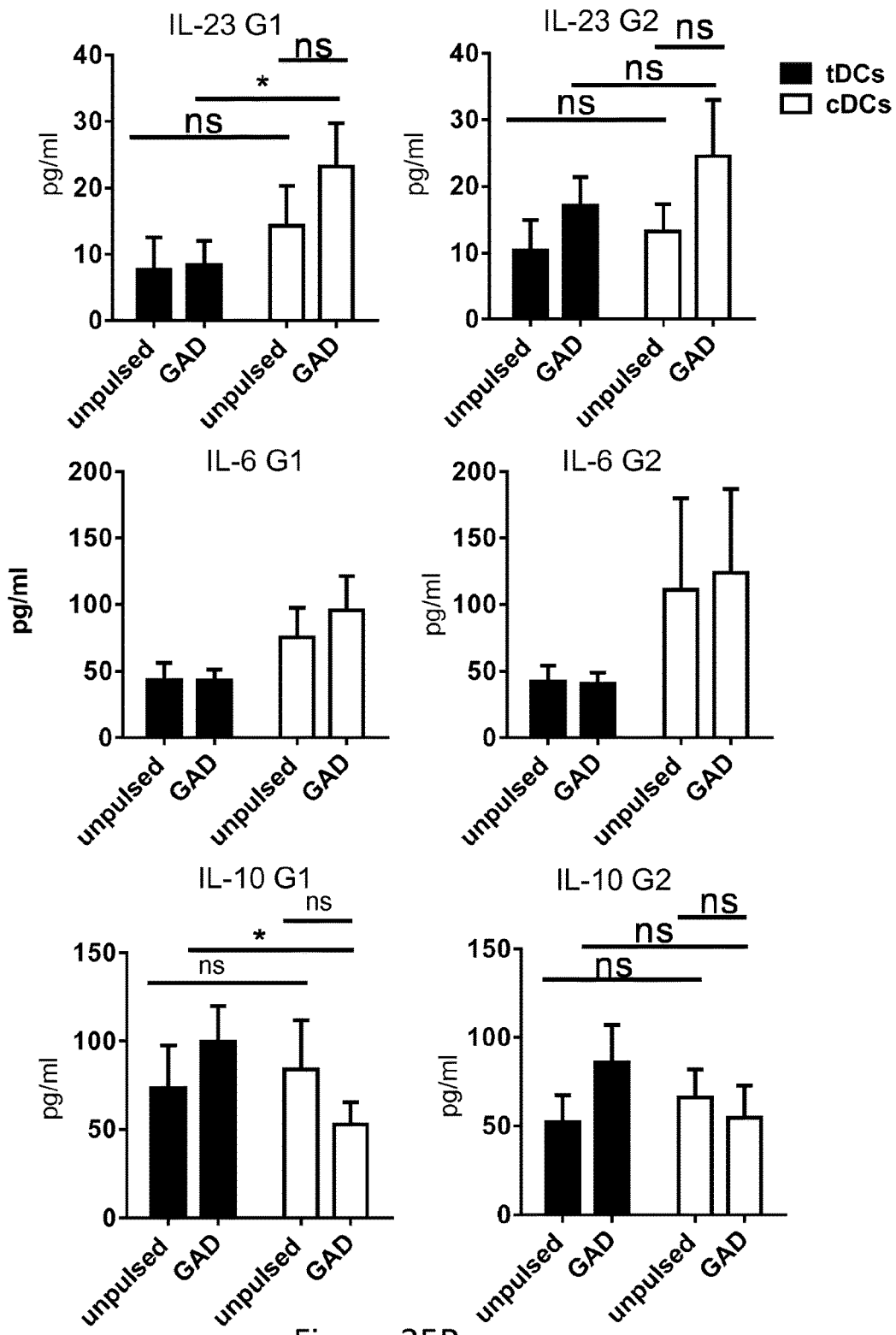

FIG. 25A-25B: tDCs induce lower amounts of pro-inflammatory cytokines in DC and T cell cultures. Autologous T cells were stimulated with unpulsed or GAD-loaded tDCs or cDCs from patients with HbA1c≤60 mmol (group 1, G1) or HbA1c>60 mmol (group 2, G2). Graphs represent the concentration of cytokines in cultures of T cells and tDCs or cDCs quantified by multiplex cytokine assay at day 6. Data are expressed as mean±SEM from at least 3 independent experiments of minimal 8 donors. *p≤0.05, p≤0.01, *p≤0.001 (paired t-test). ns, not significant.

Figure 26:
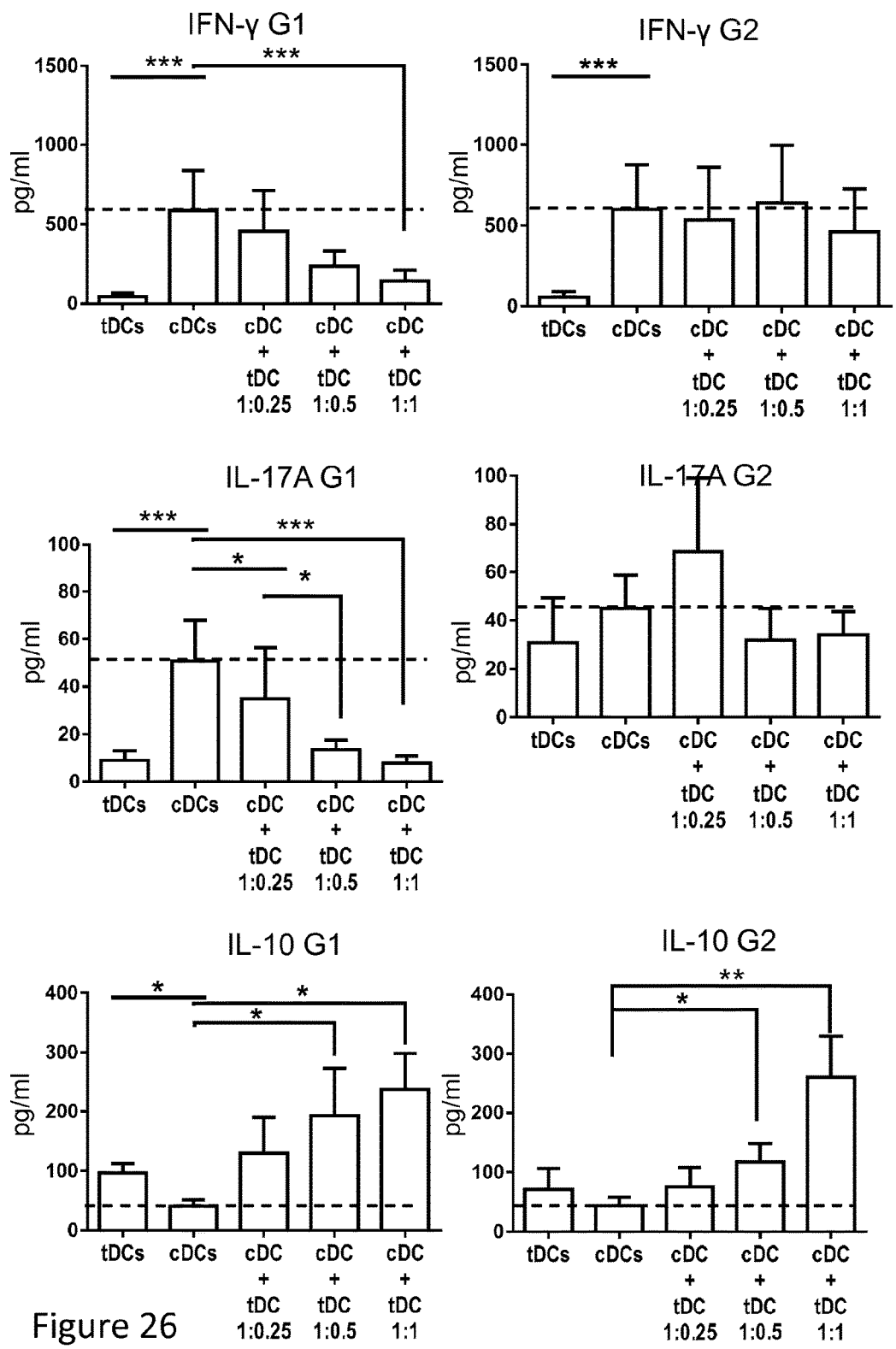

FIG. 26: tDCs are able to suppress cDC-induced T cell activation. Autologous T cells were stimulated with GAD-loaded tDCs or cDCs from patients with HbA1c≤60 mmol (group 1, G1) or HbA1c>60 mmol (group 2, G2). Various number of GAD-loaded tDCs was added to cultures of GAD-loaded cDCs and T cells (T cells:cDCs:tDCs ratio was 10:1:0.25, 10:1:0.5 or 10:1:1, respectively). Graphs represent the concentration of cytokines in cultures of T cells and tDCs and/or cDCs quantified by multiplex cytokine assay at day 6. Data are expressed as mean±SEM from at least 3 independent experiments of minimal 8 donors. *p≤0.05, **p≤0.01 (paired t-test).

Figure 27:
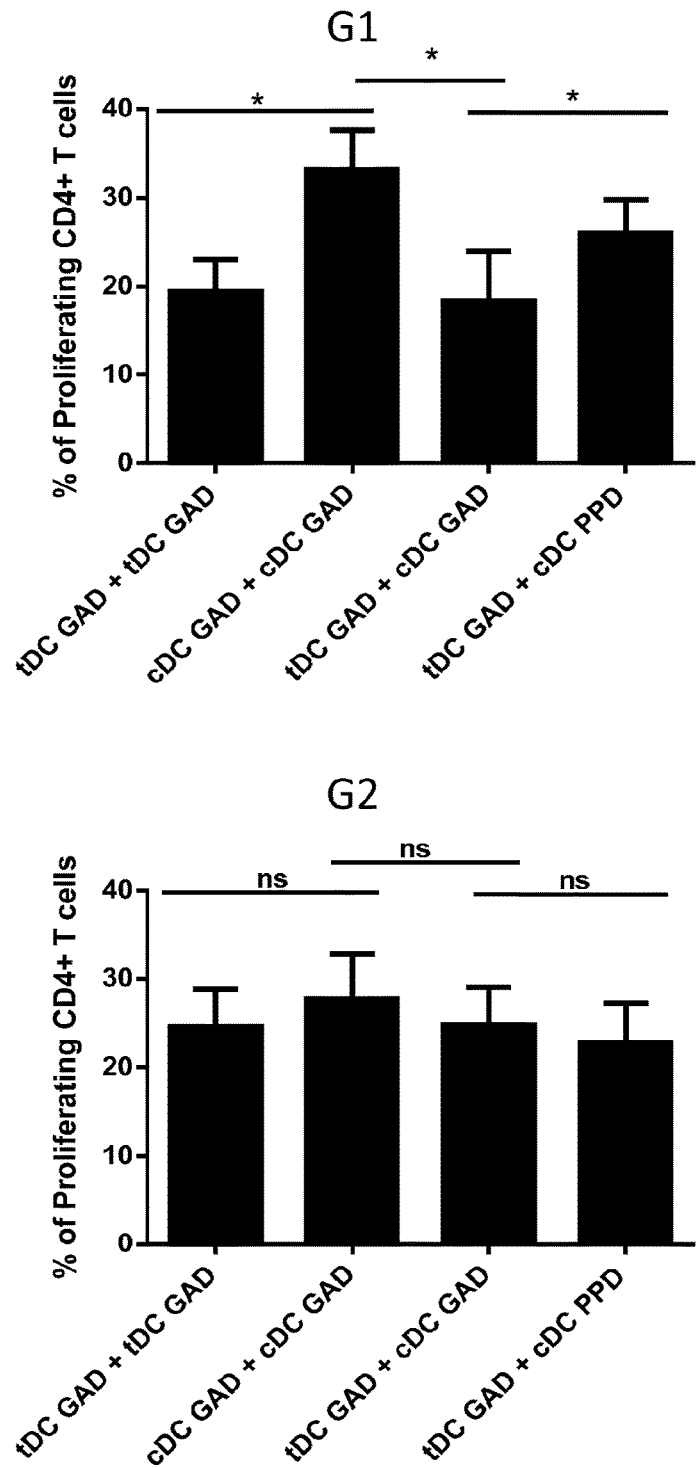

FIG. 27: Tolerogenic DC induce stable, antigen-specific hyporesponsiveness in GAD65-reactive T cells from a group of T1D patients. Lymphocytes from group 1 or group 2 of T1D patients previously stimulated with autologous GAD65-loaded cDC or tDC were stained with CFSE and rechallenged with GAD-loaded cDC or PPD-loaded cDCs. T cels proliferation was analyzed by CFSE stainig 6 days later. Data are expressed as mean±SEM from 5 independent experiments of 8 donors. **p≤0.01 (paired t-test). ns, not significant.

Figure 28:
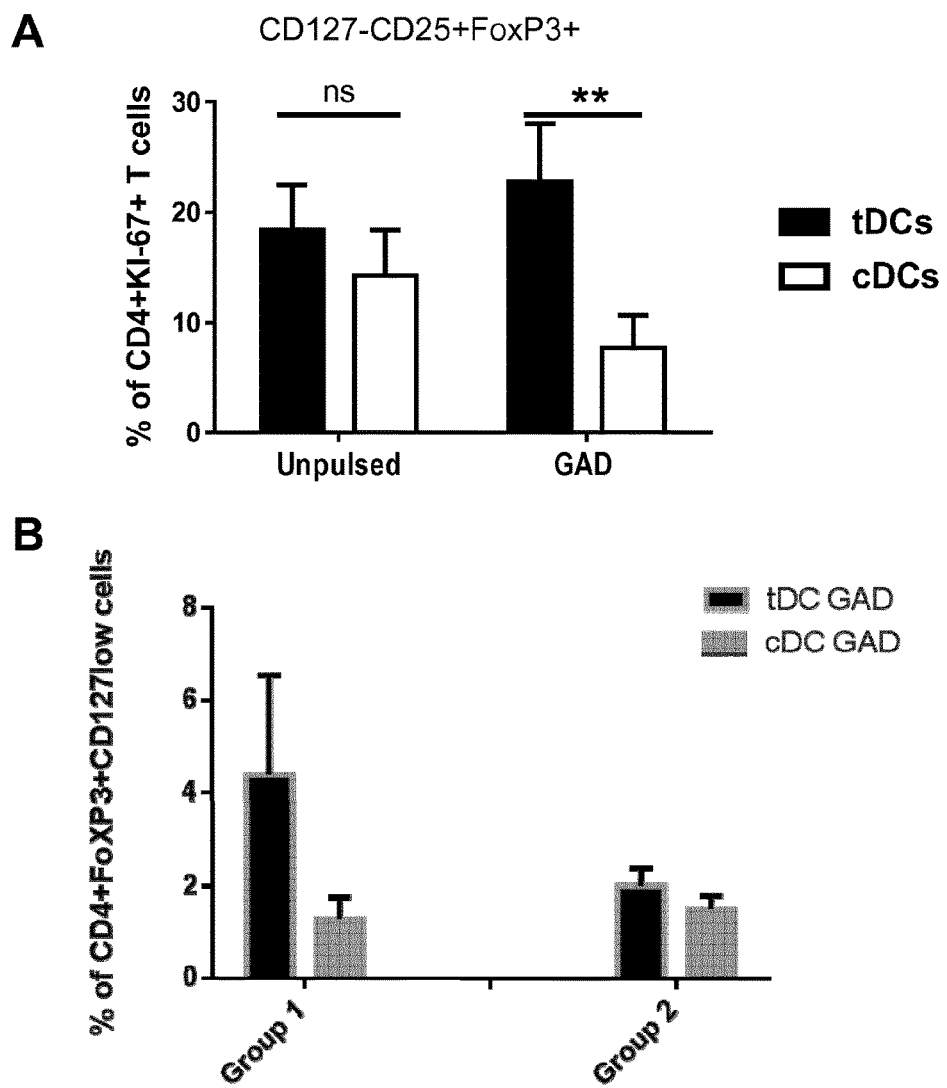

FIG. 28: tDCs are able to induce differentiation of naïve CD4+ T cells into regulatory FoxP3+ T cells. (A) Autologous naïve CD4+ T cells were stimulated with unpulsed or GAD-loaded tDCs or cDCs. Graph represents the percentage of CD127-CD25+FoxP3+ from CD4+KI-67+ T cells induced by unpulsed or GAD-loaded tDCs or DCs detected by flow cytometry at day 9. Data are expressed as mean±SEM from 5 independent experiments of 7 donors. **p≤0.01 (paired t-test). ns, not significant. (B) Induction of CD127-CD25+FoxP3+ from CD4+KI-67+ T cells induced GAD-loaded tolDCs or cDCs from patients with HbA1c≤60 mmol (group 1, G1) or HbA1c>60 mmol (group 2, G2).

Figure 29A:
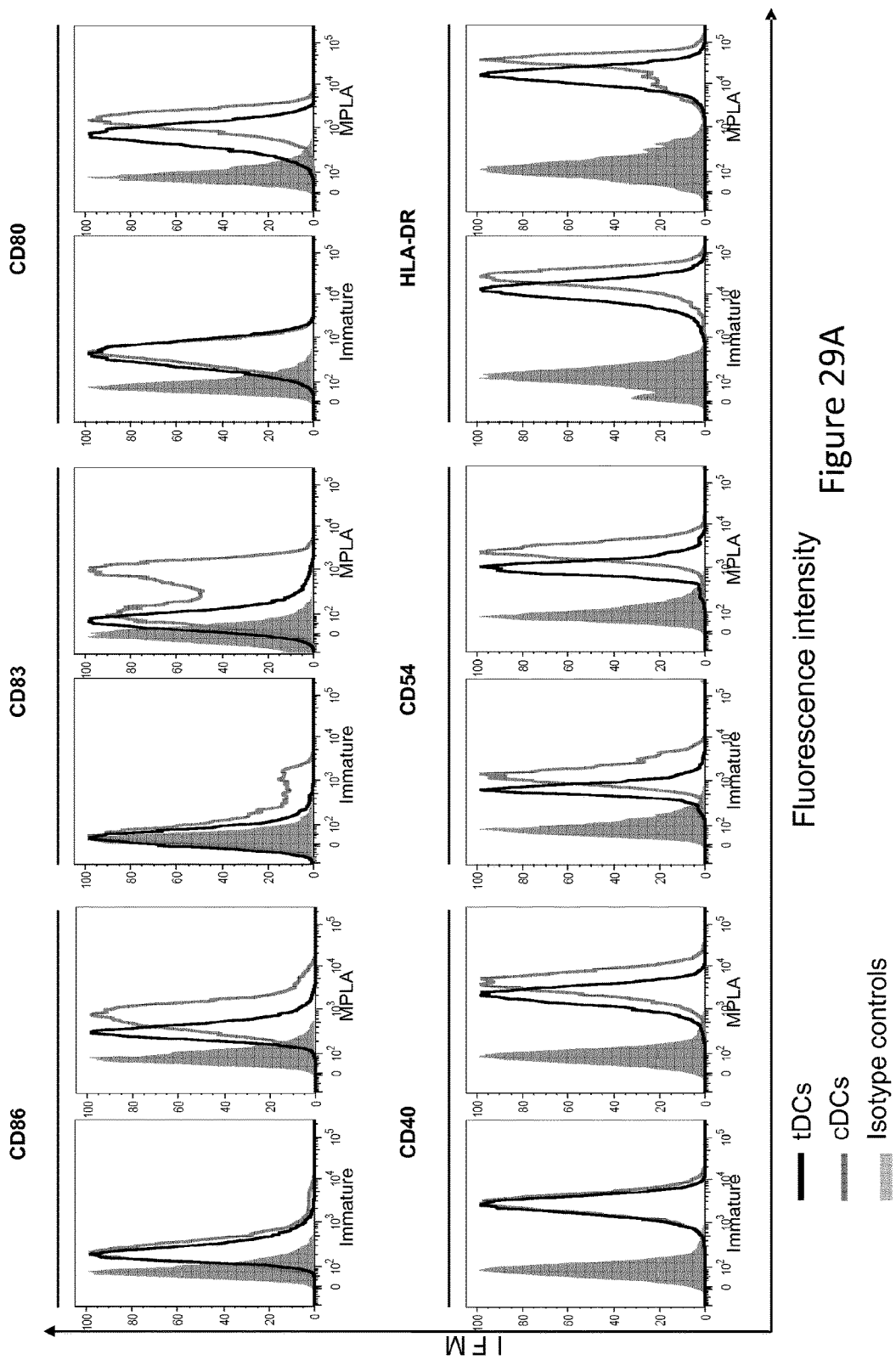
Figure 29B:
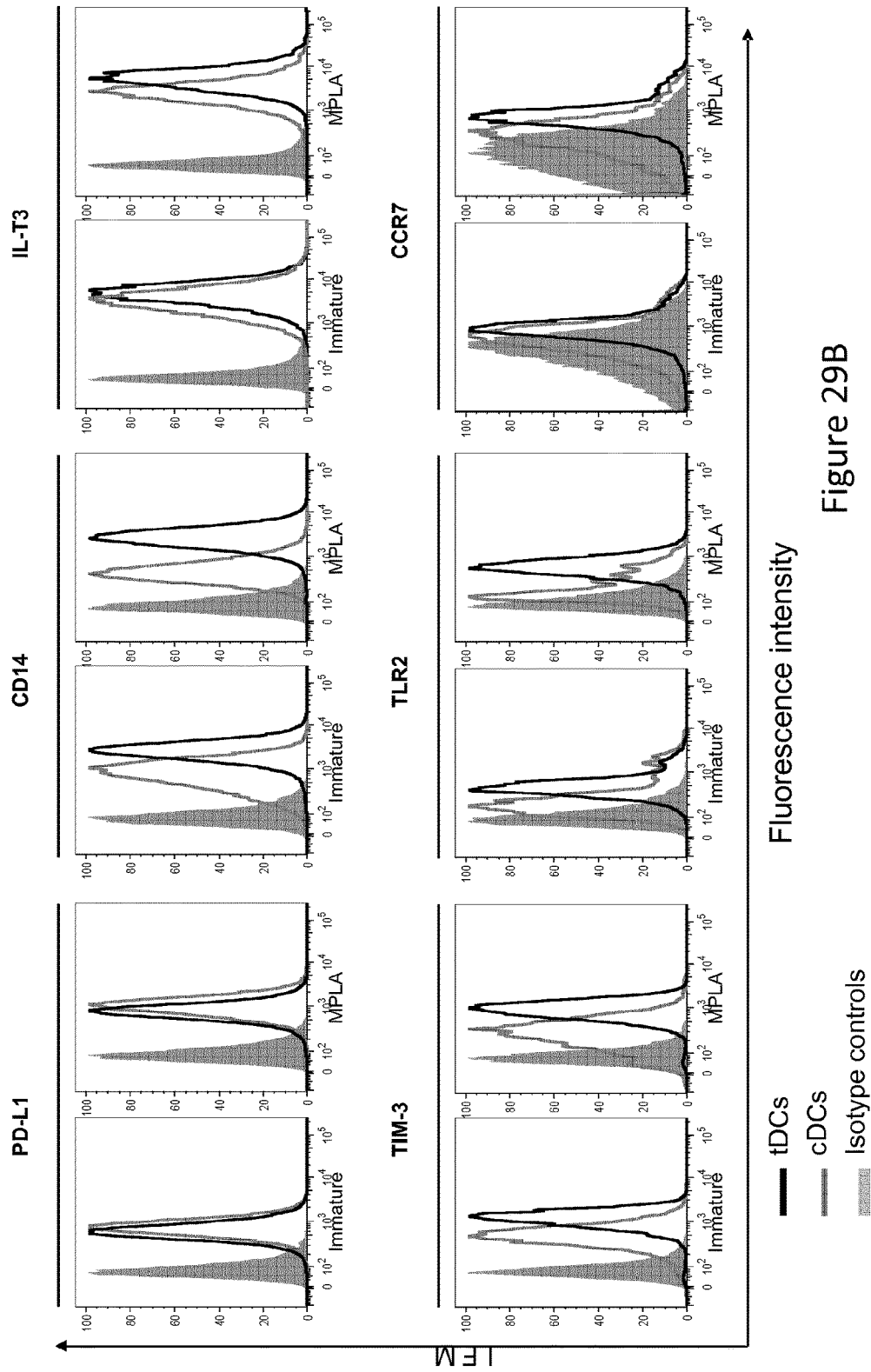
Figure 29C:
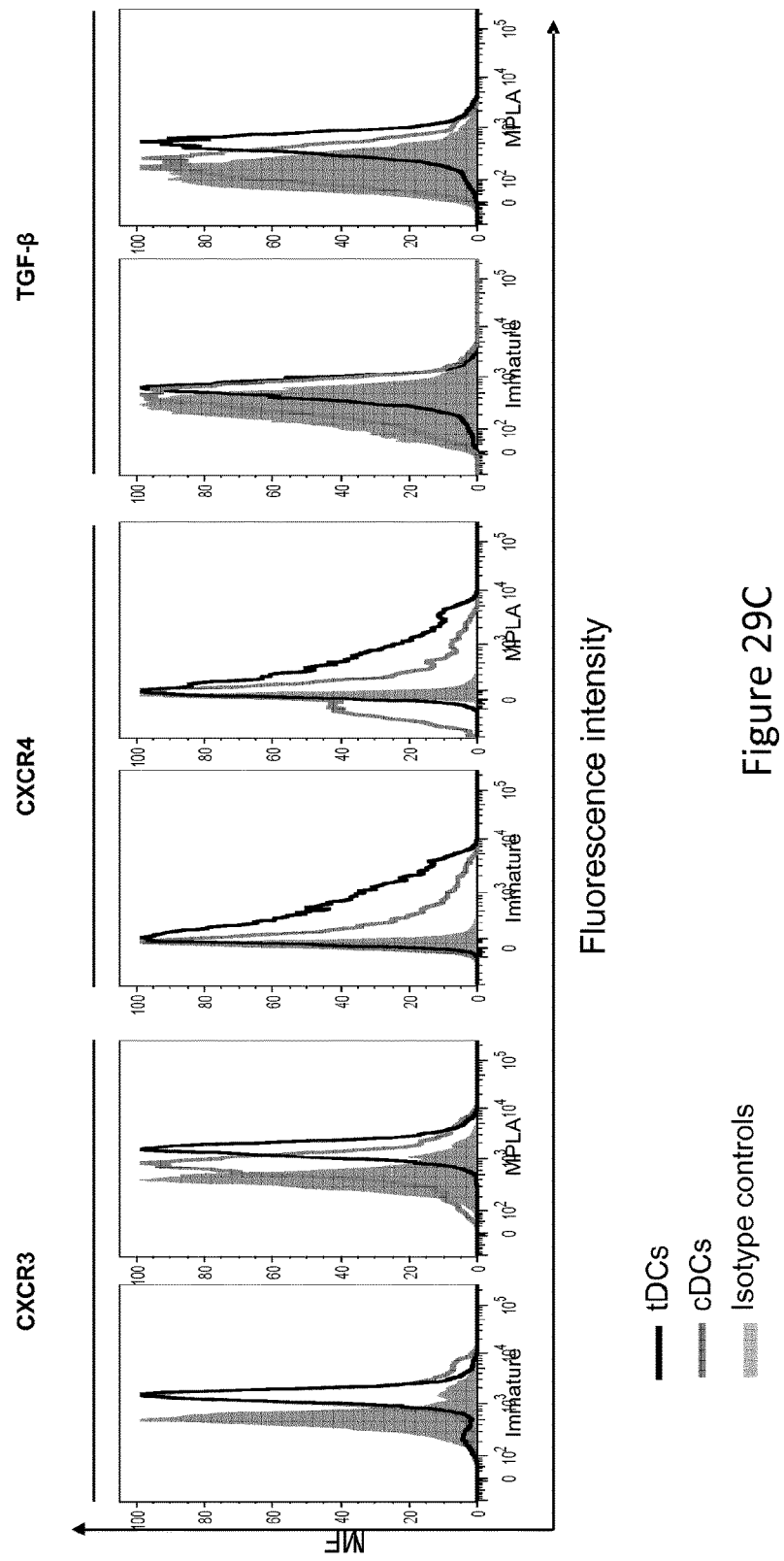

FIG. 29A-29C: tDCs prepared from monocytes of T1D patients exhibited semimature phenotype. Expression of surface markers on tDCs (black lines) or cDCs (grey lines) before maturation (Immature) and after MPLA maturation (MPLA). Light gray filled histograms represent isotype control mAb staining. Data were acquired by flow cytometry. Representative histograms of minimal 10 independent donors are shown.

Figure 30:
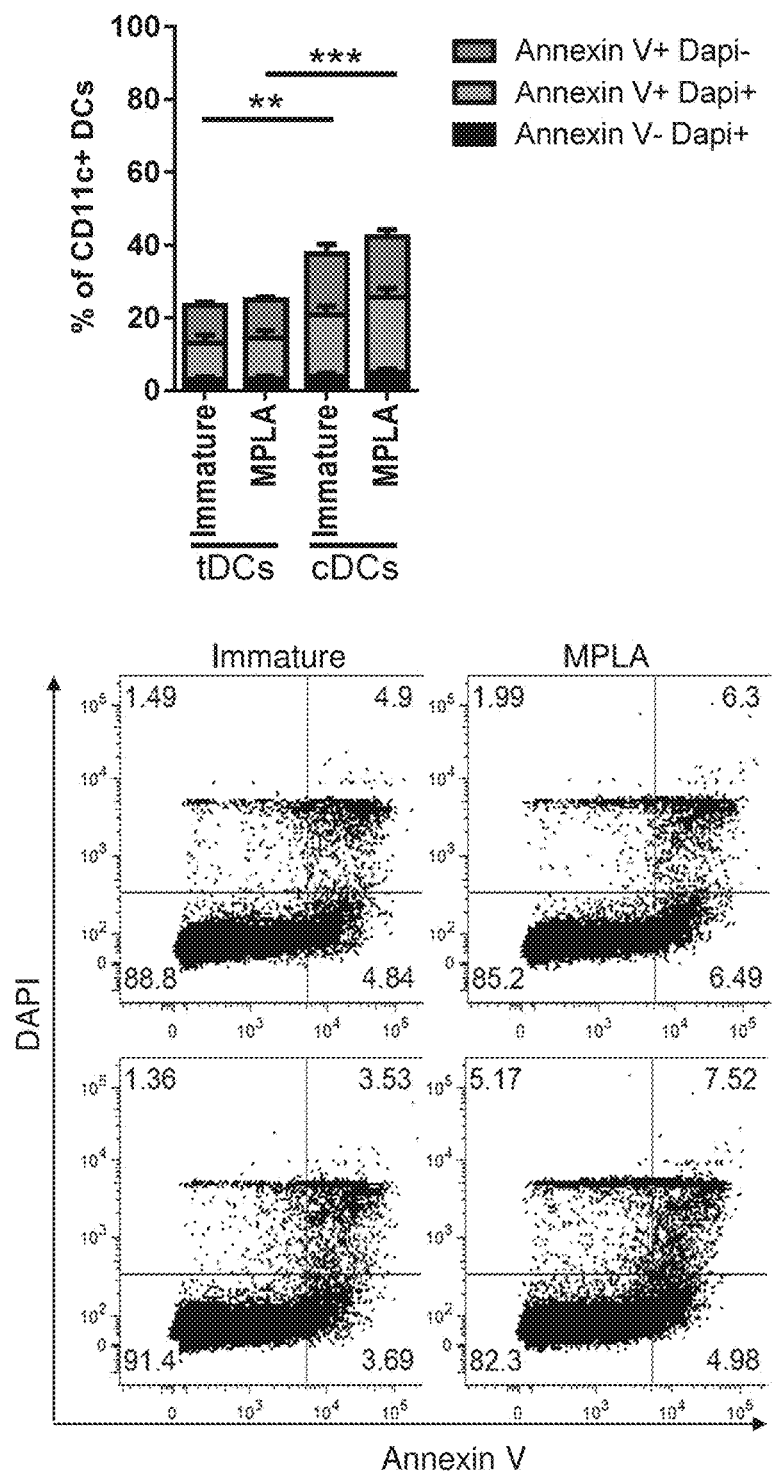

FIG. 30: Dex and VitD2 used for tDC generation did not affect DC viability. (A) The viability of tDCs or cDCs before maturation (Immature) and after MPLA maturation (MPLA). (B) The viability of thawed and restimulated MPLA-matured tDCs or cDCs. MPLA-matured tDCs or cDCs from CellGro (CG), were frozen and stored for at least 1 month in liquid nitrogen, then were thawed, washed and recultured in RPMI supplemented with 5% human serum (HS) without tolerising factors and restimulated with following stimuli: cytokine cocktail (CC) consisting of IL-1β, TNF-α, IL-6 (all 10 ng/ml) and IFN-γ (100 ng/ml) or LPS (1 μg/ml) or CD40L (1 μg/ml) or they were left unstimulated (5% HS). Data were acquired by flow cytometry and assessed based on Annexin V and DAPI staining. Results are expressed as mean±SEM from at least 3 independent experiments of minimal 5 donors. p≤0.01, *p≤0.001 (paired t-test). ns, not significant. Representative dot plots of minimal 5 independent donors are shown.

Figure 31:
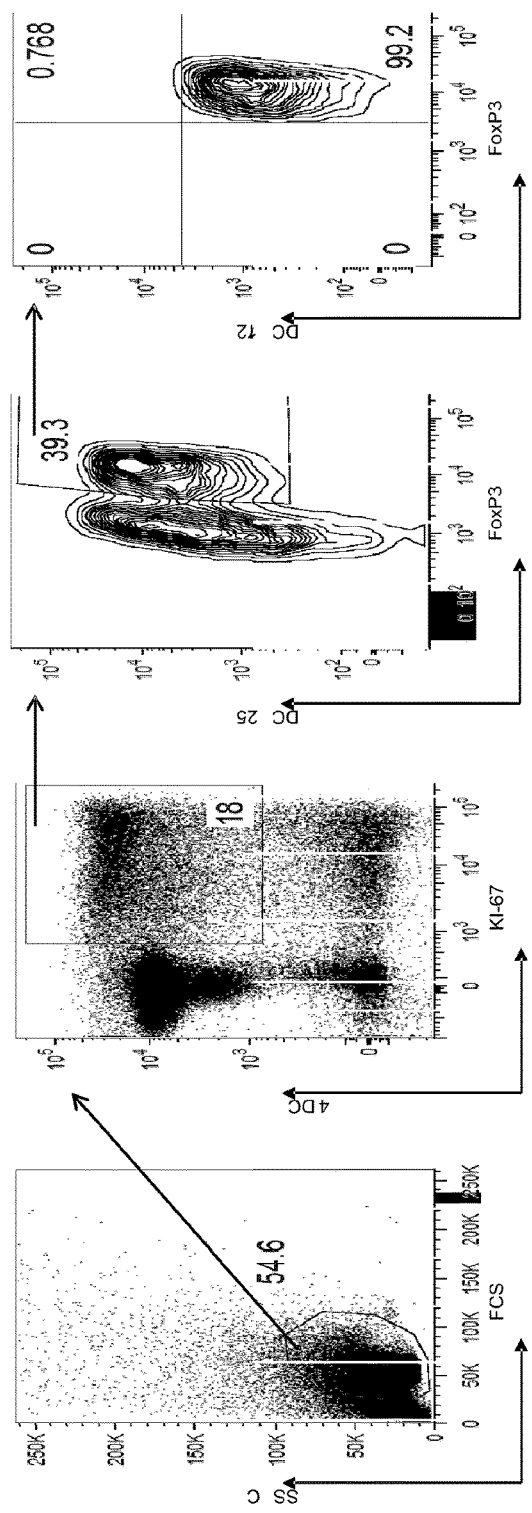

FIG. 31: Gating strategy for the analysis of regulatory T cells generation after priming of naïve CD4+ T cells with various DC groups. First dot plot depicts T cells in a gate based on forward scatter and side scatter. Second dot plot depicts gating on CD4+ and KI-67+ T cells. Third plot shows the expression of CD25 and FoxP3. CD25+FoxP3+ T cells were subsequently analyzed for the expression of CD127.

Figure 32:
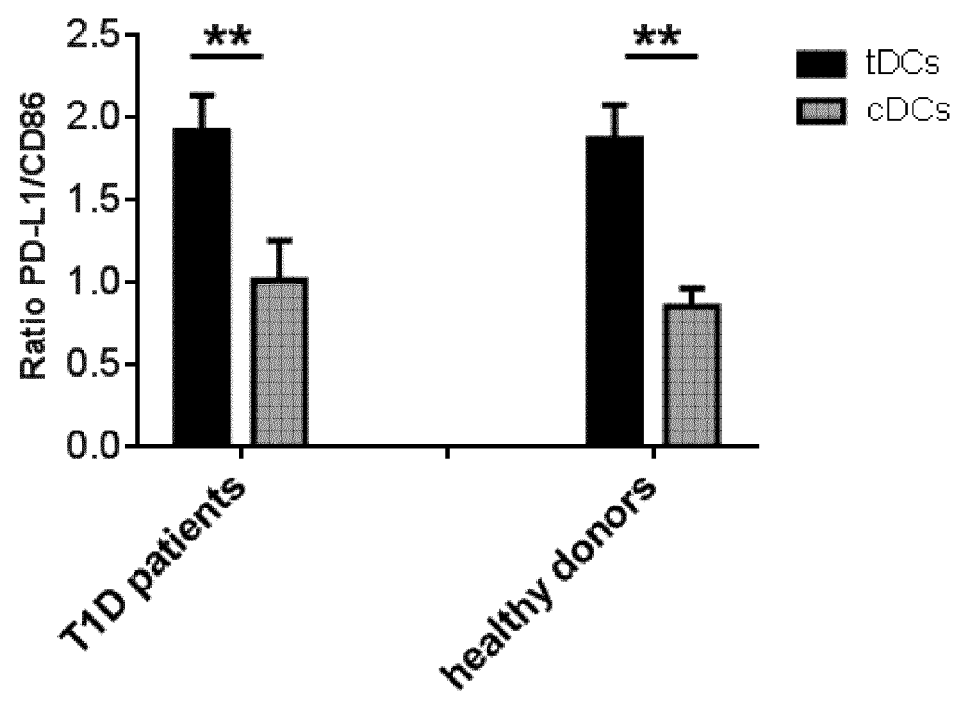

FIG. 32: Dex/VitD2 tDCs exhibit a higher ratio of PD-L1/CD86 than cDCs. The ratio of PD-L1/CD86 is a marker of tolerogenicity. The ratio of cell surface markers PD-L1 and CD86 is higher in tolDCs than is cDCs. tDCs or cDCs were prepared from monocytes of T1D patients and from monocytes from healthy donors. DCs were differentiated from monocytes in Cell Gro supplemented with GM-CSF and IL-4 in presence (tDCs, black bars) or absence of Dex and VitD2 (cDCs, grey bars) to obtain immature tDCs or immature cDCs. Cells were finally activated with MPLA for 24 h. Surface marker expression was analyzed by flow cytometry.

5. DETAILED DESCRIPTION

5.1 Terminology

In describing and claiming the invention, the following terms should be understood as follows.

As used herein, unless otherwise specified, the terms "protein(s)" and "polypeptide(s)" interchangeably refer to a chain of amino acids linked together by peptide bonds. In some embodiments, the terms "protein(s)" and "polypeptide(s)" refer to a macromolecule which comprises amino acids that are linked together by peptide bonds.

As used herein, the term "expand" in context of expanding regulatory T cells (Tregs) in culture means to culture a mixed or pure population of cells that contains a small number of Tregs so that the Tregs proliferate to greater numbers.

An "autologous cell" refers to a cell which was derived from the same subject that is being treated by cell therapy.

A "donor cell" refers to a cell that was derived from a subject other than the subject being treated by cell therapy.

An "allogeneic cell" refers to a genetically distinct cell.

As used herein, the terms "treat", "treating", and "treatment" in the context of the administration of a therapy to a subject refer to the beneficial effects that a subject derives from a therapy. In certain embodiments, treatment of a subject with an autoimmune disease in accordance with the methods described herein achieves at least one, two, three, four or more of the following effects: (i) the reduction or amelioration of the severity of one or more symptoms of the autoimmune disease; (ii) the reduction in the duration of one or more symptoms associated with the autoimmune disease; (iii) the protection against the recurrence of a symptom associated with the autoimmune disease; (iv) the reduction in hospitalization of a subject; (v) a reduction in hospitalization length; (vi) the increase in the survival of a subject; (vii) the enhancement or improvement of the therapeutic effect of another therapy; (viii) an increase in the survival rate of subjects; (xiii) a decrease in hospitalization rate; (ix) the protection against the development or onset of one or more symptoms associated with the autoimmune disease; (x) the reduction in the number of symptoms associated with the autoimmune disease; (xi) an increase in symptom-free survival of autoimmune disease subjects; (xii) improvement in quality of life as assessed by methods well known in the art; (xiii) a reduction in mortality; (xiv) an increase in the autoimmune disease-free survival rate of patients; (xv) an increase in relapse free survival; (xvi) an increase in the number of patients in remission; and/or (xvi) an increase in the length of remission in patients.

In certain embodiments, treatment of a subject with graft rejection or graft-versus-host disease in accordance with the methods described herein achieves at least one, two, three, four or more of the following effects: (i) the reduction or amelioration of the severity of one or more symptoms of the graft rejection or graft-versus-host disease; (ii) the reduction in the duration of one or more symptoms associated with the graft rejection or graft-versus-host disease; (iii) the protection against the recurrence of a symptom associated with the graft rejection or graft-versus-host disease; (iv) the reduction in hospitalization of a subject; (v) a reduction in hospitalization length; (vi) the increase in the survival of a subject; (vii) the enhancement or improvement of the therapeutic effect of another therapy; (viii) an increase in the survival rate of subjects; (xiii) a decrease in hospitalization rate; (ix) the protection against the development or onset of one or more symptoms associated with the graft rejection or graft-versus-host disease; (x) the reduction in the number of symptoms associated with the graft rejection or graft-versus-host disease; (xi) an increase in symptom-free survival of graft rejection or graft-versus-host disease subjects; (xii) improvement in quality of life as assessed by methods well known in the art; (xiii) a reduction in mortality; (xiv) an increase in the graft rejection or graft-versus-host disease-free survival rate of patients; (xv) an increase in relapse free survival; (xvi) an increase in the number of patients in remission; and/or (xvi) an increase in the length of remission in patients.

As used herein, the term "dendritic cell" (sometimes referred to herein as "DC") refers to a type of antigen presenting cell capable of initiating the primary immune responses. In specific embodiments, a dendritic cell refers to a cell performing one or all of the following functions for the immune system: 1) uptake, processing, and presentation of antigens, 2) activation of effector cells such as T-cells, B-cells and NK-cells, and/or 3) secretion of cytokines and other immune-modulating molecules to direct the immune response. Under homeostasis (steady state conditions), dendritic cells can be found in an immature state in the blood. When activated, they migrate into the lymph nodes where they interact with T-cells and B-cells.

As used herein, the term "maturation" refers to a process when immature DCs undergo morphological, phenotypic, and functional changes that culminate in complete transition from antigen-capturing cells to fully mature antigen presenting cell. Maturation can be characterized by increased expression of costimulatory molecules such as CD40, CD80, and CD86, MHC-upregulation, the loss of the capacity to take up and process antigens and the production of wide spectrum of inflammatory cytokines and chemokines (IL-1β, IL-6, IL-8, IL-12). Once activated or mature, DCs can migrate to the lymph nodes where they interact with T-cells and B-cells to initiate and shape the adaptive immune response.

As used herein, the terms "mature dendritic cell" and "activated dendritic cell" refer to a dendritic cell presenting antigens and characterized by the expression of costimulatory molecules such as CD40, CD80, and CD86, MHC-upregulation, the loss of the capacity to take up and process antigens, and the production of wide spectrum of inflammatory cytokines and chemokines (e.g., IL-1β, IL-6, IL-8, IL-12).

As used herein, the term "tolerogenic dendritic cell" or "tolDC" or "tDC" refers to antigen presenting cells with immunosuppressive properties. TolDcs have a low ability to activate effector T cells, but have a high ability to induce and activate regulatory T cells. TolDCs can induce tolerance through the presentation of antigen with inadequate co-stimulation and cytokine production for effector cell activation. TolDCs are commonly defined by low or intermediate levels of MHC II, costimulatory molecules CD80, CD86 and CD40, and chemokine receptor CCR7, in addition to a remarkably increased antigen uptake capacity. TolDCs express high levels of inhibitory molecules such as Ig-like transcripts (ILT) molecules (ILT3/ILT4) and/or PD-L molecules (PD-L1, PD-L2). Additionally, tolDCs secrete low amounts of proinflammatory cytokines (IL-12p70) and high quantities of anti-inflammatory cytokines, such as IL-10. TolDCs induce T cell anergy, T cell suppression and the generation of regulatory T cells by several mechanisms, including conversion of naïve T cells into Tregs, release of immunosuppressive cytokines, and expression of functional indoleamine-2,3 dioxygenase (IDO).

As used herein, the term "semi-mature tolerogenic dendritic cell" or "semi-mature tolDC" refers dendritic cells characterized by low expression levels of cell surface markers CD86, CD83, CD80 and CD40 and upregulated expression of TLR-2, CD14, TIM-3 and ILT-3 relative to dendritic cells cultured in culture medium comprising GM-CSF and IL-4 without tolerising agents, such as Dexamethasone and vitamin D2, as described, e.g., in Section 6, 7 and/or 8, infra. In contrast to immature dendritic cells, semi-mature dendritic cells are able to migrate towards lymph nodes.

As used herein, the terms "stable semi-mature tolerogenic dendritic cells" and "stable semi-mature tolDCs" refers to tolDCs retaining their semi-mature tolerogenic properties in the absence of tolerogenic agents and in the presence of inflammatory signals. In a specific embodiment, stable semi-mature tolDCs remain functionally stable in terms of maturation and cytokine production after restimulation of DC activation is mimicked in vivo by inflammation for instance. In another embodiment, the stable tolDCs remain able to induce Tregs and to reduce the secretion of cytokines associated with autoimmune diseases after restimulation. In another specific embodiment, stable semi-mature tolDCs are functional stable after encountering physiological environments similar to therapeutic conditions. In another specific embodiment, stable semi-mature tolDCs remain functionally stable in terms of maturation and cytokine production after re-stimulation with lipopolysaccharide (LPS), poly (I:C), or a mixture of pro-inflammatory cytokines, such as a mixture of IL-1 beta, TNF-alpha, IL-6 and IFN-gamma, in the absence of tolerogenic agents, such as Dexamethasone and vitamin D2, and can be used in immune tolerance treatments. In another specific embodiment, stable semi-mature tolerogenic dendritic cells maintain their semi-mature tolerogenic properties after stimulation with lipopolysaccharide (LPS), poly (I:C), or a mixture of pro-inflammatory cytokines, such as a mixture of IL-1 beta, TNF-alpha, IL-6 and IFN-gamma, in the absence of tolerogenic agents, such as Dexamethasone and vitamin D2. In another specific embodiment, stable semi-mature tolerogenic dendritic cells are stable as assessed by one, two or all of the methods described in Section 6, 7 and/or 8, infra.

As used herein, the term "a stable semi-mature tolerogenic phenotype" in context of tolerogenic dendritic cells (tolDCs) refers to tolDCs that retain their semi-mature tolerogenic properties in the absence of tolerogenic agents and in the presence of inflammatory signals. In a specific embodiment, tolDCs that maintain a stable semi-mature tolerogenic phenotype remain functionally stable in terms of maturation and cytokine production after restimulation of DC activation is mimicked in vivo by inflammation for instance. In another embodiment, tolDCs that maintain a stable semi-mature tolerogenic phenotype remain able to induce Tregs and to reduce the secretion of cytokines associated with autoimmune diseases after restimulation. In another specific embodiment, tolDCs that maintain a stable semi-mature tolerogenic phenotype remain functional stable after encountering physiological environments similar to therapeutic conditions. In another specific embodiment, tolDCs that maintain a stable semi-mature tolerogenic phenotype remain functionally stable in terms of maturation and cytokine production after re-stimulation with lipopolysaccharide (LPS), poly (I:C), or a mixture of pro-inflammatory cytokines, such as a mixture of IL-1 beta, TNF-alpha, IL-6 and IFN-gamma, in the absence of tolerogenic agents, such as Dexamethasone and vitamin D2, and can be used in immune tolerance treatments. In another specific embodiment, tolDCs that maintain a stable semi-mature tolerogenic phenotype remain semi-mature tolerogenic properties after stimulation with lipopolysaccharide (LPS), poly (I:C), or a mixture of pro-inflammatory cytokines, such as a mixture of IL-1 beta, TNF-alpha, IL-6 and IFN-gamma, in the absence of tolerogenic agents, such as Dexamethasone and vitamin D2. In another specific embodiment, tolDCs that maintain a stable semi-mature tolerogenic phenotype are stable as assessed by one, two or all of the methods described in Section 6, 7 and/or 8, infra.

As used herein, terms "tolerizing agents," "tolerising agents," and "tolerogenic agents" refer to agents that can produce tolerogenic dendritic. Examples of tolerogenic agents include Dexamethasone, vitamin D2 or analogue thereof, vitamin D3 or an analogue thereof, neuropeptides, such as vasoactive intestinal peptide or pituitary adenylate cyclase-activating polypeptide.

As used herein, the term "regulatory T cells" or "Tregs" refers to a cell form a specialized sub-population of T cells which acts by suppressing the activation of the immune system, thus maintaining the homeostasis of the immune system and favoring tolerance towards self antigens. Regulatory T cells can be characterized as $CD4^+CD25^+FoxP3^+$ cells.

As used herein, the term "monocytes" refers to a leukocytes circulating in the blood characterized by a bean-shaped nucleus and by the absence of granules. Monocytes can give rise to dendritic cells.

As used herein, the term "vitamin D2" refers to active forms of vitamin D2. Active forms of vitamin D2 include paracalcitol, 19-nor-1,25-dihydroxyvitamin D2, Zemplar and all other forms of active vitamin D2 known in the art, including vitamin D2 analogues. In a specific embodiment, the vitamin D2 is the form referenced in Section 6, 7 and/or 8, infra. In another specific embodiment, the vitamin D2 is the one referenced in Section 6, 7 and/or 8, infra. Vitamin D2 is sometimes referred to herein as vitD2.

As used herein, the term "Dexamethasone" refers to soluble Dexamethasone sodium phosphate, to Dexamethasone and to all other forms of Dexamethasone and names for Dexamethasone knows in the art. In a specific embodiment, the Dexamethasone is the one referenced in Section 6, 7 and/or 8, infra. Dexamethasone is sometimes referred to herein as Dex.

As used herein, the term "monophosphoryl lipid A" or "MPLA" refers to natural derivate of the lipid A fraction from Gram-negative bacteria including *Salmonella enterica* Minnesota R595 lipopolysaccharide or to synthetic forms of the same derivative or any available form known in the art. MPLA purified from bacteria can contain a mixture of 4, 5, 6, 7 or 8 acyl lipid A. The synthetic MPLA can contain only one type of acyl Lipid A, such as 6 acyl lipid A. In a specific embodiment, the MPLA is the one referenced in Section 6, 7 and/or 8, infra.

As used herein, the terms "subject" and "patient" are used interchangeably and refer to an animal. In a specific embodiment, such terms refer to a mammal such as a non-primate (e.g., cows, pigs, horses, cats, dogs, rats etc.) and a primate (e.g., monkey and human), most preferably a human.

As used herein, the term "significant," as in "significant" amount, change or effect, for example, means that the amount, change, or effect produced would not be likely to have occurred by random chance, as determined by any standard method for statistical analysis, such as a p test, wherein a p value less than the critical alpha level indicates that an event would be unlikely. Thus, a "significant" change in the context described herein indicates the P value is less than the critical alpha level, and that the probability is small that the change happened by chance.

As used herein, the term "effective amount" in the context of the administration of a therapy to a subject refers to the amount of a therapy that achieves a desired prophylactic or therapeutic effect. Examples of effective amounts are provided in Sections 5.8.2 and 5.8.3, infra.

All terms used herein, unless otherwise defined, will be given their ordinary technical or scientific meaning as would be commonly understood by one of ordinary skill in the art at the time of the disclosure.

5.2 Methods for Generating Dendritic Cells

Techniques known to one skilled in the art may be used to obtain/generate dendritic cells from peripheral blood mononuclear cells. In a specific embodiment, a whole blood sample is obtained from a patient and peripheral blood mononuclear cells are isolated. Mononuclear cells may be isolated from peripheral blood of a patient by, for example, Ficoll-Paque Plus gradient centrifugation. In addition, mononuclear cells can be fractionated using an elutriation or by using the CliniMACS® system. Dendritic cells can be enriched by sequential density centrifugation of apheresis peripheral blood mononuclear cells. The monocytes isolated from the blood of a patient may be cultured in the presence of factors, such as the combination GM-CSF and IL-4, IL-13, IL-15 and IFNα, or Flt3L, to differentiate into immature DCs after a period of, e.g., 4 to 5 days. To generate mature dendritic cells, the cells may be activated with TNF-α, IFN-γ, LPS, MPLA, CpG, IL-1 or CD40L. In a specific embodiment, mature dendritic cells are activated using TLR-3 and/or TLR-4 activators, such as poly (I:C) and/or LPS and/or MPLA. Further, CMRF-44 antigen, CD1c, BDCA-4 and other dendritic cell-specific markers may also be used to promote DC maturation. In a specific embodiment, dendritic cells are generated as described in Section 6, 7 and/or 8, infra.

Techniques known to one skilled in the art can be used to assess/confirm the presence of dendritic cells. For example, the presence of dendritic cells can be assessed/confirmed by detecting the expression of dendritic cell surface markers using techniques, such as FACS. In a specific embodiment, the presence of dendritic cells is assessed/confirmed using the methods in Section 6, 7 and/or 8, infra.

5.3 Methods for Generating tolDCs

Techniques known to one skilled in the art may be used to induce/generate tolDCs. Dendritic cells can be generated from peripheral blood mononuclear cells using the methods described in Section 5.2, supra. Dendritic cells can be induced into tolDCs with a large array of mediators, including, e.g., IL-10 and other cytokines, corticosteroids such as Dexamethasone, vitamin D3 or vitamin D2, rapamycin, neuropeptides, and combinations of vitamin D3 or vitamin D2 and Dexamethasone. In certain embodiments, Dexamethasone and vitamin D2 are utilized to generate tolDCs.

In a specific embodiment, a method for generating stable tolerogenic dendritic cells comprises: (a) isolating monocytes from a subject's blood; (b) culturing the monocytes in culture medium comprising one or more factors that induce the differentiation of monocytes into dendritic cells (e.g., GM-CSF and IL-4); (c) after a first period of time in culture, culturing the cells from step (b) in culture medium comprising Dexamethasone; (d) after a second period of time in culture, culturing the cells from step (c) in culture medium comprising Dexamethasone and vitamin D2 for a third period of time to generate tolerogenic dendritic cells to establish tolerogenic dendritic cells; and (d) after a third period of time, culturing the tolerogenic dendritic cells in cGMP medium comprising MPLA or MPLA and an antigen of associated with an autoimmune disease, graft rejection or graft-versus-host disease. In certain embodiments, the culture medium comprises one or more factors that induce the differentiation of monocytes into dendritic cells throughout the method for generating stable semi-mature tolDCs. Examples of factors that induce differentiation of monocytes into dendritic cells include the combination of GM-CSF and IL-4, IL-13, IL-15 or IFN-alpha, or Flt3L. In a specific embodiment, the culture medium comprises GM-CSF and IL-4 throughout the method for generating stable semi-mature tolDCs. In certain embodiments, the starting point for the method for generating stable semi-mature tolerogenic dendritic cells is step (b). In certain embodiments, GM-CSF is added to the culture medium to achieve a final concentration of 250 IU/ml, 300 IU/ml, 350 IU/ml, 400 IU/ml, 450 IU/ml, 500 IU/ml, 550 IU/ml, 600 IU/ml, 650 IU/ml, 700 IU/ml or 750 IU/ml. In some embodiments, GM-CSF is added to the culture medium to achieve a final concentration of 250 IU/ml to 500 IU/ml, 300 IU/ml to 400 IU/ml, 300 IU/ml to 600 IU/ml, 500 IU/ml to 750 IU/ml, or 250 IU/ml to 750 IU/ml. In a specific embodiment, GM-CSF is added to the culture medium to achieve a final concentration of 500 IU/ml. In certain embodiments, the IL-4 is added to culture medium to achieve a final concentration of 10 ng/ml, 15 ng/ml, 20 ng/ml, 25 ng/ml, 30 ng/ml, 35 ng/ml, 40 ng/ml, 45 ng/ml or 50 ng/ml. In some embodiments, the IL-4 is added to culture medium to achieve a final concentration of 10 ng/ml to 20 ng/ml, 20 ng/ml to 40 ng/ml, 25 ng/ml to 50 ng/ml or 10 ng/ml to 50 ng/ml. In a specific embodiment, the IL-4 is added to culture medium to achieve a final concentration of 20 ng/ml.

Monocytes can be isolated from a subject's blood by any technique known to one of skill in the art or described herein (see, e.g., Section 5.2, supra). In some embodiments, the monocytes used in accordance with the methods described herein are from a type 1 diabetes mellitus subject with a HbA1c level of less than or equal to 60 mmol/mol Hb. In other embodiments, the monocytes used in accordance with the methods described herein are from a type 1 diabetes mellitus subject with a HbA1c level of higher than 60 mmol/mol Hb. In certain embodiments, the method for generating stable semi-mature tolDCs takes approximately 8 days of cell culture. In some embodiments, the step of culturing the tolDCs with antigen involves culturing with one, two, three or more antigens associated with an autoimmune disease, graft rejection or graft-versus-host disease. See, e.g., Table 1, infra, for a list of autoimmune diseases and antigens associated with those autoimmune diseases.

In specific embodiments, the cells from step (b) above are cultured in culture medium comprising Dexamethasone on the $3^{rd}$ day of culture. In certain embodiments, the cells from step (b) are cultured in culture medium comprising Dexamethasone approximately 60, 61, 62, 63, 64, 65, 66, 67, 68, 69, 70, 71 or 72 hours after the monocytes were first cultured in culture medium comprising one or more factors that induce the differentiation of monocytes into dendritic cells, such as GM-CSF and IL-4. In specific embodiments, Dexamethasone is added to culture medium on the $3^{rd}$ day of culture of the cells. In specific embodiments, the culture medium comprises Dexamethasone and one or more factors that induce the differentiation of monocytes into dendritic cells, such as GM-CSF and IL-4. In certain embodiments, Dexamethasone is added to culture medium achieve a final concentration of Dexamethasone is added to the culture media at a final concentration between 0.5 and 3 micromole per liter. In some embodiments, Dexamethasone is added to culture medium to achieve a final concentration of 0.5, 1, 1.5, 2, 2.5, 3, 3.5 or 4 micromole per liter. In yet another embodiment, Dexamethasone is added to culture media at a final concentration of 1 micromole per liter. In certain embodiments, GM-CSF is added to the culture medium to achieve a final concentration of 250 IU/ml, 300 IU/ml, 350 IU/ml, 400 IU/ml, 450 IU/ml, 500 IU/ml, 550 IU/ml, 600 IU/ml, 650 IU/ml, 700 IU/ml or 750 IU/ml. In some embodiments, GM-CSF is added to the culture medium to achieve a final concentration of 250 IU/ml to 500 IU/ml, 300 IU/ml to 400 IU/ml, 300 IU/ml to 600 IU/ml, 500 IU/ml to 750 IU/ml, or 250 IU/ml to 750 IU/ml. In a specific embodiment, GM-CSF is added to the culture medium to achieve a final concentration of 500 IU/ml. In certain embodiments, the IL-4 is added to culture medium to achieve a final concentration of 10 ng/ml, 15 ng/ml, 20 ng/ml, 25 ng/ml, 30 ng/ml, 35 ng/ml, 40 ng/ml, 45 ng/ml or 50 ng/ml. In some embodiments, the IL-4 is added to culture medium to achieve a final concentration of 10 ng/ml to 20 ng/ml, 20 ng/ml to 40 ng/ml, 25 ng/ml to 50 ng/ml or 10 ng/ml to 50 ng/ml. In a specific embodiment, the IL-4 is added to culture medium to achieve a final concentration of 20 ng/ml.

In specific embodiments, the cells from step (c) above are cultured in culture medium comprising Dexamethasone and vitamin D2 on the $6^{th}$ day of culture. In some embodiments, the cells from step (c) are cultured in culture medium comprising Dexamethasone and vitamin D2 approximately 135, 136, 137, 138, 139, 140, 141, 142, 143, 144, 145, 146, 147, 148, 149 or 150 hours after the monocytes were first cultured in culture medium comprising one or more factors that induce the differentiation of monocytes into dendritic cells, such as GM-CSF and IL-4. In certain embodiments, Dexamethasone and vitamin D2 are added to culture medium simultaneously approximately 135, 136, 137, 138, 139, 140, 141, 142, 143, 144, 145, 146, 147, 148, 149 or 150 hours after the monocytes were first cultured in culture medium comprising one or more factors that induce the differentiation of monocytes into dendritic cells, such as GM-CSF and IL-4. In some embodiments, Dexamethasone and vitamin D2 are added to the cells from step (c) in cell culture simultaneously on the 6$^{th}$ day in culture. In certain embodiments, vitamin D2 and Dexamethasone are added to the cells in cell culture separately during the 6$^{th}$ day of culture (e.g., within 5 minutes, 10 minutes, 15 minutes, 30 minutes, 45 minutes, 1 hour, 1.5 hours, 2 hours or more of each other). In specific embodiments, the culture medium comprises Dexamethasone, vitamin D2 and one or more factors that induce the differentiation of monocytes into dendritic cells, such as GM-CSF and IL-4. In certain embodiments, Dexamethasone is added to culture medium achieve a final concentration of Dexamethasone is added to the culture media at a final concentration between 0.5 and 3 micromole per liter. In some embodiments, Dexamethasone is added to culture medium to achieve a final concentration of 0.5, 1, 1.5, 2, 2.5, 3, 3.5 or 4 micromole per liter. In a specific embodiment, Dexamethasone is added to culture media at a final concentration of 1 micromole per liter. In certain embodiments, vitamin D2 is added to culture medium to achieve a final concentration of between 0.1 and 10 nM. In some embodiments, vitamin D2 is added to culture medium to achieve a final concentration of 0.1, 0.5, 1, 2, 3, 4, 5, 6, 7, 8, 9 or 10 nM. In a specific embodiment, vitamin D2 is added to culture medium to achieve a final concentration of 3.6 nM. In certain embodiments, GM-CSF is added to the culture medium to achieve a final concentration of 250 IU/ml, 300 IU/ml, 350 IU/ml, 400 IU/ml, 450 IU/ml, 500 IU/ml, 550 IU/ml, 600 IU/ml, 650 IU/ml, 700 IU/ml or 750 IU/ml. In some embodiments, GM-CSF is added to the culture medium to achieve a final concentration of 250 IU/ml to 500 IU/ml, 300 IU/ml to 400 IU/ml, 300 IU/ml to 600 IU/ml, 500 IU/ml to 750 IU/ml, or 250 IU/ml to 750 IU/ml. In a specific embodiment, GM-CSF is added to the culture medium to achieve a final concentration of 500 IU/ml. In certain embodiments, the IL-4 is added to culture medium to achieve a final concentration of 10 ng/ml, 15 ng/ml, 20 ng/ml, 25 ng/ml, 30 ng/ml, 35 ng/ml, 40 ng/ml, 45 ng/ml or 50 ng/ml. In some embodiments, the IL-4 is added to culture medium to achieve a final concentration of 10 ng/ml to 20 ng/ml, 20 ng/ml to 40 ng/ml, 25 ng/ml to 50 ng/ml or 10 ng/ml to 50 ng/ml. In a specific embodiment, the IL-4 is added to culture medium to achieve a final concentration of 20 ng/ml.

In specific embodiments, the tolerogenic dendritic cells are cultured in culture medium comprising MPLA, or MPLA and an antigen(s) associated with an autoimmune disease, graft rejection, or graft-versus-host disease on the 7$^{th}$ day of culture. In some embodiments, the tolerogenic dendritic cells are cultured in culture medium comprising MPLA, or MPLA and an antigen associated with an autoimmune disease, graft rejection, or graft-versus-host disease 156, 157, 158, 159, 160, 161, 162, 163, 164, 165, 166, 167, 168, 169 or 170, hours after the monocytes were first cultured in culture medium comprising one or more factors that induce the differentiation of monocytes into dendritic cells, such as GM-CSF and IL-4. In specific embodiments, the culture medium comprises MPLA and one or more factors that induce the differentiation of monocytes into dendritic cells (e.g., GM-CSF and IL-4), or MPLA, one or more factors that induce the differentiation of monocytes into dendritic cells (e.g., GM-CSF and IL-4), and an antigen(s) associated with an autoimmune disease, graft rejection or graft-versus-host disease. In certain embodiments, the tolerogenic dendritic cells are cultured in culture medium comprising MPLA, or MPLA and an antigen associated with an autoimmune disease, graft rejection or graft-versus-host disease for 18, 19, 20, 21, 22, 23, 24, 25, 26, 27, 28, 29 or 30 hours before the cells are harvested. In some embodiments, the tolerogenic dendritic cells are cultured in culture medium comprising MPLA and one or more factors that induce the differentiation of monocytes into dendritic cells (e.g., GM-CSF and IL-4), or MPLA, one or more factors that induce the differentiation of monocytes into dendritic cells (e.g., GM-CSF and IL-4), and an antigen(s) associated with an autoimmune disease, graft rejection, or graft-versus-host disease for 18, 19, 20, 21, 22, 23, 24, 25, 26, 27, 28, 29 or 30 hours before the cells are harvested.

In certain embodiments, MPLA, MPLA and an antigen associated with an autoimmune disease, graft rejection, or graft-versus-host disease is/are added to culture medium approximately 135, 136, 137, 138, 139, 140, 141, 142, 143, 144, 145, 146, 147, 148, 149 or 150 hours after the monocytes were first cultured in culture medium comprising factors, such as GM-CSF and IL-4. In some embodiments, MPLA, or MPLA and an antigen(s) associated with an autoimmune disease, graft rejection, or graft-versus-host disease is/are added to culture medium on the 7$^{th}$ day of culture. In some embodiments, MPLA and an antigen(s) associated with an autoimmune disease, graft rejection, or graft-versus-host disease are added to the tolerogenic dendritic cells in cell culture simultaneously on the 7$^{th}$ day in culture. In certain embodiments MPLA and an antigen(s) associated with an autoimmune disease, graft rejection, or graft-versus-host disease are added to the tolerogenic dendritic cells in cell culture separately during the 7$^{th}$ day of culture (e.g., within 5 minutes, 10 minutes, 15 minutes, 30 minutes, 45 minutes, 1 hour, 1.5 hours, 2 hours or more of each other). When added separately, antigen is added before the MPLA. In certain embodiments, the tolerogenic dendritic cells are cultured in culture medium comprising MPLA, or MPLA and an antigen associated with an autoimmune disease, graft rejection or graft-versus-host disease for 18, 19, 20, 21, 22, 23, 24, 25, 26, 27, 28, 29 or 30 hours before the cells are harvested. In specific embodiments, the culture medium further comprises one or more factors that induce the differentiation of monocytes into dendritic cells (e.g., GM-CSF and IL-4).

In certain embodiments, MPLA is added to culture medium to achieve a final concentration of between 0.1 and 10 nM. In some embodiments, MPLA is added to culture medium to achieve a final concentration of between 1 and 3 microgram per milliliter. In a specific embodiment, MPLA is added to culture medium to achieve a final concentration of 2 microgram per milliliter. In certain embodiments, GM-CSF is added to the culture medium to achieve a final concentration of 250 IU/ml, 300 IU/ml, 350 IU/ml, 400 IU/ml, 450 IU/ml, 500 IU/ml, 550 IU/ml, 600 IU/ml, 650 IU/ml, 700 IU/ml or 750 IU/ml. In some embodiments, GM-CSF is added to the culture medium to achieve a final concentration of 250 IU/ml to 500 IU/ml, 300 IU/ml to 400 IU/ml, 300 IU/ml to 600 IU/ml, 500 IU/ml to 750 IU/ml, or 250 IU/ml to 750 IU/ml. In a specific embodiment, GM-CSF is added to the culture medium to achieve a final concentration of 500 IU/ml. In certain embodiments, the IL-4 is added to culture medium to achieve a final concentration of 10 ng/ml, 15 ng/ml, 20 ng/ml, 25 ng/ml, 30 ng/ml, 35 ng/ml, 40 ng/ml, 45 ng/ml or 50 ng/ml. In some embodiments, the IL-4 is added to culture medium to achieve a final concentration of 10 ng/ml to 20 ng/ml, 20 ng/ml to 40 ng/ml, 25 ng/ml to 50 ng/ml or 10 ng/ml to 50 ng/ml. In a specific embodiment, the IL-4 is added to culture medium to achieve a final concentration of 20 ng/ml.

In some embodiments, an antigen(s) associated with an autoimmune disease, graft rejection, or graft-versus-host disease is added to culture medium to achieve a final concentration of between 1 nM to 500 nM. In certain embodiments, an antigen associated with an autoimmune disease is added to culture medium to achieve a final concentration of between 10 nM to 200 nM. In a specific embodiment, the antigen is a purified GAD65 polypeptide. In certain embodiments, the purified GAD65 polypeptide is added to culture medium to achieve a final concentration of 20, 30, 40, 50, 60, 70, 80, 90, 100 or 110 nM. In another embodiment, the purified GAD65 polypeptide is added to culture medium to achieve a final concentration of 80 nM. In another specific embodiment, the antigen is a purified insulin polypeptide. In certain embodiments, the purified insulin polypeptide is added to culture medium to achieve a final concentration of 50, 100, 150, 200, 250, 300, 350 or 400 nM. In a specific embodiment, the purified insulin polypeptide is added to culture medium to achieve a final concentration of 170 nM. In some embodiments, the antigens are purified GAD65 polypeptide and purified insulin polypeptide. In certain embodiments, the purified GAD65 polypeptide is added to culture medium to achieve a final concentration of 20, 30, 40, 50, 60, 70, 80, 90, 100 or 110 nM and the purified insulin polypeptide is added to culture medium to achieve a final concentration of 50, 100, 150, 200, 250, 300, 350 or 400 nM. In certain embodiments, a cell lysate(s) or a MHC-peptide(s) obtained or derived from the donor of the graft (e.g., tissue or cell sample) is used as an antigen(s) associated with graft rejection and/or graft-versus-host disease. Techniques known to one skilled in the art can be used to generate a cell lysate(s) or MHC-peptide from the donor (see, e.g., Lu et al, 1995, Transplantation 62: 659-665, Hayamizu et al., 1998, Transplantation 66:1285-1291). In a specific embodiment, the donor is a subject (preferably, a human subject).

In specific embodiments, the culture medium used in accordance with the methods described herein is medium suitable for culturing monocytes, dendritic cells and/or tolerogenic dendritic cells. In particular embodiments, the culture medium used in accordance with the methods described herein is cGMP medium. In a specific embodiment, the culture medium used in accordance with the methods described herein is the culture medium described in Section 6, 7 and/or 8, infra.

In a specific embodiment, stable semi-mature tolDCs are generated by following the methodology in FIG. 6. In a preferred embodiment, stable semi-mature tolDCs are generated from peripheral blood mononuclear cells utilizing vitamin D2 and Dexamethasone as described in Section 6, 7 and/or 8, infra.

In certain embodiments, a method described herein for generating stable semi-mature tolDCs result in a yield of dendritic cells in culture at the time the cells are harvested is similar to the yield of dendritic cells obtained by culturing the monocytes in culture medium comprising GM-CSF and IL-4 without tolerising agents, such as Dexamethasone and vitamin D2. In some embodiments, the method described herein for generating tolDCs result in a yield of dendritic cells in culture at the time the cells are harvested is similar to the yield of non-adherent dendritic cells obtained by culturing the monocytes in culture medium comprising GM-CSF and IL-4 without tolerising agents, such as Dexamethasone and vitamin D2. In specific embodiments, the term "similar" in this paragraph means that there is less than a 50%, 45%, 40%, 35%, 30%, 25%, 20%, 15%, or 10% difference in the yield of dendritic cells.

In some embodiments, a method described herein for generating stable semi-mature tolDCs results in a percentage of CD11c$^+$ dendritic cells in culture at the time the tolDCs are harvested that is equivalent or superior to the percentage of CD11c$^+$ dendritic cells obtained by culturing monocytes in culture medium comprising GM-CSF and IL-4 without tolerising agents, such as Dexamethasone and vitamin D2. In specific embodiments, the percentage of CD11c$^+$ dendritic cells in culture at the time the tolDCs are harvested is at least 20 percent, at least 25 percent, at least 30 percent, at least 35 percent, at least 40 percent, at least 45 percent or at least 50 percent. In certain embodiments, the percentage of CD11c$^+$ dendritic cells in culture at the time the tolDCs are harvested is between 20 percent to 30 percent, 25 percent to 50 percent, or 20 percent to 40 percent. In accordance with these embodiments, in specific embodiments, the percentage of CD11c$^+$ dendritic cells culture is assessed after same length of time in culture.

In certain embodiments, a method described herein for generating stable semi-mature tolDCs results in PD-L1 expression on the population of tolerogenic dendritic cells in culture at the time the cells are harvested that is lower than the PD-L1 expression on the population of dendritic cells obtained by culturing monocytes in culture medium comprising GM-CSF and IL-4 without tolerising agents, such as Dexamethasone and vitamin D2. In some embodiments, the PL-L1 expression on the population of tolDCs is approximately 70%, 65%, 60%, 55%, 50%, 45%, 40%, 35%, 30%, 25%, 20%, 15%, 10% or 5% lower than the PD-L1 expression on the population of dendritic cells obtained by culturing monocytes in culture medium comprising GM-CSF and IL-4 without tolerising agents. In accordance with these embodiments, in specific embodiments, the PD-L1 expression on the population of tolDCs and the population of dendritic cells obtained by culturing monocytes in culture medium comprising GM-CSF and IL-4 without tolerising agents, such as Dexamethasone and vitamin D2, are assessed after same length of time for cell culture.

In certain embodiments, a method described herein for generating stable semi-mature tolDCs results CD14 expression on the population of tolerogenic dendritic cells in culture at the time the cells are harvested that is at least 3 times higher than the CD14 expression on the population of dendritic cells obtained by culturing monocytes in culture medium comprising GM-CSF and IL-4 without tolerising agents, such as Dexamethasone and vitamin D2. In some embodiments, the CD14 expression is 3.5 times, 4 times, 4.5 times, 4 times, 4.5 times, 5 times, 5.5 times, 6 times, 6.5 times, 7 times, 7.5 times, 8 times, 8.5 times, 9 times, 9.5 times, 10 times, 10.5 times, 11 times, 11.5 times, 12 times, 12.5 times or 13 times higher than the CD14 expression on the population of dendritic cells obtained by culturing monocytes in culture medium comprising GM-CSF and IL-4 without tolerising agents. In certain embodiments, the CD14 expression is between 3 to 4 times, 3 to 5 times, 3 to 6 times, 3 to 10 times, 3 to 15 times, 4 to 6 times, 5 to 10 times, 10 to 15 times, 5 to 12 times, 10 to 13 times, or 5 to 15 times higher than the CD14 expression on the population of dendritic cells obtained by culturing monocytes in culture medium comprising GM-CSF and IL-4 without tolerising agents. In accordance with these embodiments, in specific embodiments, the CD14 expression on the population of tolDCs and the population of dendritic cells obtained by culturing monocytes in culture medium comprising GM-CSF and IL-4 without tolerising agents, such as Dexamethasone and vitamin D2, are assessed after same length of time for cell culture.

In certain embodiments, a method described herein for generating stable semi-mature tolDCs results in CD86 expression on the population of tolerogenic dendritic cells in culture at the time the cells are harvested that is lower than the CD86 expression on the population of dendritic cells obtained by culturing monocytes in culture medium comprising GM-CSF and IL-4 without tolerising agents, such as Dexamethasone and vitamin D2. In some embodiments, the CD86 expression on the population of tolDCs is approximately 70%, 65%, 60%, 55%, 50%, 45%, 40%, 35%, 30%, 25%, 20%, 15%, or 10% lower than the CD86 expression on the population of dendritic cells obtained by culturing monocytes in culture medium comprising GM-CSF and IL-4 without tolerising agents. In accordance with these embodiments, in specific embodiments, the CD86 expression on the population of tolDCs and the population of dendritic cells obtained by culturing monocytes in culture medium comprising GM-CSF and IL-4 without tolerising agents, such as Dexamethasone and vitamin D2, are assessed after same length of time for cell culture.

In certain embodiments, a method described herein for generating stable semi-mature tolDCs results in a ratio of PD-L1/CD86 expression on the population of tolerogenic dendritic cells in culture at the time the cells are harvested that is higher than the ratio of PD-L1/CD86 expression on the population of dendritic cells obtained by culturing monocytes in culture medium comprising GM-CSF and IL-4 without tolerising agents, such as Dexamethasone and vitamin D2. In some embodiments, the ratio is 1.5 times, 2 times, 2.5 times, 3 times, 3.5 times, 4 times, 4.5 times, 4 times, 4.5 times, 5 times, 5.5 times, 6 times, 6.5 times, 7 times, 7.5 times, 8 times, 8.5 times, 9 times, 9.5 times, 10 times, 10.5 times, 11 times, 11.5 times, 12 times, 12.5 times or 13 times higher than the same ratio on the population of dendritic cells obtained by culturing monocytes in culture medium comprising GM-CSF and IL-4 without tolerising agents. In a specific embodiment, a method described herein for generating stable semi-mature tolDCs results in a ratio of PD-L1/CD86 expression on the population of tolerogenic dendritic cells in culture at the time the cells are harvested that is higher than the ratio of PD-L1/CD86 expression on the population of dendritic cells obtained by culturing monocytes in culture medium comprising GM-CSF and IL-4 without tolerising agents, such as Dexamethasone and vitamin D2, by the same or similar amount as depicted in FIG. 32. In accordance with this embodiment, the term "similar" means within 5%, 10%, 15%, 20%, 25%, or 30% of the values in FIG. 32.

In certain embodiments, a method described herein for generating stable semi-mature tolDCs results in CXCR3 expression on the population of tolerogenic dendritic cells in culture at the time the cells are harvested that is higher than the CXCR3 expression on the population of dendritic cells obtained by culturing monocytes in culture medium comprising GM-CSF and IL-4 without tolerising agents, such as Dexamethasone and vitamin D2. In some embodiments, the CXCR3 expression on the population of tolDCs is approximately 200%, 175%, 150%, 125%, 100%, 95%, 90%, 85%, 80%, 75%, 70%, 65%, 60%, 55%, 50%, 45%, 40%, 35%, 30%, 25%, 20%, 15%, or 10% higher than the CXCR3 expression on the population of dendritic cells obtained by culturing monocytes in culture medium comprising GM-CSF and IL-4 without tolerising agents. In accordance with these embodiments, in specific embodiments, the CXCR3 expression on the population of tolDCs and the population of dendritic cells obtained by culturing monocytes in culture medium comprising GM-CSF and IL-4 without tolerising agents, such as Dexamethasone and vitamin D2, are assessed after same length of time for cell culture.

In certain embodiments, a method described herein for generating stable semi-mature tolDCs results in CD83 expression on the population of tolerogenic dendritic cells in culture at the time the cells are harvested that is lower than the CD83 expression on the population of dendritic cells obtained by culturing monocytes in culture medium comprising GM-CSF and IL-4 without tolerising agents, such as Dexamethasone and vitamin D2. In some embodiments, the CD83 expression on the population of tolDCs is approximately 10%, 15%, 20%, 25%, 30%, 35%, 40%, 45%, 50%, 55%, 60%, 65%, 70%, 75%, 80%, 85%, 90%, 95%, 98% or 100% lower than the CD83 expression on the population of dendritic cells obtained by culturing monocytes in culture medium comprising GM-CSF and IL-4 without tolerising agents. In accordance with these embodiments, in specific embodiments, the CD83 expression on the population of tolDCs and the population of dendritic cells obtained by culturing monocytes in culture medium comprising GM-CSF and IL-4 without tolerising agents, such as Dexamethasone and vitamin D2, are assessed after same length of time for cell culture.

In certain embodiments, a method described herein for generating stable semi-mature tolDCs results in ITL-3 expression on the population of tolerogenic dendritic cells in culture at the time the cells are harvested that is higher than the ITL-3 expression on the population of dendritic cells obtained by culturing monocytes in culture medium comprising GM-CSF and IL-4 without tolerising agents, such as Dexamethasone and vitamin D2. In some embodiments, the ITL-3 expression on the population of tolDCs is approximately 200%, 175%, 150%, 125%, 100%, 95%, 90%, 85%, 80%, 75%, 70%, 65%, 60%, 55%, 50%, 45%, 40%, 35%, 30%, 25%, 20%, 15%, or 10% higher than the ILT-3 expression on the population of dendritic cells obtained by culturing monocytes in culture medium comprising GM-CSF and IL-4 without tolerising agents. In accordance with these embodiments, in specific embodiments, the ITL-3 expression on the population of tolDCs and the population of dendritic cells obtained by culturing monocytes in culture medium comprising GM-CSF and IL-4 without tolerising agents, such as Dexamethasone and vitamin D2, are assessed after same length of time for cell culture.

In certain embodiments, a method described herein for generating stable semi-mature tolDCs results in CD40 expression on the population of tolerogenic dendritic cells in culture at the time the cells are harvested that is lower than the CD40 expression on the population of dendritic cells obtained by culturing monocytes in culture medium comprising GM-CSF and IL-4 without tolerising agents, such as Dexamethasone and vitamin D2. In some embodiments, the CD40 expression on the population of tolDCs is approximately 10%, 15%, 20%, 25%, 30%, 35%, 40%, 45%, 50%, 55%, 60%, 65%, 70%, 75%, 80%, 85%, 90%, 95%, 98% or 100% lower than the CD40 expression on the population of dendritic cells obtained by culturing monocytes in culture medium comprising GM-CSF and IL-4 without tolerising agents. In accordance with these embodiments, in specific embodiments, the CD40 expression on the population of tolDCs and the population of dendritic cells obtained by culturing monocytes in culture medium comprising GM-CSF and IL-4 without tolerising agents, such as Dexamethasone and vitamin D2, are assessed after same length of time for cell culture.

In certain embodiments, a method described herein for generating stable semi-mature tolDCs results in TLR-2 expression on the population of tolerogenic dendritic cells in culture at the time the cells are harvested that is higher than the TLR-2 expression on the population of dendritic cells obtained by culturing monocytes in culture medium comprising GM-CSF and IL-4 without tolerising agents, such as Dexamethasone and vitamin D2. In some embodiments, the TLR-2 expression on the population of tolDCs is approximately 200%, 175%, 150%, 125%, 100%, 95%, 90%, 85%, 80%, 75%, 70%, 65%, 60%, 55%, 50%, 45%, 40%, 35%, 30%, 25%, 20%, 15%, or 10% higher than the TLR-2 expression on the population of dendritic cells obtained by culturing monocytes in culture medium comprising GM-CSF and IL-4 without tolerising agents. In accordance with these embodiments, in specific embodiments, the TLR-2 expression on the population of tolDCs and the population of dendritic cells obtained by culturing monocytes in culture medium comprising GM-CSF and IL-4 without tolerising agents, such as Dexamethasone and vitamin D2, are assessed after same length of time for cell culture.

In certain embodiments, a method described herein for generating stable semi-mature tolDCs results in IL-10 secretion by the population of tolerogenic dendritic cells in culture at the time the cells are harvested that is higher than the IL-10 secretion by the population of dendritic cells obtained by culturing monocytes in culture medium comprising GM-CSF and IL-4 without tolerising agents, such as Dexamethasone and vitamin D2. In some embodiments, the IL-10 secretion by the population of tolDCs is approximately 200%, 175%, 150%, 125%, 100%, 95%, 90%, 85%, 80%, 75%, 70%, 65%, 60%, 55%, 50%, 45%, 40%, 35%, 30%, 25%, 20%, 15%, or 10% higher than the IL-10 secretion by the population of dendritic cells obtained by culturing monocytes in culture medium comprising GM-CSF and IL-4 without tolerising agents. In accordance with these embodiments, in specific embodiments, the IL-10 secretion by the population of tolDCs and the population of dendritic cells obtained by culturing monocytes in culture medium comprising GM-CSF and IL-4 without tolerising agents, such as Dexamethasone and vitamin D2, are assessed after same length of time for cell culture.

In certain embodiments, a method described herein for generating stable semi-mature tolDCs results in TGF-beta secretion by the population of tolerogenic dendritic cells in culture at the time the cells are harvested that is higher than the TGF-beta secretion by the population of dendritic cells obtained by culturing monocytes in culture medium comprising GM-CSF and IL-4 without tolerising agents, such as Dexamethasone and vitamin D2. In some embodiments, the TGF-beta secretion by the population of tolDCs is approximately 200%, 175%, 150%, 125%, 100%, 95%, 90%, 85%, 80%, 75%, 70%, 65%, 60%, 55%, 50%, 45%, 40%, 35%, 30%, 25%, 20%, 15%, or 10% higher than the TGF-beta secretion by the population of dendritic cells obtained by culturing monocytes in culture medium comprising GM-CSF and IL-4 without tolerising agents. In accordance with these embodiments, in specific embodiments, the TGF-beta secretion by the population of tolDCs and the population of dendritic cells obtained by culturing monocytes in culture medium comprising GM-CSF and IL-4 without tolerising agents, such as Dexamethasone and vitamin D2, are assessed after same length of time for cell culture.

In certain embodiments, a method described herein for generating stable semi-mature tolDCs results in TIM-3 expression on the population of tolerogenic dendritic cells in culture at the time the cells are harvested that is higher than the TIM-3 expression on the population of dendritic cells obtained by culturing monocytes in culture medium comprising GM-CSF and IL-4 without tolerising agents, such as Dexamethasone and vitamin D2. In some embodiments, the TIM-3 expression on the population of tolDCs is approximately 200%, 175%, 150%, 125%, 100%, 95%, 90%, 85%, 80%, 75%, 70%, 65%, 60%, 55%, 50%, 45%, 40%, 35%, 30%, 25%, 20%, 15%, or 10% higher than the TIM-3 expression on the population of dendritic cells obtained by culturing monocytes in culture medium comprising GM-CSF and IL-4 without tolerising agents. In accordance with these embodiments, in specific embodiments, the TIM-3 expression on the population of tolDCs and the population of dendritic cells obtained by culturing monocytes in culture medium comprising GM-CSF and IL-4 without tolerising agents, such as Dexamethasone and vitamin D2, are assessed after same length of time for cell culture.

In certain embodiments, a method described herein for generating stable semi-mature tolDCs results in IL-12p70 secretion by the population of tolerogenic dendritic cells in culture at the time the cells are harvested that is lower than the IL-12p70 secretion by the population of dendritic cells obtained by culturing monocytes in culture medium comprising GM-CSF and IL-4 without tolerising agents, such as Dexamethasone and vitamin D2. In some embodiments, the IL-12p70 secretion by the population of tolDCs is approximately 10%, 15%, 20%, 25%, 30%, 35%, 40%, 45%, 50%, 55%, 60%, 65%, 70%, 75%, 80%, 85%, 90%, 95%, 98% or 100% lower than the IL-12p70 secretion by the population of dendritic cells obtained by culturing monocytes in culture medium comprising GM-CSF and IL-4 without tolerising agents. In accordance with these embodiments, in specific embodiments, the IL-12p70 secretion by the population of tolDCs and the population of dendritic cells obtained by culturing monocytes in culture medium comprising GM-CSF and IL-4 without tolerising agents, such as Dexamethasone and vitamin D2, are assessed after same length of time for cell culture.

In certain embodiments, a method described herein for generating stable semi-mature tolDCs results in a population of tolerogenic dendritic cells that induce low levels of IL-17 production by T cells when the tolerogenic dendritic cells are co-cultured with T cells as described herein (see, e.g., Sections 6, 7 and/or 8, infra) relative to the IL-17 production by T cells co-cultured with a population of dendritic cells obtained by culturing monocytes in culture medium comprising GM-CSF and IL-4 without tolerising agents, such as Dexamethasone and vitamin D2. In some embodiments, the IL-17 production induced by the tolDCs is approximately 10%, 15%, 20%, 25%, 30%, 35%, 40%, 45%, 50%, 55%, 60%, 65%, 70%, 75%, 80%, 85%, 90%, 95%, 98% or 100% lower than the IL-17 production induced by a population of dendritic cells obtained by culturing monocytes in culture medium comprising GM-CSF and IL-4 without tolerising agents. In accordance with these embodiments, in specific embodiments, the IL-17 production induced by the population of tolDCs and the IL-17 production induced by a population of dendritic cells obtained by culturing monocytes in culture medium comprising GM-CSF and IL-4 without tolerising agents, such as Dexamethasone and vitamin D2, are assessed after same length of time for cell culture.

In certain embodiments, a method described herein for generating stable semi-mature tolDCs results in: (i) CD86, CD83, and CD40 expression on the population of tolerogenic dendritic cells in culture at the time the cells are harvested that is lower than the CD86, CD83, and CD40 expression on the population of dendritic cells obtained by culturing monocytes in culture medium comprising GM-CSF and IL-4 without tolerising agents, such as Dexamethasone and vitamin D2; and (ii) ILT-3, TIM-3, TLR-2, and PD-L1 expression on the population of tolerogenic dendritic cells in culture at the time the cells are harvested that is higher than the ILT-3, TIM-3, TLR-2, and PD-L1 expression on the population of dendritic cells obtained by culturing monocytes in culture medium comprising GM-CSF and IL-4 without tolerising agents, such as Dexamethasone and vitamin D2. In some embodiments, the ILT-3, TIM-3, TLR-2, and PD-L1 expression on the population of tolDCs is approximately 200%, 175%, 150%, 125%, 100%, 95%, 90%, 85%, 80%, 75%, 70%, 65%, 60%, 55%, 50%, 45%, 40%, 35%, 30%, 25%, 20%, 15%, or 10% higher than the ILT-3, TIM-3, TLR-2, and PD-L1 expression on the population of dendritic cells obtained by culturing monocytes in culture medium comprising GM-CSF and IL-4 without tolerising agents. In some embodiments, the CD86, CD83, and CD40 expression on the population of tolDCs is approximately 10%, 15%, 20%, 25%, 30%, 35%, 40%, 45%, 50%, 55%, 60%, 65%, 70%, 75%, 80%, 85%, 90%, 95%, 98% or 100% lower than the CD86, CD83, and CD40 expression on the population of dendritic cells obtained by culturing monocytes in culture medium comprising GM-CSF and IL-4 without tolerising agents. In accordance with these embodiments, in specific embodiments, the CD86, CD83, CD40, ILT-3, TIM-3, TLR-2, and PD-L1 expression on the population of tolDCs and the population of dendritic cells obtained by culturing monocytes in culture medium comprising GM-CSF and IL-4 without tolerising agents, such as Dexamethasone and vitamin D2, are assessed after same length of time for cell culture.

In certain embodiments, the stable semi-mature tolDCs generated by the methods described herein and following treatment with an inflammatory stimuli (e.g., a cytokine cocktail) have enhanced glycolysis relative to the glycolysis by a population of dendritic cells obtained by culturing monocytes in culture medium comprising GM-CSF and IL-4 without tolerising agents, such as Dexamethasone and vitamin D2, and treated with an inflammatory stimuli. In some embodiments, the glycolysis by a population of tolDCs following treatment with an inflammatory stimuli is approximately 200%, 175%, 150%, 125%, 100%, 95%, 90%, 85%, 80%, 75%, 70%, 65%, 60%, 55%, 50%, 45%, 40%, 35%, 30%, 25%, 20%, 15%, or 10% higher than the glycolysis by the population of dendritic cells obtained by culturing monocytes in culture medium comprising GM-CSF and IL-4 without tolerising agents and treated with an inflammatory stimuli. In accordance with these embodiments, in specific embodiments, the glycolysis by the population of tolDCs following treatment with an inflammatory stimuli and the glycolysis by the population of dendritic cells obtained by culturing monocytes in culture medium comprising GM-CSF and IL-4 without tolerising agents, such as Dexamethasone and vitamin D2, and treated with an inflammatory stimuli are assessed after same length of time for cell culture. In a specific embodiment, the glycolysis by a population of tolDCs following treatment with an inflammatory stimuli (e.g., a cytokine cocktail) is enhanced relative to the glycolysis by the population of dendritic cells obtained by culturing monocytes in culture medium comprising GM-CSF and IL-4 without tolerising agents, such as Dexamethasone and vitamin D2, and treated with an inflammatory stimuli as assessed by the techniques described in Section 7, infra. In another specific embodiment, the glycolysis by a population of tolDCs following treatment with an inflammatory stimuli (e.g., a cytokine cocktail) is enhanced relative to the glycolysis by the population of dendritic cells obtained by culturing monocytes in culture medium comprising GM-CSF and IL-4 without tolerising agents, such as Dexamethasone and vitamin D2, and treated with an inflammatory stimuli by as much as described in Section 7, infra. In accordance with these embodiments, in specific embodiments, the level of glycolysis by the population of tolDCs following treatment with an inflammatory stimuli (e.g., a cytokine cocktail) and the the level of glycolysis by the population of dendritic cells obtained by culturing monocytes in culture medium comprising GM-CSF and IL-4 without tolerising agents, such as Dexamethasone and vitamin D2, and treated with an inflammatory stimuli are assessed after same length of time for cell culture. In a specific embodiment, the accumulation of lactate is assessed as a measurement of glycolysis. Techniques for measuring lactate accumulation are known in the art (see, e.g., Section 7, infra). Thus, in some embodiments, the accumulation of lactate is 10%, 15%, 20%, 25%, 30%, 35%, 40%, 45%, 50%, 55%, 60%, 65%, 70%, 75%, 80%, 85%, 90%, 95%, 98% or 100% higher by a population of tolDCs following treatment with an inflammatory stimuli (e.g., a cytokine cocktail) than the accumulation of lactate by a population of dendritic cells obtained by culturing monocytes in culture medium comprising GM-CSF and IL-4 without tolerising agents, such as Dexamethasone and vitamin D2, and treated with an inflammatory stimuli.

In specific embodiments, different intracellular signaling pathways are triggered in a population of the tolDCs described herein following treatment with an inflammatory stimuli (e.g., a cytokine cocktail) relative to the signal pathways triggered in a population of dendritic cells obtained by culturing monocytes in culture medium comprising GM-CSF and IL-4 without tolerising agents, such as Dexamethasone and vitamin D2, and treated with an inflammatory stimuli (e.g., a cytokine cocktail). In another specific embodiment, the MAPK, JNK, SAPK, ERK1/2, and IDO are differentially activated in a population of the tolDCs described herein following treatment with an inflammatory stimuli (e.g., a cytokine cocktail) relative to MAPK, JNK, SAPK, ERK1/2, and IDO activation in a population of dendritic cells obtained by culturing monocytes in culture medium comprising GM-CSF and IL-4 without tolerising agents, such as Dexamethasone and vitamin D2, and treated with an inflammatory stimuli (e.g., a cytokine cocktail). In a specific embodiment, the tolDCs described herein exhibit one, two, three or more, or all of the signaling properties described in Sections 6 and/or 7, infra.

In another specific embodiment, the levels of JNK and/or ERK1/2 activation (i.e. phosphorylation) in the stable semi-mature tolDCs described herein following treatment with inflammatory stimuli (e.g., a cytokine cocktail) are higher than the levels of JNK and/or ERK1/2 activation (i.e. phosphorylation) in a population of dendritic cells obtained by culturing monocytes in culture medium comprising GM-CSF and IL-4 without tolerising agents, such as Dexamethasone and vitamin D2, and treated with an inflammatory stimuli (e.g., a cytokine cocktail). In some embodiments, the levels of JNK and/or ERK1/2 activation in the population of tolDCs following treatment with an inflammatory stimuli (e.g., a cytokine cocktail) is approximately 200%, 175%, 150%, 125%, 100%, 95%, 90%, 85%, 80%, 75%, 70%, 65%, 60%, 55%, 50%, 45%, 40%, 35%, 30%, 25%, 20%, 15%, or 10% higher than the levels of JNK and/or ERK1/2 activation in a population of dendritic cells obtained by culturing monocytes in culture medium comprising GM-CSF and IL-4 without tolerising agents, and treated with an inflammatory stimuli. In particular embodiments, the JNK and/or ERK1/2 activation may be assessed by measuring the phosporylation of JNK and/or ERK1/2. Techniques for measuring phosphorylation are known in the art (see, e.g., Sections 6 and/or 7, infra). In accordance with these embodiments, in specific embodiments, the levels of JNK and/or ERK1/2 activation in the population of tolDCs and the population of dendritic cells obtained by culturing monocytes in culture medium comprising GM-CSF and IL-4 without tolerising agents, such as Dexamethasone and vitamin D2, are assessed after same length of time for cell culture.

In another specific embodiment, the levels of p38MAPK activation (i.e. phosphorylation) in the stable semi-mature tolDCs described herein following treatment with inflammatory stimuli (e.g., a cytokine cocktail) are lower than the levels of p38MAPK activation (i.e. phosphorylation) in a population of dendritic cells obtained by culturing monocytes in culture medium comprising GM-CSF and IL-4 without tolerising agents, such as Dexamethasone and vitamin D2, and treated with an inflammatory stimuli (e.g., a cytokine cocktail). In some embodiments, the levels of p38MAPK activation in the population of tolDCs following treatment with an inflammatory stimuli (e.g., a cytokine cocktail) is approximately 200%, 175%, 150%, 125%, 100%, 95%, 90%, 85%, 80%, 75%, 70%, 65%, 60%, 55%, 50%, 45%, 40%, 35%, 30%, 25%, 20%, 15%, or 10% lower than the levels of p38MAPK activation in a population of dendritic cells obtained by culturing monocytes in culture medium comprising GM-CSF and IL-4 without tolerising agents, and treated with an inflammatory stimuli. In particular embodiments, the p38MAPK activation may be assessed by measuring the phosporylation of p38MAPK. Techniques for measuring phosphorylation are known in the art (see, e.g., Sections 6 and/or 7, infra). In accordance with these embodiments, in specific embodiments, the levels of p38MAPK activation in the population of tolDCs and the population of dendritic cells obtained by culturing monocytes in culture medium comprising GM-CSF and IL-4 without tolerising agents, such as Dexamethasone and vitamin D2, are assessed after same length of time for cell culture.

In another specific embodiment, the level of NF-κB activation in the stable semi-mature tolDCs described herein following treatment with inflammatory stimuli (e.g., a cytokine cocktail) is lower than the level of NF-κB activation in a population of dendritic cells obtained by culturing monocytes in culture medium comprising GM-CSF and IL-4 without tolerising agents, such as Dexamethasone and vitamin D2, and treated with an inflammatory stimuli (e.g., a cytokine cocktail). In some embodiments, the level of NF-κB activation in the population of tolDCs following treatment with an inflammatory stimuli (e.g., a cytokine cocktail) is approximately 10%, 15%, 20%, 25%, 30%, 35%, 40%, 45%, 50%, 55%, 60%, 65%, 70%, 75%, 80%, 85%, 90%, 95%, 98% or 100% lower than the levels of NF-κB activation in a population of dendritic cells obtained by culturing monocytes in culture medium comprising GM-CSF and IL-4 without tolerising agents, and treated with an inflammatory stimuli. In particular embodiments, the NF-κB activation may be assessed by measuring the phosporylation of NF-κB. Techniques for measuring phosphorylation are known in the art (see, e.g., Sections 6 and/or 7, infra). In accordance with these embodiments, in specific embodiments, the level of NF-κB activation in the population of tolDCs and the population of dendritic cells obtained by culturing monocytes in culture medium comprising GM-CSF and IL-4 without tolerising agents, such as Dexamethasone and vitamin D2, are assessed after same length of time for cell culture.

In another specific embodiment, the levels of IDO in the stable semi-mature tolDCs described herein following treatment with inflammatory stimuli (e.g., a cytokine cocktail) are higher than the levels of IDO in a population of dendritic cells obtained by culturing monocytes in culture medium comprising GM-CSF and IL-4 without tolerising agents, such as Dexamethasone and vitamin D2, and treated with an inflammatory stimuli (e.g., a cytokine cocktail). In some embodiments, the levels of IDO in the population of tolDCs following treatment with an inflammatory stimuli (e.g., a cytokine cocktail) is approximately 200%, 175%, 150%, 125%, 100%, 95%, 90%, 85%, 80%, 75%, 70%, 65%, 60%, 55%, 50%, 45%, 40%, 35%, 30%, 25%, 20%, 15%, or 10% higher than the levels of IDO in a population of dendritic cells obtained by culturing monocytes in culture medium comprising GM-CSF and IL-4 without tolerising agents, and treated with an inflammatory stimuli. In particular embodiments, the levels of IDO may be assessed techniques known in the art (see, e.g., Sections 6 and/or 7, infra). In accordance with these embodiments, in specific embodiments, the levels IDO in the population of tolDCs and the population of dendritic cells obtained by culturing monocytes in culture medium comprising GM-CSF and IL-4 without tolerising agents, such as Dexamethasone and vitamin D2, are assessed after same length of time for cell culture.

In another specific embodiment, the levels of mTOR and/or STAT3 activation in the stable semi-mature tolDCs described herein following treatment with inflammatory stimuli (e.g., a cytokine cocktail) are higher than the levels of mTOR and/or STAT3 activation in a population of dendritic cells obtained by culturing monocytes in culture medium comprising GM-CSF and IL-4 without tolerising agents, such as Dexamethasone and vitamin D2, and treated with an inflammatory stimuli (e.g., a cytokine cocktail). In some embodiments, the levels of mTOR and/or STAT3 activation in the population of tolDCs following treatment with an inflammatory stimuli (e.g., a cytokine cocktail) is approximately 200%, 175%, 150%, 125%, 100%, 95%, 90%, 85%, 80%, 75%, 70%, 65%, 60%, 55%, 50%, 45%, 40%, 35%, 30%, 25%, 20%, 15%, or 10% higher than the levels of mTOR and/or STAT3 activation in a population of dendritic cells obtained by culturing monocytes in culture medium comprising GM-CSF and IL-4 without tolerising agents, and treated with an inflammatory stimuli. In particular embodiments, the activation of mTOR and/or STAT3 are assessed by measuring the phosporylation of mTOR and/or STAT3. Techniques for measuring phosphorylation are known in the art (see, e.g., Section 7, infra). In accordance with these embodiments, in specific embodiments, the levels of mTOR and/or STAT3 activation in the population of tolDCs and the population of dendritic cells obtained by culturing monocytes in culture medium comprising GM-CSF and IL-4 without tolerising agents, such as Dexamethasone and vitamin D2, are assessed after same length of time for cell culture.

In certain embodiments, a method described herein for generating stable semi-mature tolDCs results in tolDCs that induce a higher number of CD4$^+$CD25$^+$FoxP3$^+$ regulatory T cells than dendritic cells obtained by culturing monocytes in culture medium comprising GM-CSF and IL-4 without tolerising agents, such as Dexamethasone and vitamin D2. In certain embodiments, a method described herein for generating stable semi-mature tolDCs results in tolDCs that induce approximately 250%, 225%, 200%, 175%, 150%, 125%, 100%, 95%, 90%, 85%, 80%, 75%, 70%, 65%, 60%, 55%, 50%, 45%, 40%, 35%, 30%, 25%, 20%, 15%, or 10% higher number of CD4$^+$CD25$^+$FoxP3$^+$ regulatory T cells than dendritic cells obtained by culturing monocytes in culture medium comprising GM-CSF and IL-4 without tolerising agents, such as Dexamethasone and vitamin D2. In a specific embodiment, the Tregs were induced as described in Section 6, 7 and/or 8, infra.

In a specific embodiment, a method for generating stable semi-mature tolDCs described herein results in tolDCs with one, two, three or more of the functional properties of the Dex/Vitamin D2 tolDCs described in Section 6, 7 and/or 8, infra. In another specific embodiment, a method for generating stable semi-mature tolDCs described herein results in tolDCs with all of the functional properties of the Dex/Vitamin D2 tolDCs described in Section 6, 7 and/or 8, infra.

5.4 Method for Expanding and Detecting Tregs

Techniques known to one skilled in the art may be used to expand and detect Tregs. To define the capacity of tolDC to induce regulatory T cells expansion, tolDC can be cultured with allogeneic naïve CD4+ T cells. In certain embodiments, the T cells are obtained from a subject with type 1 diabetes mellitus with a HbA1c level of less than or equal to 60 mmol/mol Hb. In other embodiments, the T cells are obtained from a subject with type 1 diabetes mellitus with a HbA1c level of greater than to 60 mmol/mol Hb. In some embodiments, the T cells and the monocytes used to produce the tolDCs described herein are from the same subject. In other embodiments, the T cells and the monocytes used to produce the tolDCs described herein are from different subjects. The percentage of Tregs induced by the co-culture with tolDCs can be measured by flow cytometry using antibodies against CD4, CD25 and FoxP3+. In order to expand Tregs after the incubation with tolDCs, Tregs can be sorted by FACS sorter using antibodies against CD4, CD 25 and CD127. The sorted Tregs can subsequently be cultured in the presence of IL-2 and autologous serum, and proliferation can be stimulated with antibodies against CD3, CD28 or with a second incubation with tolDCs. Tregs can be further expanded in bioreactors. Tregs obtained in GMP conditions can transferred back to the patient to be treated.

5.5 Compositions

In one aspect, provided herein is a composition comprising stable semi-mature tolerogenic dendritic cells. In certain embodiments, the composition further comprises a physiologically acceptable carrier, such as saline or phosphate buffered saline (PBS). In some embodiments, the composition may further comprise another therapy. The composition may be a vaccine.

In another aspect, provided herein is a composition comprising Tregs. In certain embodiments, the composition further comprises a physiologically acceptable carrier, such as saline or PBS. In some embodiments, the composition may further comprise another therapy. The composition may be a vaccine.

In some embodiments, stable semi-mature tolDCs are aliquoted and cryopreserved in 3, 4, 5, 6, 7, 8, 9, 10 or more cryovials. In some embodiment each cryovial will contain 3×10$^6$, 4×10$^6$, 5×10$^6$, 6×10$^6$, 7×10$^6$, 8×10$^6$, 9×10$^6$, 10×10$^6$, or more cells. In some embodiments, stable semi-mature tolDCs are cryopreserved in a final solution containing 5, 6, 7, 8, 9, 10, 11, 12, 13, 14, 15 or more % of DMSO. In certain embodiments, stable semi-mature tolDCs are cryopreserved in CryoStor CS10. In some embodiments, any cryopreservation methods and cryopreserving media known in the art may be used to preserve stable semi-mature tolDCs. In a specific embodiment, the cryopreserved tolDCs maintain phenotypic stability after thawing as assessed by techniques known in the art. In another specific embodiment, the cryopreserved tolDCs maintain phenotypic stability as assessed by the techniques described in Sections 6, 7 and/or 8, infra.

In a specific embodiment, provided herein is a cryovial containing cryropreserved the stable semi-mature tolDCs described herein. In certain eobmdients, the cryovial contains 3×10$^6$, 4×10$^6$, 5×10$^6$, 6×10$^6$, 7×10$^6$, 8×10$^6$, 9×10$^6$, 10×10$^6$, or more cells. In a specific embodiment, the cryopreserved tolDCs maintain phenotypic stability after thawing as assessed by techniques known in the art. In another specific embodiment, the cryopreserved tolDCs maintain phenotypic stability as assessed by the techniques described in Sections 6, 7 and/or 8, infra.

5.6 Methods for Treating Autoimmune Diseases, Graft Rejection and Graft-Versus-Host Disease In another aspect, provided herein is a method for treating an autoimmune disease in a subject, comprising administering to the subject the stable semi-mature tolDCs described herein which were cultured in culture medium comprising MPLA, or MPLA and an antigen associated with the autoimmune disease, or a composition comprising such stable semi-mature tolerogenic dendritic cells. In a specific embodiment, provided herein is a method for treating type 1 diabetes in a subject, comprising administering to the subject stable semi-mature tolerogenic dendritic cells which were cultured in culture medium comprising MPLA and an antigen associated with type 1 diabetes, such as a GAD65 polypeptide or an insulin polypeptide, or a composition comprising such stable semi-mature tolerogenic dendritic cells. In specific embodiments, the tolerogenic dendritic cells are derived from monocytes that are autologous to the subject being treated. In specific embodiments, the subject is a human subject.

In another aspect, provided herein is a method for treating an autoimmune disease in a subject, comprising: (a) culturing stable semi-mature tolerogenic dendritic cells, which were cultured in culture medium comprising MPLA, or MPLA and an antigen associated with the autoimmune disease, in culture medium with T cells to induce Tregs; (b) isolating the Tregs; and (c) administering the Tregs to the subject. Techniques known to one skilled in the art or described herein (e.g., Section 5.4, supra, and Section 6, 7 and/or 8, infra) can be used be used to isolate Tregs. For example, flow cytometry as described in Section 5.4, supra, can be used to isolate Tregs. In certain embodiments, the Tregs are expanded in culture after being isolated and before being administered to the subject. Techniques known to one skilled in the art or described herein (e.g., Section 5.4, supra) can be used to expand Tregs in culture. In specific embodiments, the tolerogenic dendritic cells are derived from monocytes that are autologous to the subject being treated. In specific embodiments, the Tregs are derived from T cells that are autologous to the subject being treated. In specific embodiments, the subject is a human subject.

In a specific embodiment, provided herein is a method for treating type 1 diabetes in a subject, comprising: (a) culturing stable semi-mature tolerogenic dendritic cells, which were cultured in culture medium comprising MPLA, or MPLA and an antigen associated with type 1 diabetes, such as a GAD65 polypeptide or an insulin polypeptide, in culture medium with T cells to induce Tregs; (b) isolating the Tregs; and (c) administering the Tregs or a composition comprising such Tregs to the subject. Techniques known to one skilled in the art or described herein (e.g., Section 5.4, supra, and Section 6, 7 and/or 8, infra) can be used be used to isolate Tregs. For example, flow cytometry as described in Section 5.4, supra, can be used to isolate Tregs. In certain embodiments, the Tregs are expanded in culture after being isolated and before being administered to the subject. Techniques known to one skilled in the art or described herein (e.g., Section 5.4, supra) can be used to expand Tregs in culture. In certain embodiments, the tolerogenic dendritic cells are derived from monocytes that are from a patient with a HbA1c level of less than or equal to 60 mmol/mol Hb. In other embodiments, the tolerogenic dendritic cells are derived from monocytes that are from a patient with a HbA1c level of greater than 60 mmol/mol Hb. In specific embodiments, the tolerogenic dendritic cells are derived from monocytes that are autologous to the subject being treated. In certain embodiments, the T cells are derived from a patient with a HbA1c level of less than or equal to 60 mmol/mol Hb. In other embodiments, the T cells are derived from monocytes that are from a patient with a HbA1c level of greater than 60 mmol/mol Hb. In specific embodiments, the Tregs are derived from T cells that are autologous to the subject being treated. In specific embodiments, the subject is a human subject.

In certain embodiments, stable semi-mature tolDCs or a composition thereof is administered in combination with another therapy to treat an autoimmune disease. In some embodiments, Tregs or a composition thereof is administered in combination with another therapy to treat an autoimmune disease.

In certain embodiments, the autoimmune disease to be treated is type 1 diabetes or Juvenile diabetes. In another embodiment, the autoimmune disease to be treated is Acute Disseminated Encephalomyelitis (ADEM), Acute necrotizing hemorrhagic leukoencephalitis, Alopecia areata, Ankylosing spondylitis, Anti-GBM disease, Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune oophoritis, Autoimmune pancreatitis, Autoimmune retinopathy, Autoimmune thrombocytopenic purpura (ATP)/Idiopathic thrombocytopenic purpura (ITP), Autoimmune thyroid disease, Autoimmune urticarial, Behcet's disease, Bullous pemphigoid, Celiac disease, Churg-Strauss syndrome, Cicatricial pemphigoid/benign mucosal pemphigoid, Crohn's disease, Cogans syndrome, Cold agglutinin disease, Coxsackie myocarditis, Dermatitis herpetiformis, Dermatomyositis, Devic's disease (neuromyelitis optica), Discoid lupus, Dressler's syndrome, Evans syndrome, Glomerulonephritis, Goodpasture's syndrome, Granulomatosis with Polyangiitis (GPA) (formerly called Wegener's Granulomatosis), Graves' disease, Guillain-Barre syndrome, Hashimoto's encephalitis, Hashimoto's thyroiditis, Inclusion body myositis, Juvenile arthritis, Kawasaki syndrome, Lambert-Eaton syndrome, Lichen planus, Lupus (SLE), Microscopic polyangiitis, Mixed connective tissue disease (MCTD), Multiple sclerosis (MS), Myasthenia gravis, Myositis, Neuromyelitis optica (Devic's), Neutropenia, Ocular cicatricial pemphigoid, PANDAS (Pediatric Autoimmune Neuropsychiatric Disorders Associated with Streptococcus), Paraneoplastic cerebellar degeneration, Parry Romberg syndrome, Pemphigus, Type I, II, & III autoimmune polyglandular syndromes, Polymyositis, Postmyocardial infarction syndrome, Progesterone dermatitis, Primary biliary cirrhosis, Primary sclerosing cholangitis, Psoriasis, Psoriatic arthritis, Pure red cell aplasia, Reactive Arthritis, Reflex sympathetic dystrophy, Reiter's syndrome, Rheumatic fever, Rheumatoid arthritis, Schmidt syndrome, Scleroderma, Sjogren's syndrome, Sperm & testicular autoimmunity, Susac's syndrome, Sympathetic ophthalmia, Takayasu's arteritis, Undifferentiated connective tissue disease (UCTD), or Wegener's granulomatosis (now termed Granulomatosis with Polyangiitis (GPA).

TABLE 1

Autoimmune Disease And Antigen Associated Therewith.

| AUTOIMMUNE DIEASE | ANTIGEN |
|---|---|
| Type 1 diabetes or Juvenile diabetes | Insulin, GAD65 |
| Acute Disseminated Encephalomyelitis (ADEM) | Myelin |
| Alopecia areata | trichohyalin and keratin 16 |
| Anti-TBM nephritis | Tubulointerstitial nephritis antigen |
| Anti-GBM disease | alpha-3 chain of type IV collagen |
| Antiphospholipid syndrome (APS) | Apolipoprotein H/β2 glycoprotein I, cardiolipin |
| Autoimmune dysautonomia | Alpha 3 Acetylcholine Receptor |
| Autoimmune inner ear disease (AIED) | COCH5B2 |
| Autoimmune myocarditis | Cardiac myosin |
| Autoimmune thrombocytopenic purpura (ATP)/Idiopathic thrombocytopenic purpura (ITP) | glycoproteins IIb-IIIa or Ib-IX |
| Autoimmune thyroid disease | thyroid peroxidase, thyrotropin (TSH) receptor, thyroglobulin |
| Behcet's disease | Kinectin |
| Bullous pemphigoid | Dystonin/Bullous Pemphigoid Antigen 1, type XVII collagen/Bullous Pemphigoid Antigen 2 |
| Celiac disease | Gliadin, Epidermal transglutaminase (TGase 3) |
| Crohn's disease | *Saccharomyces cerevisiae* mannans, *Saccharomyces cerevisiae* 200 kDa glycoprotein |
| Cogans syndrome | DEP-1/CD148, connexin 26 |
| Dermatitis herpetiformis | Epidermal transglutaminase (TGase 3) |
| Devic's disease (neuromyelitis optica) | Aquaporin 4 |
| Glomerulonephritis | phospholipase A2 receptor |
| Granulomatosis with Polyangiitis (GPA) (formerly called Wegener's Granulomatosis) | Proteinase 3, myeloperoxidase (MPO), bacterial permeability increasing factor (BPI), HMG1, HMG2, alpha enolase, catalase, beta glucuronidase, azurocidin, actin and h-lamp-2 |
| Graves' disease | thyrotropin receptor (TSH receptor) |
| Guillain-Barre syndrome | Gangliosides |
| Hashimoto's encephalitis | alpha-enolase |
| Hashimoto's thyroiditis | thyroid peroxidase, thyrotropin receptor, thyroglobulin |
| Lambert-Eaton syndrome | voltage-dependent calcium channels |
| Lupus (SLE) | Sjögren syndrome type B antigen |
| Myasthenia gravis | nicotinic acetylcholine receptor (nAChR) |
| Myositis | aminoacyl tRNA-synthetase enzymes, signal-recognition particle, Mi-2 protein, CADM-140, SAE (small ubiquitin-like modifier activating enzyme), p155/140, p140 |
| Ocular cicatricial pemphigoid | BP1 and BP2 hemidesmosome |
| Pemphigus | Desmoglein |

TABLE 1-continued

Autoimmune Disease And Antigen Associated Therewith.

| AUTOIMMUNE DIEASE | ANTIGEN |
|---|---|
| Progesterone dermatitis | Progesterone |
| Primary biliary cirrhosis | pyruvate dehydrogenase complex (PDC-E2) |
| Schmidt syndrome | Anti-citrullinated proteins |
| Sjogren's syndrome | Sjögren syndrome type B antigen |

In another aspect, provided herein is a method for treating graft rejection or graft-versus-host disease in a subject, comprising administering to the subject the stable semi-mature tolDCs described herein which were cultured in culture medium comprising MPLA, or MPLA and an antigen associated with the graft rejection or graft-versus-host disease, or a composition comprising such stable semi-mature tolerogenic dendritic cells. In specific embodiments, the tolerogenic dendritic cells are derived from monocytes that are autologous to the subject being treated. In specific embodiments, the subject is a human subject.

In another aspect, provided herein is a method for treating graft rejection or graft-versus-host disease in a subject, comprising: (a) culturing stable semi-mature tolerogenic dendritic cells, which were cultured in culture medium comprising MPLA, or MPLA and an antigen associated with the graft rejection or graft-versus-host disease, in culture medium with T cells to induce Tregs; (b) isolating the Tregs; and (c) administering the Tregs to the subject. Techniques known to one skilled in the art or described herein (e.g., Section 5.4, supra, and Section 6, 7 and/or 8, infra) can be used be used to isolate Tregs. For example, flow cytometry as described in Section 5.4, supra, can be used to isolate Tregs. In certain embodiments, the Tregs are expanded in culture after being isolated and before being administered to the subject. Techniques known to one skilled in the art or described herein (e.g., Section 5.4, supra) can be used to expand Tregs in culture. In specific embodiments, the tolerogenic dendritic cells are derived from monocytes that are autologous to the subject being treated. In specific embodiments, the Tregs are derived from T cells that are autologous to the subject being treated. In specific embodiments, the subject is a human subject.

In certain embodiments, stable semi-mature tolDCs or a composition thereof is administered in combination with another therapy to treat graft rejection or graft-versus-host disease. In some embodiments, Tregs or a composition thereof is administered in combination with another therapy to treat graft rejection or graft-versus-host disease.

5.7 Patient Populations

In some embodiments, stable semi-mature tolDCs described herein, a composition(s) comprising such stable semi-mature tolDCs, or combination therapies are administered to a subject suffering from or diagnosed with an autoimmune disease, graft rejection or graft-versus-host disease. In other embodiments stable semi-mature tolDCs described herein, a composition(s) comprising such stable semi-mature tolDCs, or combination therapies are administered to a subject predisposed or susceptible to developing an autoimmune disease, graft rejection or graft-versus-host disease.

In some embodiments, stable semi-mature tolDCs described herein, a composition(s) comprising such stable semi-mature tolDCs, or combination therapies are administered to a mammal. In certain embodiments, stable semi-mature tolDCs described herein, a composition(s) comprising such stable semi-mature tolDCs, or combination therapies are administered to a mammal which is 0 to 6 months old, 6 to 12 months old, 1 to 5 years old, 5 to 10 years old, 10 to 15 years old, 15 to 20 years old, 20 to 25 years old, 25 to 30 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old.

In certain embodiments, stable semi-mature tolDCs described herein, a composition(s) comprising such stable semi-mature tolDCs, or combination therapies are administered to a human at risk developing an autoimmune disease, graft rejection or graft-versus-host disease. In some embodiments, stable semi-mature tolDCs described herein, a composition(s) comprising such stable semi-mature tolDCs, or combination therapies are administered to a human with an autoimmune disease, graft rejection or graft-versus-host disease. In certain embodiments stable semi-mature tolDCs described herein, a composition(s) comprising such stable semi-mature tolDCs, or combination therapies are administered to a human diagnosed with an autoimmune disease, graft rejection or graft-versus-host disease. In certain embodiments, the patient is a human 0 to 6 months old, 6 to 12 months old, 1 to 5 years old, 5 to 10 years old, 5 to 12 years old, 10 to 15 years old, 15 to 20 years old, 20 to 25 years old, 25 to 30 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old. In specific embodiments, the patient has or is at risk of developing type 1 diabetes mellitus. In certain embodiments, the patient is a human that has an HbA1c level of less than or equal to 60 mmol/mol Hb. In other embodiments, the patient is a human that has an HbA1c level of greater than 60 mmol/mol Hb. In some embodiments, the human patient to be treated is assessed for HbA1c levels. Techniques for measuring HbA1c levels are known to one skilled in the art (see, e.g., Section 8, infra).

In some embodiments, the subject being administered stable semi-mature tolDCs described herein, a composition(s) comprising such stable semi-mature tolDCs, or combination therapies has not received a therapy prior to the administration of the stable semi-mature tolDCs described herein, a composition(s) comprising such stable semi-mature tolDCs, or combination therapies. In other embodiments, stable semi-mature tolDCs described herein, a composition(s) comprising such stable semi-mature tolDCs, or combination therapies are administered to a subject who has received a therapy prior to administration of stable semi-mature tolDCs described herein, a composition(s) comprising such stable semi-mature tolDCs, or combination therapies. In some embodiments, the subject administered stable semi-mature tolDCs described herein, a composition(s) comprising such stable semi-mature tolDCs, or combination therapies was refractory to a prior therapy or experienced adverse side effects to the prior therapy or the prior therapy was discontinued due to unacceptable levels of toxicity to the subject.

In some embodiments, Tregs generated in accordance with a method described herein, a composition(s) comprising such Tregs, or combination therapies are administered to a subject suffering from or diagnosed with an autoimmune disease, graft rejection or graft-versus-host disease. In other embodiments, Tregs generated in accordance with a method described herein, a composition(s) comprising such Tregs, or combination therapies are administered to a subject predisposed or susceptible to developing an autoimmune disease, graft rejection or graft-versus-host disease.

In some embodiments, Tregs generated in accordance with a method described herein, a composition(s) comprising such Tregs, or combination therapies are administered to a mammal. In certain embodiments, Tregs generated in accordance with a method described herein, a composition(s) comprising such Tregs, or combination therapies are administered to a mammal which is 0 to 6 months old, 6 to 12 months old, 1 to 5 years old, 5 to 10 years old, 10 to 15 years old, 15 to 20 years old, 20 to 25 years old, 25 to 30 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old.

In certain embodiments, Tregs generated in accordance with a method described herein, a composition(s) comprising such Tregs, or combination therapies are administered to a human at risk developing an autoimmune disease, graft rejection or graft-versus-host disease. In some embodiments, Tregs generated in accordance with a method described herein, a composition(s) comprising such Tregs, or combination therapies are administered to a human with an autoimmune disease, graft rejection or graft-versus-host disease. In certain embodiments, Tregs generated in accordance with a method described herein, a composition(s) comprising such Tregs, or combination therapies are administered to a human diagnosed with an autoimmune disease, graft rejection or graft-versus-host disease. In certain embodiments, the patient is a human 0 to 6 months old, 6 to 12 months old, 1 to 5 years old, 5 to 10 years old, 5 to 12 years old, 10 to 15 years old, 15 to 20 years old, 20 to 25 years old, 25 to 30 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old. In specific embodiments, the patient has or is at risk of developing type 1 diabetes mellitus. In certain embodiments, the patient is a human that has an HbA1c level of less than or equal to 60 mmol/mol Hb. In other embodiments, the patient is a human that has an HbA1c level of greater than 60 mmol/mol Hb. In some embodiments, the human patient to be treated is assessed for HbA1c levels. Techniques for measuring HbA1c levels are known to one skilled in the art (see, e.g., Section 8, infra).

In some embodiments, the subject being Tregs generated in accordance with a method described herein, a composition(s) comprising such Tregs, or combination therapies has not received a therapy prior to the administration of the Tregs generated in accordance with a method described herein, a composition(s) comprising such Tregs, or combination therapies. In other embodiments, Tregs generated in accordance with a method described herein, a composition(s) comprising such Tregs, or combination therapies are administered to a subject who has received a therapy prior to administration of Tregs generated in accordance with a method described herein, a composition(s) comprising such Tregs, or combination therapies. In some embodiments, the subject administered Tregs generated in accordance with a method described herein, a composition(s) comprising such Tregs, or combination therapies was refractory to a prior therapy or experienced adverse side effects to the prior therapy or the prior therapy was discontinued due to unacceptable levels of toxicity to the subject.

5.8 Administration and Dosage
5.8.1. Mode of Administration

Stable semi-mature tolDCs described herein or a composition(s) comprising such stable semi-mature tolDCs can be administered via any route known in the art. Stable semi-mature tolDCs described herein or a composition(s) comprising such stable semi-mature tolDCs can be administered by, for example, infusion or bolus injection, and may be administered together with another biologically active agent. Administration can be systemic or local. Various delivery systems are known and can be used to deliver stable semi-mature tolDCs described herein or a composition(s) comprising such stable semi-mature tolDCs.

Methods of administration include but, are not limited to, parenteral, intradermal, intramuscular, intraperitoneal, intravenous, subcutaneous or intracerebral. In a specific embodiment, stable semi-mature tolDCs described herein or a composition(s) comprising such stable semi-mature tolDCs are/is intravenously, intradermally or subcutaneously administered to the patient. In another specific embodiment, stable semi-mature tolDCs described herein or a composition(s) comprising such stable semi-mature tolDCs are/is administered to the patient by direct intranodal delivery. The mode of administration is left to the discretion of the practitioner.

In specific embodiments, it may be desirable to administer stable semi-mature tolDCs described herein or a composition(s) comprising such stable semi-mature tolDCs locally. In specific embodiments, stable semi-mature tolDCs described herein or a composition(s) comprising such stable semi-mature tolDCs are/is administrated at the site of the autoimmune disease, graft rejection or graft-versus-host disease by local infusion. For example, in the case of rheumatoid arthritis, stable semi-mature tolDCs described herein or a composition(s) comprising such stable semi-mature tolDCs can be administrated directly intra-articularly.

Tregs generated in accordance with a method described herein or a composition(s) comprising Tregs can be administered via any route known in the art. Tregs generated in accordance with a method described herein or a composition(s) comprising Tregs can be administered by, for example, infusion or bolus injection, and may be administered together with another biologically active agent. Administration can be systemic or local. Various delivery systems are known and can be used to deliver Tregs generated in accordance with a method described herein or a composition(s) comprising Tregs.

Methods of administration include but, are not limited to, parenteral, intradermal, intramuscular, intraperitoneal, intravenous, subcutaneous or intracerebral. In a specific embodiment, Tregs generated in accordance with a method described herein or a composition(s) comprising Tregs are/is intravenously, intradermally or subcutaneously administered to the patient. In another specific embodiment, Tregs generated in accordance with a method described herein or a composition(s) comprising Tregs are/is administered to the patient by direct intranodal delivery. The mode of administration is left to the discretion of the practitioner.

In specific embodiments, it may be desirable to administer Tregs generated in accordance with a method described herein or a composition(s) comprising Tregs locally. In specific embodiments, Tregs generated in accordance with a method described herein or a composition(s) comprising Tregs are/is administrated at the site of the autoimmune disease, graft rejection or graft-versus-host disease by local infusion. For example, in the case of rheumatoid arthritis, Tregs generated in accordance with a method described herein or a composition(s) comprising Tregs can be administrated directly intra-articularly.

5.8.2. Dosage of Stable Semi-Mature Tolerogenic Dendritic Cells

The amount stable semi-mature tolDCs described herein, or the amount of a composition comprising stable semi-mature tolDCs, that will be effective in the treatment of an autoimmune disease, graft rejection or graft-versus-host disease can be determined by standard clinical techniques. In vitro or in vivo assays may optionally be employed to help identify optimal dosage ranges. The precise dose to be employed will also depend, e.g., on the route of administration, the type of symptoms, and the seriousness of the symptoms, and should be decided according to the judgment of the practitioner and each patient's or subject's circumstances.

Doses of stable semi-mature tolDCs for administration to a subject by any route of administration can be at least 100, 200, 300, 400, 500, 700, 1,000, 5,000, 10,000, 25,000, 50,000, or 100,000 cells. In specific embodiments, the number of stable semi-mature tolDCs is at least 100, 200, 300, 400, 500 cells. In other embodiments, the number of stable semi-mature tolDCs is at least 300, 400, 500, 700, 1,000 cells. In yet other specific embodiments, the number of stable semi-mature tolDCs is at least 700, 1,000, 5,000, 10,000 cells. In some embodiments, the number of stable semi-mature tolDCs at least 5,000, 10,000, 25,000, 50,000, or 100,000 cells. In yet another embodiment, the number of stable semi-mature tolDCs is at least 50,000, or 100,000 cells. In other embodiments, the number of stable semi-mature tolDCs is at least $1\times10^6$, $5\times10^6$, $1\times10^7$, $5\times10^7$, $1\times10^8$, $5\times10^8$ or more cells. In specific embodiments, the number of stable semi-mature tolDCs is between $1\times10^2$ to $1\times10^4$, $5\times10^4$ to $5\times10^6$, $1\times10^5$ to $1\times10^7$, $1\times10^5$ to $5\times10^8$, $1\times10^6$ to $1\times10^8$, or $1\times10^6$ to $1\times10^7$, or $1\times10^4$ to $1\times10^5$ cells.

In certain embodiments, a subject is administered stable semi-mature tolDCs described herein or a composition thereof in an amount effective to inhibit or reduce symptoms associated with the autoimmune disease, graft rejection or graft-versus-host disease by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In certain embodiments to treat, a subject is administered stable semi-mature tolDCs described herein or a composition thereof in an amount effective to inhibit or reduce symptoms associated with the autoimmune disease, graft rejection or graft-versus-host disease by at least 1.5-fold, 2-fold, 2.5-fold, 3-fold, 4-fold, 5-fold, 8-fold, 10-fold, 15-fold, 20-fold, or 2- to 5-fold, 2- to 10-fold, 5- to 10-fold, or 5- to 20-fold relative to a negative control as determined using an assay described herein or other known to one of skill in the art.

In certain embodiments to, a subject is administered stable semi-mature tolDCs described herein or a composition thereof in an amount effective to decrease an autoimmune response or graft rejection by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In some embodiments, a subject is administered stable semi-mature tolDCs described herein or a composition thereof in an amount effective to decrease an autoimmune response or graft rejection by at least 1.5-fold, 2-fold, 2.5-fold, 3-fold, 4-fold, 5-fold, 8-fold, 10-fold, 15-fold, 20-fold, or 2 to 5-fold, 2 to 10-fold, 5 to 10-fold, or 5 to 20-fold relative to a negative control as determined using an assay described herein or others known to one of skill in the art.

In certain embodiments to, a subject is administered stable semi-mature tolDCs described herein or a composition thereof in an amount effective to increase or enhance the number of Tregs (in some embodiments, in a specific target body compartment) by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In some embodiments, a subject is administered stable semi-mature tolDCs described herein or a composition thereof in an amount effective to increase or enhance the number of Tregs (in some embodiments, in a specific target body compartment) by at least 1.5-fold, at least 2-fold, at least 2.5-fold, at least 3-fold, at least 4-fold, at least 5-fold, at least 8-fold, at least 10-fold, at least 15-fold, or at least 20-fold; or by approximately 2 to 5-fold, 2 to 10-fold, 5 to 10-fold, or 5 to 20-fold relative to a negative control as determined using an assay described herein or others known to one of skill in the art. In particular embodiments, the specific target body compartment where the number of Tregs is increased or enhanced is the body compartment affected by the autoimmune disease, graft rejection or graft-versus-host disease.

In certain embodiments, a dose of stable semi-mature tolDCs described herein or a composition thereof is administered to a subject every day, every other day, every couple of days, every third day, once a week, twice a week, three times a week, or once every two weeks or once a month, or less. In other embodiments, two, three or four doses of stable semi-mature tolDCs described herein or composition thereof is administered to a subject every day, every couple of days, every third day, once a week or once every two weeks. In some embodiments, a dose(s) of stable semi-mature tolDCs described herein or a composition thereof is administered for 2 days, 3 days, 5 days, 7 days, 14 days, 21 days, 28 days or 31 days. In certain embodiments, a dose of stable semi-mature tolDCs described herein or a composition thereof is administered for 0.5 month, 1 month, 1.5 months, 2 months, 2.5 months, 3 months, 4 months, 5 months, 6 months or more.

In a particular embodiment, a patient is administered multiple doses of stable semi-mature tolDCs described herein or a composition thereof, wherein each dose of the stable semi-mature tolDCs described herein or a composition thereof comprises tolDCs pulsed with an antigen(s) associated with an autoimmune disease (e.g., type 1 diabetes), graft rejection or graft-versus-host disease. In some embodiments, the stable semi-mature tolDCs administered to the patient were pulsed the same antigen(s). In other embodiments, the stable semi-mature tolDCs were pulsed with different antigens. In another embodiment, a patient is administered multiple doses of stable semi-mature tolDCs described herein or a composition thereof, wherein each dose of the stable semi-mature tolDCs described herein or a composition thereof comprises tolDCs pulsed with GAD65 and/or insulin peptides. In a specific embodiment, a batch of stable semi-mature tolDCs described herein (which had been pulsed with an antigen associated with an autoimmune disease, e.g., GAD65 and/or insulin peptides, graft rejection or graft-versus-host disease) is frozen and stored in separate containers (e.g., 2, 3, 4, 5, 6, 7, 8, 9, 10, 11, 12, 13, 14, 15, 16, 17, 18, 19, 20 or more containers, such as vials) and one container, such as a vial, or optionally more than 1 container, is thawed for delivery of the stable semi-mature tolDCs described herein to a patient.

The dosages of prophylactic or therapeutic agents which have been or are currently used for the treatment of autoimmune diseases, graft rejection, or graft-versus-host disease can be determined using references available to a clinician such as, e.g., the Physicians' Desk Reference (68th ed. 2014).

The above-described administration schedules are provided for illustrative purposes only and should not be considered limiting.

5.8.3. Dosage of Tregs

The amount Tregs generated in accordance with a method described herein, or the amount of a composition comprising Tregs, that will be effective in the treatment of an autoimmune disease, graft rejection, or graft-versus-host disease can be determined by standard clinical techniques. In vitro or in vivo assays may optionally be employed to help identify optimal dosage ranges. The precise dose to be employed will also depend, e.g., on the route of administration, the type of symptoms, and the seriousness of the symptoms, and should be decided according to the judgment of the practitioner and each patient's or subject's circumstances.

Doses of Tregs for administration to a subject by any route of administration can be at least 100, 200, 300, 400, 500, 700, 1,000, 5,000, 10,000, 25,000, 50,000, or 100,000 cells. In specific embodiments, the number of Tregs is at least 100, 200, 300, 400, 500 cells. In other embodiments, the number of Tregs is at least 300, 400, 500, 700, 1,000 cells. In yet other specific embodiments, the number of Tregs is at least 700, 1,000, 5,000, 10,000 cells. In some embodiments, the number of Tregs at least 5,000, 10,000, 25,000, 50,000, or 100,000 cells. In yet another embodiment, the number of Tregs is at least 50,000, or 100,000 cells. In other embodiments, the number of Tregs is at least $1\times10^6$, $5\times10^6$, $1\times10^7$, $5\times10^7$, $1\times10^8$, $5\times10^8$ or more cells. In specific embodiments, the number of Tregs is between $1\times10^2$ to $1\times10^4$, $5\times10^4$ to $5\times10^6$, $1\times10^5$ to $1\times10^7$, $1\times10^5$ to $5\times10^8$, $1\times10^6$ to $1\times10^8$, or $1\times10^6$ to $1\times10^7$, or $1\times10^4$ to $1\times10^5$ cells.

In certain embodiments, a subject is administered Tregs generated in accordance with a method described herein, or a composition comprising Tregs in an amount effective to inhibit or reduce symptoms associated with the autoimmune disease, graft rejection, or graft-versus-host disease by at least 20% to 25%, preferably at least 25% to 30%, at least 30% to 35%, at least 35% to 40%, at least 40% to 45%, at 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In certain embodiments to treat, a subject is Tregs generated in accordance with a method described herein, or a composition comprising Tregs in an amount effective to inhibit or reduce symptoms associated with the autoimmune disease, graft rejection, or graft-versus-host disease by at least 1.5-fold, 2-fold, 2.5-fold, 3-fold, 4-fold, 5-fold, 8-fold, 10-fold, 15-fold, 20-fold, or 2- to 5-fold, 2- to 10-fold, 5- to 10-fold, or 5- to 20-fold relative to a negative control as determined using an assay described herein or other known to one of skill in the art.

In certain embodiments to, a subject is administered Tregs generated in accordance with a method described herein, or a composition comprising Tregs in an amount effective to decrease an autoimmune response or graft rejection, or graft-versus-host disease by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In some embodiments, a subject is administered Tregs generated in accordance with a method described herein, or a composition comprising Tregs in an amount effective to decrease an autoimmune response or graft rejection, or graft-versus-host disease by at least 1.5-fold, 2-fold, 2.5-fold, 3-fold, 4-fold, 5-fold, 8-fold, 10-fold, 15-fold, 20-fold, or 2 to 5-fold, 2 to 10-fold, 5 to 10-fold, or 5 to 20-fold relative to a negative control as determined using an assay described herein or others known to one of skill in the art.

In certain embodiments, a dose of Tregs generated in accordance with a method described herein, or a composition comprising Tregs is administered to a subject every day, every other day, every couple of days, every third day, once a week, twice a week, three times a week, or once every two weeks or once a month, or less. In other embodiments, two, three or four doses of Tregs generated in accordance with a method described herein, or a composition comprising Tregs are administered to a subject every day, every couple of days, every third day, once a week or once every two weeks. In some embodiments, a dose(s) of Tregs generated in accordance with a method described herein, or a composition comprising Tregs is administered for 2 days, 3 days, 5 days, 7 days, 14 days, 21 days, 28 days or 31 days. In certain embodiments, a dose of Tregs generated in accordance with a method described herein, or a composition comprising Tregs is administered for 0.5 month, 1 month, 1.5 months, 2 months, 2.5 months, 3 months, 4 months, 5 months, 6 months or more.

In a specific embodiment, a batch of Tregs is frozen and stored in separate containers (e.g., 2, 3, 4, 5, 6, 7, 8, 9, 10, 11, 12, 13, 14, 15, 16, 17, 18, 19, 20 or more containers, such as vials) and one container, such as a vial, or optionally more than 1 container, is thawed for delivery of the Tregs to a patient.

The dosages of prophylactic or therapeutic agents which have been or are currently used for the treatment of autoimmune diseases, graft rejection, or graft-versus-host disease can be determined using references available to a clinician such as, e.g., the Physicians' Desk Reference (68th ed. 2014).

The above-described administration schedules are provided for illustrative purposes only and should not be considered limiting.

5.9 Biological Assays

The immune tolerance induction capability of tolDCs can be assessed using techniques known to one skilled in the art. Various assays known in the art can be used to assess whether tolDCs described herein induce immune tolerance. In one aspect, a tolDCs described herein induce immune tolerance by creating an anti-inflammatory environment through the increased secretion anti-inflammatory of cytokines (e.g. IL-10) and attenuated secretion of pro-inflammatory cytokines (e.g. IL-12p70, IL-6, TNFα). In a specific embodiment, the ability of tolDCs to secrete IL-10, IL-12p70, IL-6 and TNFα is assessed using ELISA assays or Luminex xMAP assays as described in Section 6, 7 and/or 8, infra.

ELISA assays can also be used to evaluate the stability of tolDCs. In a specific embodiment, stability of tolDCs can be assessed through the measurement of cytokines (e.g., Il-10 and IL-12p70) secreted after re-stimulation of established tolDCs with TLR ligands, cytokine cocktails or molecules mimicking activated T cells. In a specific embodiments, the TLR ligands are LPS or poly (I:C). In another specific embodiment, cytokine cocktails contain IL-1β, TNFα, IL-6 and IFNγ. In yet another specific embodiment, a molecule mimicking activated T cells is CD40L.

T cells proliferation may be used to test the reduced potential in allogeneic stimulatory properties of tolDCs. Well-known methods in the art, e.g., flow cytometry, CFSE staining, 3H-thymidine incorporation can be used to assess T cell proliferation. More specifically, proliferation of T cells can be assessed by a flow cytometric analysis of cell division by dilution of CFSE and related dyes as described in the art. In a specific embodiment, proliferation of CD4+ and CD8+ T cells after incubation with tolDCs is assessed by the CFSE dilution method as described in Section 6 and/or 7, infra.

The reduced potential in allogeneic stimulatory of tolerogenic properties of tolDCs can be tested by measuring cytokine (e.g. IFNγ or IL-10) production by T cell incubated with tolDCs. In one embodiment, IFNγ production by T cells is assessed by IFNγ intracellular immunocytochemistry as described in Section 6, 7 and/or 8, infra. Immunocytochemistry for FoxP3 can also be used to assess the de novo induction of Tregs differentiation from naïve CD4$^+$ T cells upon incubation of allogeneic T cells with tolDCs.

In specific embodiments, tolDCs described herein induce or enhance Tregs proliferation in a subject that by at least 0.2 to 5 times, 5 to 20 times, 10 to 30 times, 20 to 50 times, 50 to 200 times, 100 to 500, 200 to 1000 times, or 500 to 2,000 times higher relative to T cell proliferation in a negative control as determined by methods well known in the art.

An ELISPOT assay can be used to measure cytokine release by lymphocytes cocultured by pulsed tolDCs described herein. Cytokine secretion can be detected by antibodies which are specific for a particular cytokine, e.g., IL-2, IL-4, IL-10, IL-17, IFN-γ, or chemokines. In a specific embodiment, a cytokine secretion of autologous T cells incubated with autologous tolDCs can be assessed using the techniques described in Section 6, 7 and/or 8, infra. In specific embodiments, tolDCs described herein decrease or increase the expression and secretion of cytokine of autologous T cells in a subject by at least 0.2 to 5 times, 5 to 20 times, 10 to 30 times, 20 to 50 times, 50 to 200 times, 100 to 500, 200 to 1000 times, or 500 to 2,000 times higher relative to cytokine secretion of autologous T cells in a control experiment with non-tolDCs.

In a specific embodiment, one, two, three or more of the assays described in Section 6, 7 and/or 8, infra, can be used to assess the functional properties and characteristics of the stable semi-mature tolDCs described herein, including the stability of the stable semi-mature tolDCs. In addition, techniques known to one skilled in the art can be assess the functional properties and characteristics of the stable semi-mature tolDCs described herein, including the stability of the stable semi-mature tolDCs.

6. EXAMPLE 1

This example demonstrates that tolerogenic DCs generated using dexamethasone and vitamin D2 are stable phenotypically and functionally even upon stimulation with a variety of biologically relevant inflammatory stimuli in the absence of tolerising factors.

6.1 Materials and Methods:

Reagents and Abs:

Flow cytometry: commercial antibodies anti-CD86-FITC, CD274 (PD-L1)-FITC, CD273 (PD-L2)-PE, HLA-DR-PE-Cy7, IFNγ-FITC were purchased from BD Biosciences; CD83-PerCP-Cy5.5 was purchased from Beckman Coulter; CD80-FITC, CD40-PerCP-eFluor710, CD1a-PE-Cy7, CD4-PE-Cy7, FoxP3-AF488 were purchased from eBiosciences; TLR2-FITC, CD25-PerCP-Cy5.5, IL-10-PE were purchased from BioLegend; TIM-3-PE, CD14-PE-DL594, CD11c-APC, CD3-AF700, CD8-PE-Dy590 were purchased from Exbio; CD85k (IL-T3)-PE, CD85d (IL-T4)-FITC were purchased from R&D Systems.

For western blot, anti-p-pP38, anti-p-ERK1/2, anti-p-JNK/SAPK, anti-p-IκB-α, anti-IDO, anti-p-mTOR, anti-p-STAT3, anti-p-p70S6K, anti-p38mAPK, anti-ERK1/2, anti-JNK/SAPK, and anti-STAT3 Ab were purchased from Cell Signaling Technology; anti-actin was from BioLegend.

DC Differentiation and Stimulation:

Immature DCs were obtained from buffy coats of healthy donors as previously described (Palova-Jelinkova et al. 2005, J Immunol 175: 7038-7045). Briefly, human PBMC were isolated by Ficoll gradient and monocytes were separated by allowing 2 h of cell adhesion in 75 cm$^2$ culture flasks (Nunc). DC were generated by culturing monocytes for 6 days in cGMP-grade Cell Gro DC medium (CellGenix) containing penicillin and streptomycin solution (100 U/ml and 100 μg/ml, respectively, Gibco) in the presence of GM-CSF (500 IU/ml, Gentaur) and IL-4 (20 ng/ml, CellGenix). Medium and cytokines were replenished on day 3. On day 6, DC were harvested and seeded in 96-well plates (Nunc) at 1×10$^6$ cells/ml.

Tolerogenic DCs (tolDCs) were cultured using the same medium described above (namely, cGMP-grade Cell Gro DC medium (CellGenix) containing penicillin and streptomycin solution (100 U/ml and 100 μg/ml, respectively, Gibco) in the presence of GM-CSF (500 IU/ml, Gentaur) and IL-4 (20 ng/ml, CellGenix)) supplemented as follows, depending on the experiment:

1. Dexamethasone (Dex) on day 3 (1 μM, Medochemie) and Dex and paricalcitol (VitD2) (1.5 ng/ml, Zemplar, Abbott Laboratories) on day 6 (the tolDCs generated using this protocol are referred to herein as "tolDCs 1")

2. Paricalcitol (Vit D2) (1.5 ng/ml, Zemplar, Abbott Laboratories) on day 0, 3 and 6 and Dex on day 3 and 6 (the tolDCs generated using this protocol are referred to herein as "tolDCs 2")

3. Paricalcitol (VitD2) (1.5 ng/ml, Zemplar, Abbot Laboratories) on day 0, 3 and 6 (the tolDCs generated using this protocol are referred to herein as "tolDCs 3")

4. Dexamethasone (Dex) on day 3 (1 μM, Medochemie) and Dex and Vitamin D3 (1.5 ng/ml, Calcijex) on day 6 (the tolDCs generated using this protocol are referred to herein as "tolDCs 4")

To induce maturation, DC were treated with vaccine grade monophosphoryl lipid A (MPLA) (2 μg/ml, Cayla-Invivo-Gen) on day 6 or on day 7. On day 7 or on day 8, DC were harvested, washed and functional assays were performed. Control DC (cDC) were cultured without tolerising factors. For restimulation assays, tolDC and cDC were extensively washed and recultured in complete RPMI 1640 medium (Gibco) in the absence of tolerising factors for 24-72 h, with or without lipopolysaccharide (LPS, 1 μg/ml, Sigma-Aldrich), poly I:C (25 μg/ml, Cayla-InvivoGen), CD40L (1000 ng/ml, Enzo) or a mixture of pro-inflammatory cytokines containing IL-1β (10 ng/ml), TNFα (10 ng/ml), IL-6 (10 ng/ml) and IFNγ (100 ng/ml) (all from R&D systems). Supernatant and cells were collected for further analysis. Signaling inhibitors were added 1 h before the start of experiments under the specified stimulation conditions. SB203580 (p38 MAPK inhibitor at 10 µM), SP600125 (JNK/SAPK inhibitor at 20 µM), PD98059 (ERK1/2 inhibitor at 20 µM), Bay 11-7082 (NF-κB inhibitor at 10 µM), Stattic (STAT3 inhibitor at 5 µM) and rapamycin (mTOR inhibitor at 100 nM) were obtained from Calbiochem and dissolved in DMSO.

Differentiation and Stimulation of DC from Type 1 Diabetic (T1D) Patients:

Immature DC from T1D patients were differentiated from monocytes using the same protocol as for preparation of immature DC from buffy coats of healthy donors. On day 6, DC were harvested and seeded in 96-well plates (Nunc) at $1\times10^6$ cells/ml. To induce antigen specific maturation, DC were loaded with recombinant human Insulin (1 µg/ml, Sigma Aldrich) or recombinant human Glutamic Acid Decarboxylase (GAD65, 5 µg/ml, Diamyd Medical) and after 3 hours DC were activated by vaccine grade monophosphoryl lipid A (MPLA) (2 µg/ml, Cayla-InvivoGen) on day 7. On day 8, DCs were harvested, washed and functional assays were performed. To induce tolerogenic DC (tolDC), DC were treated with Dexamethasone (Dex) on day 3 (1 µM, Medochemie) and Dex and paricalcitol (1.5 ng/ml, Zemplar, Abbott Laboratories) on day 6. Control DC (cDC) were cultured without tolerising factors.

Restimulation assay of tolDC and DC from T1D patients was prepared as described for DCs from buffy coats of healthy donors.

Flow Cytometry Analysis:

Cells were stained with fluorochrome-conjugated mAbs for 30 min at 4° C. in PBS, washed and analysed on LSRFortessa cell analyzer (BD Biosciences). Appropriate isotype controls were included. Data were analyzed using FlowJo software (Tree Star). DCs were gated according to the FSC, SSC and CD11c+ parameters for analysis. Dead cells were excluded from the analysis based on DAPI staining. For intracellular cytokine staining, T cells were stimulated with phorbol-12-myristate-13-acetate (PMA) (50 ng/ml, Sigma-Aldrich) plus ionomycin (1 µg/ml, Sigma-Aldrich) for 4-16 hours in the presence of Brefeldin A (5 µg/ml, BioLegend) before cell analysing. After stimulation, cells were washed, incubated in Fixation/Permeabilization Buffer (eBiosciences) for 30 min at 4° C., then washed in Permeabilization Buffer (eBiosciences) and stained with appropriate mAb for 30 min at 4° C.

DC Cytokine Detection:

Cell supernatants were harvested after 24 hours of DC stimulation and frozen at −80° C. until analysis. IL-10, IL-12p70, IL-6 and TNFα concentrations were determined in cell culture supernatants of activated DCs using Luminex assay (MILLIPLEX™ Human Cytokine/Chemokine Kit, Merck Millipore) and ELISA assay (DuoSet ELISA Kit, R&D systems) according to manufacturer's instructions.

DC and T Cells Cultures:

T cells were obtained from PBMC non-adherent fraction. Naïve CD4+ T cells were purified by negative selection with The EasySep™ Human Naïve CD4+ T Cell Enrichment Kit (StemCell Technologies). tolDC or cDC were cultured with allogeneic T cells in complete RPMI medium containing 5% human AB serum (Invitrogen), 1% L-glutamine (Gibco), penicillin and streptomycin (100 U/ml and 100 µg/ml, respectively, Gibco), 1% non-essential amino acids (Gibco), 1 mM sodium pyruvate (Gibco) and 50 µM beta-mercaptoethanol (Gibco). Cells were cultured at 1:10 ratio (DC/T cells) in 96-well, round-bottom plates. IL-2 (20 U/ml, PeproTech) was added on day 3, 6 and 9.

Allostimulatory Assay:

For primary MLR assays, allogeneic T cells ($2\times10^5$) labelled with 5 µM carboxyfluorescein succinimidyl ester (CFSE, Invitrogen) were incubated with tolDC or cDC ($2\times10^4$) in 96-well, round-bottom plates. T cell proliferation was determined by the sequential dilution of CFSE fluorescence of T cells, as detected by flow cytometry on day 6.

T Cell Cytokine Production:

For detection of IFNγ and IL-10 production by T cells, $2\times10^4$ tolDC or cDC were cultured with $2\times10^5$ allogeneic T cells. Cytokine production was determined by intracellular staining by flow cytometry on day 6 and day 9, respectively.

Expansion and Detection of Regulatory T Cells:

To define the capacity of tolDC to induce regulatory T cells expansion, $2\times10^4$ tolDC or cDC were cultured with $2\times10^5$ allogeneic naïve CD4+ T cells. The percentage of regulatory T cells defined as CD4+CD25+FoxP3+ was measured by flow cytometry on day 9.

Western Blotting:

Cell lysates ($2\times10^6$ DCs) were prepared from cells cultured in Cell Gro or recultured in complete RPMI alone or with a cytokine cocktail, LPS, poly(I:C) or CD40L for 1 hour as previously described (Palova-Jelinkova et al. 2005, J Immunol 175: 7038-7045). When indicated, rapamycin (100 nM) was added 1 hour before stimulation. Equal amounts of the lysates were subjected to 10% SDS-PAGE and transferred to nitrocellulose membranes before being immunoblotted with the indicated specific mAbs. The membranes were revealed by HRP-conjugated secondary Ab (Cell Signaling Technology) using the West Femto Maximum Sensitivity Substrate (Pierce). After stripping, the membranes were reprobed with an appropriate mAb as loading control.

Preparation of Nuclear Extract and Colorimetric NF-kB Assay

Nuclear extract were prepared from DC cultured in Cell Gro or recultured in complete RPMI alone or with cytokine cocktail, LPS, poly(I:C) or CD40 L for 90 min using a nuclear extract kit (Active Motif). NF-kB DNA binding activity of p50, p65, c-Rel and Rel-b was measured as previously described (Palova-Jelinkova et al. 2005, J Immunol 175: 7038-7045).

Cytokine ELISPOT Analysis:

The ELISPOT analysis was performed in accordance with the manufacturer's instructions. PVDF bottomed, 96-well microtitre plates were first treated with 35% ethanol and then coated with anti-human IFNγ monoclonal Ab (Millipore, Bedford, Mass.) overnight at 4° C. Unbound antibodies were removed by washing three times with sterile PBS solution. After blocking with RPMI with 10% FCS, $3\times10^4$ tolDC or cDC established from T1D patients loaded either with insulin (1 µg/ml) or GAD65 (5 µg/ml) were seeded together with $3\times10^5$ autologous T cells per well and incubated at 37° C. for 48 h. Spots representing IFNγ-producing cells were developed using a biotinylated anti-IFNγ detection antibody and streptavidin—alkaline phosphatase conjugated with BCIP/NBT buffer and quantified using the Series-1 Immunospot Analyzer. Even though the spots varied greatly in size and density, homogeneously stained spots were seen in positive wells, whereas the small dense spots that were occasionally seen both in wells with cells and in control wells without cells were distinguished as artifacts.

Statistical Analysis:

Results are given as mean±standard error of the mean (SEM) of at least 3 samples. Two-tailed paired t-test was applied for data analysis using GraphPad Prism 6. A value of $p \leq 0.05$ was considered statistically significant.

6.2 Results

Figure 1B:
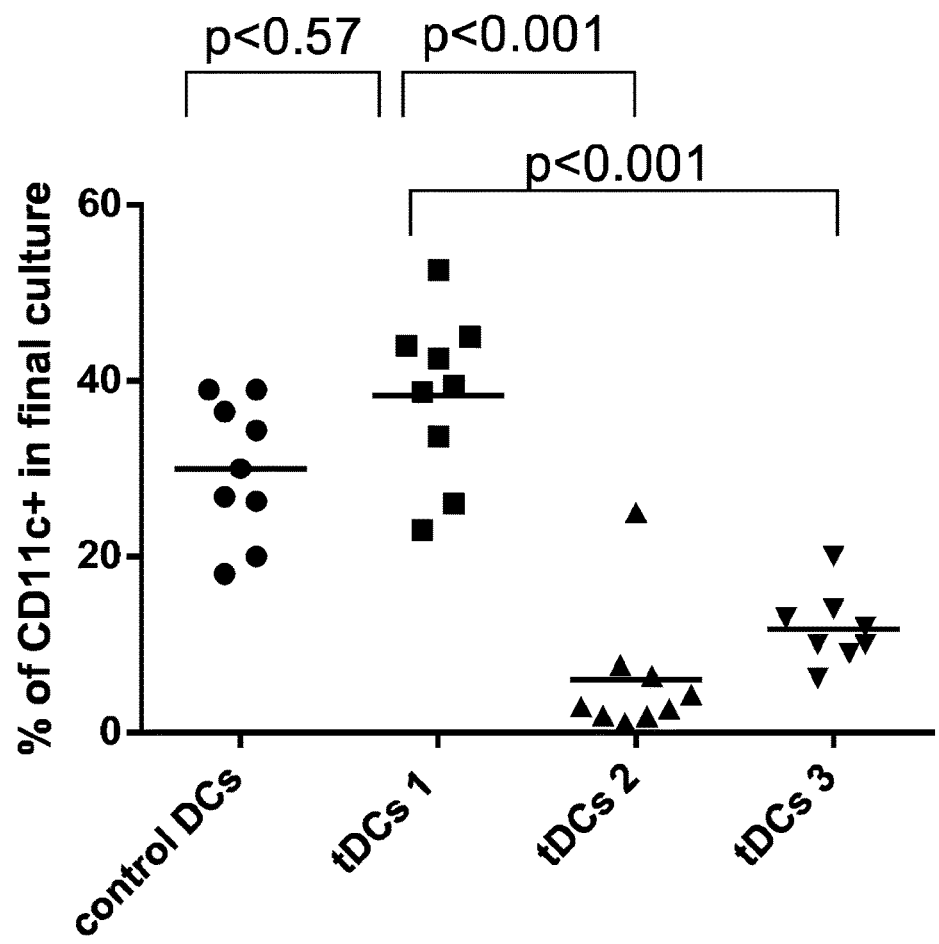

Comparison of Various Protocols for Establishment of Tolerogenic DCs by Using Dex and VitD2:

In the first set of experiments, different protocols for establishing tolerogenic DCs were assessed to determine whether the type of protocol affects the process of differentiation of monocytes into immature DCs. TolDCs generated for 8 days by protocol tolDCs1 were found to have a comparable yield of non-adherent cells in the final culture and a comparable percentage of $CD11c^+$ non-adherent DCs in final culture when compared to control DCs generated without tolerogenic factors (FIG. 1A, Table 2 and Table 3). tolDCs generated by protocol tolDCs 2 and tolDCs 3 revealed significantly lower yield of cells and significantly lower percentage of $CD11c^+$ DCs in final culture when compared to tolDCs 1 (FIG. 1B, Table 2 and Table 3).

TABLE 2

Normalized Yield Of tolDCs Compared To Yield Of cDCs (in % of cDCs)

| Experiment | tolDC 1 | tolDC 2 | tolDC 3 |
|---|---|---|---|
| 1 | 48.97959184 | | |
| 2 | 4.347826087 | | |
| 3 | 9.411764706 | | |
| 4 | 37.77777778 | | |
| 5 | −37.14285714 | | |
| 6 | −28.30188679 | | |
| 7 | −18.84057971 | −69.56521739 | |
| 8 | −9.647058824 | −74.11764706 | −72.89719626 |
| 9 | −25.23364486 | −95.3271028 | −70.71129707 |
| 10 | −19.66527197 | | |
| 11 | −17.43970315 | −70.87198516 | −48.05194805 |

TABLE 3

Normalized Yield Of $CD11c^+$ Cells In tolDCs Compared To The Yield Of $CD11c^+$ Cells cDCs Culture (in % $CD11c^+$ cells of cDCs)

| Experiment | tolDC 1 | tolDC 2 | tolDC 3 |
|---|---|---|---|
| 1 | 1.282051282 | −88.92307692 | −76.92307692 |
| 2 | 29.33333333 | −93.5 | −56.66666667 |
| 3 | 25.74626866 | −93.09701493 | −47.76119403 |
| 4 | 16.71232877 | −91.80821918 | −67.12328767 |
| 5 | 52.90697674 | −92.09302326 | −70.93023256 |
| 6 | 71.1026616 | −95.51330798 | −23.95437262 |
| 7 | 15 | −67.9 | |
| 8 | 44.44444444 | −57.22222222 | −65.55555556 |
| 9 | 12.82051282 | −35.8974359 | −74.35897436 |

Figure 2A:
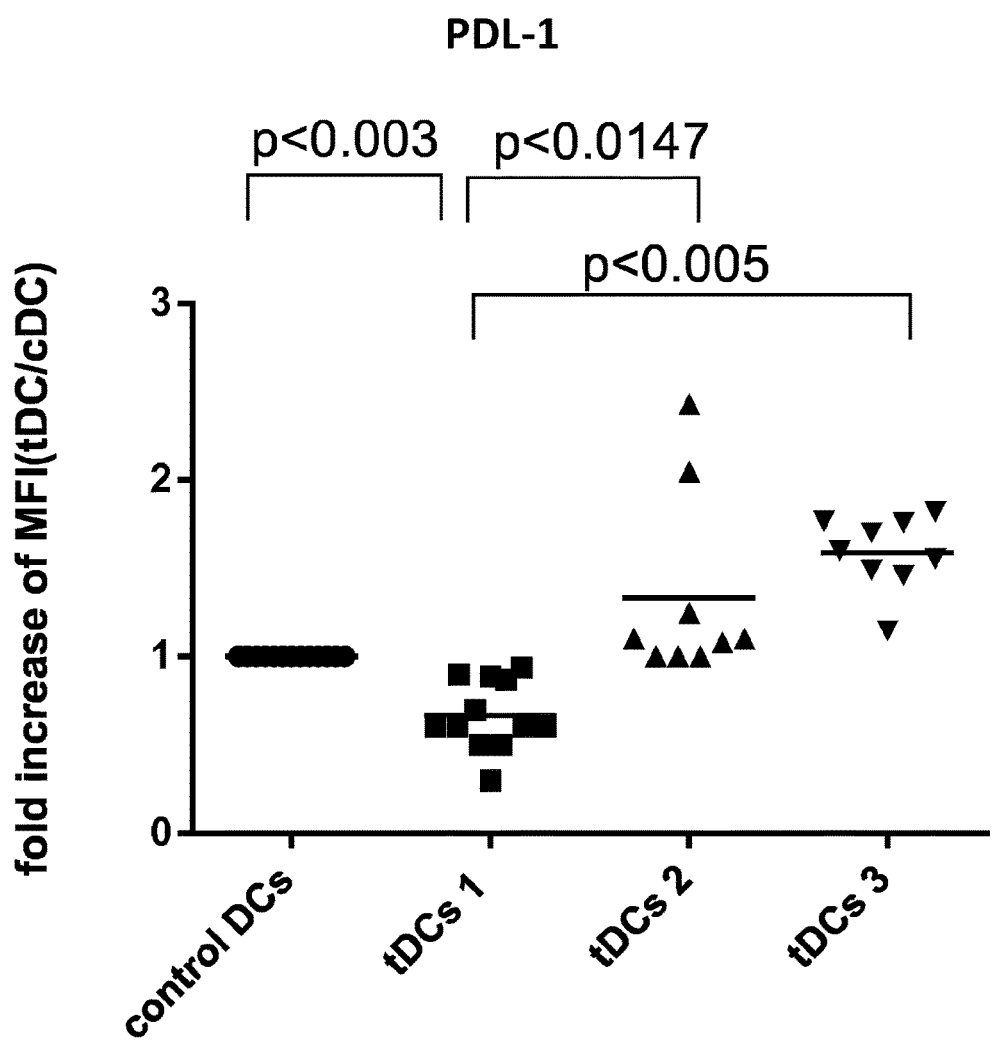
Figure 2B:
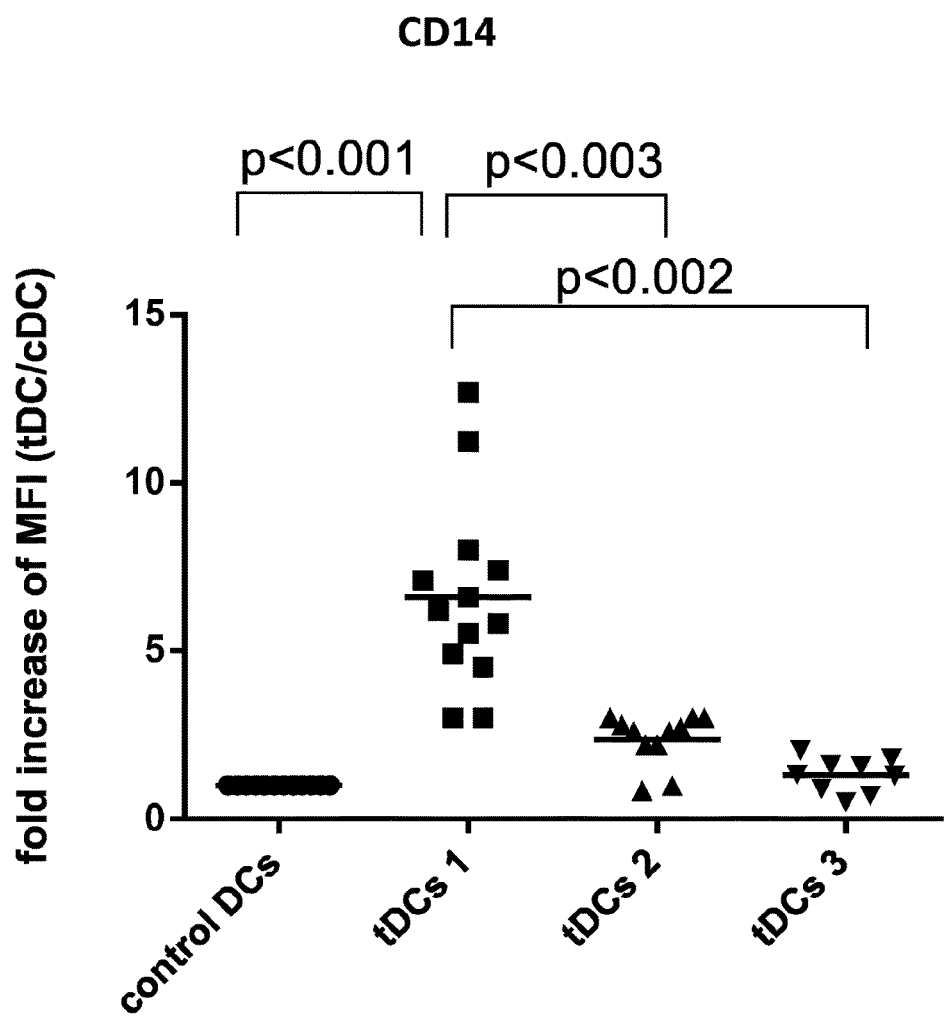
Figure 3A:
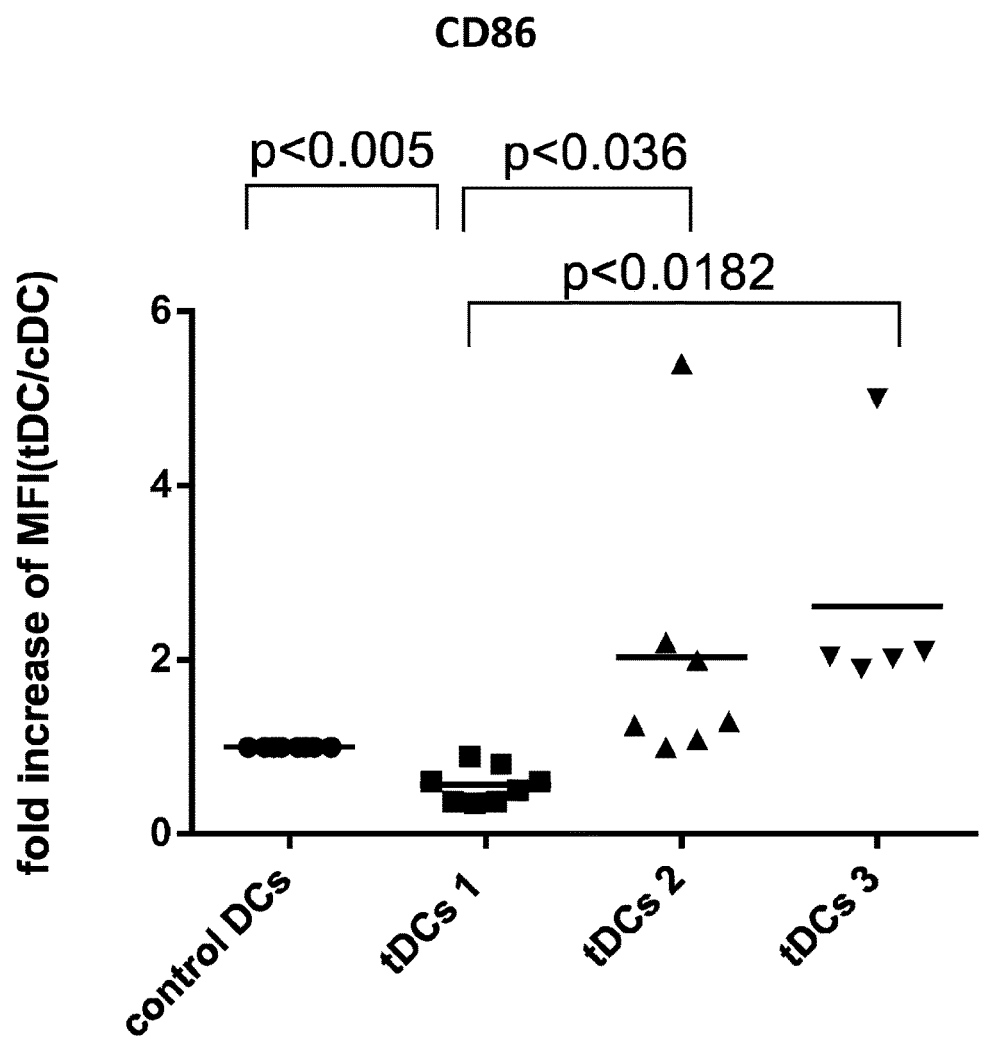
Figure 3B:
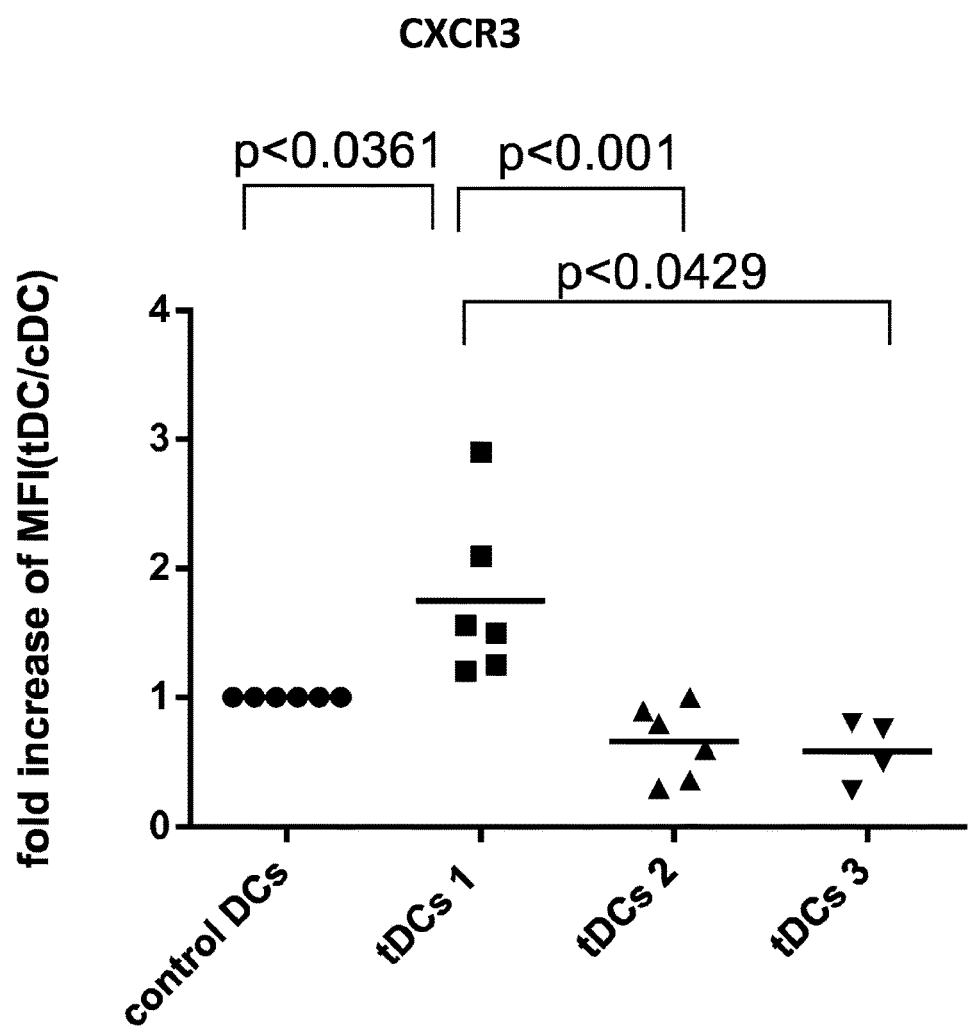

Phenotype of tolDCs Generated by Various Protocols:

Next, the expression of maturation marker CD86, tolerogenic marker PD-1, chemokine receptor CXCR3 and CD14 molecule was analyzed (FIGS. 2 and 3. Table 4, 5, 6 and 7). Expression of CD86 and PD-L1 was significantly lower on tolDCs generated by protocol tolDCs 1 when compared to control DCs (FIGS. 2A and 3A, Table 4 and 6). tolDCs generated by protocol tolDCs 2 and protocol tolDCs 3 express a significantly higher level of CD86 and PD-L1 when compared to tolDCs generated by protocol tolDCs 1 (FIGS. 2A and 3A, Table 4 and 6). In contrast, expression of CD14 and CXCR3 on tolDCs generated by protocol tolDCs 1 was significantly higher when compared to control DCs (FIGS. 2B and 3B, Table 5 and 7). tolDCs generated by protocol tolDCs 2 and protocol tolDCs 3 express significantly lower levels of CD14 and CXCR3 in comparison with tolDCs generated by protocol tolDCs 1 (FIGS. 2B and 3B, Table 5 and 7).

TABLE 4

Fold Increase Of PD-L1 Expression Between tolDCs And cDCs

| Experiment | tolDC 1 | tolDC 2 | tolDC 3 |
|---|---|---|---|
| 1 | 0.94 | | 1.147 |
| 2 | 0.6 | | 1.6 |
| 3 | 0.9 | 2.05 | |
| 4 | 0.6 | 2.43 | |
| 5 | 0.87 | 1 | |
| 6 | | | 1.76 |
| 7 | 0.6 | 1 | 1.46 |
| 8 | 0.7 | 1.1 | 1.49 |
| 9 | 0.3 | | 1.556 |
| 10 | 0.89 | 1.25 | |
| 11 | 0.5 | 1.08 | 1.7 |
| 12 | 0.6 | 1.1 | 1.77 |
| 13 | 0.5 | 1 | 1.82 |

TABLE 5

Fold Increase Of CD14 Expression Between tolDCs And cDCs

| Experiment | tolDC 1 | tolDC 2 | tolDC 3 |
|---|---|---|---|
| 1 | 12.68 | 2.59 | |
| 2 | 7.4 | 0.84 | |
| 3 | 11.23 | 1 | |
| 4 | 8 | | 1.3 |
| 5 | 4.91 | | 1.57 |
| 6 | | | 2.05 |
| 7 | 3 | 3 | 0.9 |
| 8 | 6.2 | 2.6 | 1.8 |
| 9 | 6.6 | 4 | 1.6 |
| 10 | 5.8 | 3 | |
| 11 | 5.5 | 2.8 | 1.32 |
| 12 | 4.5 | 2.2 | 0.7 |
| 13 | 2.6 | 2.2 | 0.5 |
| 14 | 7.1 | 2.7 | |

TABLE 6

Fold Increase Of CD86 Expression Between tolDCs And cDCs

| Experiment | tolDC 1 | tolDC 2 | tolDC 3 |
|---|---|---|---|
| | 0.9 | 5.4 | 5 |
| | 0.35 | 2.2 | 2.1 |
| | 0.6 | 1.3 | 1.9 |
| | 0.8 | 2 | |
| | 0.37 | | |
| | 0.37 | 1 | |
| | 0.5 | 1.09 | 2.02 |
| | 0.6 | 1.25 | 2.04 |

TABLE 7

Fold increase of CXCR3 expression between tolDCs and cDCs

| Experiment | tolDC 1 | tolDs 2 | tolDC 3 |
|---|---|---|---|
| 1 | 1.2 | 0.3 | 0.5 |
| 2 | 1.56 | 0.8 | 0.8 |
| 3 | 1.5 | 0.6 | |

TABLE 7-continued

Fold increase of CXCR3 expression between tolDCs and cDCs

| Experiment | tolDC 1 | tolDs 2 | tolDC 3 |
|---|---|---|---|
| 4 | 2.1 | 1 | |
| 5 | 2.9 | 0.9 | 0.76 |
| 6 | 1.25 | 0.36 | 0.28 |

Differences in Induction of CD4+CD25+FoxP3+ Regulatory T Cells from Naive T Cells by tolDCs Prepared by Using Vit D2 or Vit D3:

Next, the capacity of tolDCs established by protocol tolDCs 1 using VitD2, tolDCs established by protocol tolDCs 1 using VitD3 (calcitriol) and control DCs to promote de novo differentiation of Tregs was tested. Allogeneic naive T cells were co-cultured with DC at a ratio of 10:1 for 9 days. As shown in FIG. 4 and Table 8, tolDCs generated with VitD2 induced significantly higher level of CD4+CD25+FoxP3+ Tregs in comparison with control DCs. However, tolDCs generated with VitD3 induce comparable level of CD4+CD25+FoxP3+ Tregs in comparison with control DCs.

TABLE 8

Fold Increase of the Yield Tregs Generated by tolDCs Compared to the Yield of Tregs Generated by cDCs

| Experiment | tolDC 1 | tolDC 4 |
|---|---|---|
| 1 | 1.6916996047 | 0.664031621 |
| 2 | 1.3029315961 | 0.631921824 |
| 3 | 1.1811320755 | 0.950943396 |
| 4 | 1.3867403315 | 0.947513812 |
| 5 | 1.1627218935 | 1.405325444 |
| 6 | 1.2857142857 | 0.847826087 |

Differences in Induction of CD4+CD25+FoxP3+ Regulatory T Cells from Naive T Cells by tolDCs Prepared by tolDC 1 Protocol for 7 or 8 Days:

Next, the capacity of tolDCs established by protocol tolDCs 1 for 7 days (MPLA was added at day 6 and cell were finally matured for 24 hrs) and tolDCs established by tolDCs 1 protocol for 8 days (MPLA was added at day 7 and cells were finally matured for 24 hrs) to promote de novo differentiation of Tregs was assessed. Allogeneic naive T cells were co-cultured with DC at a ratio of 10:1 for 9 days. As shown in FIG. 5 and Table 9, tolDCs generated by 8 day protocol induced significantly higher level of CD4+CD25+FoxP3+ Tregs in comparison with tolDCs established by the 7 day protocol.

TABLE 9

Fold Increase of the Yield of Tregs Generated By tolDCs Compared To Yield Of Tregs Generated By cDCs

| Experiment | 7 days | 8 days |
|---|---|---|
| 1 | 2.43781095 | 3.383928571 |
| 2 | 0.42368421 | 2.909090909 |
| 3 | 1.74637681 | 2.807486631 |
| 4 | 0.98913043 | 1.232804233 |
| 5 | 1.07079646 | 1.517412935 |
| 6 | 0.18802817 | 1.863247863 |
| 7 | 0.78840348 | 1.792243767 |
| 8 | 1.06434316 | 1.198369565 |

Dex/VitD2-Treated tolDC (tolDCs 1) Maintain a Stable Semi-Mature Tolerogenic Phenotype Even after Restimulation with LPS, CC, Poly(I:C) and CD40L:

To study the stability and functional properties of tolDC, freshly isolated human monocytes were cultured in cGMP-medium Cell Gro in the presence of GM-CSF, IL-4, Dex, VitD2 and MPLA. Control DC were cultured without Dex and VitD2. As shown in FIG. 7A (1-4), tolDCs 1 cultured in Cell Gro exhibited semi-mature phenotype with significantly lower surface levels of CD86, CD83, CD80 and CD40, but not CD1a, CD11c and HLA-DR, in comparison with control DC. In contrast, tolDCs 1 had higher expression of TLR-2, CD14 and inhibitory molecule T cell immunoglobulin and mucin protein 3 (TIM-3) and ILT-3. The expression of tolerogenic markers ILT-4, PD-L1 and PD-L2 on tolDCs 1 was not altered. Next, the phenotype of control DCs and tolDCs 1 generated in Cell Gro were recultured in complete RPMI without tolerising agents and subsequently stimulated with LPS, CC, poly(I:C) or CD40L for 24, 48 and 72 hours were analyzed. Restimulation with CC, LPS, poly(I:C) or CD40L led to a slight upregulation of CD86, CD83 and CD40 on tolDC 1, however, it remained low when compared to their non-tolerogenic counterparts even at 72 hours after stimulation (FIG. 7B (1-4)). Importantly, the expression of TLR2, CD14 and ILT-3 on tolDC 1 remained high after the secondary stimulation when compared to control DC even after 72 h. The expression of TIM-3 decreased approximately two-fold after CC, LPS and CD40L stimulation, however, it remained higher in comparison with control DC. The expression of tolerogenic molecule PD-L1, that was low on tolDC 1, dramatically increased after restimulation of tolDC 1 for 24 hours with LPS as well as CC and slightly after poly(I:C) and CD40L stimulation. Collectively, these data demonstrate that, in spite of the presence of maturation stimuli, Dex/VitD2 tolDC maintain stable phenotype and are able to increase expression of tolerogenic markers.

Figure 8A:
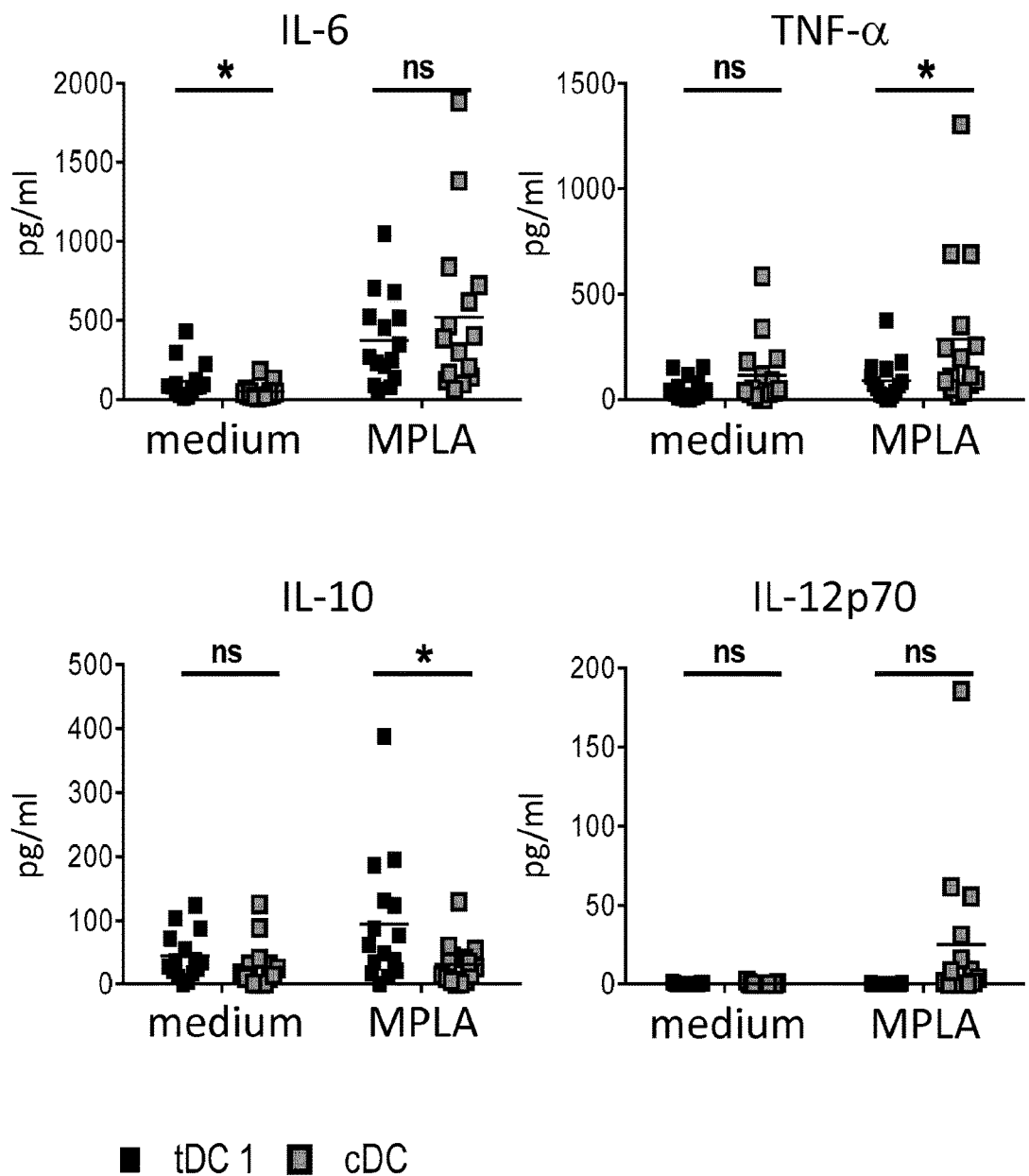
Figure 8B:
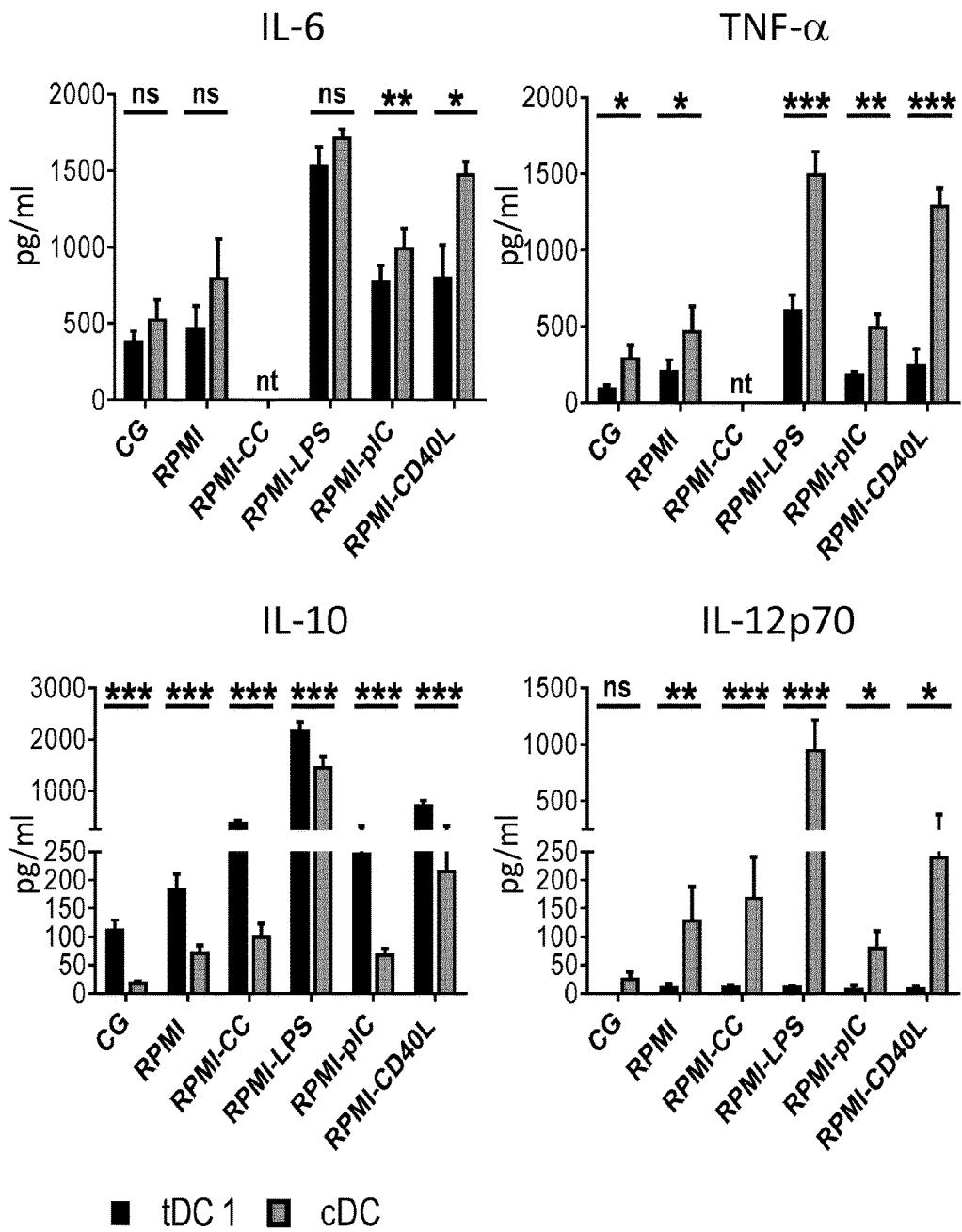
Figures 1, 9A:
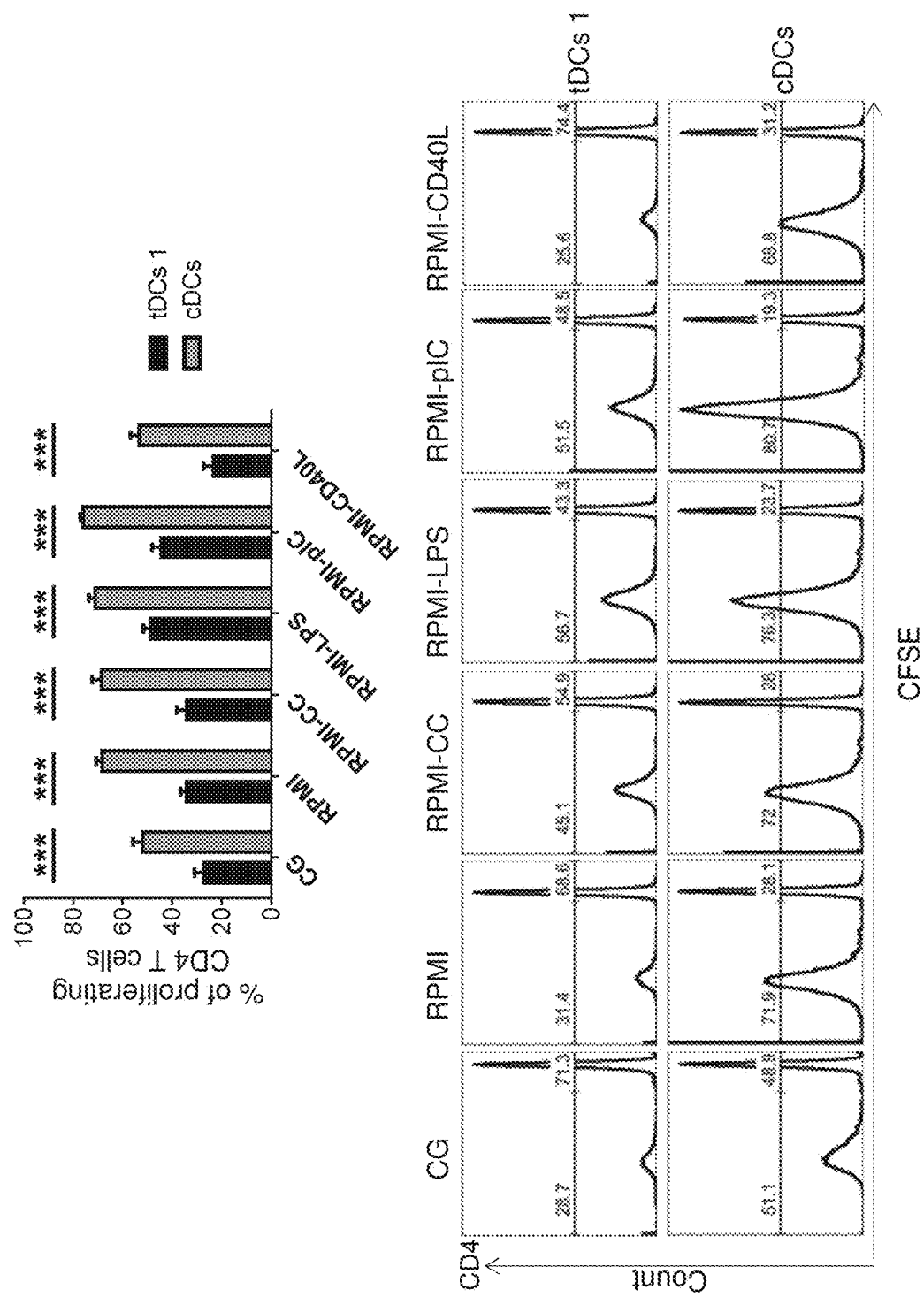
Figures 2, 9A:
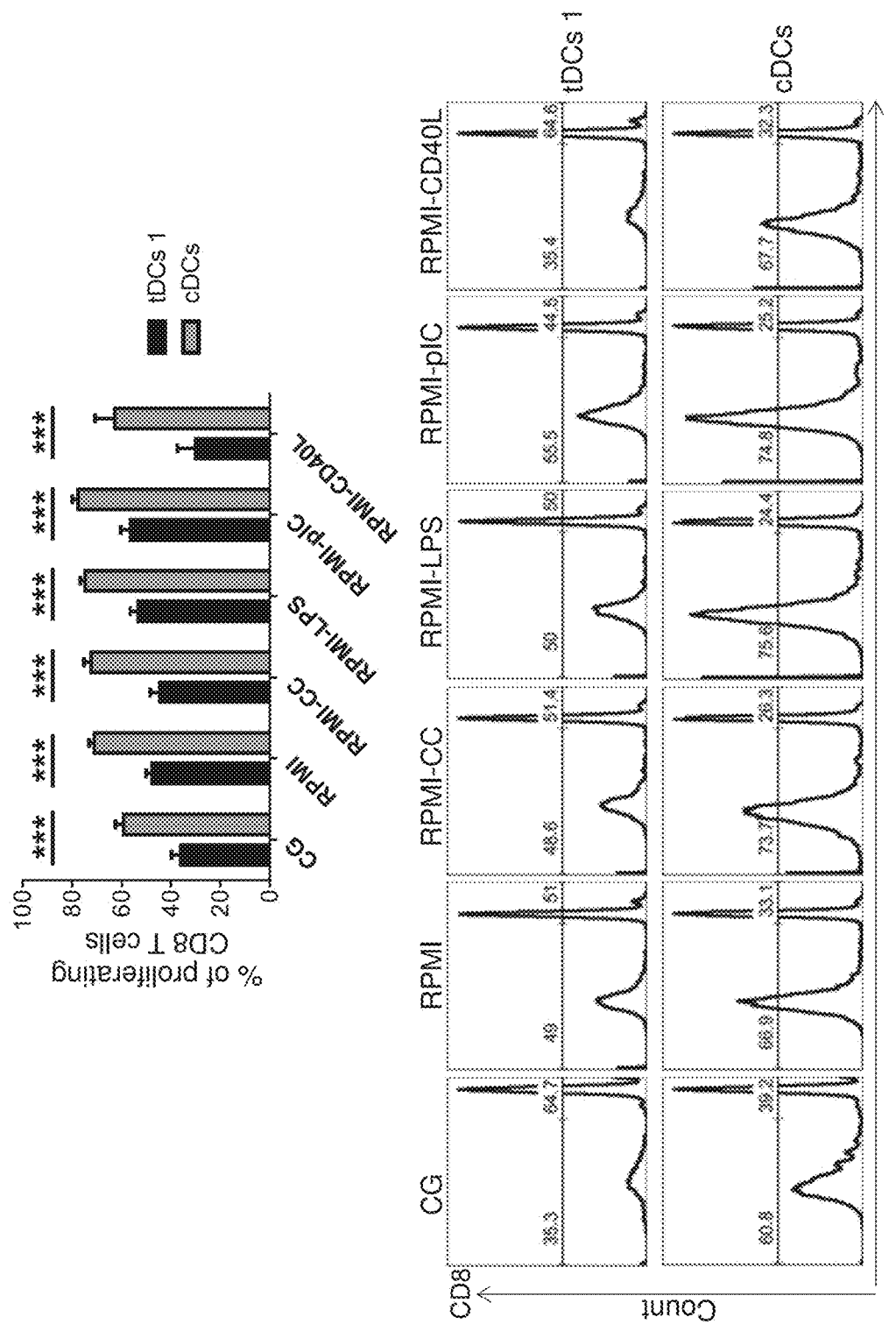
Figure 9B:
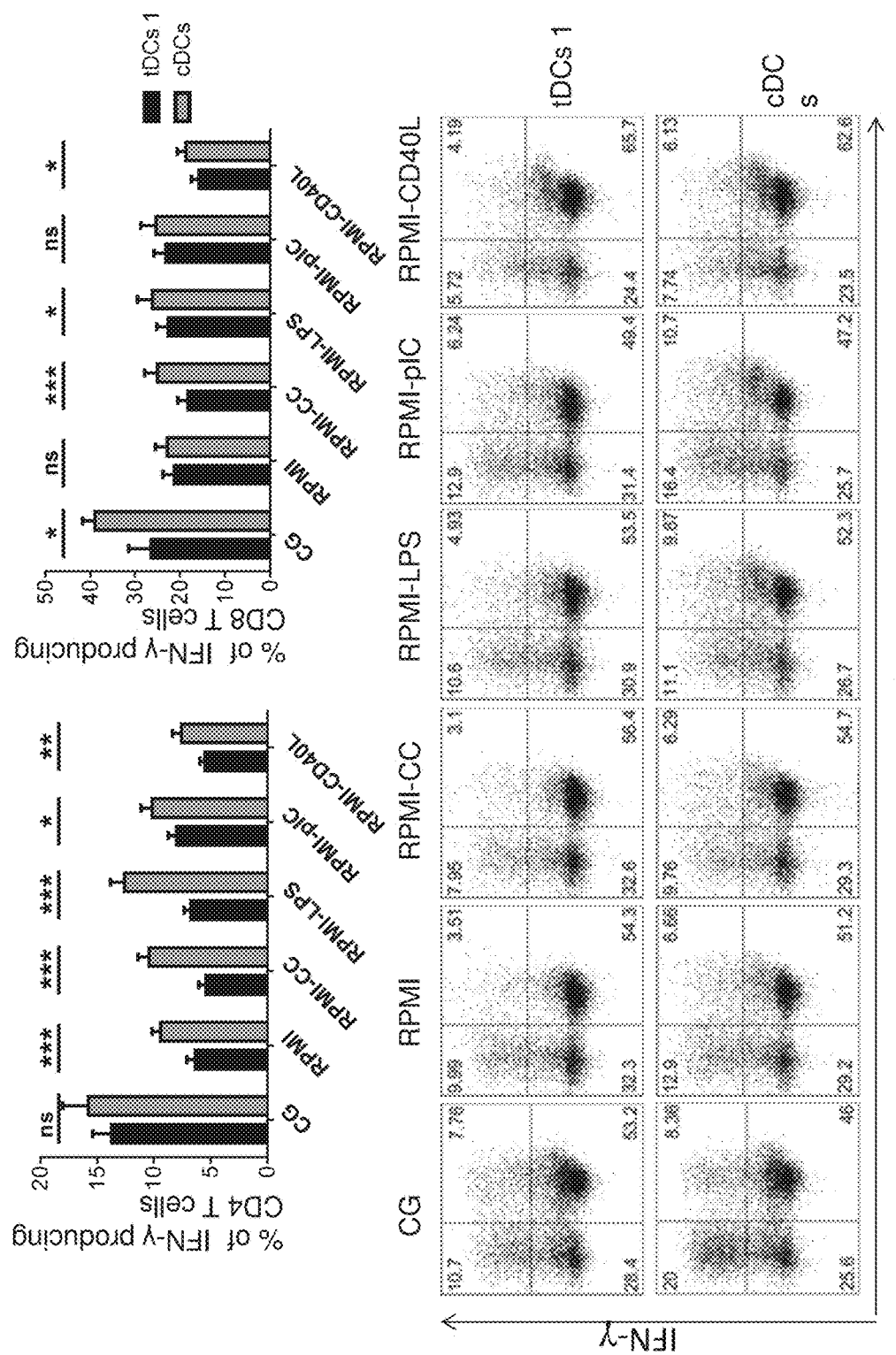
Figure 9C:
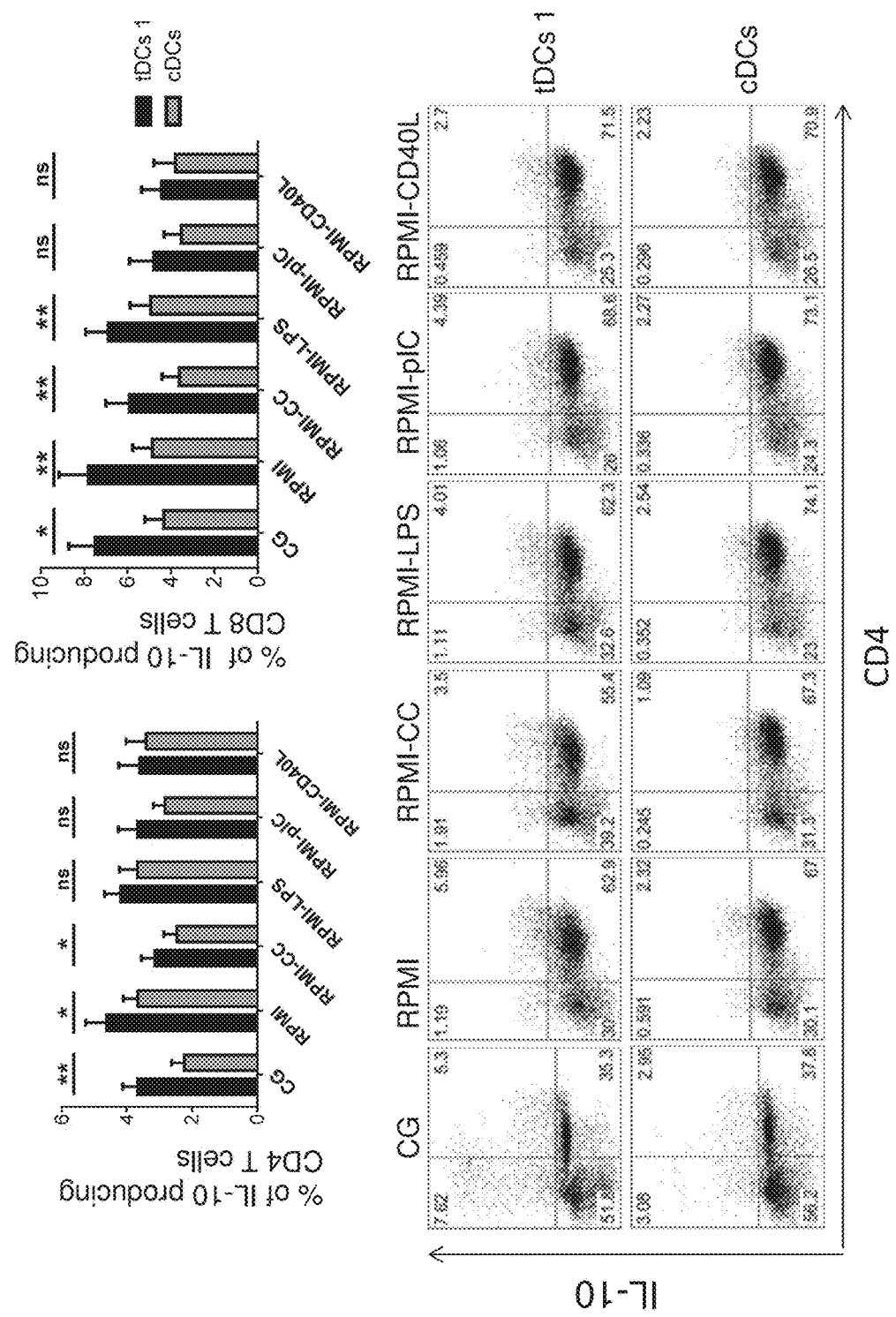

Tolerogenic DCs Preserve High IL-10/IL-12 Ratio:

Next, the cytokine production of tolDC 1 and control DC was evaluated. In comparison to control DC, tolDC 1 produced high levels of IL-10, low quantities of TNF-α, almost identical levels of IL-6, and no IL-12p70 (FIG. 8A). Subsequent restimulation of tolDC 1 with the CC, LPS, poly(I:C) or CD40L led to a robust increase of IL-10 production accompanied by minimal IL-12p70 secretion, suggesting that the increased preferential IL-10 secretion is the characteristic of tolDC 1 in response to maturation stimuli. The levels of TNF-α and IL-6 produced by tolDC 1 remained reduced after restimulation with all the maturation agents tested with the exception that IL-6 production was markedly upregulated after LPS stimulation when compared to control DC. DC produced slightly higher levels of IL-10 after restimulation with CC, poly(I:C) and CD40L and robust increase of IL-10 after LPS restimulation. Moreover, they markedly elevated IL-12, IL-6 and TNF-α levels after secondary restimulation, especially after LPS and CD40L restimulation (FIG. 8B). Collectively, these data support stable non-proinflammatory profile of tolDC 1.

TolDCs 1 Display an Impaired Allostimulatory Capacity and Skew the T Cell Cytokine Profile to Higher IL-10 and Lower IFN-γ Production Even after Restimulation:

Next, the ability tolDC 1 to reduce T cell proliferation and maturation stimuli can reverse the inhibitory function of tolDC 1 for T cell proliferation was assessed. Thus, tolDC 1 or control DCs were cultured with allogeneic T cells at a ratio of 1:10. Tolerogenic DCs established in Cell Gro were weak inducers of T cell proliferation. Allostimulatory capacity of tolDC 1 remained low even after the restimulation by any of the restimulatory conditions tested compared to control DC (FIG. 9A (1-2)).

Next, allogeneic T cell differentiation induced by tolDC 1 or control DC was characterized by measuring the frequency of IFN-γ and IL-10 producing T cells. As documented in FIGS. 9B and 9C, co-incubation of allogeneic T cells with tolDC 1 cultured in Cell Gro skewed the T cell cytokine profile towards markedly reduced IFN-γ production and significantly increased IL-10 production by CD4+ as well as CD8+ T cells, in comparison to control DC. In addition, co-incubation of T cells with tolDC 1 restimulated with CC, LPS, poly(I:C) and CD40L led to marked reduction of CD4+ IFN-γ producing T cells together with stable numbers of CD4+ IL-10 producing cells. The percentage of CD8+ IFN-γ T cells remained stable or slightly decreased after CC and CD40L restimulation of tolDCs 1, while the amount of CD8+ IL-10 producing T cells remained almost the same after restimulation of tolDC 1 with LPS and slightly decreased after restimulation of tolDC 1 with CC, poly(I:C) and CD40L.

TolDCs 1 Induce CD4+CD25+FoxP3+ T Differentiation from Naïve CD4+ T Cells:

Increased capacity to promote differentiation/induction of Tregs from naïve precursors seems to be one of the most important hallmarks of tolDC (Mahnke et al. 2003, Blood 101: 4862-4869). To test the capacity of tolDC 1 to promote de novo differentiation of Tregs, allogeneic naïve CD4+ T cells were co-cultured with DC at a ratio 10:1 for 9 days. As shown in FIG. 10, tolDC 1 generated in Cell Gro significantly expanded the number of CD4+CD25+FoxP3 cells generated from naïve T cells in comparison with control DCs. Importantly, tolDCs 1 maintain the ability to induce de novo CD4+CD25+FoxP3+ T cells even after restimulation. TolDCs 1 restimulated with CC and LPS maintained a significantly higher ability to induce CD4+CD25+FoxP3+ T cells from naïve CD4+T cells when compared to control DCs counterpart.

Tolerogenic or Control DC Utilize Distinct Signaling Pathways after Restimulation:

To decipher the molecular mechanisms that play a role in maintaining the tolerogenic properties of tolDC, signaling pathways including p38 MAPK, JNK/SAPK, ERK1/2, NF-κB, mTOR, and STAT3, which have been previously reported to influence DC maturation and orchestrate the IL-10 and IL-12 production, were analyzed (Weichhart et al. 2008, Immunity 29: 565-577; Qian et al. 2006, Blood 108: 2307-2315; Jackson et al. European Cytokine Network 21: 319-328).

Figures 11A, 11B:
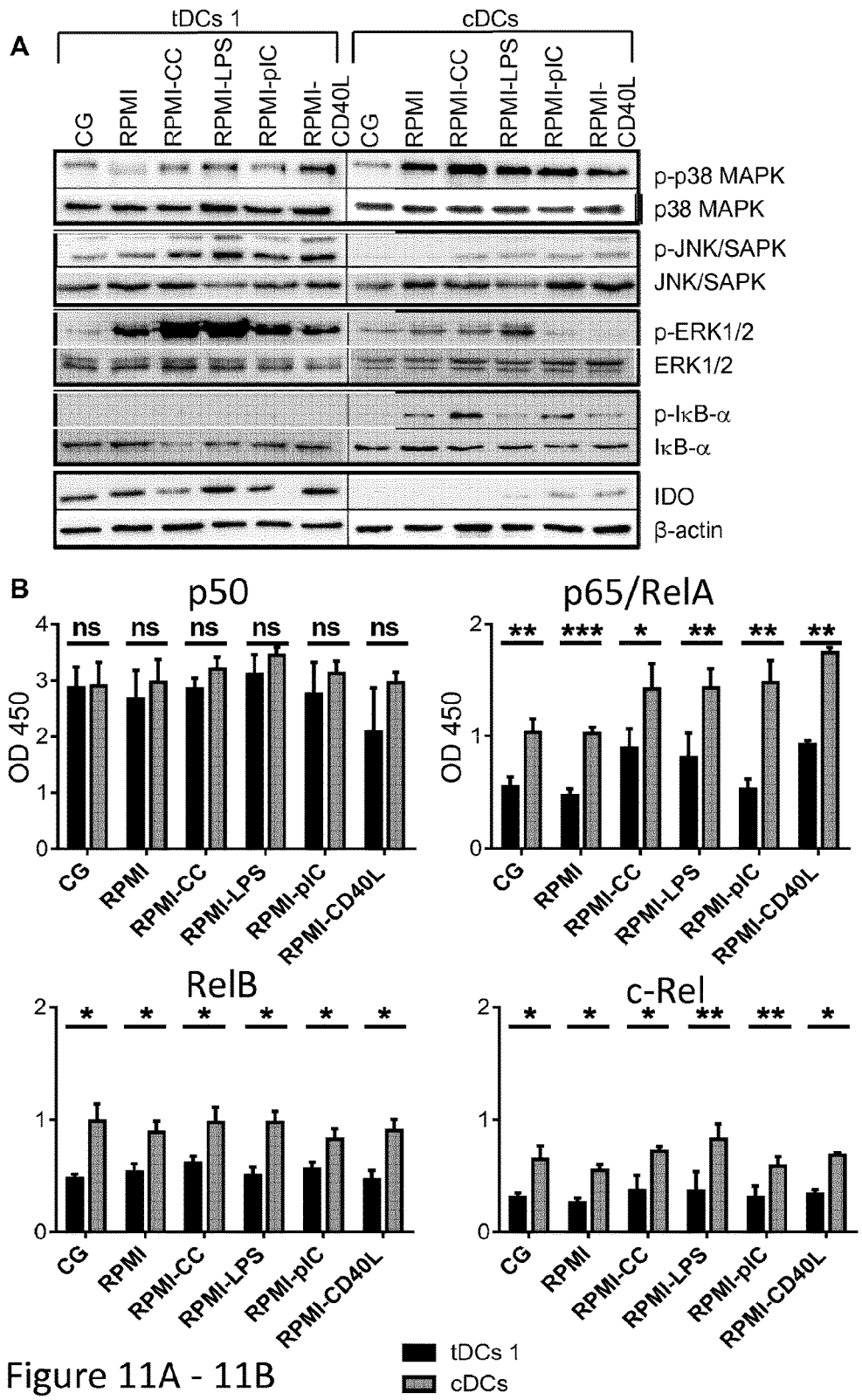

First, MAPK, including p38 MAPK, JNK/SAPK and ERK1/2, were assessed to determine whether they differentially regulated in tolDC 1 and control DC. As shown in FIG. 11A, tolDC 1 from Cell Gro expressed higher levels of activated JNK/SAPK; however p38 MAPK and ERK1/2 were comparably activated in tolDC 1 and control DC. Then, the activation of MAPK in DCs conditioned in RPMI was compared to the activation of MAPK in DCs stimulated with CC, LPS, poly (I:C) and CD40L. Similarly to the prestimulation, tolDC 1 in the presence of RPMI or stimulated with CC, LPS, poly(I:C) and CD40L expressed higher level of activated JNK/SAPK, but a lower level of the activated p38 MAPK. ERK1/2 was significantly up-regulated after all stimulatory conditions tested in tolDC 1, but only after LPS stimulation in control DC. The results suggest that p38 MAPK, JNK/SAPK and ERK1/2 are differentially regulated in tolDC 1 compared to control DC, which might play a role in maintaining the tolerogenic properties of tolDC 1 after rechallenge.

Given that DC differentiation and maturation is associated with activation of NF-κB and Dex/VitD tolDC were shown to be generated through suppression of NF-κB pathway (Adorini et al 2009, Handbook of Experimental Pharmacology: 251-273; van Kooent et al, Handbook of Experimental Pharmacology: 233-249), TLR agonists, CC or CD40L were assessed for their ability to reverse NF-κB suppression in the absence of tolerising factors. In contrast to control DC, the phosphorylation of IkB-α was dramatically reduced in tolDC 1 in all the stimulatory conditions tested was analyzed (FIG. 11A). To quantify NF-κB activation, DNA binding activity of NF-κB subunits p50, p65/RelA, c-Rel and RelB in the nucleus (FIG. 11B). DEX/VitD2 tolDC 1 from CG exhibited low levels of RelB, shown to reflect DC maturation (Scheinman et al. 1995, Mol Cell Biol 15: 943-953) and low levels of c-Rel shown to be involved in IL-12 production (Grumont et al 2001, J Exp Med 194: 1021-1032) in nuclear extracts when compared to control DC. Rel-B and c-Rel levels remained lower even when rechallenge in the absence of VitD2 and DEX in tolDC 1. Moreover, tolDC 1 exhibited markedly decreased p65 levels and almost identical p50 levels compared to control DC (FIG. 11B).

Finally tolDC 1 were found to express high levels of IDO, an immune tolerance-promoting enzyme. IDO expression remained stable even after subsequent restimulation with CC, LPS, poly(I:C) and CD40L. Control DC expressed no detectable or very low levels of IDO after restimulation (FIG. 11A).

Figures 1, 11C:
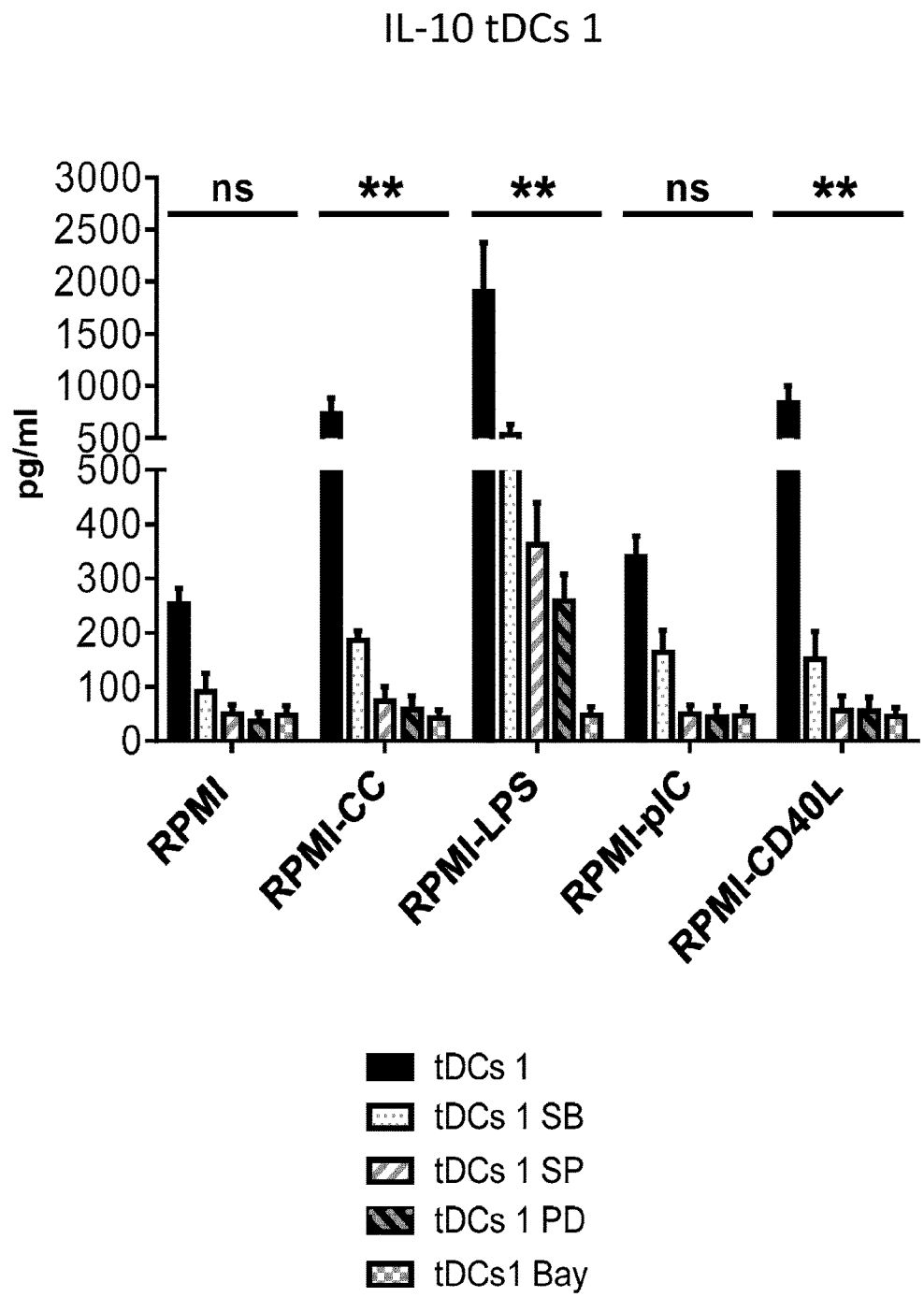
Figures 3, 11C:
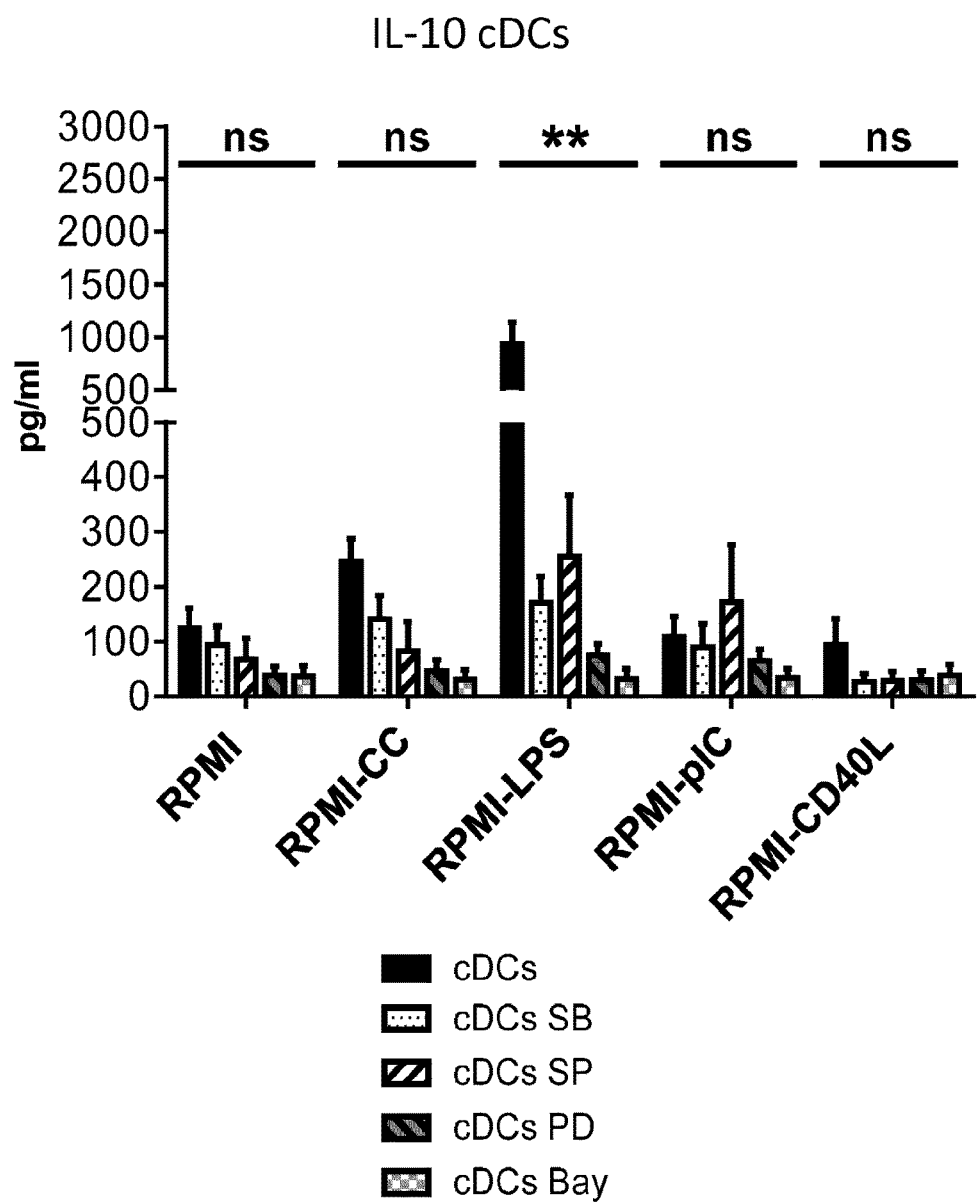
Figures 5, 11C:
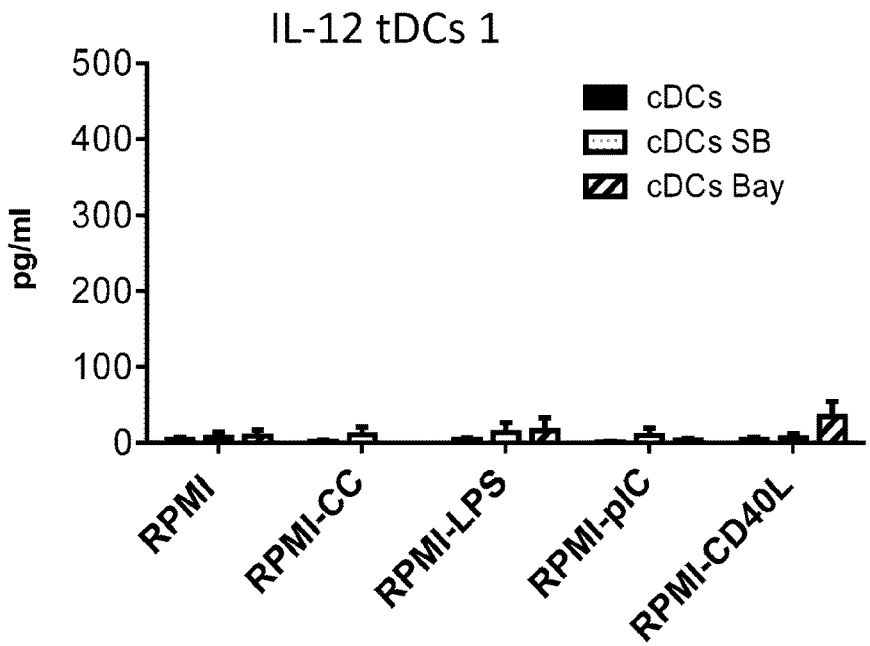
Figures 6, 11C:
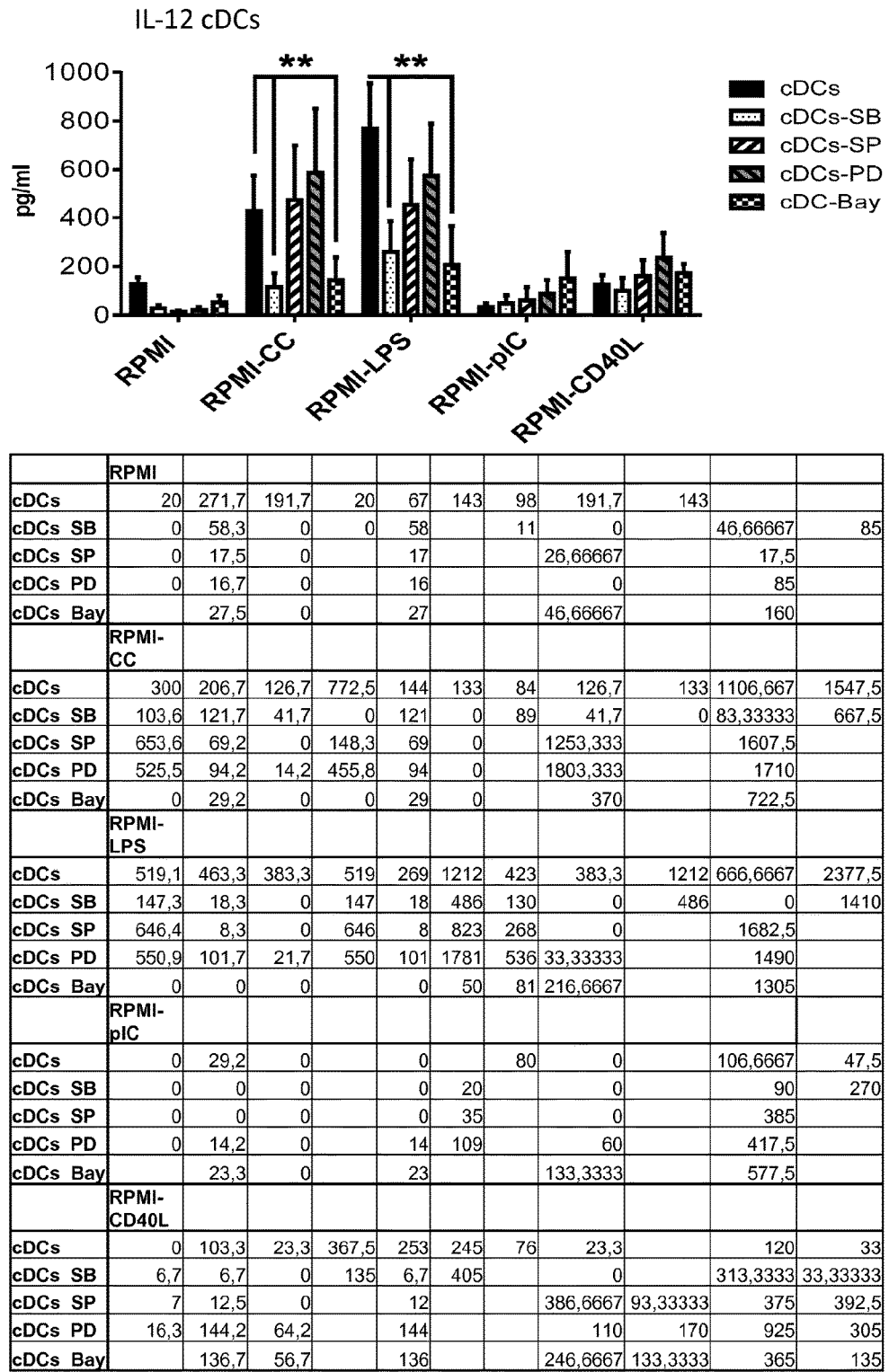
Figures 1, 11D:
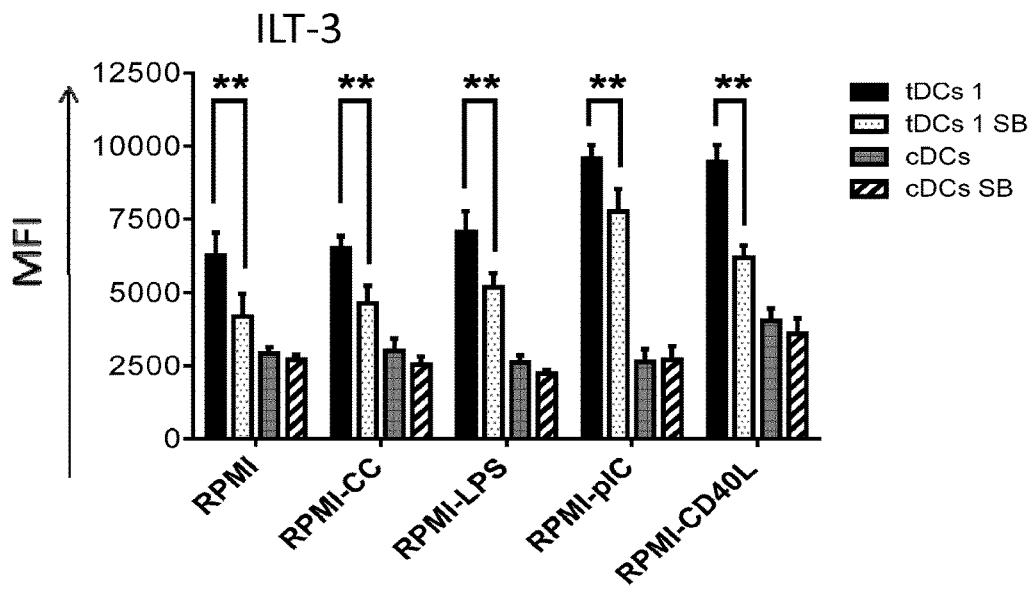
Figures 2, 11D:
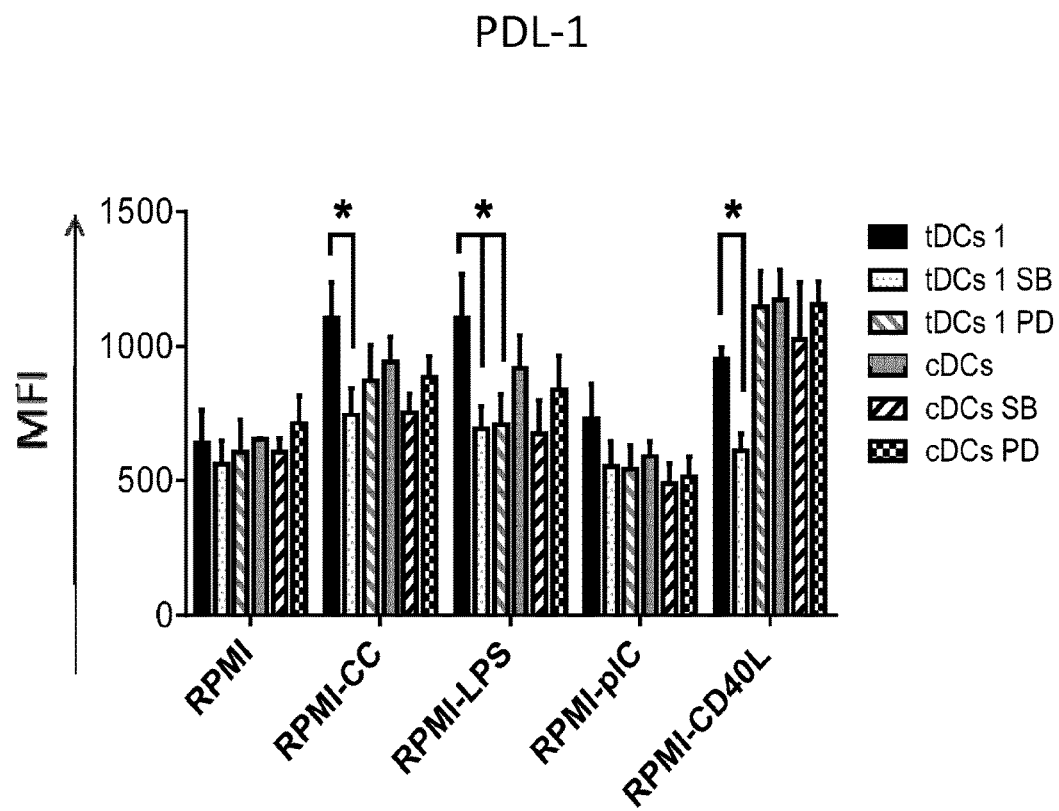
Figures 12A, 12B:
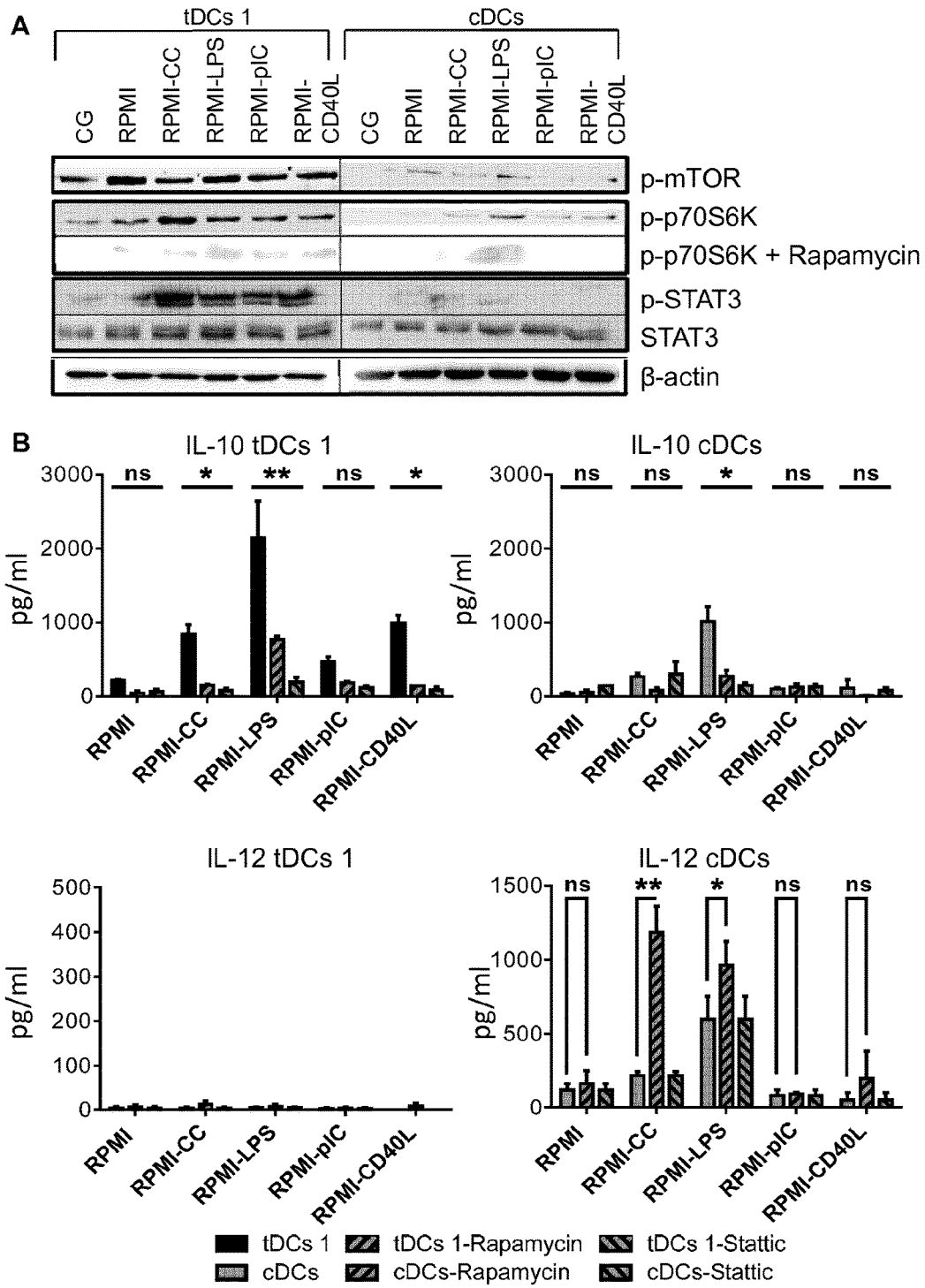
Figures 1, 12C:
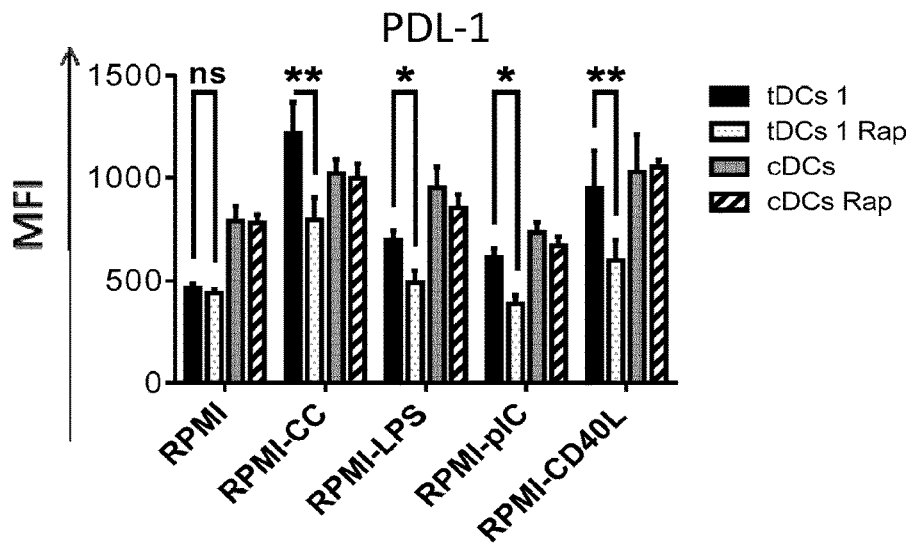
Figures 2, 12C:
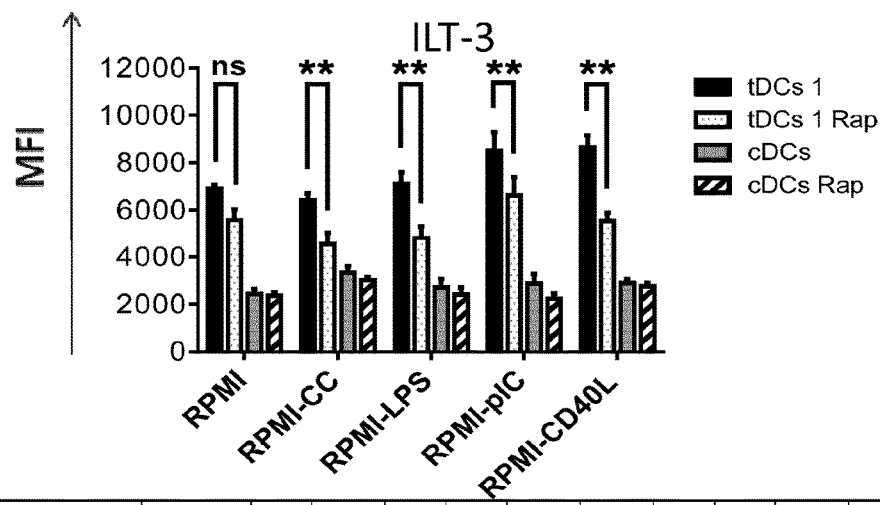
Figures 3, 12C:
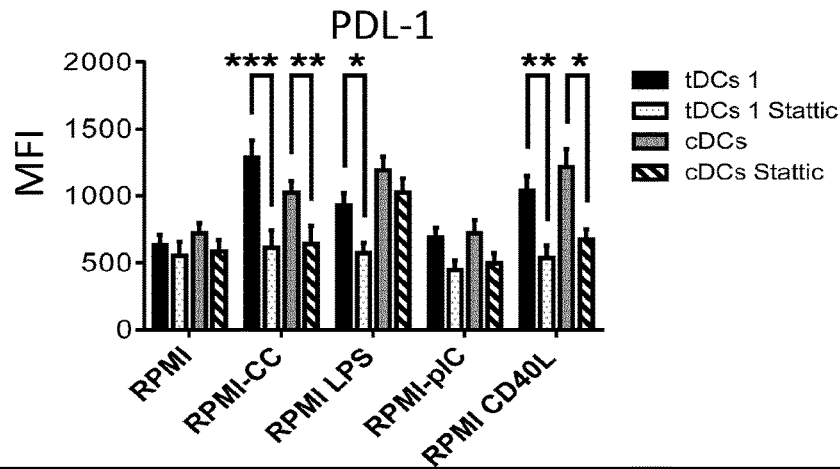
Figures 4, 12C:
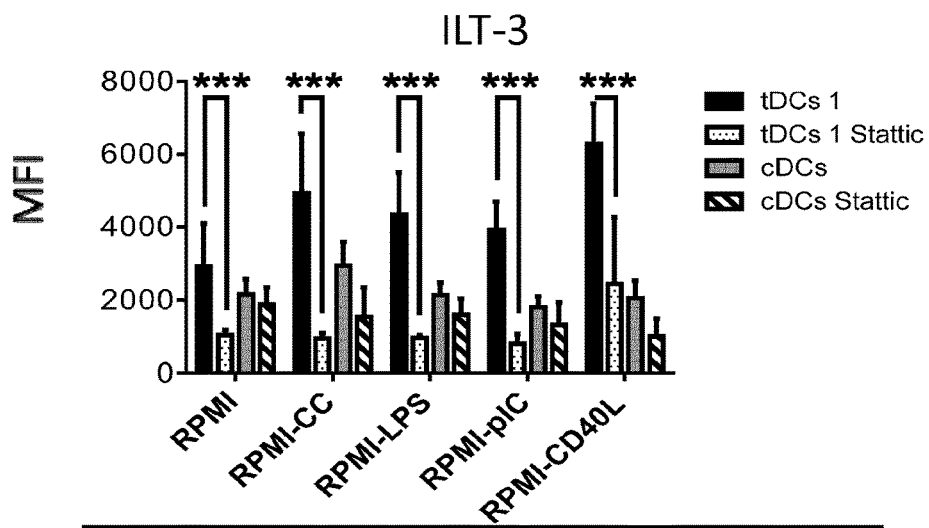

Next, the relative contribution of MAPK and NF-κB signaling pathway on the levels of IL-10 and IL-12 production and the expression of tolerogenic markers in response to LPS, CC, poly(I:C) and CD40L in the presence of p38 MAPK, JNK1/2, ERK1/2, and NF-κB inhibitors SB203580, SP600125, PD98059 and Bay 11-7082, respectively, were assessed (FIG. 11C (1-6) and 11D (1-3)). The production of IL-10 was significantly dependent on p38 MAPK, JNK/SAPK, ERK1/2 and NF-κB activation pathway after CC, LPS and CD40L restimulation in tolDC 1, however the same situation only after LPS triggering in control DC was observed (FIG. 11C (1-6)). On the other hand, p38 MAPK and NF-κB inhibitor markedly down-regulated IL-12 production in control DC after RPMI, LPS and CC triggering, but did not changed IL-12 production in tolDC 1. In terms of tolerogenic molecule expression, tolDC 1 expressed ILT-3 and PD-L1 molecule in p38 MAPK dependent manner in all the conditions tested or after CC and LPS trigger, respectively, in contrast to control DC. ERK1/2 inhibitor down-regulated PD-L1 expression after LPS trigger in tolDC 1 as well as control DC. Other inhibitors tested had no significant effect on IL-12 production (FIG. 11C (1-6)) and ILT-3 and PD-L1 expression in both types of DC (data not shown).

mTOR and STAT-3 are Markedly Up-Regulated in tolDC 1 after Restimulation and Supports Tolerogenic Properties of tolDC 1:

Recently, mTOR was found to coordinate pro-versus anti-inflammatory events in human DCs by attenuating NF-κB and up-regulating STAT3 activity (Weichhart et al. 2008, Immunity 29: 565-577). Western blot analysis revealed that tolDC 1, in contrast to control DC, markedly up-regulated phosphorylation of mTOR and STAT3 molecules after restimulation with CC, LPS, poly(I:C) and CD40L. mTOR phosphorylation led to phosphorylation of p70S6K, and mTOR dependent event, that was confirmed by using mTOR specific inhibitor rapamycin (FIG. 12A). To further corroborate the link between mTOR and STAT3 activation and IL-10, IL-12 production as well as ILT-3 and PD-L1 molecules expression, blocking experiments of mTOR and STAT3 using chemical inhibitors rapamycin and Stattic-3, respectively, were performed. Treatment of tolDC 1 with mTOR inhibitor rapamycin and STAT3 inhibitor Stattic reduced IL-10 production (FIG. 12B). Rapamycin and Stattic down-regulated IL-10 production after LPS restimulation in control DCs (FIG. 12B). However, in contrast to control DCs, where rapamycin treatment markedly increased IL-12 production after CC and LPS treatment, rapamycin was not able to restore IL-12 production in all the restimulated tolDCs 1 (FIG. 12B). IL-12 production was unaffected after Stattic treatment in both DCs tested (FIG. 12B). Furthermore, expression of tolerogenic markers ILT-3 and PD-L1 were reduced in tolDCs after rapamycin and Stattic treatment suggesting mTOR and STAT3 activation plays a role in maintaining tolerogenic properties of tolDCs (FIG. 12C (1-4)).

Figures 1, 13A:
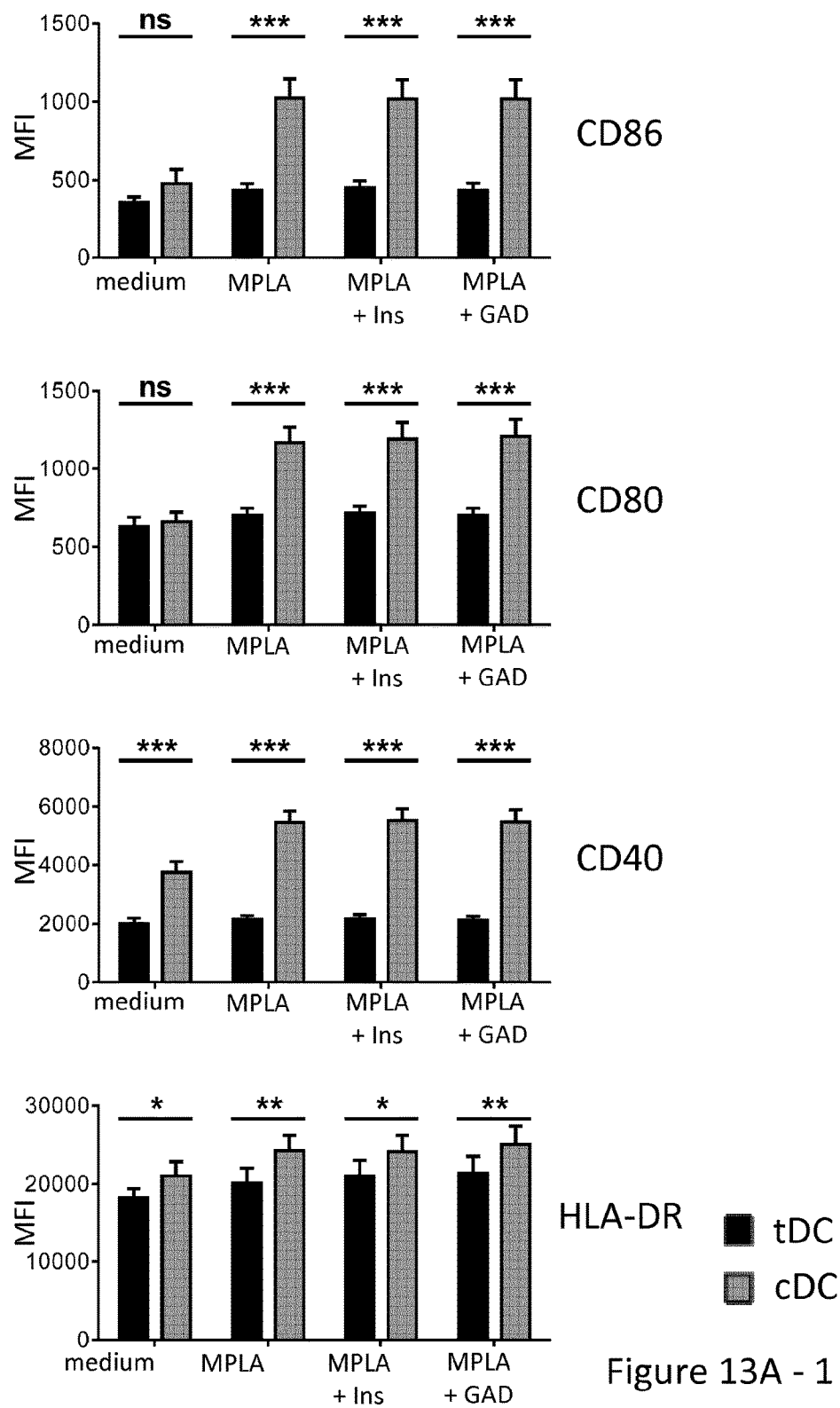
Figures 2, 13A:
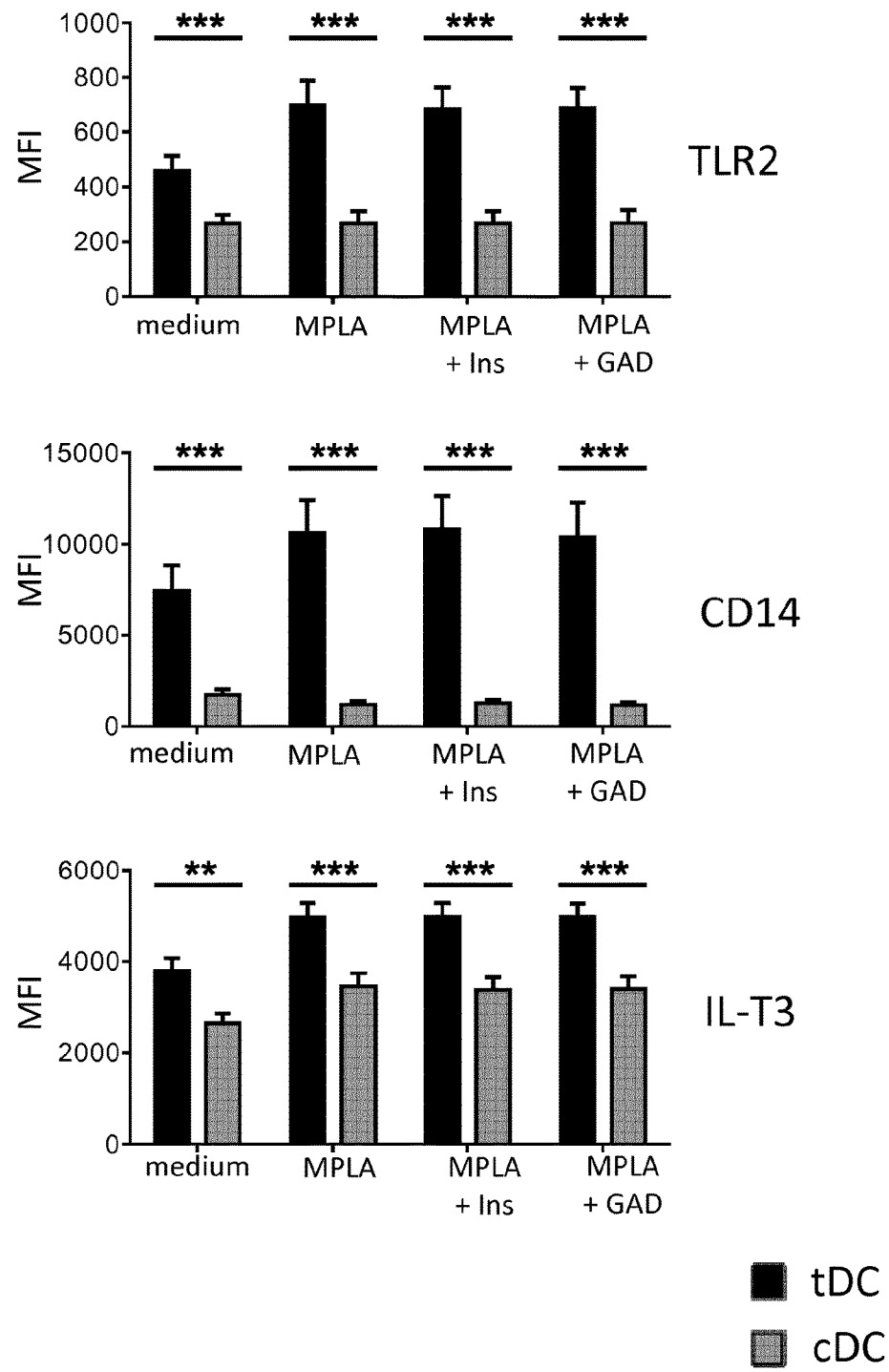
Figures 3, 13A:
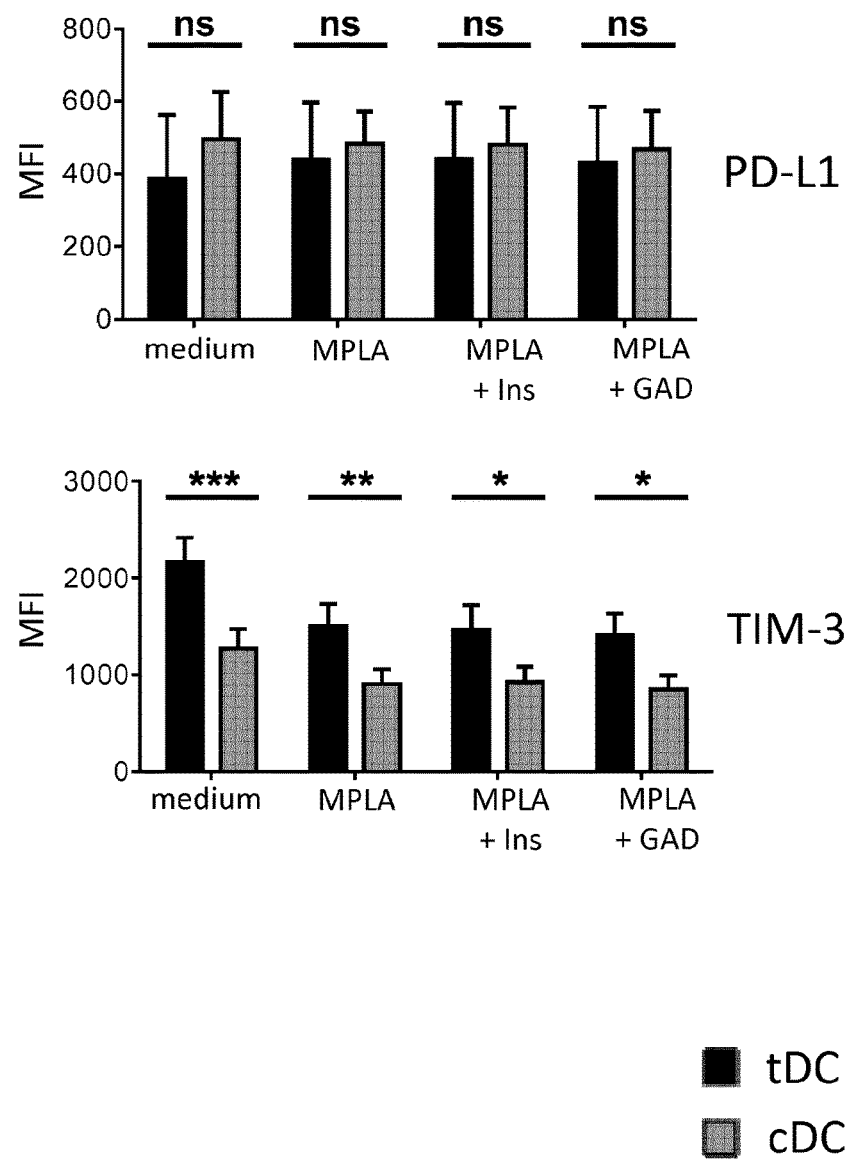
Figures 1, 13B:
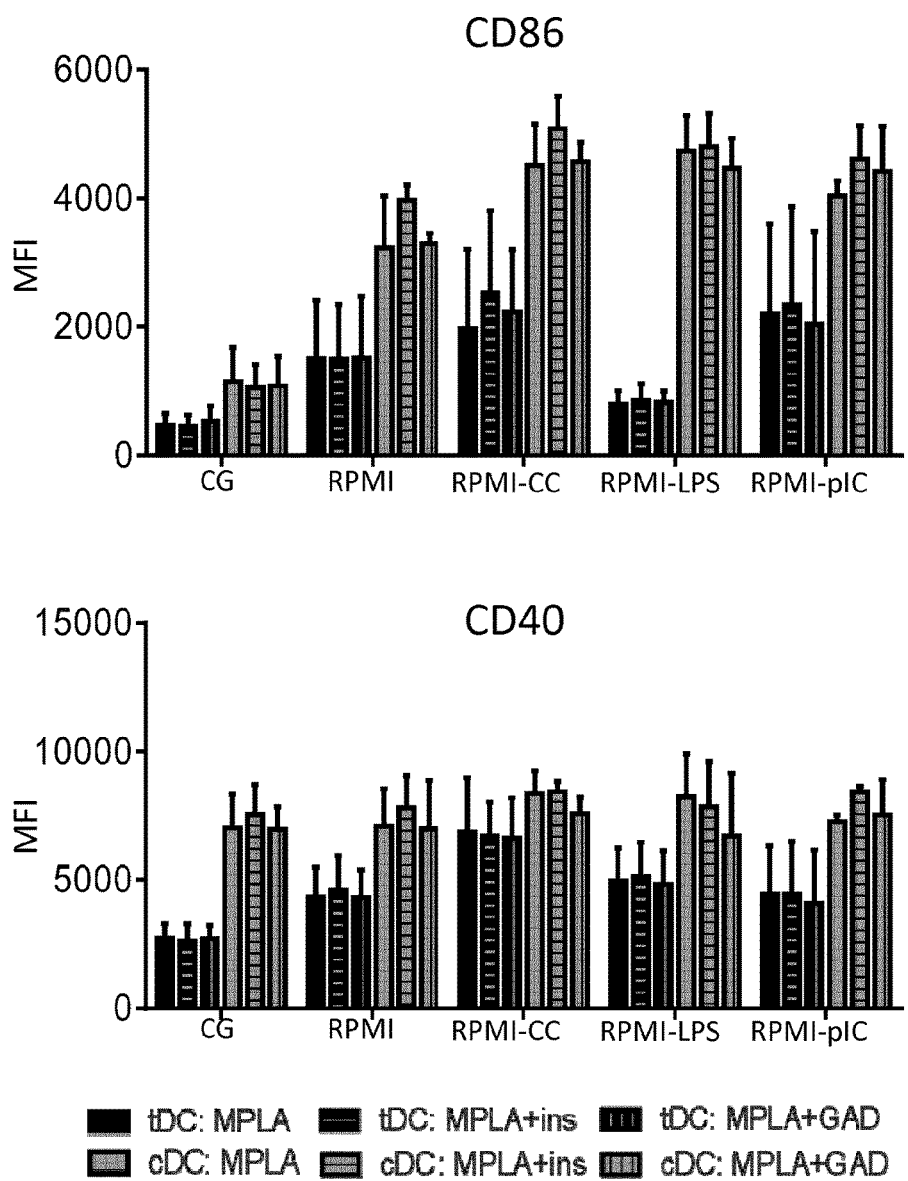
Figures 2, 13B:
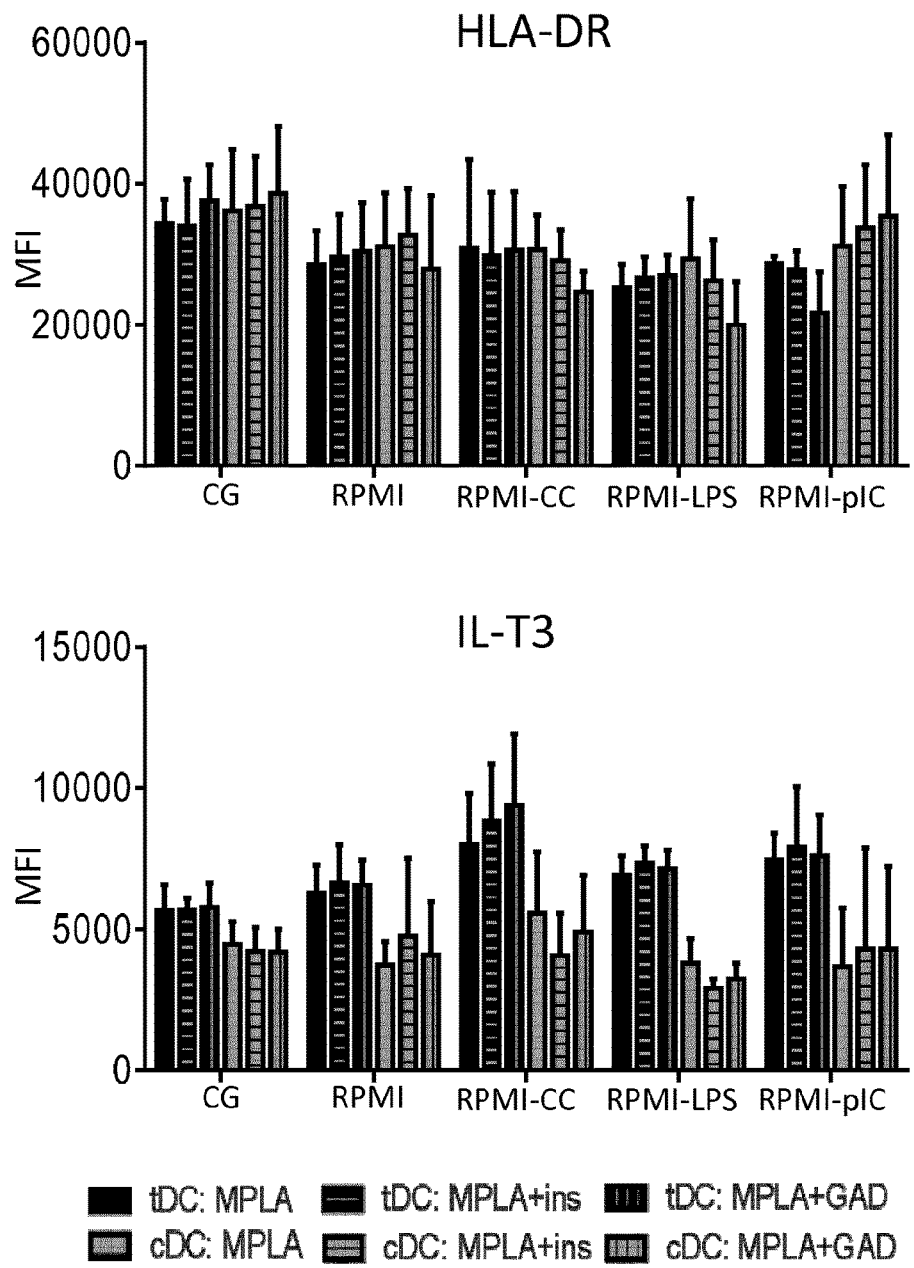

Tolerogenic DC Established from T1D Patients Exhibit a Stable Semi-Mature Phenotype:

The surface phenotype of tolDC 1 from type 1 diabetes patients, established using the cGMP medium CellGro, VitD2, DEX and maturation factor MPLA, as compared with control DC was investigated. Before final maturation, DCs were loaded with GAD65 (5 ug/ml) or insulin (1 ug/ml). As shown in FIG. 13A (1-3) and B (1-2), tolDC 1 cultured in Cell Gro exhibited a semi-mature phenotype with significantly lower surface levels of CD86, CD80, CD40 and HLA-DR expression in comparison with control DC. In contrast, tolDC 1 upregulated the expression of TLR-2, CD14 and inhibitory molecules Tim-3 and ILT-3. The expression of tolerogenic marker PD-L1 on tolDC 1 was not altered. Secondary restimulation with cytokine cocktail, LPS or poly(I:C) led to a slight upregulation of CD86 and CD40 on tolDC 1, however, it remained lower when compared to their non-tolerogenic counterparts. Moreover, the levels of tolerogenic marker ILT-3 remained higher or even increased after secondary rechallenge with maturation stimuli.

Tolerogenic DC Established from T1D Patients Reduce IFNγ Secretion from Autologous T Cells:

In patients with T1D, spontaneous production of IFNγ in T cells incubated with DC treated with MPLA only was present at similar, very low levels (for tolDC 2±1 spots per $3 \times 10^5$ T cells; for cDC 5±1 spots per $3 \times 10^5$ T cells) (FIG. 14). In the presence of insulin or GAD65 protein, however, there were major differences in responsiveness between T cells cultivated with tolDC 1 or cDC (FIG. 14). IFNγ responses to GAD65 presented by control DC were seen in the majority of patients (n=7/11; on average 20±5 spots per $3 \times 10^5$ T cells) and were markedly reduced when T cells were incubated with tolDCs 1 (on average 2±1 spots per $3 \times 10^5$ T cells). Cultivation of T cells with cDC loaded with insulin led to production of IFNγ in cells from 3/11 patients (on average 13±1 spots per $3 \times 10^5$ T cells) and was decreased when T cells were cultivated with tolDCs 1 loaded with insulin (on average 2±1 spots per $3 \times 10^5$ T cells).

6.3 Discussion

Administration of stable tolDCs resistant to subsequent activation by an inflammatory signal(s) is a prerequisite for achieving downregulation of pathologic immune reactions in autoimmune diseases. This example describes the preparation of tolDCs in the presence of Dex, VitD2 and MPLA in GMP-compliant Cell Gro media and comprehensive testing of their stability after removal of tolerising factors and mimicking in vivo DC activation by LPS, a cytokine cocktail, poly(I:C) or CD40L in RPMI 1640 media with 5% AB serum.

The tolDCs 1 described herein after restimulation with LPS, CC or CD40L have a phenotypic profile of low to intermediate CD80, CD86, CD83 and CD40 expression, which is indicative of the preservation of anti-inflammatory phenotype of tolDCs. The data provided herein also demonstrates stable increased levels of inhibitory and tolerogenic markers ILT-3, TIM-3, stable high expression of TLR2 and CD14 and markedly up-regulated PD-L1 expression after mimicking in vivo tolDCs maturation. High expression of ILT-3 after treatment of DCs with VitD3 has been reported to participate in the induction of CD4$^+$FoxP3$^+$ Tregs (Manavalan et al. 2003, Transpl Immunol 11: 245-258; Penna et al. 2005, Blood 106:3490-3497). TIM-3 was shown as an inhibitory molecule on Th1/cytotoxic T cells, however the role of TIM-3 on antigen presenting cells (APC) is elusive. TIM-3 signaling in APC was initially reported to synergize with TLRs to promote inflammation (Anderson et al. 2007, Science 318: 1141-1143), however, a recent study suggested that TIM-3 serves as a negative regulator of TLR-driven IL-12 production, dependent on TIM-3 expresssion level (Zhang et al. 2012, J Leukoc Biol 91: 189-196). The tolDCs 1 described herein had high levels of TIM-3 compared to control DCs. The expression of TIM-3 by tolDCs decreased after CC, LPS or poly(I:C) stimulation. However, whether TIM-3 has the role in maintaining regulatory properties of tolDCs remains to be elucidated.

TLR-2 up-regulation on tolDCs after TLR triggering was shown to lead to an enhanced IL-10 production and a reduced proinflammatory profile (Chamorro et al. 2009, J Immunol 183: 2984-2994). Together with PD-L1, TLR-2 signaling was reported to participate in Tregs induction (Unger et al. 2009, Eur J Immunol 39: 3147-315915; Sutmuller et al. 2006, J Clin Invest 116: 485-494). The data described herein demonstrates that restimulation of tolDCs 1, especially with CC or LPS, leads to a significant up-regulation of PD-L1 expression, IL-10 production and a high capacity to induce CD4$^+$CD25$^+$FoxP3$^+$ Tregs. Therefore, the data described herein predicts that stable expression of TLR2 and up-regulation of PD-L1 after restimulation of tolDCs 1 might play a role in tolerance induction.

TolDCs 1 restimulated by inflammatory signals also maintained a stable cytokine profile with high IL-10 production, reduced TNF-α expression and virtually no IL-12 expression. These results confirm that the pattern of high IL-10 and low or no IL-12 production is the steady and intrinsic characteristic of tolDCs (Naranjo-Gomez et al. 2011, J Transl Medicine 9: 893; Chamorro et al. 2009, J Immunol 183: 2984-2994).

Next, the stability of restimulated tolDCs 1 from the functional point of view, with respect to their capacity to polarize T cells and induce Tregs was comprehensively tested. Compared to control DCs, tolDCs 1 showed a reduced ability to induce T cell proliferation in primary MLR. This feature of tolDCs 1 remains preserved even after second activation of tolDCs with all inflammatory stimuli.

The tolDCs 1 described herein were restimulated by inflammatory signals induced T cells with low IFN-γ production and high IL-10 production, by both CD8$^+$ and CD8$^+$ compartments when compared to T cell responses induced by control DCs. Similarly, stable down-regulated induction of allogeneic IFN-γ positive T cells was shown when Dex tolDCs were stimulated with heat-killed gram-negative bacteria (Cabezon et al. 2012, PloS One 7:e52456). The reduction of IFN-γ positive T cells after restimulation with concomitant stable IL-10 positive T cells might be caused by switching T cell response rather toward Th2 due to higher IL-10 production from restimulated tolDCs and control DCs (Langenkamp et al. 2000, Nature Immunology 1: 311-316).

One important and novel observation of this example is that tolDCs 1 are able to induce de novo CD4$^+$CD25$^+$FoxP3$^+$T cells even after the restimulation.

Newly, activation pathways triggered in tolDCs 1 upon mimicking subsequent proinflammatory activation were assessed. This example describes for the first time regulation of numerous activation pathways after restimulation of tolDCs in the absence of tolerogenic agents. The proinflammatory DC maturation is normally associated with the activation of numerous signaling pathways including transcription factors NF-κB and p38 MAPK (Nakahara et al. 2006, J Derm Science 42: 1-11; Katholnig et al. 2013, J Immunol 190: 1519-1527). Cell signaling events triggered in tolDCs are profoundly different and involve the activation of ERK1/2, non-canonical NF-κB pathway, STAT3 and IDO (Qian et al. 2006, Blood 108: 2307-2315; Harden et al. 2012, Immunol Invest 41: 738-764; Manches et al. 2012, PNAS 109: 14122-14127; Farias et al. 2013, CNS 19: 269-277).

The results described herein demonstrate stable down-regulated NF-κB activation in tolDCs 1 presented by abrogated phosphorylation of IκB-α. Furthermore, nuclear translocation of NF-κB subunits p65/RelA, RelB and c-Rel in tolDCs 1 maintain reduced after restimulation. These data are consistent with observation that nuclear expression of RelB as a p50/RelB heterodimer in DCs correlates with the degree of maturation (Scheinman et al. 1995, Mol Cel Biol 15: 943-953). As c-Rel plays a role in IL-12 production (Grumont et al. 2001, J Exp Med 194: 1021-1032), down-regulated levels of c-Rel in Dex/VitD2 tolDCs 1 reflect their abrogated ability to produce IL-12 even after secondary stimulation when the tolerogenic agents are absent. High levels of p50 in nucleus of tolDCs can reflect the fact that p50 homodimers serve as transcriptional activators of IL-10 (Cao et al. 2006, J Biol Chem 281: 26041-26050). The link between high levels of p50 and high production of IL-10 in tolDCs can be supported by strong reduction of IL-10 production after treatment with NF-κB inhibitor Bay reported previously to block phosphorylation of p50 (Lee at al. 2012, Med Inflamm 2012: 416036).

The data described herein supports the use of a distinctive MAPK activation pathway in tolDCs vs control DCs after restimulation with inflammatory stimuli. In tolDCs 1, activation of p38 MAPK after restimulation is low compared to control DCs. However, the experiments with p38 MAPK inhibitor show that p38 MAPK plays an important role in IL-10 production and expression of tolerogenic molecules ILT-3 and PD-L1 in tolDCs. In contrast, p38 MAPK is markedly activated in control DCs after restimulation and controls mainly IL-12 production, but had no significant effect on expression of tolerogenic molecules. These data suggest the distinct role of p38 MAPK in tolerogenic vs proinflammatory maturation. The role of p38 MAPK in tolerogenic maturation was reported by the fact that PD-L1 expression is regulated in p38/cytokine/STAT3-dependent manner (Wolfle et al. 2011, Eur J Immunol 41: 413-424).

The data also shows that ERK1/2 was markedly phosphorylated after restimulation with all stimuli tested in tolDCs but only after LPS restimulation in control DCs. This might correlate with marked up-regulation of IL-10 production in these stimulatory conditions. The blocking experiments with ERK1/2 inhibitor PD98059 confirmed the role of ERK1/2 in IL-10 production after inflammatory trigger in tolDCs and support reportedly linked ERK1/2 activation with IL-10 secretion (Saraiva et al. 2010, Nature Immunol 10: 170-181).

Next, the data demonstrates that tolDCs 1 express high levels of IDO that remains stable even after restimulation. As expression of IDO in tolDCs and the ensuing production of tryptophan metabolites has been shown to induce direct suppression of effector T-cell activity and concurrent expansion of Tregs (Harden et al. 2012, Immunol Invest 41: 738-764; Manches et al. 2012, PNAS 109: 14122-14127; Farias et al. 2013, CNS 19: 269-277), stable IDO expression might support tolerogenic properties of tolDCs 1.

Finally, the data demonstrates that the activation of mTOR and STAT3 molecules participate in maintaining of tolerogenic properties of tolDCs 1 after restimulation. Blocking experiments with a specific inhibitor of mTOR and STAT3 led to decreased IL-10 production and down-regulation of ILT-3 and PD-L1 expression in tolDCs. Recently, JAK/STAT signaling pathway was shown to be involved in PD-L1 expression in APCs (Song et al. 2014, Int Immunopharmacol 20: 117-123). The data described herein are consistent with observation that mTOR acts as early regulator of IL-10 and IL-12 production in APCs (11). However, inhibition of mTOR had no effect on IL-12 production in tolDCs 1 after restimulation, in contrast to control DCs.

Taken together, the results described herein demonstrates that clinical grade tolDCs 1 maintain stable phenotypic and functional properties even upon stimulation with a variety of biologically relevant inflammatory stimuli in the absence of tolerising factors. Furthermore, tolerogenic and control DCs employ distinctive activation pathways after restimulation with inflammatory stimuli. Tolerogenic DCs employ p38 MAPK, ERK1/2, IDO, mTOR and STAT3 to maintain their tolerogenic properties in contrast to control DC characterized by strong activation of p38 MAPK and NF-κB. Distinct pattern of signaling pathways triggered by inflammatory stimuli can also serve as a feasible test that would distinguish inflammatory and tolerogenic DC in culture. This example provides a rationale for using Dex/VitD2 tolDCs (e.g., tolDCs 1) in clinical settings, such as in autoimmune diseases or transplantation (e.g., graft rejection or graft-versus-host disease).

7. EXAMPLE 2

This example demonstrates that tolerogenic DCs (tDCs) generated using dexamethasone and vitamin D2 are stable phenotypically and functionally even upon stimulation with a variety of biologically relevant inflammatory stimuli in the absence of tolerising factors. This example further demonstrates that stability of tDCs in the inflammatory environment is regulated by multiple signaling pathways.

7.1 Materials and Methods:

Reagents and Abs:

Flow cytometry: commercial antibodies anti-CD86-FITC (clone 2231 FUN-1), CD274 (PD-L1)-FITC (clone MIH1), CD273 (PD-L2)-PE (clone MIH-18), HLA-DR-PE-Cy7 (clone L243), IFN-γ-FITC (clone 4SB3) were purchased from BD Biosciences; CD83-PerCP-Cy5.5 (clone HB15a) was purchased from Beckman Coulter; CD80-FITC (clone MAB104), CD40-PerCP-eFluor710 (clone 5C3), CD1a-PE-Cy7 (clone HI149) and CD4-PE-Cy7 (clone RPA-T4) were purchased from eBioscience; TLR2-FITC (clone T2.5), TIM-3-PE (clone F38-2E2), IL-10-PE (clone JES3-9D7), KI-67-PE (clone Ki-67) were purchased from BioLegend; CD14-PE-DL594 (clone MEM-15), CD11c-APC (clone BU15), CD3-AF700 (clone MEM-57), CD8-PE-Dy590 (clone MEM-31) were purchased from Exbio; CD85k (ILT-3)-PE (clone 293623), CD85d (IL-T4)-FITC (clone 287219) were purchased from R&D Systems. For western blot, anti-p-p38 MAPK, anti-p-ERK1/2, anti-p-JNK/SAPK, anti-p-IκB-α, anti-IDO, anti-p-mTOR, anti-p-STAT3, anti-p- p70S6K, anti-p38 MAPK, anti-ERK1/2, anti-JNK/SAPK and anti-STAT3 Ab were purchased from Cell Signaling Technology; anti-actin was from BioLegend.

DC Differentiation, Stimulation and Inhibition:

Immature DCs were obtained from buffy coats of healthy donors as previously described [Palova-Jelinkova L, Rozkova D, Pecharova B, Bartova J, Sediva A, Tlaskalova-Hogenova H, Spisek R, Tuckova L: Gliadin fragments induce phenotypic and functional maturation of human dendritic cells. J Immunol 2005; 175:7038-7045]. Briefly, human peripheral blood mononuclear cells (PBMC) were isolated by Ficoll gradient and monocytes were separated by allowing 2 h of cell adhesion in 75-cm$^2$ culture flasks (Nunc). DCs were generated by culturing monocytes for 6 days in GMP-grade Cell Gro DC medium (CellGenix) containing penicillin and streptomycin (100 U/ml and 100 µg/ml, respectively, Gibco) in the presence of GM-CSF (500 IU/ml, Gentaur) and IL-4 (20 ng/ml, CellGenix). Medium and cytokines were replenished on day 3. On day 6, DCs were harvested and seeded in 96-well plates (Nunc) at $1\times10^6$ cells/ml. On day 7, immature DCs were activated with vacci grade MPLA (2 µg/ml, Cayla-InvivoGen) for 24 hrs. To induce tDCs, DCs were treated with Dex on day 3 (1 µM, Medochemie) and Dex and VitD2-paricalcitol (1.5 ng/ml, Zemplar, Abbott Laboratories) on day 6. Control DCs (cDCs) were cultured without tolerising factors. For restimulation assays, tDCs and cDCs were washed and recultured in complete RPMI medium (Gibco) containing 5% human AB serum (Invitrogen) in the absence of tolerising factors for 24 h, with or without LPS (1 µg/ml, Sigma-Aldrich), polyI:C (25 µg/ml, Cayla-InvivoGen), megaCD40L™ (1000 ng/ml, Enzo Life Sciences) or mixture of pro-inflammatory cytokines containing IL-1β, TNF-α, IL-6 (all 10 ng/ml) and IFN-γ (100 ng/ml) (all from R&D systems). Signaling inhibitors were added 1 h before the start of experiments under the specified stimulation conditions. SB203580 (p38 MAPK inhibitor at 10 µM), SP600125 (JNK/SAPK inhibitor at 20 µM), PD98059 (ERK1/2 inhibitor at 20 µM), Bay 11-7082 (NF-κB inhibitor at 10 µM), Stattic (STAT3 inhibitor at 5 µM) and rapamycin (mTOR inhibitor at 100 nM) were obtained from Calbiochem and dissolved in dimethyl sulfoxide. Supernatants and cells were collected for further analysis.

Flow Cytometry:

Cells ($2\times10^5$/well) were stained with fluorochrome-conjugated mAbs for 30 min at 4° C. in PBS, washed and analysed on LSR Fortessa cell analyzer (BD Biosciences). Appropriate isotype controls were included. Data were analyzed using FlowJo software (Tree Star). DCs were gated according to the forward scatter, side scatter and CD11c+ parameters for analysis. Dead cells were excluded from the analysis based on DAPI (4',6-diamidin-2-fenylindol) staining. For intracellular cytokine staining, T cells were stimulated with phorbol 12-myristate 13-acetate (PMA) (50 ng/ml, Sigma-Aldrich) plus ionomycin (1 µg/ml, Sigma-Aldrich) for 4-16 h in the presence of Brefeldin A (5 µg/ml, BioLegend) before analysing. After stimulation, cells were washed, incubated in Fixation/Permeabilization Buffer (eBioscience) for 30 min at 4° C., then washed in Permeabilization Buffer (eBioscience) and stained with appropriate monoclonal antibody (mAb) for 30 min at 4° C.

DC Cytokine Production:

Cell supernatants were harvested after 24 h of DC stimulation and frozen at −80° C. until analysis. IL-10, IL-12p70, TNF-α and TGF-β concentrations were determined using Luminex assay (MILLIPLEX™ Human Cytokine/Chemokine Kit, Merck Millipore) and ELISA assay (DuoSet ELISA Kit, R&D systems) according to the manufacturer's instructions. Cell supernatants were acidified before measuring TGF-β levels according to the manufacturer's instructions.

DCs and T Cells Cultures, Allostimulatory Assay:

T cells were obtained from PBMC non-adherent fraction. tDCs or cDCs ($2\times10^4$) were cultured with allogeneic T cells ($2\times10^5$) in complete RPMI medium (Gibco) containing 5% human AB serum (Invitrogen). IL-2 (20 U/ml, PeproTech) was added on day 2, 5 and 7. For primary mixed lymphocyte reaction (MLR) assays, allogeneic T cells ($2\times10^5$) labelled with 5 µM carboxyfluorescein succinimidyl ester (CFSE) (Invitrogen) were incubated with tDCs or cDCs ($2\times10^4$). T cell proliferation was determined by the sequential dilution of CFSE fluorescence of T cells, as detected by flow cytometry on day 6. For detection of IFN-γ, IL-10 and IL-17A production by T cells, $2\times10^4$ tDCs or cDCs were cultured with $2\times10^5$ allogeneic T cells. Cytokine production was determined by intracellular staining by flow cytometry on day 6 (IFN-γ) and day 9 (IL-10). IL-17A production from cell culture supernatants was analyzed by ELISA on day 6.

Expansion of Regulatory T Cells and Suppression Assay:

Naïve CD4+ T cells (donor A) were purified by negative selection with The EasySep™ Human Naïve CD4+ T Cell Enrichment Kit (StemCell Technologies). Naïve CD4+ T cells were plated with allogeneic human leukocyte antigen (HLA)-mismatched Dex/VitD2 tDCs (donor B) in a 10:1 ratio for 6 d in complete RPMI (5% human AB serum) in a 24-well plate. IL-2 (20 U/ml, PeproTech) was added on day 2 and 5. Next, T cells were washed and rested for 2 d with complete RPMI (5% human AB serum) and IL-2 and subsequently restimulated with Dex/VitD2 tDCs under the same condition for 5 d. After 5 days, T cells were recovered and rested for 2 days before use in the suppression assay. T cells primed for two rounds with Dex/VitD2 tDCs are referred to as Tregs. CD4+ Tregs were tested for suppressive capacity in following MLR assay. CD4+ Tregs (donor A) were labeled with Vybrant DiD cell labeling solution (5 µM, Millipore), washed and plated in a round-bottom 96-well plate coated with 1:20 000 anti-CD3 mAb (clone MEM-57) with responder T cells (donor A) and MPLA-matured cDCs (not treated with Dex and VitD2) (donor B). cDCs were from the same donor as the Dex/VitD2 tDCs used to induce Tregs. Cells were plated in a Treg/Tresp/DCs ratio of 10:10:1 or 5:10:1. As additional controls, Tresp and Tregs were cultured alone or with cDCs. After 6 d, cells were recovered and proliferation of responder cells was analyzed by measuring Ki-67 by flow cytometry. Cell culture supernatants were recovered for IL-10, IFN-γ and IL-17A analysis.

Western Blot Analysis:

Cell lysates ($2\times10^6$ DCs) were prepared from cells cultured in Cell Gro or recultured in complete RPMI alone or with cytokine cocktail, LPS, polyI:C or CD40L for 1 h as previously described [Palova-Jelinkova L, Rozkova D, Pecharova B, Bartova J, Sediva A, Tlaskalova-Hogenova H, Spisek R, Tuckova L: Gliadin fragments induce phenotypic and functional maturation of human dendritic cells. J Immunol 2005; 175:7038-7045]. When indicated, rapamycin (100 nM) was added 1 h before stimulation. Cell lysates were subjected to 10% sodium dodecyl sulfate polyacrylamide gel electrophoresis and transferred to nitrocellulose membranes before being immunoblotted with indicated specific mAbs. The membranes were revealed by horseradish peroxidase-conjugated secondary Ab (Cell Signaling Technology) using the West Femto Maximum Sensitivity Substrate (Pierce). After stripping, the membranes were reprobed with an appropriate mAb as loading control.

Preparation of Nuclear Extracts and Colorimetric NF-κB Assay:

Nuclear extracts were prepared from DCs ($2\times10^6$) cultured in Cell Gro or recultured in complete RPMI alone or with cytokine cocktail, LPS, polyI:C or CD40L for 90 min using a nuclear extract kit (Active Motif). NF-κB DNA binding activity of p50, p65/RelA, c-Rel and RelB was measured as previously described [Palova-Jelinkova L, Rozkova D, Pecharova B, Bartova J, Sediva A, Tlaskalova-Hogenova H, Spisek R, Tuckova L: Gliadin fragments induce phenotypic and functional maturation of human dendritic cells. J Immunol 2005; 175:7038-7045].

Metabolic Quantification:

lactate, glucose and lactate dehydrogenase measurements: Concentrations of lactate and glucose in DC culture supernatants were measured with Glycolysis Cell-based assay kit (Cayman Chemicals) and Glucose colorimetric assay kit (BioVision), respectively. When indicated, glycolysis was suppressed by treatment with 10 mM 2-deoxyglucose (Sigma) 1 h prior exposition of DCs cultured in Cell Gro into RPMI, LPS, CC, polyI:C or CD40L. LDH activity of the DCs extracts was measured with Lactate dehydrogenase activity assay kit (Sigma).

Statistical Analysis:

Results were obtained from at least three independent experiments and are given as mean±SEM. Two-tailed paired t-test was applied for data analysis using GraphPad PRISM 6. A value of p≤0.05 was considered statistically significant.

7.2 Results tDCs Preserved Semimature Tolerogenic Phenotype after Restimulation with LPS, CC, polyI:C and CD40L:

To study the functional properties and stability of tDCs, freshly isolated human monocytes were cultured in GMP-compliant medium Cell Gro in the presence of GM-CSF, IL-4, and tolerogenic factors Dex and VitD2. Control DCs (cDCs) were cultured without Dex and VitD2. Finally, DCs were activated with MPLA.

Figures 1, 15A:
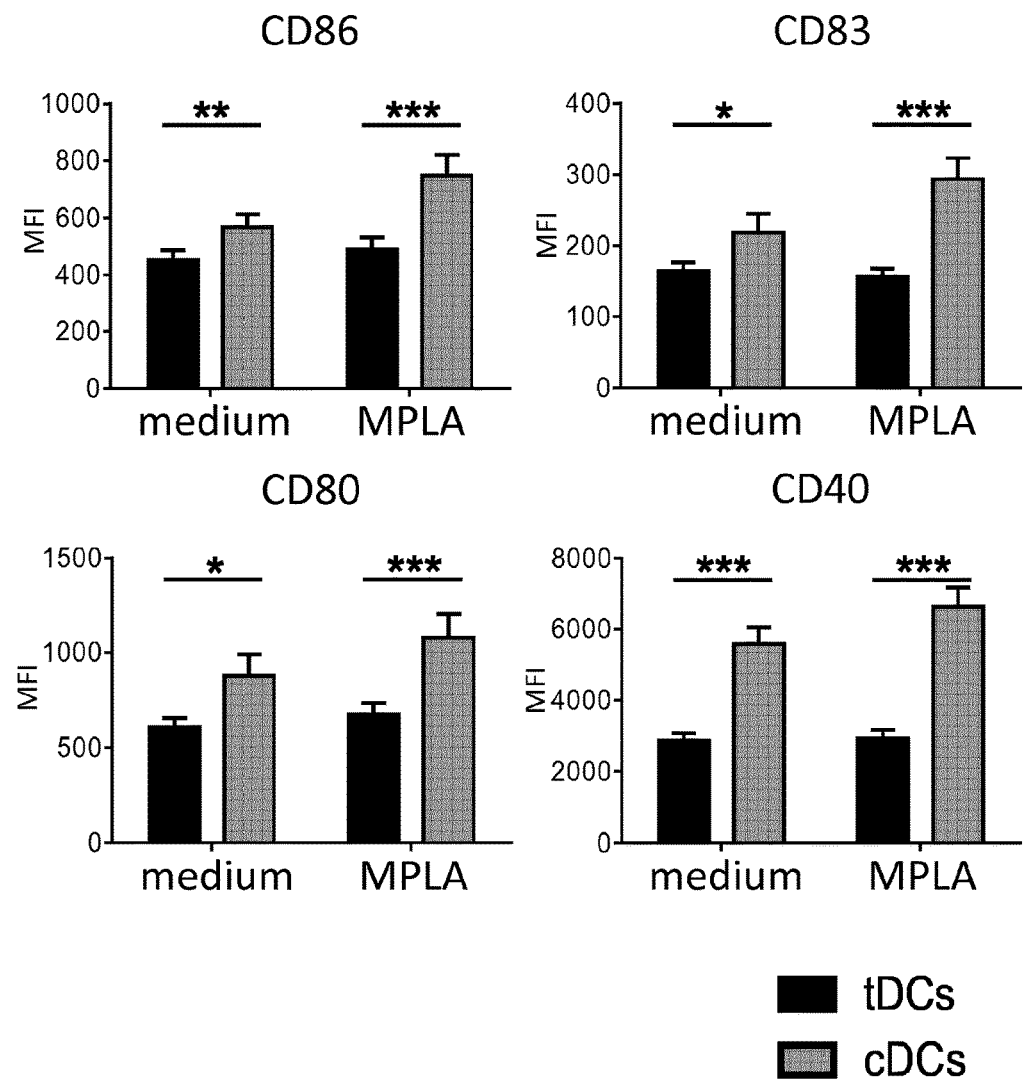
Figures 2, 15A:
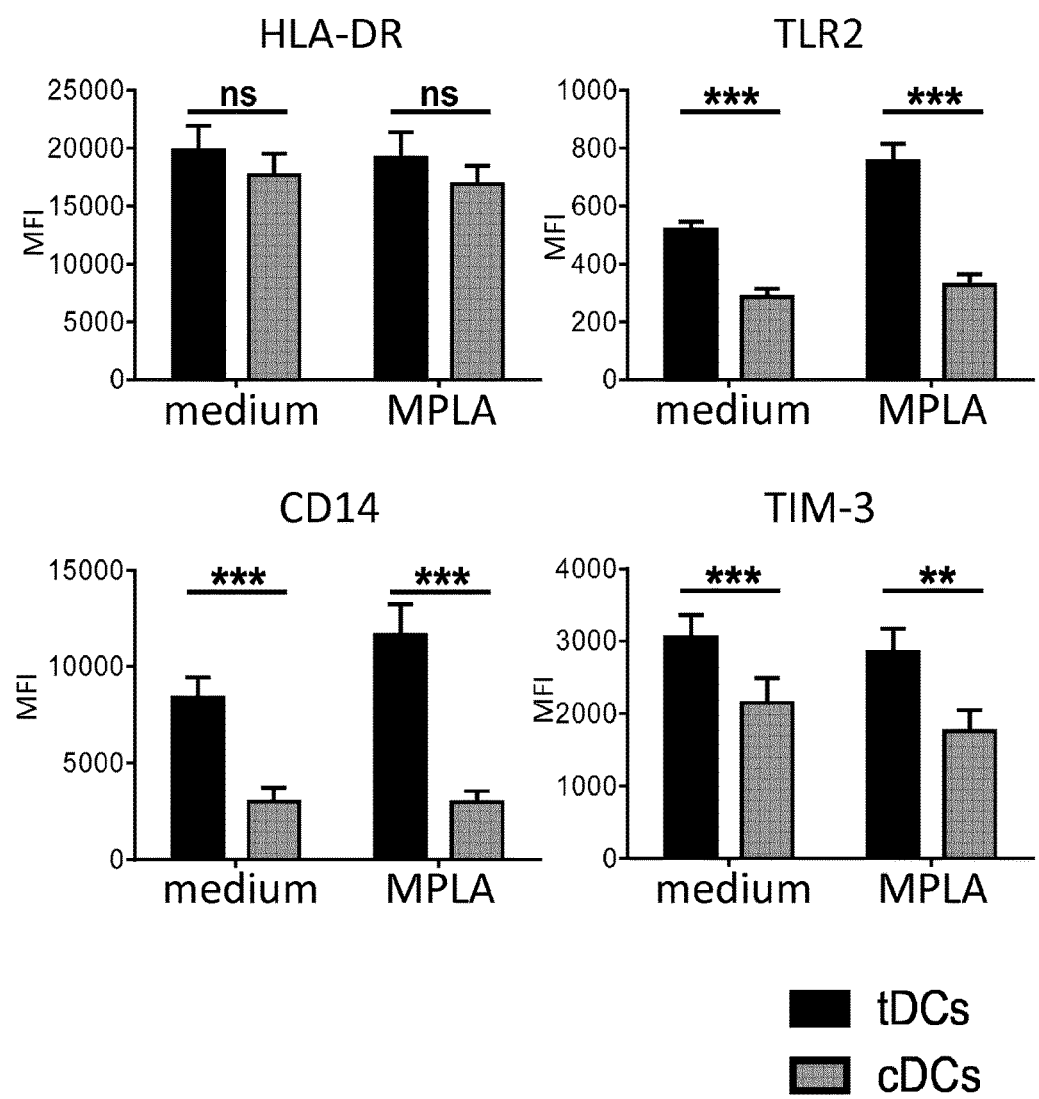
Figures 3, 15A:
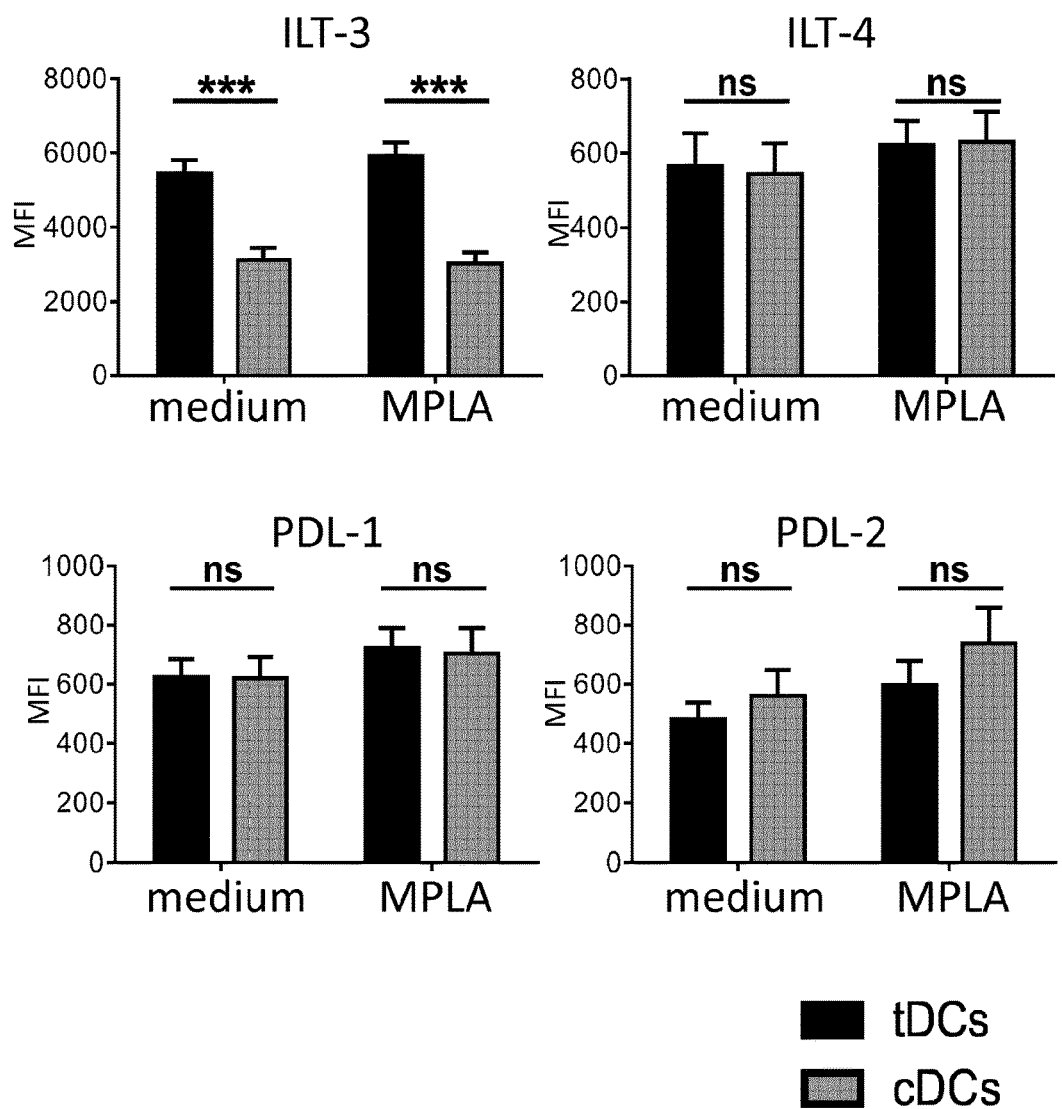
Figures 4, 15A:
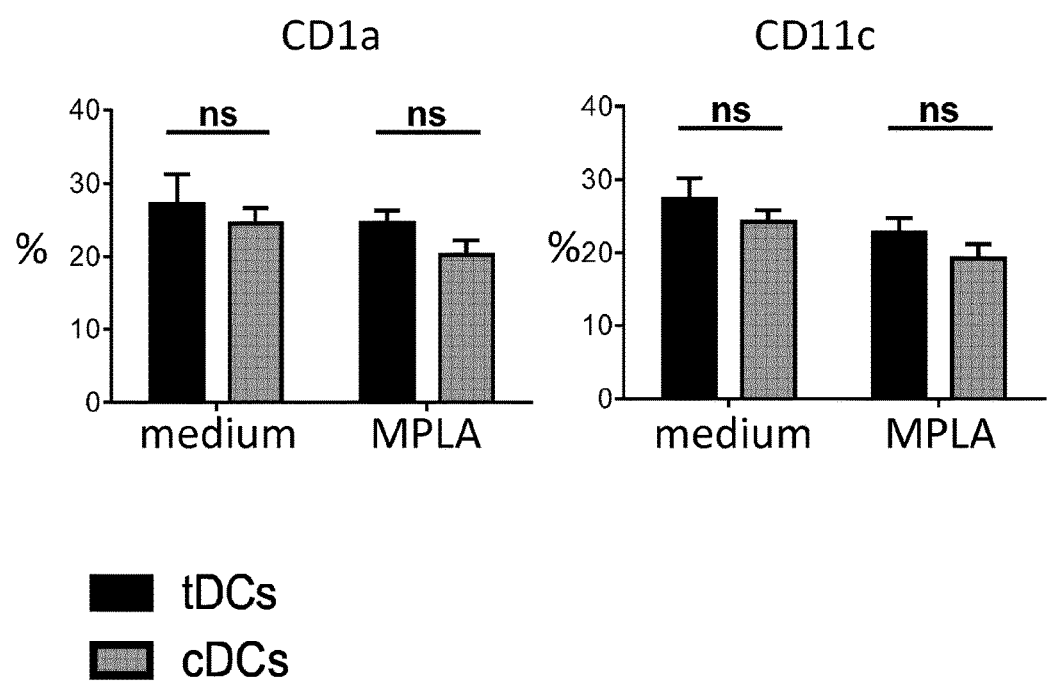
Figures 1, 15B:
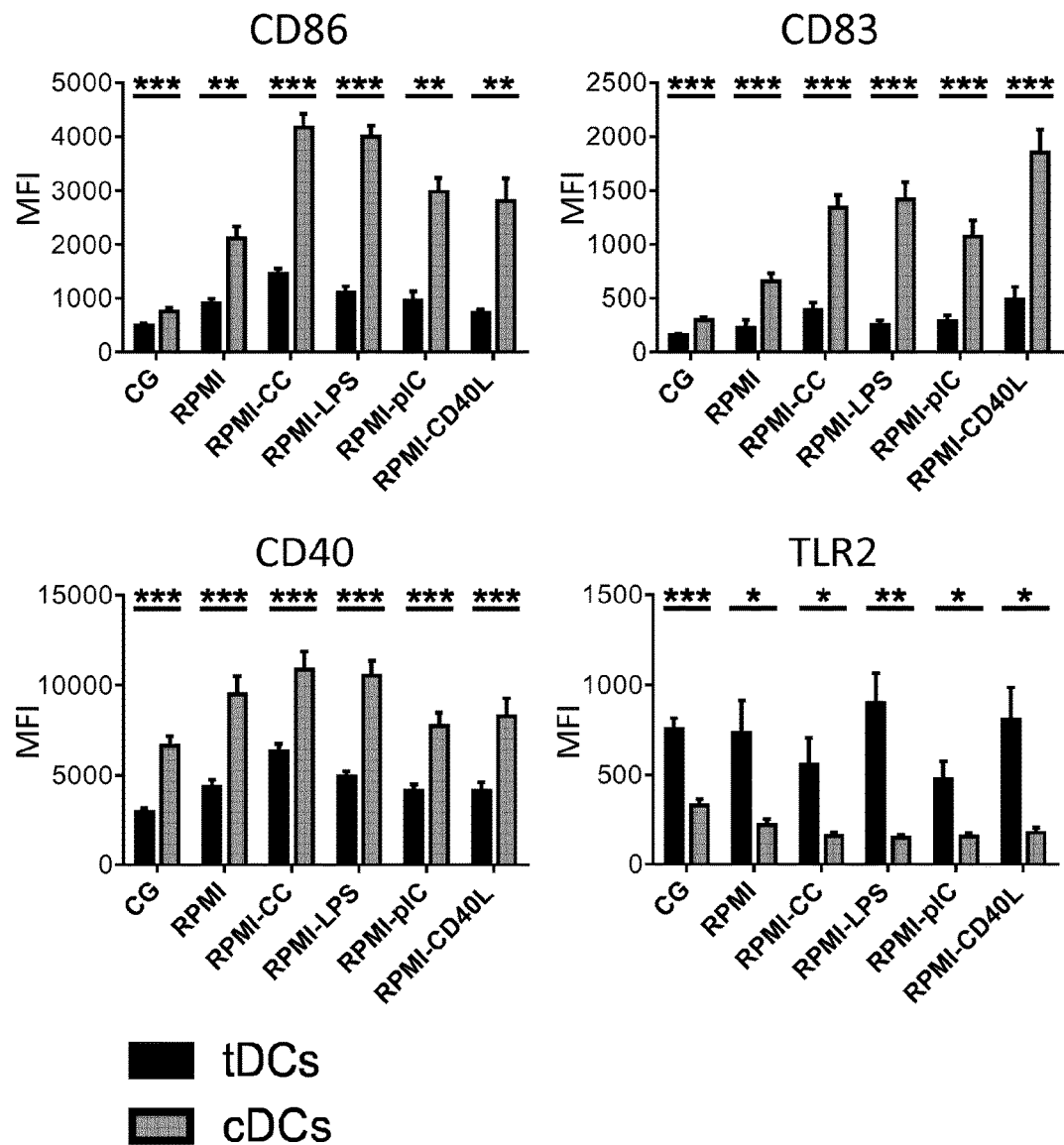
Figures 2, 15B:
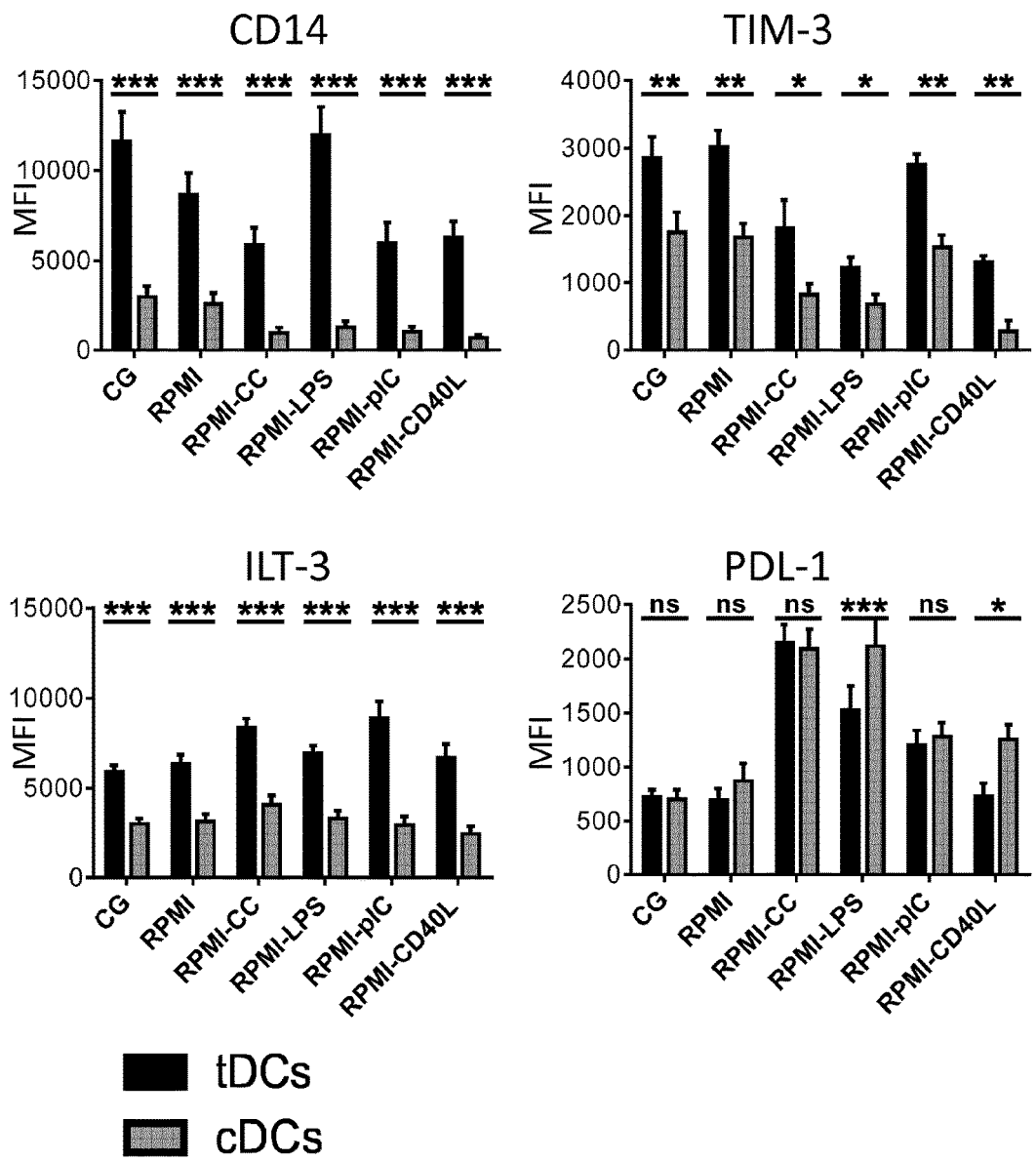

As shown in FIG. 15A (1-4), tDCs cultured in Cell Gro exhibited tolerogenic phenotype with significantly lower surface levels of CD86, CD83, CD80 and CD40 but higher levels of Toll-like receptor (TLR)-2, CD14 and inhibitory molecules TIM-3 and ILT-3 in comparison to cDCs. The level of CD1a, CD11c, HLA-DR and inhibitory molecules ILT-4, PD-L1 and PD-L2 were comparable in tDCs and cDCs. However, the ratio of PD-L1 expression over CD86 expression was higher in tolDCs than in cDCs (FIG. 32). This ratio can be used as a marker of tolerogenicity. To study the stability of DCs, cDCs and tDCs generated in Cell Gro were recultured in complete RPMI without tolerising agents and subsequently stimulated with LPS, CC, polyI:C and CD40L for 24 h (FIG. 15B (1-2)). Restimulation led to a slight upregulation of CD86, CD83 and CD40 on tDCs, however, it remained significantly lower when compared to cDCs. Importantly, the expression of TLR2, CD14 and ILT-3 on tDCs remained high after restimulation when compared to cDCs. The expression of TIM-3 decreased approximately two-fold after CC, LPS and CD40L stimulation, however, it remained higher in comparison to cDCs. The expression of tolerogenic molecule PD-L1, that was low on tDCs from Cell Gro, dramatically increased after restimulation of tDCs with CC as well as LPS and slightly after polyI:C stimulation for 24 h.

Figure 15C:
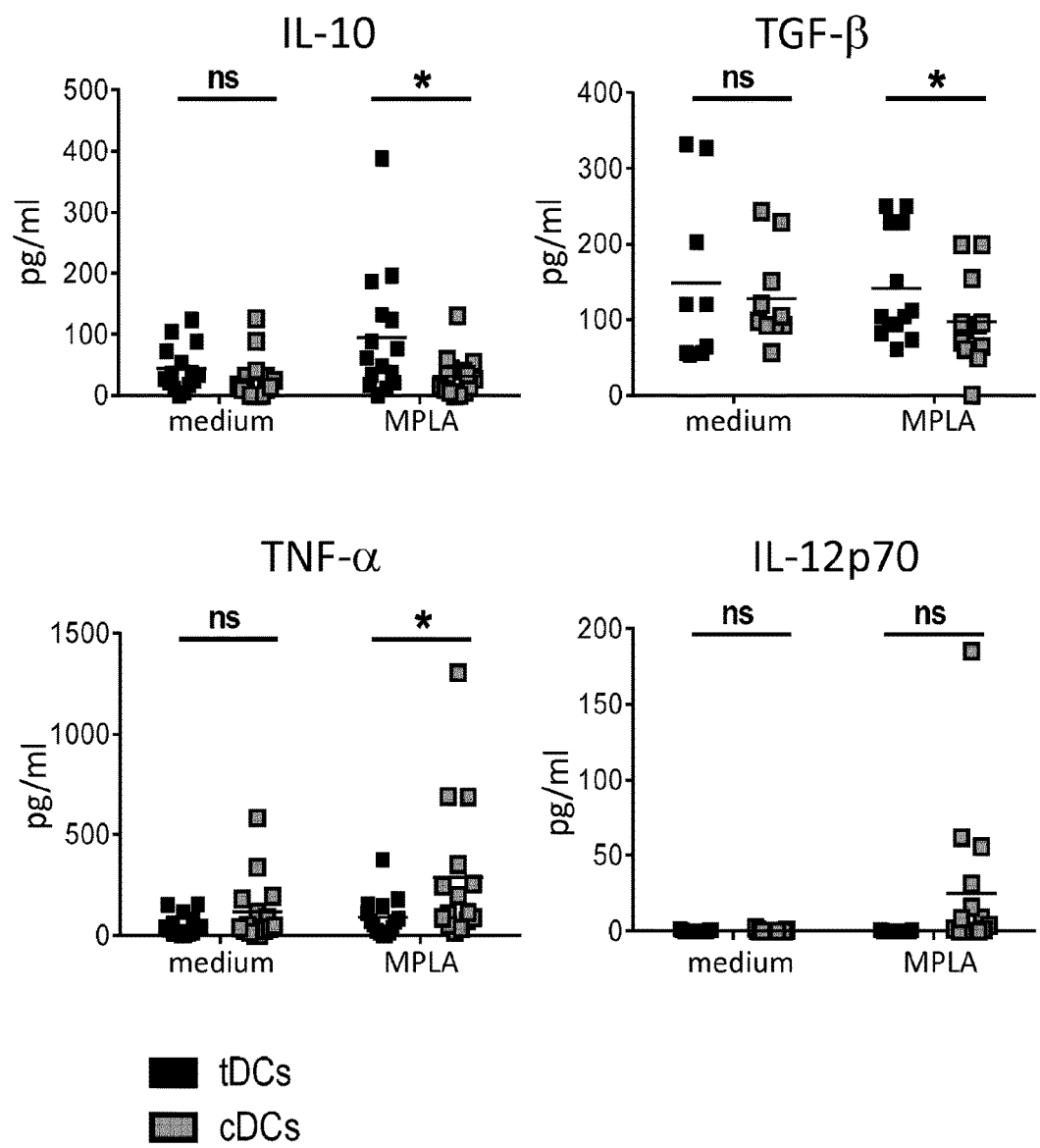
Figure 15D:
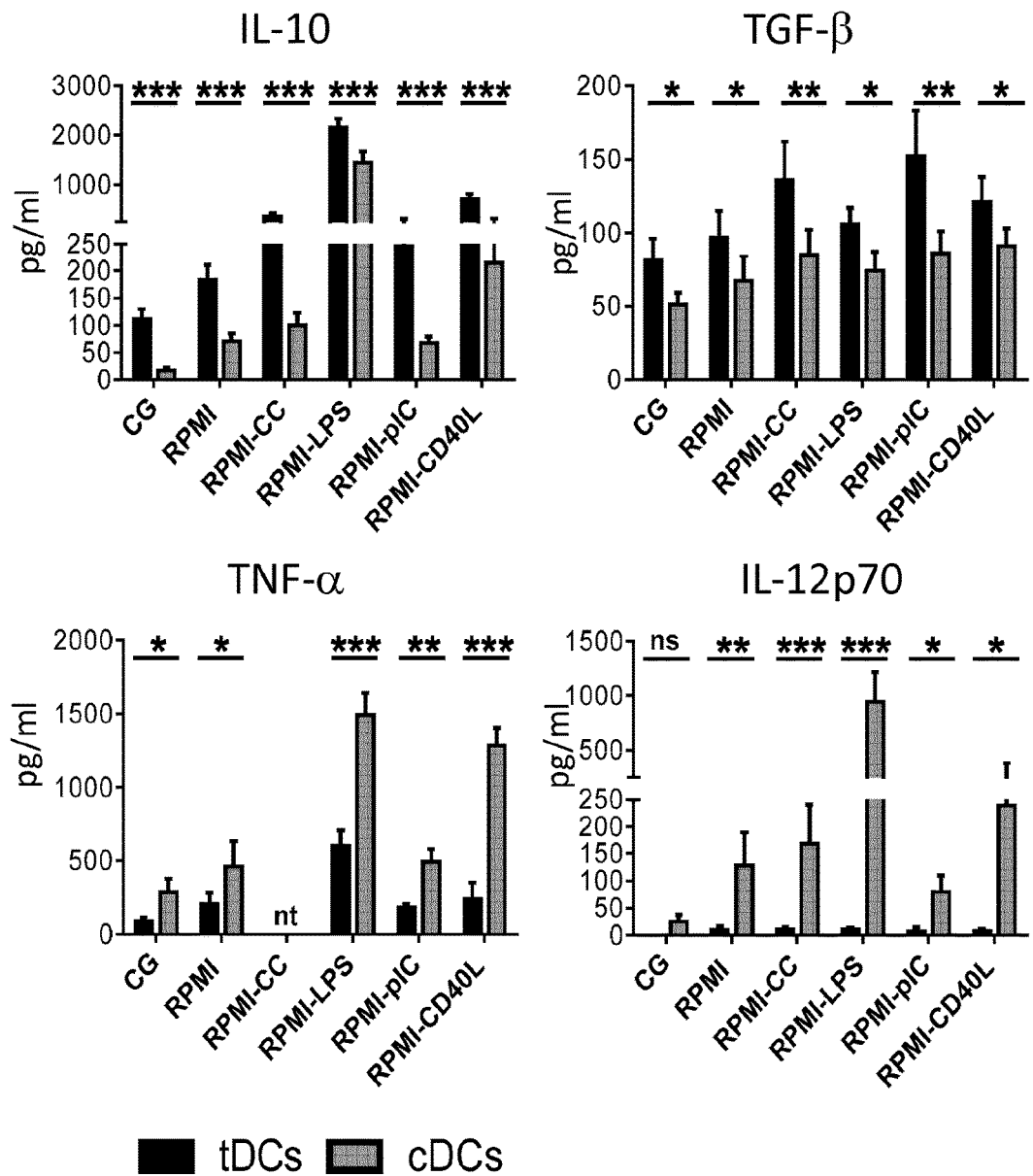

In line with tolerogenic cell-surface phenotype, tDCs produced higher levels of IL-10 and TGF-β, low quantities of TNF-α and no IL-12p70 as compared to cDCs (FIG. 15C). Subsequent restimulation of tDCs with CC, LPS, polyI:C or CD40L led to robust increase of IL-10 production, slight up-regulation of TGF-β, low production of TNF-α and minimal IL-12 production (FIG. 15D). Collectively, these data demonstrate that, in spite of the presence of maturation stimuli, Dex/VitD2 tDCs preserve non-proinflammatory profile with high expression of tolerogenic markers, high IL-10/IL-12p70 ratio and sustained TGF-β production.

Figures 16A, 16B:
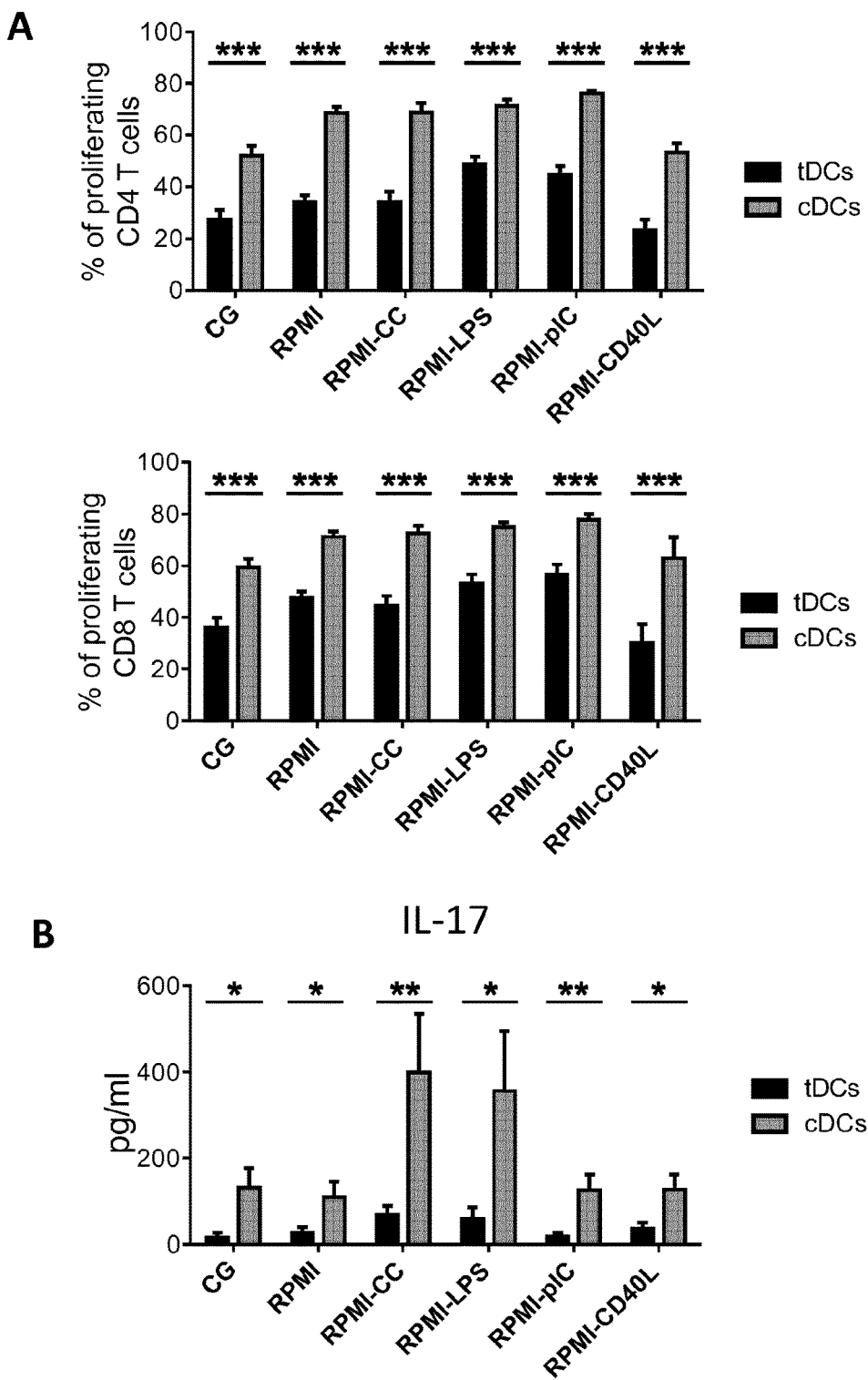
Figures 16C, 16D:
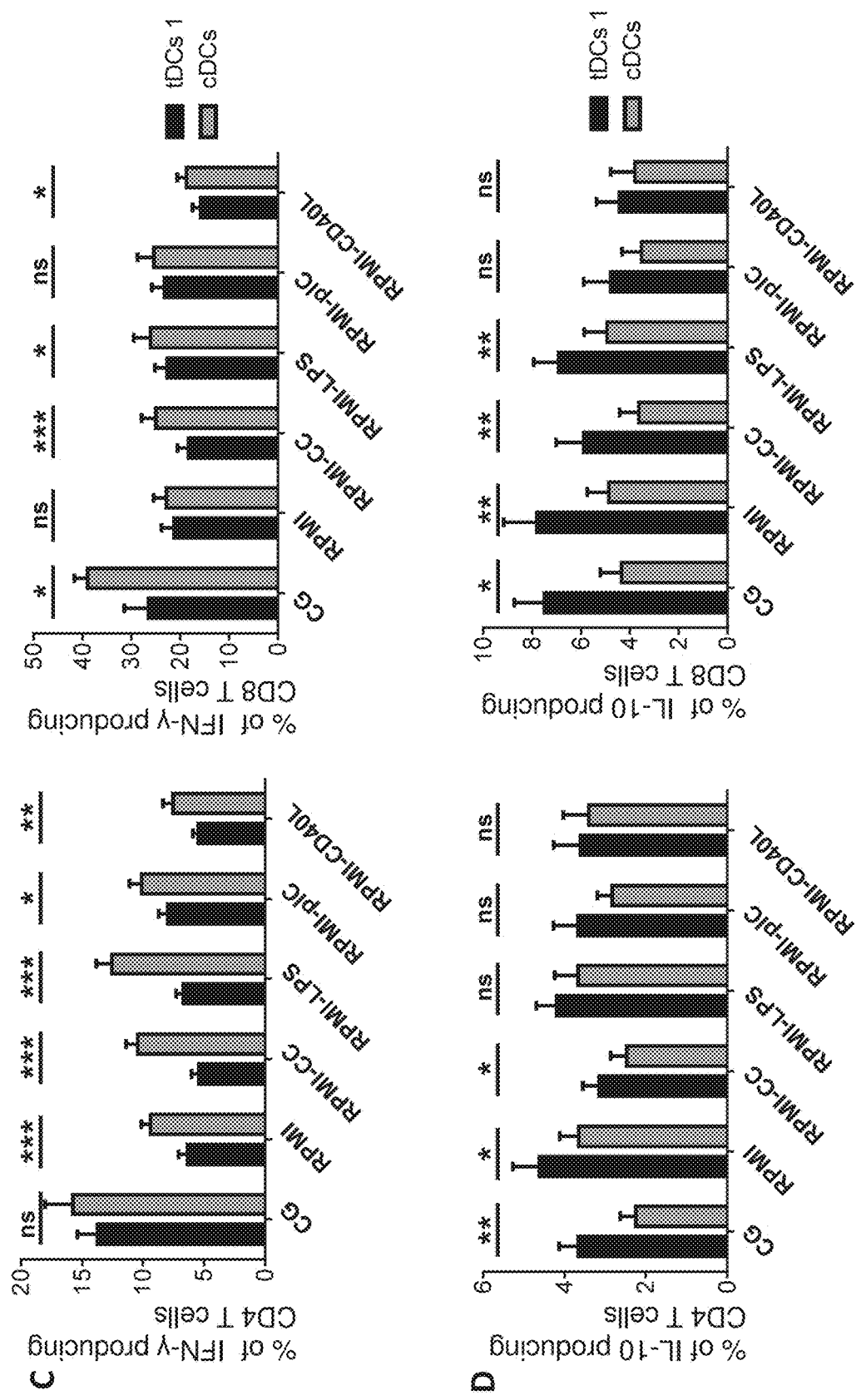

Dex/VitD2 tDCs Preserved Reduced T Cell Stimulatory Capacity after Restimulation:

TDCs or cDCs were cultured with allogeneic T cells at a ratio of 1:10. TDCs were weaker inducers of CD4+ as well as CD8+ T cell proliferation, even after the restimulation, irrespective of the maturation agent when compared to cDCs (FIG. 16A). In line with this, tDCs induced low IL-17A production by allogeneic T cells even after restimulation in contrast to cDCs that were potent inducers of IL-17A by T cells especially after CC and LPS stimulation (FIG. 16B). Moreover, co-incubation of allogeneic T cells with tDCs cultured in Cell Gro skewed the T cell cytokine profile towards reduced IFN-γ and significantly increased IL-10 production by CD4+ as well as CD8+ T cells, in comparison to cDCs (FIG. 16C, 16D). In addition, co-incubation of T cells with tDCs restimulated with CC, LPS, polyI:C and CD40L led to marked reduction of CD4+ IFN-γ producing T cells together with stable numbers of CD4+ IL-10 producing T cells. The percentage of CD8+ IFN-γ producing T cells remained stable or slightly decreased after CC and CD40L restimulation of tDCs, while the amount of CD8+ IL-10 producing T cells remained almost the same after restimulation of tDCs with LPS and slightly decreased after restimulation of tDCs with CC, polyI:C and CD40L.

Figure 17A:
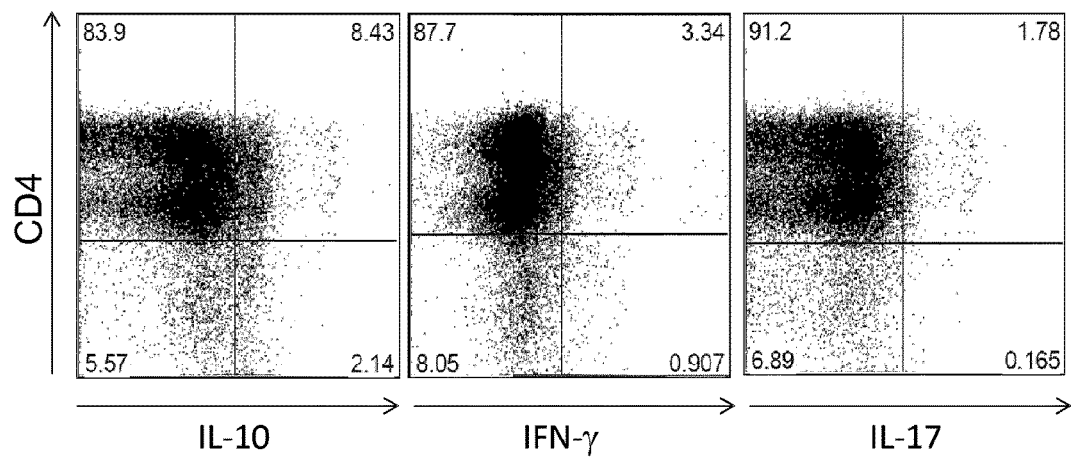
Figure 17A:
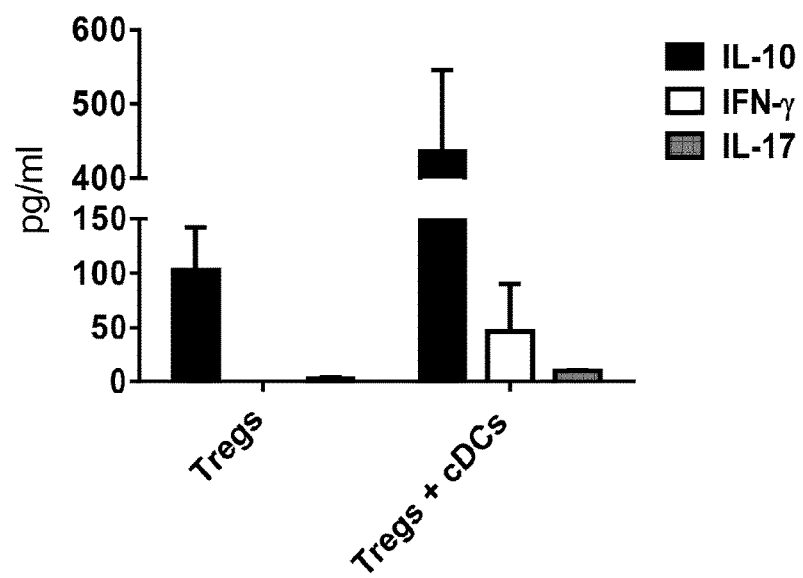
Figure 17B:
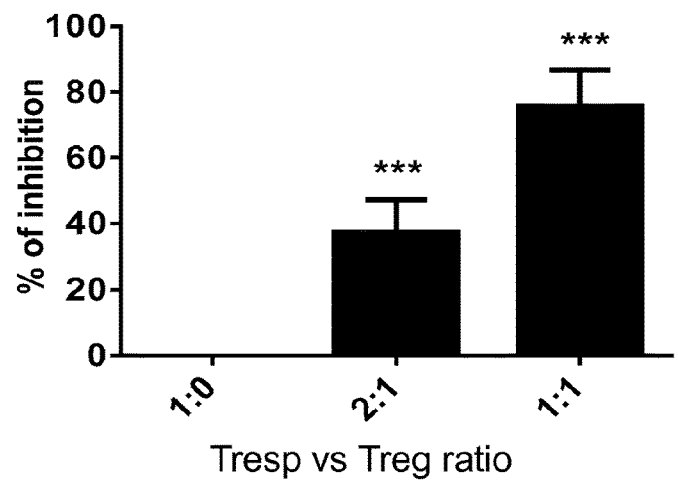
Figure 17B:
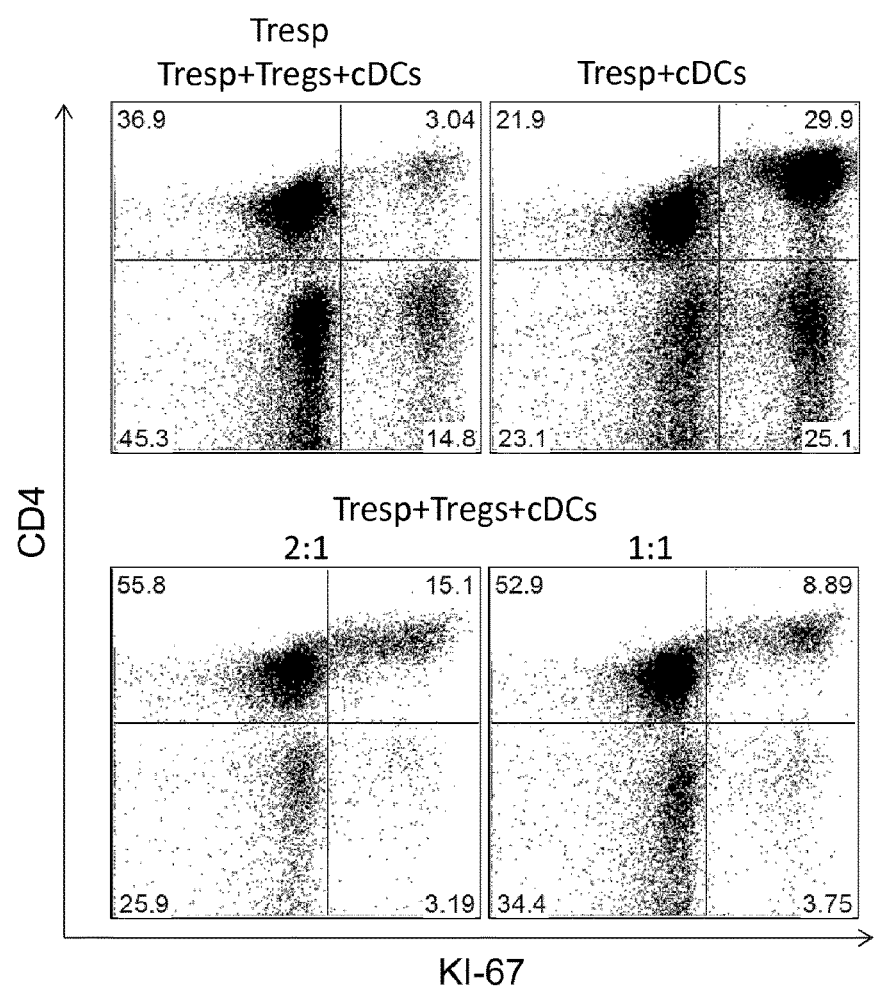
Figure 17C:
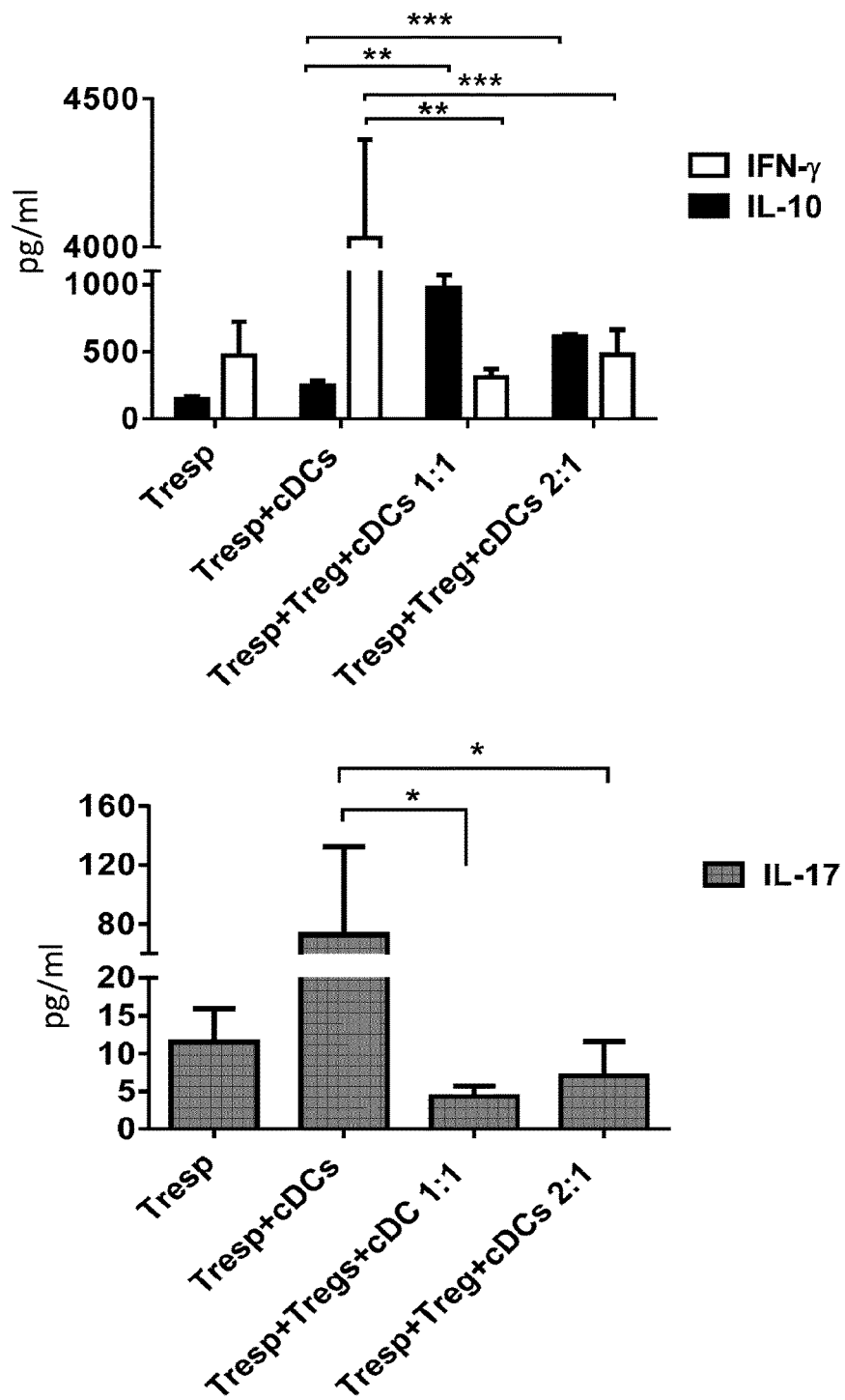

Dex/VitD2 tDCs Induced Tregs Differentiation from Naïve CD4+ T Cells:

Increased capacity to promote differentiation/induction of Tregs from naïve precursors seems to be one of the most important hallmarks of tDCs [Mahnke K, Qian Y, Knop J, Enk A H: Induction of CD4+/CD25+ regulatory T cells by targeting of antigens to immature dendritic cells. Blood 2003; 101:4862-4869]. Co-culturing of allogeneic T cells with Dex/VitD2 tDCs induced higher and stable levels of IL-10 producing CD4+ T cells when compared to cDCs. Previously, IL-10 producing CD4+ T cells generated by repetitive priming of CD4+ naïve T cells with immature DCs or tDCs generated by VitD3 were shown to display regulatory properties [Unger W W, Laban S, Kleijwegt F S, van der Slik A R, Roep B O: Induction of Treg by monocyte-derived DC modulated by vitamin D3 or dexamethasone: Differential role for PD-L1. Eur J Immunol 2009; 39:3147-3159; Jonuleit H, Schmitt E, Schuler G, Knop J, Enk A H: Induction of interleukin 10-producing, nonproliferating CD4(+) T cells with regulatory properties by repetitive stimulation with allogeneic immature human dendritic cells. J Exp Med 2000; 192:1213-1222]. Thus, to test whether IL-10 producing CD4+ T cells induced by Dex/VitD2 tDCs (referred to as Tregs) possess regulatory activity after being expanded by repetitive priming, naïve CD4+ T cells were cultured with allogeneic Dex/VitD2 tDCs for two rounds of stimulation. As shown in FIG. 17A, Tregs expanded by Dex/VitD2 tDCs produced IL-10 but virtually no IFN-γ and IL-17A. IL-10 production was increased upon specific activation with cDCs. IFN-γ and IL-17 production was only slightly increased upon specific activation with cDCs. To analyze the suppressive function of Tregs expanded after two rounds of stimulation with Dex/VitD2 tDCs, Tregs were titrated into a MLR comprising allogeneic cDCs (from the same DCs donor as used in the original stimulation) and autologous responder T cells (from the same T cell donor as Tregs). As shown in FIG. 17B, Tregs dose-dependently inhibited responder T cell proliferation. Moreover, adding of Tregs into MLR led to up-regulation of IL-10 and down-regulation of IFN-γ and IL-17A production in a dose-dependent manner (FIG. 17C). Therefore, IL-10 producing Tregs induced by Dex/VitD2 tDCs are functional and suppress proliferation of responder T cells.

Dex/VitD2 tDCs Used NF-κB, p38 MAPK and ERK1/2 to Regulate their Tolerogenic Properties in the Inflammatory Environment:

To decipher the molecular mechanisms that play a role in maintaining tolerogenic properties of tDCs, signaling pathways including p38 MAPK, c-Jun N-terminal kinases (JNK/SAPK), ERK1/2, NF-κB, indoleamine 2, 3 deoxygenase (IDO), mTOR, and STAT3, previously reported to affect DC maturation and orchestrate IL-10 and IL-12 production, were analyzed [Nakahara T, Moroi Y, Uchi H, Furue M: Differential role of MAPK signaling in human dendritic cell maturation and Th1/Th2 engagement. J Derm Sci 2006; 42:1-11; Weichhart T, Costantino G, Poglitsch M, Rosner M, Zeyda M, Stuhlmeier K M, Kolbe T, Stulnig T M, Horl W H, Hengstschlager M, Muller M, Saemann M D: The TSC-mTOR signaling pathway regulates the innate inflammatory response. Immunity 2008; 29:565-577; Qian C, Jiang X, An H, Yu Y, Guo Z, Liu S, Xu H, Cao X: TLR agonists promote ERK-mediated preferential IL-10 production of regulatory dendritic cells (diffDCs), leading to NK-cell activation. Blood 2006; 108:2307-2315; Harden J L, Egilmez N K: Indoleamine 2,3-dioxygenase and dendritic cell tolerogenicity. Immunol Invest 2012; 41:738-764; Jackson A M, Mulcahy L A, Porte J, Franks H A, El Refaee M, Wang Q, Shah S, Zhu X, Patel P M: Role of mitogen-activated protein kinase and PI3K pathways in the regulation of IL-12-family cytokines in dendritic cells and the generation of Th-responses. Eur Cyt Net 2010; 21:319-328].

Figures 18A, 18B:
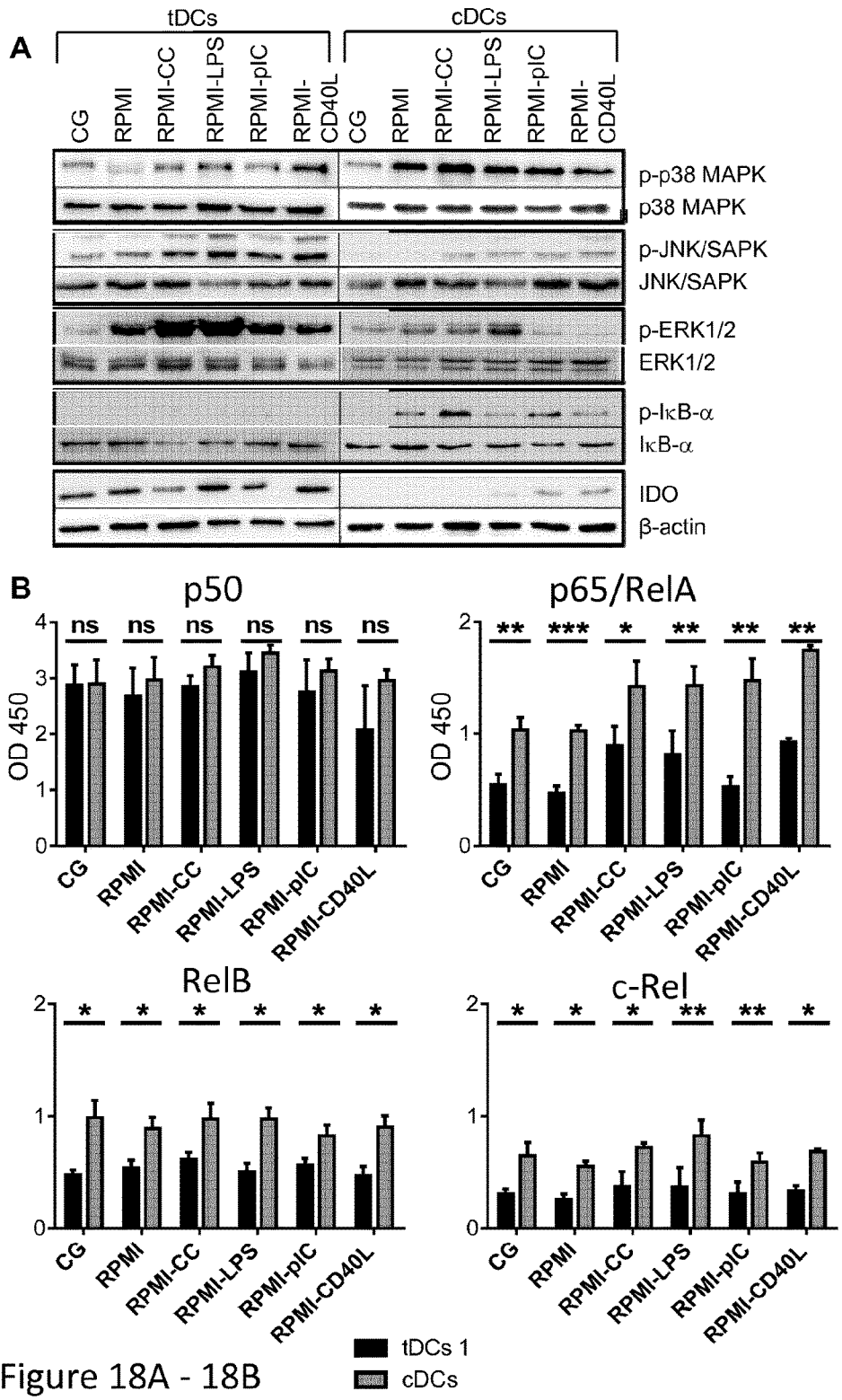

First, it was evaluated whether MAPK, including p38 MAPK, JNK/SAPK and ERK1/2, are differentially regulated in tDCs and cDCs. As shown in FIG. 18A, tDCs from Cell Gro expressed higher levels of activated JNK/SAPK, however, p38 MAPK and ERK1/2 were comparably activated in tDCs and cDCs. After re-exposing DCs to inflammatory stimuli, tDCs expressed higher level of activated JNK/SAPK, lower level of the activated p38 MAPK and markedly up-regulated ERK1/2 in contrast to cDCs.

Next, it was shown that tDCs expressed high level of immunoregulatory molecule IDO in all the stimulatory conditions tested. In contrast, IDO was absent or weakly expressed in cDCs. These results suggest that p38 MAPK, JNK/SAPK, ERK1/2 and IDO are differentially regulated in tDCs compared to cDCs, which might play a role in maintaining tolerogenic properties of tDCs after rechallenge.

Given that DC differentiation and maturation is associated with activation of NF-κB and Dex/VitD tDCs differentiation was shown to be mediated through the suppression of NF-κB pathway [Adorini L, Penna G: Induction of tolerogenic dendritic cells by vitamin D receptor agonists. Handbook of Experimental Pharmacology 2009:251-273; van Kooten C, Stax A S, Woltman A M, Gelderman K A: Handbook of experimental pharmacology "dendritic cells": The use of dexamethasone in the induction of tolerogenic DCs. Handbook of Experimental Pharmacology 2009:233-249], it was evaluated whether LPS, polyI:C, CC or CD40L can reverse NF-κB suppression in the absence of tolerogenic factors. First, it was shown that phosphorylation of IκB-α, a regulatory protein that inhibits NF-κB by complexing with and trapping it in the cytoplasm, was dramatically reduced in tDCs in all the stimulatory conditions tested. In contrast, IκB-α was phosphorylated in cDCs (FIG. 18A). To quantify NF-κB activation, DNA binding activity of NF-κB subunits p50, p65/RelA, RelB and c-Rel in the nucleus were analyzed (FIG. 18B). Dex/VitD2 tDCs from Cell Gro exhibited low binding activity of p65/RelA, and low binding activity of RelB, shown to reflect DCs maturation [Scheinman R I, Gualberto A, Jewell C M, Cidlowski J A, Baldwin A S, Jr.: Characterization of mechanisms involved in transrepression of NF-kB by activated glucocorticoid receptors. Mol Cell Biol 1995; 15:943-953], and c-Rel, shown to be involved in IL-12 production [Grumont R, Hochrein H, O'Keeffe M, Gugasyan R, White C, Caminschi I, Cook W, Gerondakis S: C-Rel regulates interleukin 12 p70 expression in CD8(+) dendritic cells by specifically inducing p35 gene transcription. J Exp Med 2001; 194:1021-1032], in nuclear extracts when compared to cDCs. DNA binding activities of p65/RelA, RelB and c-Rel in tDCs remained lower even after rechallenge in the absence of VitD2 and Dex. On the other hand, binding activity of NF-κB subunit p50, shown to create homodimers increasing production of IL-10 [Cao S, Zhang X, Edwards J P, Mosser D M: NF-kB1 (p50) homodimers differentially regulate pro- and anti-inflammatory cytokines in macrophages. J Biol Chem 2006; 281:26041-26050], was high in tDCs in all the conditions tested (FIG. 18B).

Figure 18C:
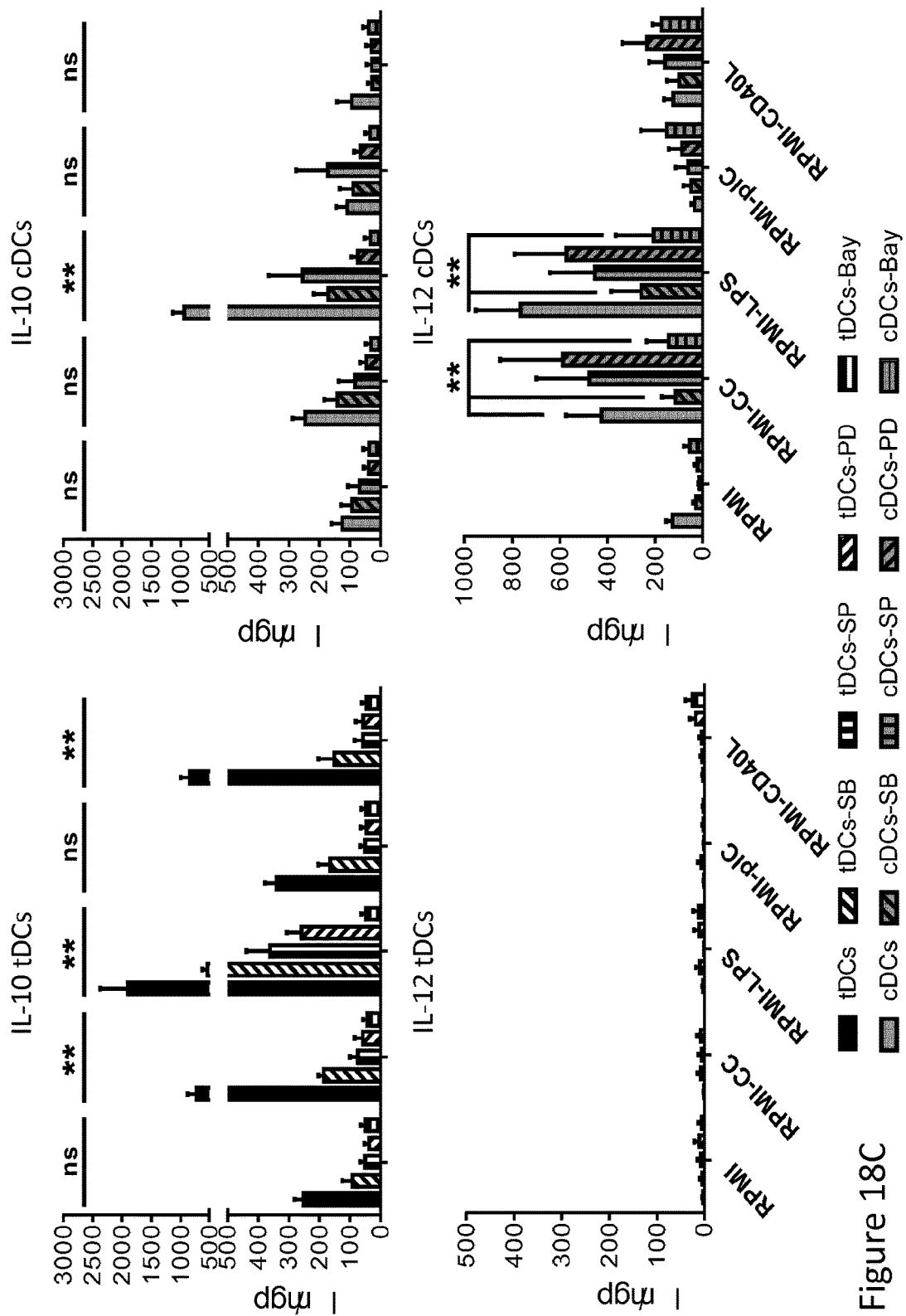
Figure 18D:
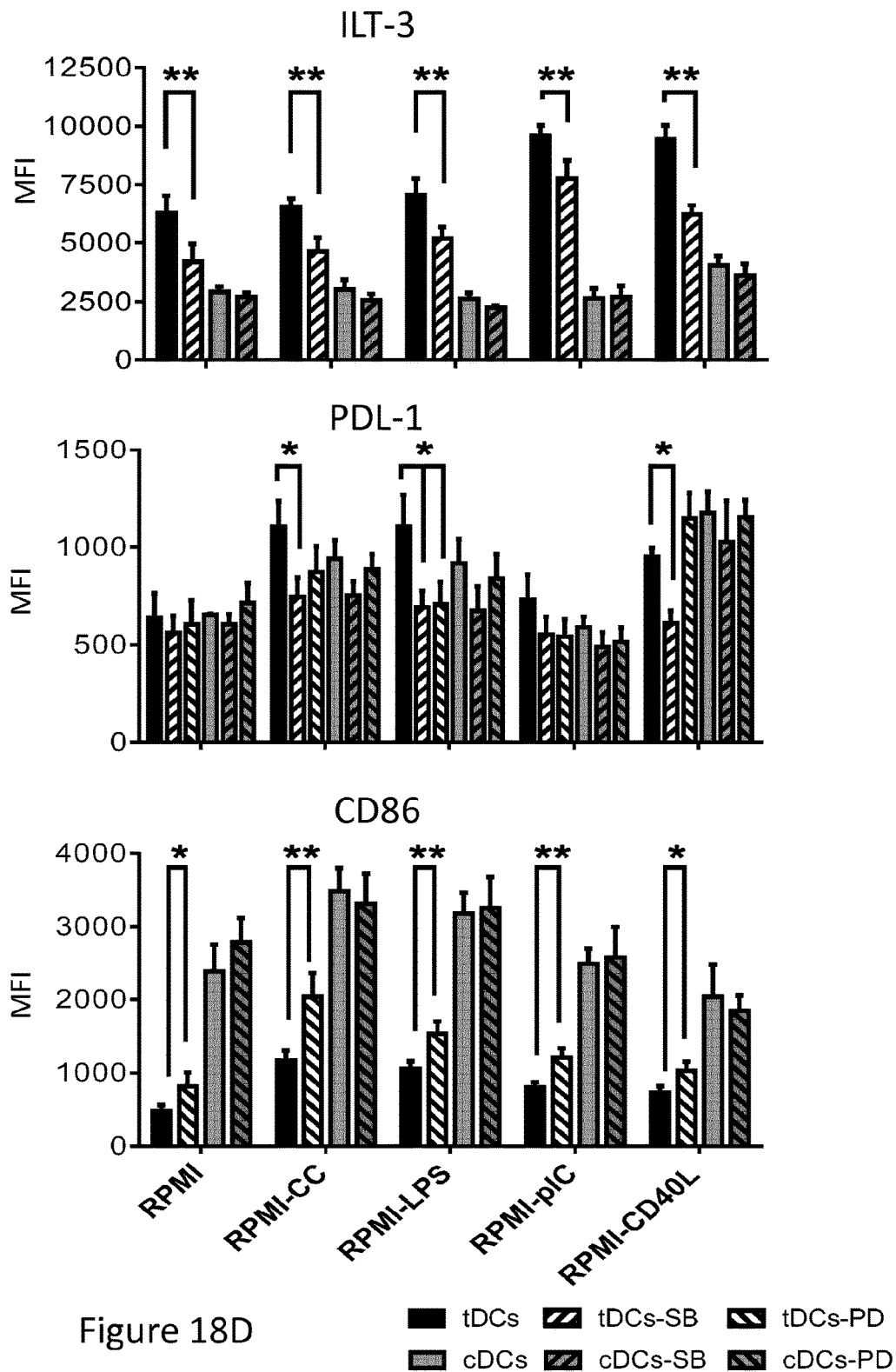
Figure 18E:
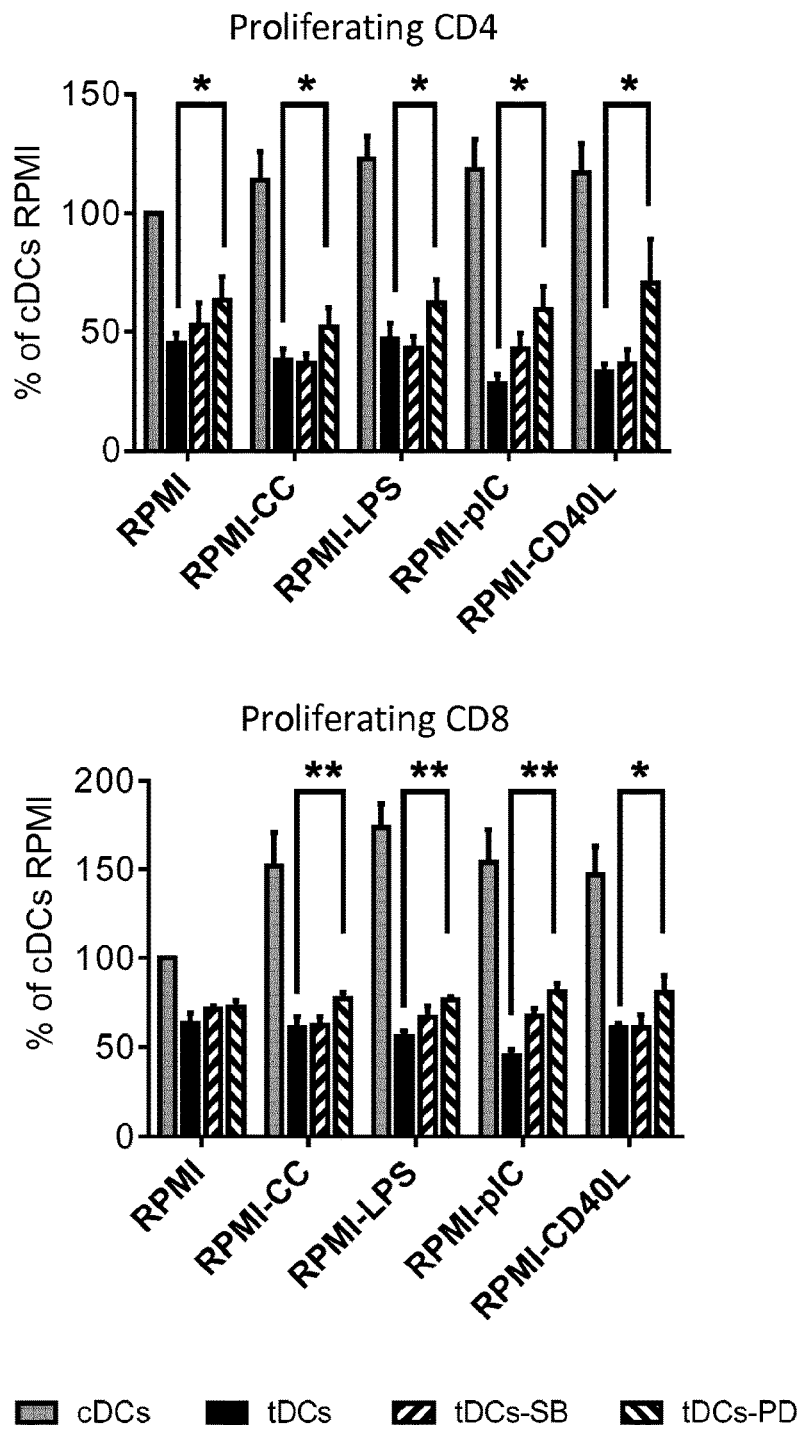
Figures 19A, 19B:
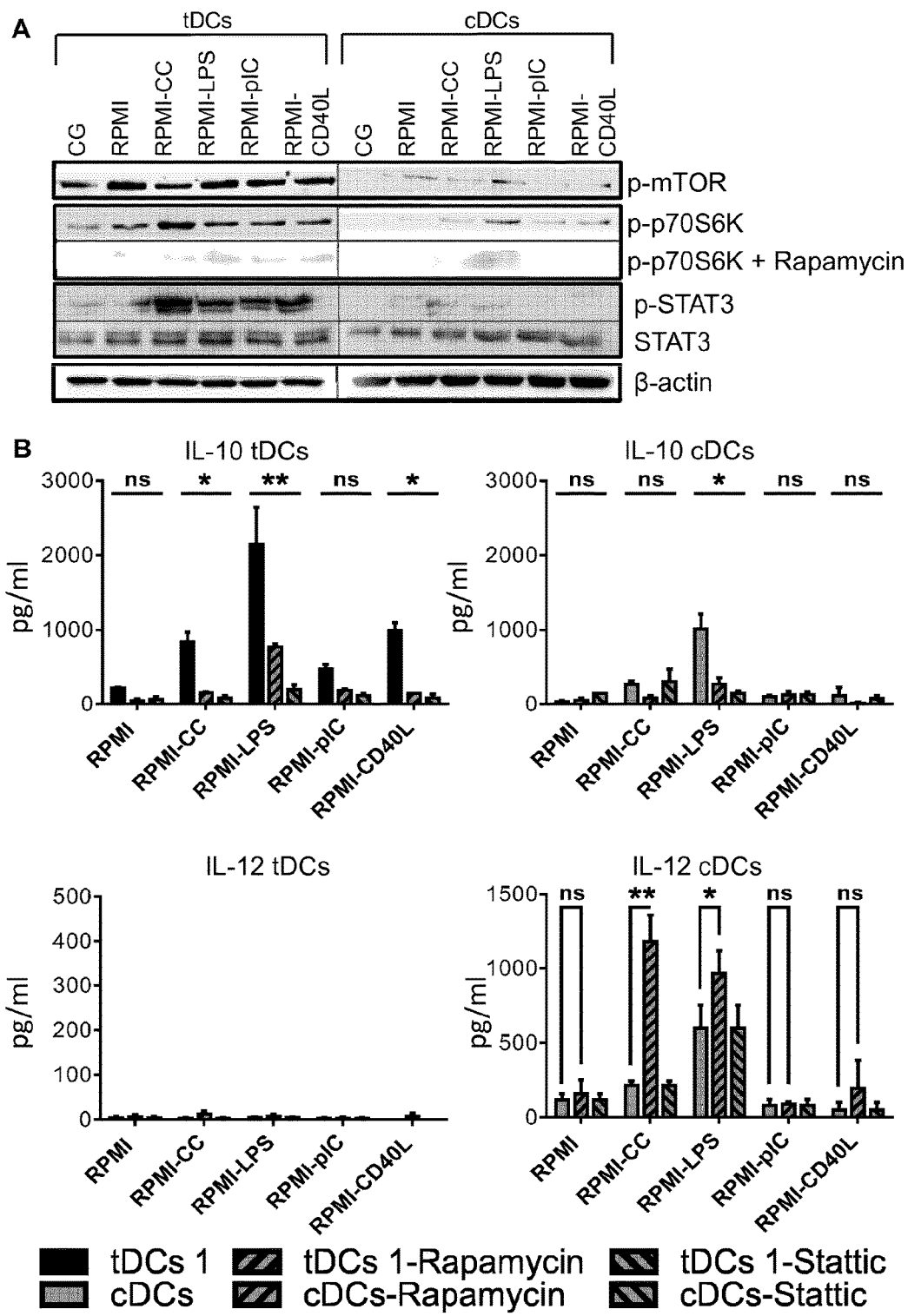
Figure 19C:
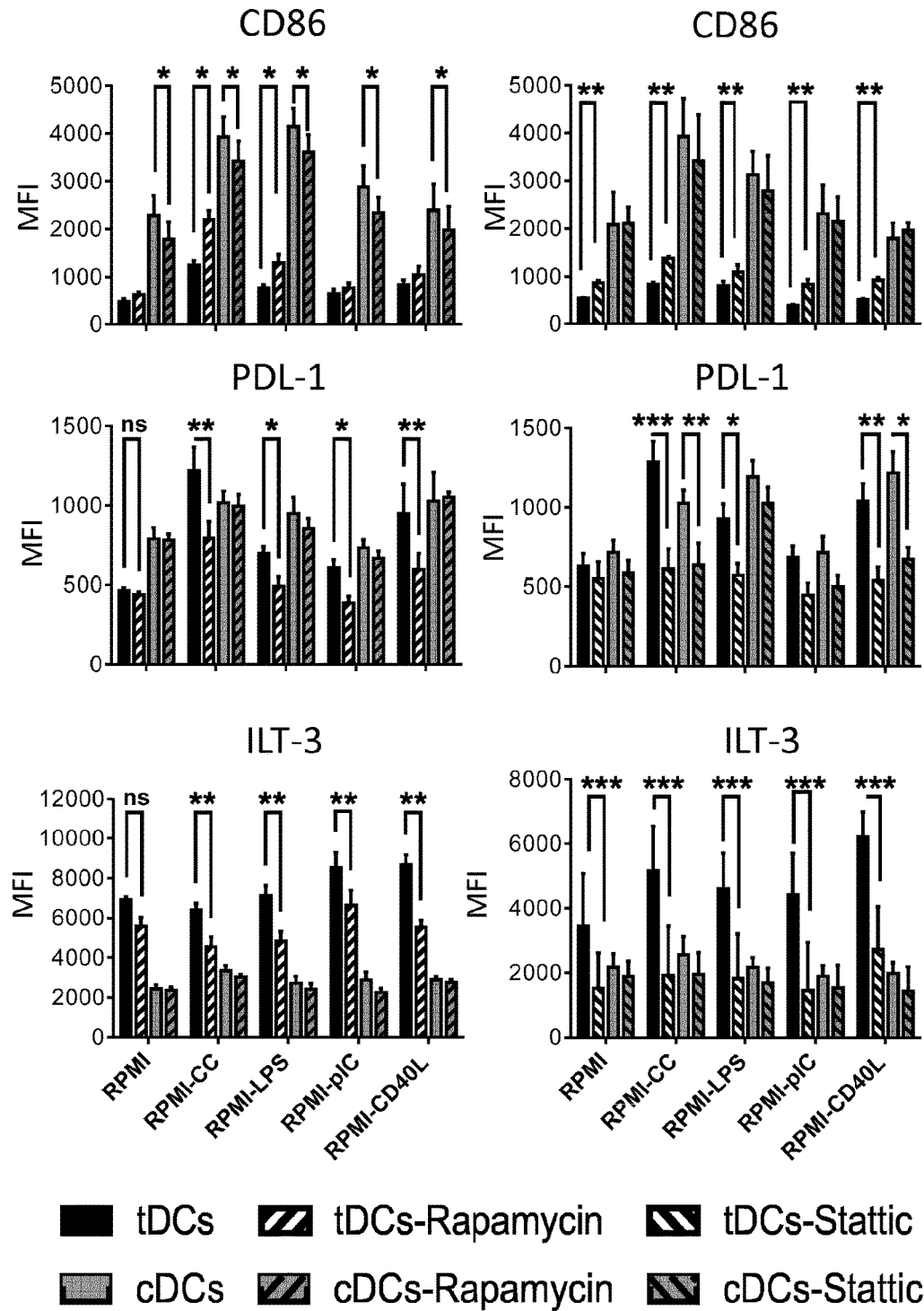
Figure 19D:
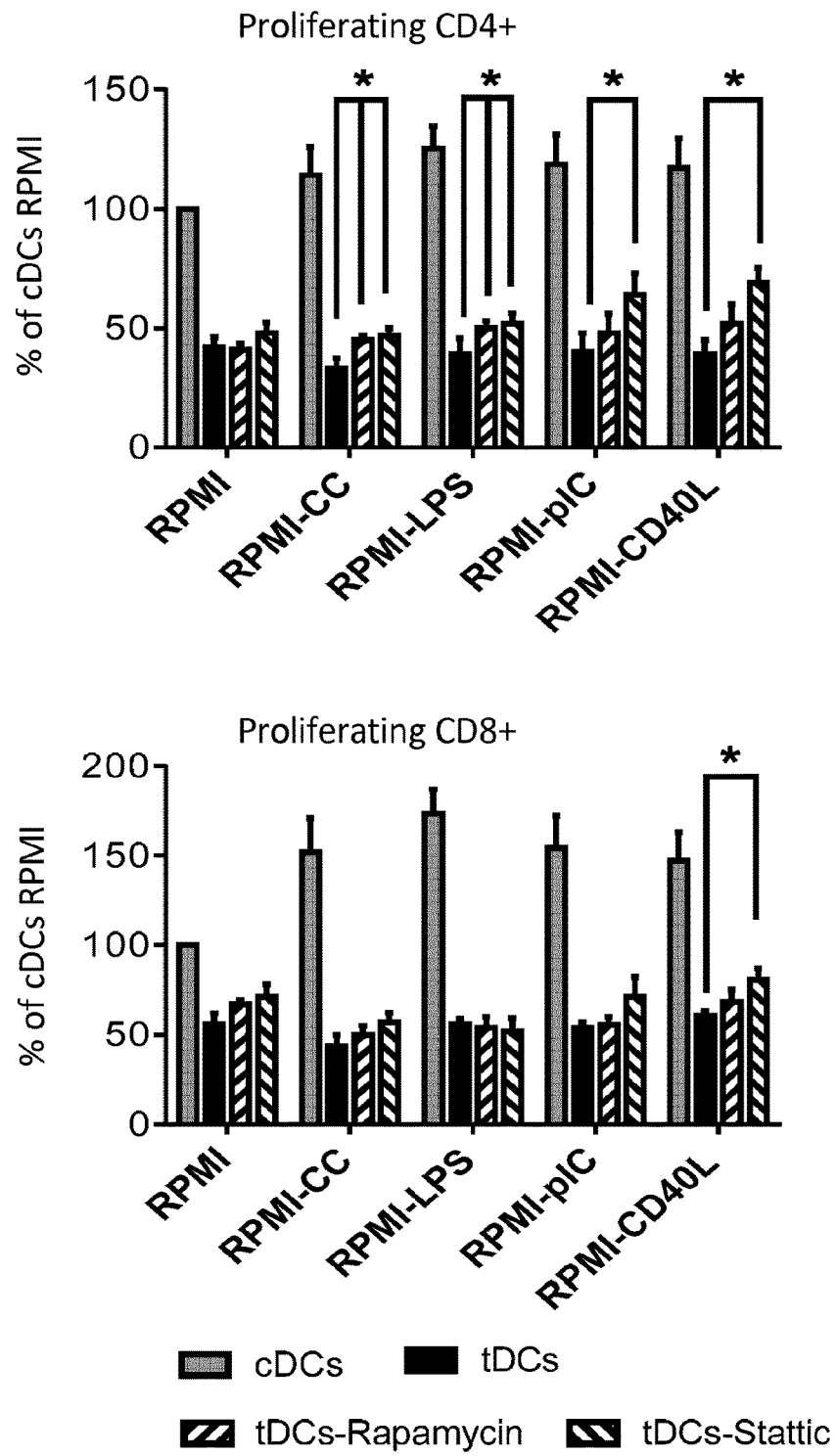

Next, it was determined how MAPK and NF-κB signaling pathway utilization contributes to inflammatory versus tolerogenic phenotype of DCs in response to LPS, CC, polyI:C and CD40L. Before stimulation, DCs were pretreated by p38 MAPK, JNK/SAPK, ERK1/2, and NF-κB inhibitor SB203580, SP600125, PD98059 and Bay 11-7082, respectively. Analyzing IL-10 and IL-12 production showed that IL-10 production was significantly dependent on p38 MAPK, JNK/SAPK and ERK1/2 activation pathways after CC, LPS and CD40L restimulation in tDCs. Also Bay 11-7082 abrogated IL-10 production in tDCs. However, the same situation was observed only after LPS triggering in cDCs (FIG. 18C). On the other hand, p38 MAPK and NF-κB inhibitor markedly down-regulated IL-12 production in cDCs after LPS and CC triggering, but did not affect IL-12 production in tDCs. Analyzing cell-surface molecules showed that p38 MAPK inhibition down-regulated ILT-3 and PD-L1 expression in tDCs, in contrast to cDCs (FIG. 18D). Moreover, ERK1/2 inhibitor down-regulated PD-L1 expression after LPS stimulation in tDCs but significantly up-regulated CD86 expression in tDCs in all the conditions tested (FIG. 18D). Other inhibitors tested had no significant effect on ILT-3, PD-L1 and CD86 expression in tDCs (data not shown). The ability of p38 MAPK and ERK1/2 inhibitors to modulate IL-10 production and expression of costimulatory and inhibitory molecules in tDCs suggests an impact on subsequent T cell activation. By employing the allogeneic T cell activation model, it was shown that ERK1/2 inhibitor increased the ability of Dex/VitD tDCs to stimulate CD4+ as well as CD8+ T cell proliferation when compared to tDCs without ERK1/2 inhibitor (FIG. 18E). Collectively, these data suggest the distinct pattern of activated signaling pathways in tDCs versus cDCs, with p38 MAPK, ERK1/2 and down-regulated NF-κB being important for maintaining down-regulated CD86 and up-regulated ILT-3 and PD-L1 expression, high IL-10 production and reduced allostimulatory potential of Dex/VitD tDCs.

mTOR and STAT3 Regulate IL-10 Production and ILT-3, PD-L1 and CD86 Expression in tDCs after Restimulation:

Recently, mTOR was found to coordinate pro-versus anti-inflammatory events in human monocytes and DCs by attenuating NF-κB and up-regulating STAT3 activity [Weichhart T, Costantino G, Poglitsch M, Rosner M, Zeyda M, Stuhlmeier K M, Kolbe T, Stulnig T M, Horl W H, Hengstschlager M, Muller M, Saemann M D: The TSC-mTOR signaling pathway regulates the innate inflammatory response. Immunity 2008; 29:565-577; Haidinger M, Poglitsch M, Geyeregger R, Kasturi S, Zeyda M, Zlabinger G J, Pulendran B, Horl W H, Saemann M D, Weichhart T: A versatile role of mammalian target of rapamycin in human dendritic cell function and differentiation. J Immunol 2010; 185:3919-3931]. Western blot analysis revealed that tDCs strongly phosphorylated mTOR and STAT3 after re-exposing to inflammatory stimuli while the phosphorylation of mTOR is weaker and phosphorylated STAT3 is barely detectable in cDCs. mTOR phosphorylation led to the phosphorylation of p70S6K, mTOR dependent event, that was abrogated by the mTOR specific inhibitor rapamycin (FIG. 19A). To further corroborate the link between mTOR and STAT3 activation and IL-10 and IL-12 production as well as CD86, ILT-3 and PD-L1 expression, blocking experiments of mTOR and STAT3 using chemical inhibitors rapamycin and Stattic, respectively, were performed. Upon mTOR and STAT3 inhibition tDCs reduced IL-10 production (FIG. 19B). Rapamycin and Stattic down-regulated IL-10 production after LPS restimulation in cDCs (FIG. 19B). However, in contrast to cDCs, where rapamycin treatment markedly increased IL-12 production after CC and LPS treatment, rapamycin was not able to restore IL-12 production in tDCs irrespective of the stimulatory agent. IL-12 production was unaffected after Stattic treatment in both DCs tested (FIG. 19B). Furthermore, mTOR and STAT3 inhibition markedly reduced expression of tolerogenic markers PD-L1 and ILT-3 but significantly increased CD86 expression in tDCs after CC and LPS trigger (mTOR inhibition) or in all the conditions tested (STAT3 inhibition), respectively. This was paralleled by a partial restoration of the ability of tDCs to stimulate especially CD4+ T cell proliferation when compared to tDCs cultivated without Rapamycin or Stattic (FIG. 19D). Altogether, these data suggest that mTOR and STAT3 controls not only IL-10 production and ILT-3, PD-L1 and CD86 expression in tDCs after restimulation but also play a role in their immunoregulatory function (FIG. 19C).

mTOR-Dependent Glycolysis Regulate Stable Tolerogenic Properties of tDCs after Restimulation:

TLR-induced proinflammatory maturation and activation of DCs was shown to be dependent upon PI3/Akt-mediated metabolic reprogramming, switching from oxidative phosphorylation (OXPHOS) to aerobic glycolysis [Krawczyk C M, Holowka T, Sun J, Blagih J, Amiel E, DeBerardinis R J, Cross J R, Jung E, Thompson C B, Jones R G, Pearce E J: Toll-like receptor-induced changes in glycolytic metabolism regulate dendritic cell activation. Blood 2010; 115:4742-4749]. mTOR is a downstream target of PI3/Akt and was shown to regulate glycolytic metabolism [Locasale J W, Cantley L C: Genetic selection for enhanced serine metabolism in cancer development. Cell Cycle 2011; 10:3812-3813]. However, the data provided herein demonstrated strong phosphorylation of mTOR in Dex/VitD tDCs after activation with TLR ligands, cytokine cocktail and CD40L which was not accompanied with tDCs maturation. In addition, mTOR inhibition down-regulated tolerogenic molecules ILT-3 and PD-L1 expression and IL-10 production in Dex/VitD tDCs. Therefore, it was investigated whether mTOR activation in tDCs was accompanied with glycolytic activation and how glycolysis regulated stable tolerogenic profile of tDCs in the inflammatory environment.

Figure 20A:
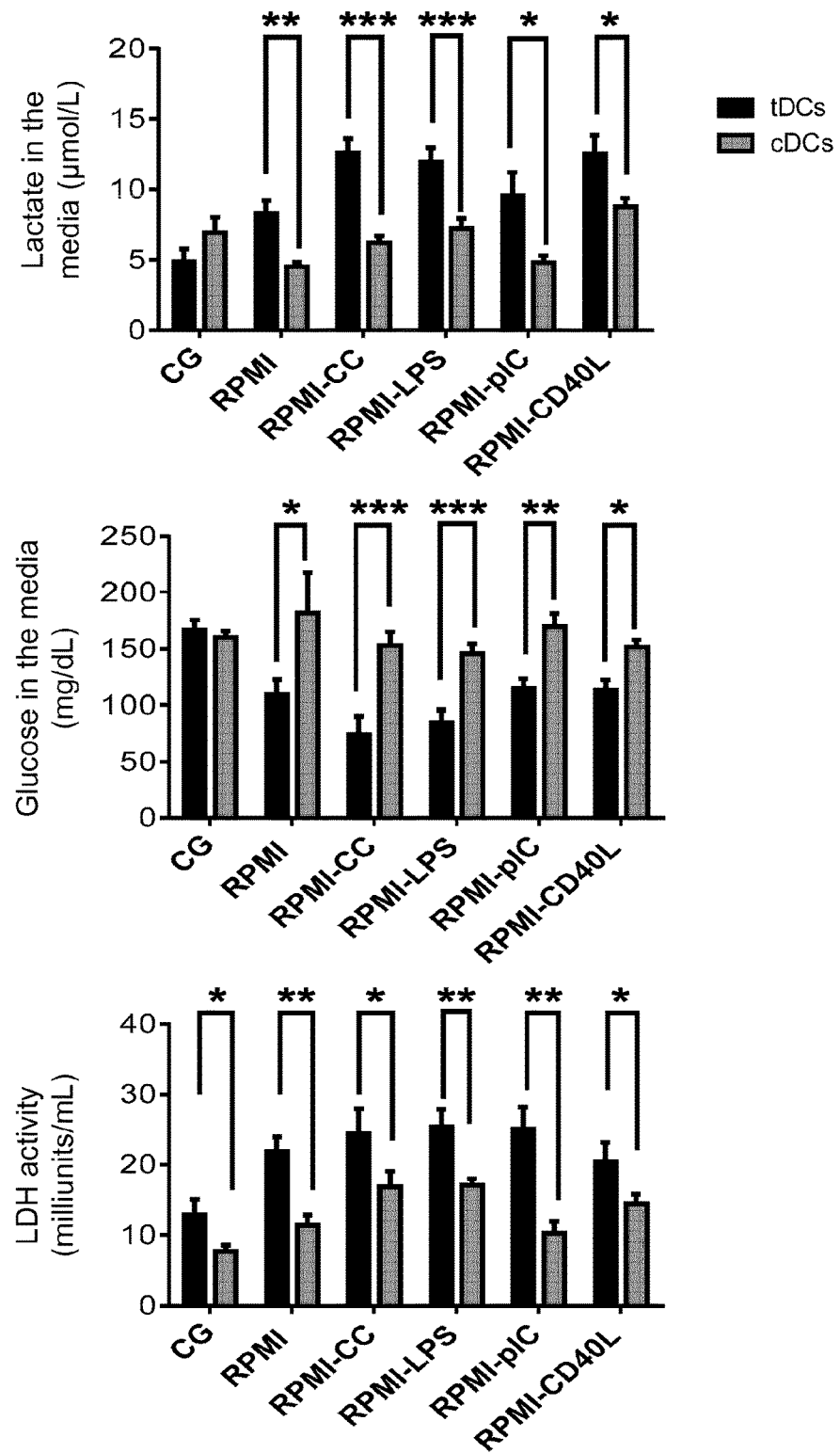
Figure 20B:
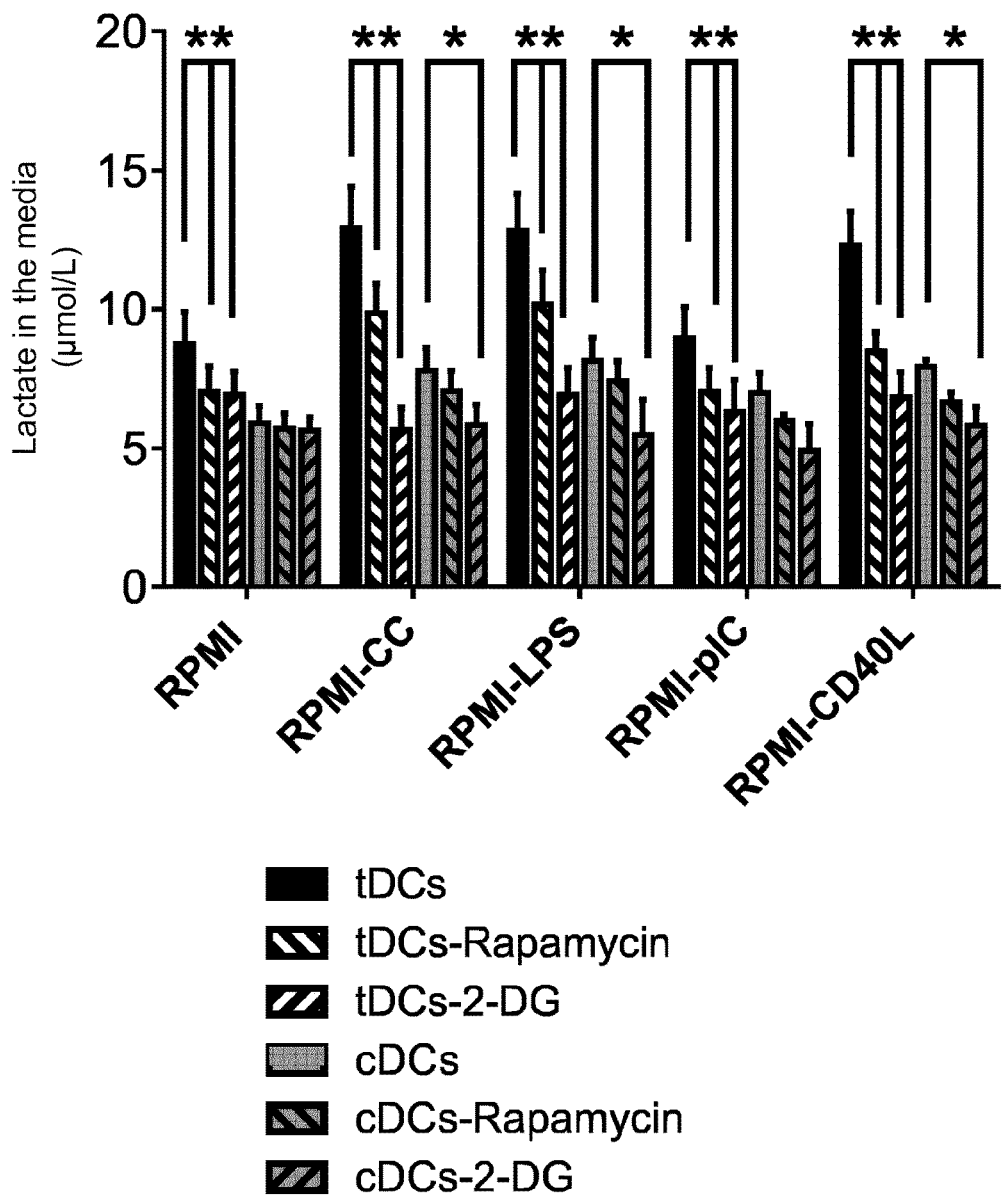
Figure 20C:
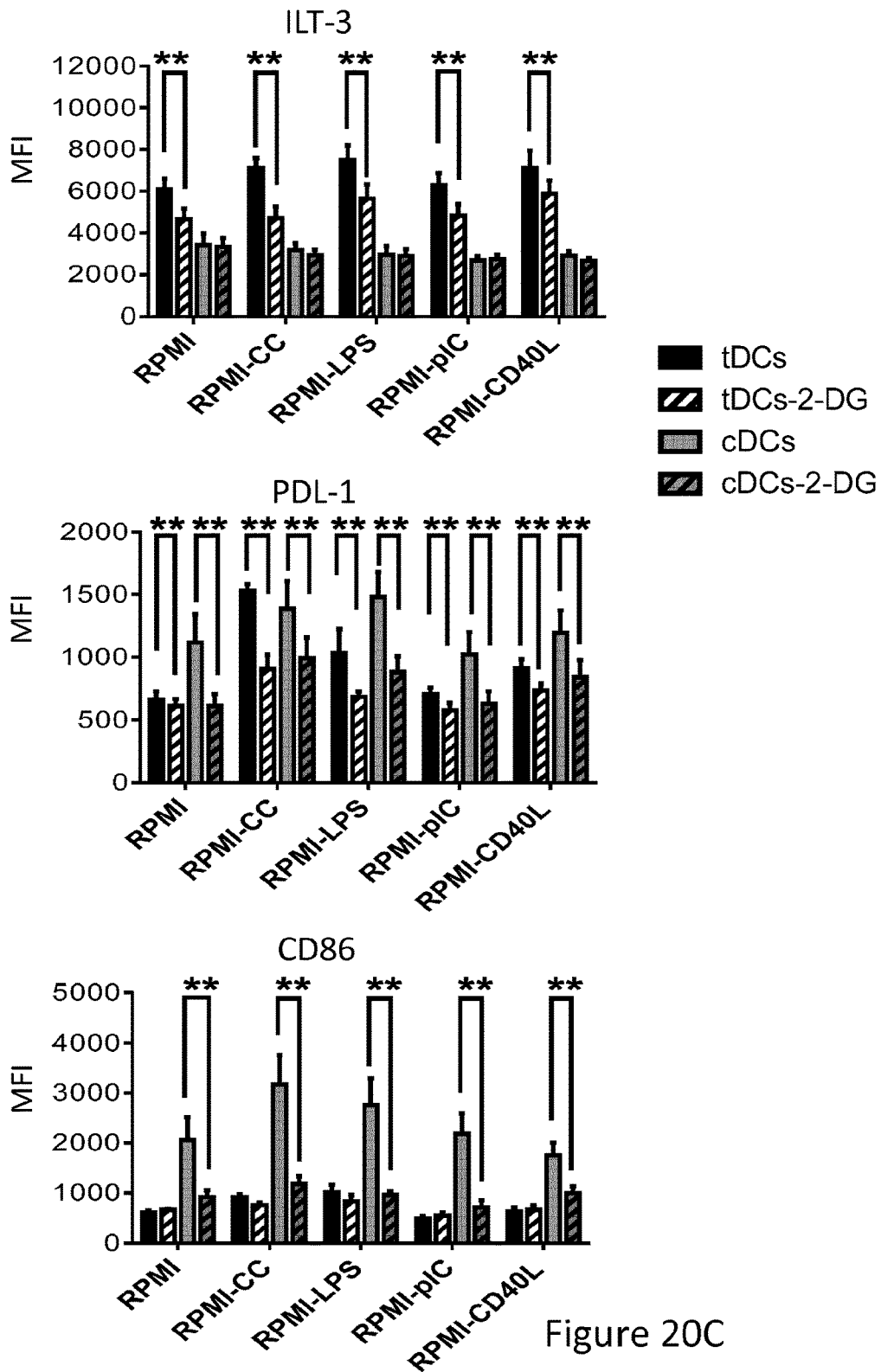
Figure 20D:
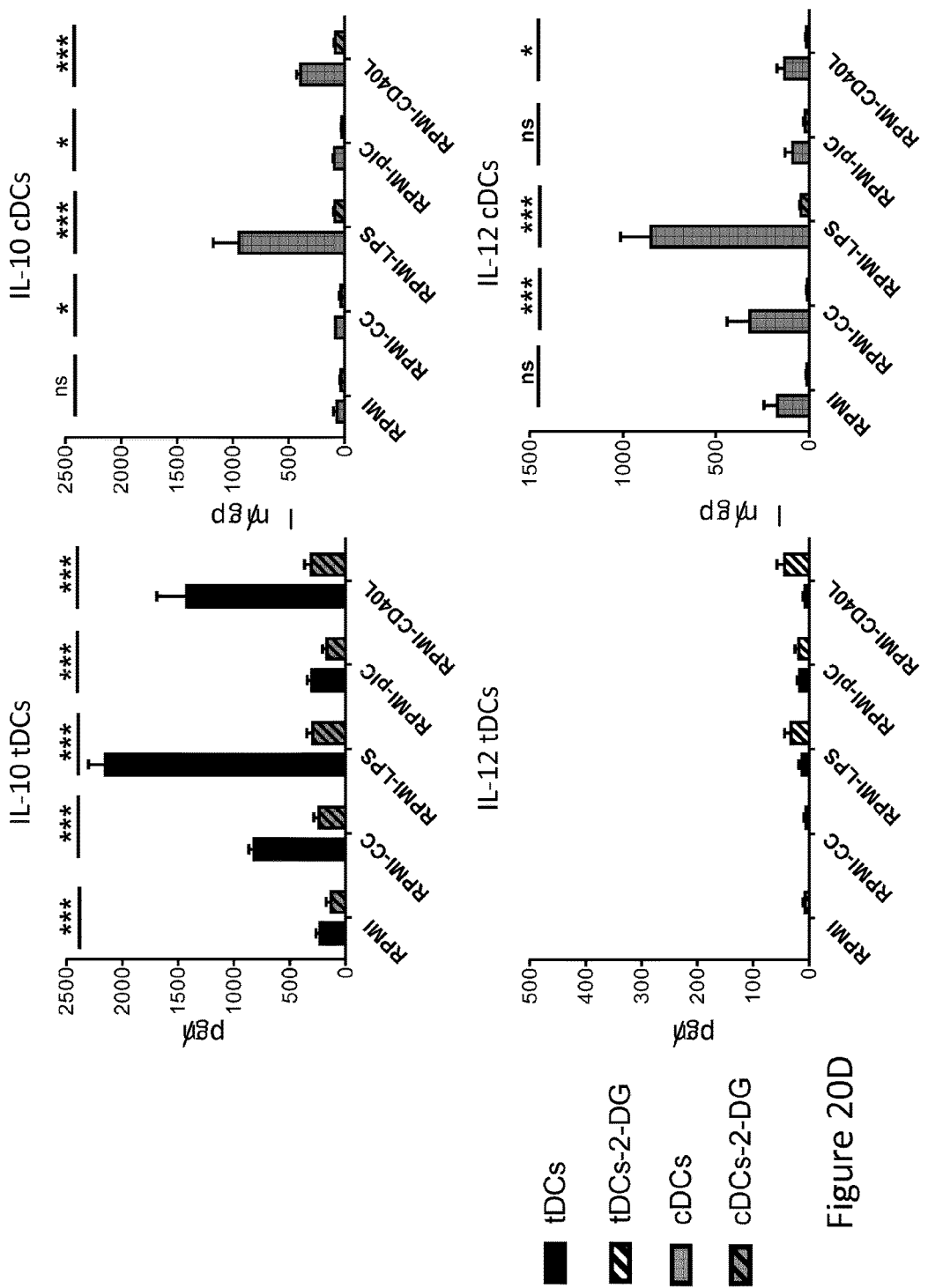
Figure 20E:
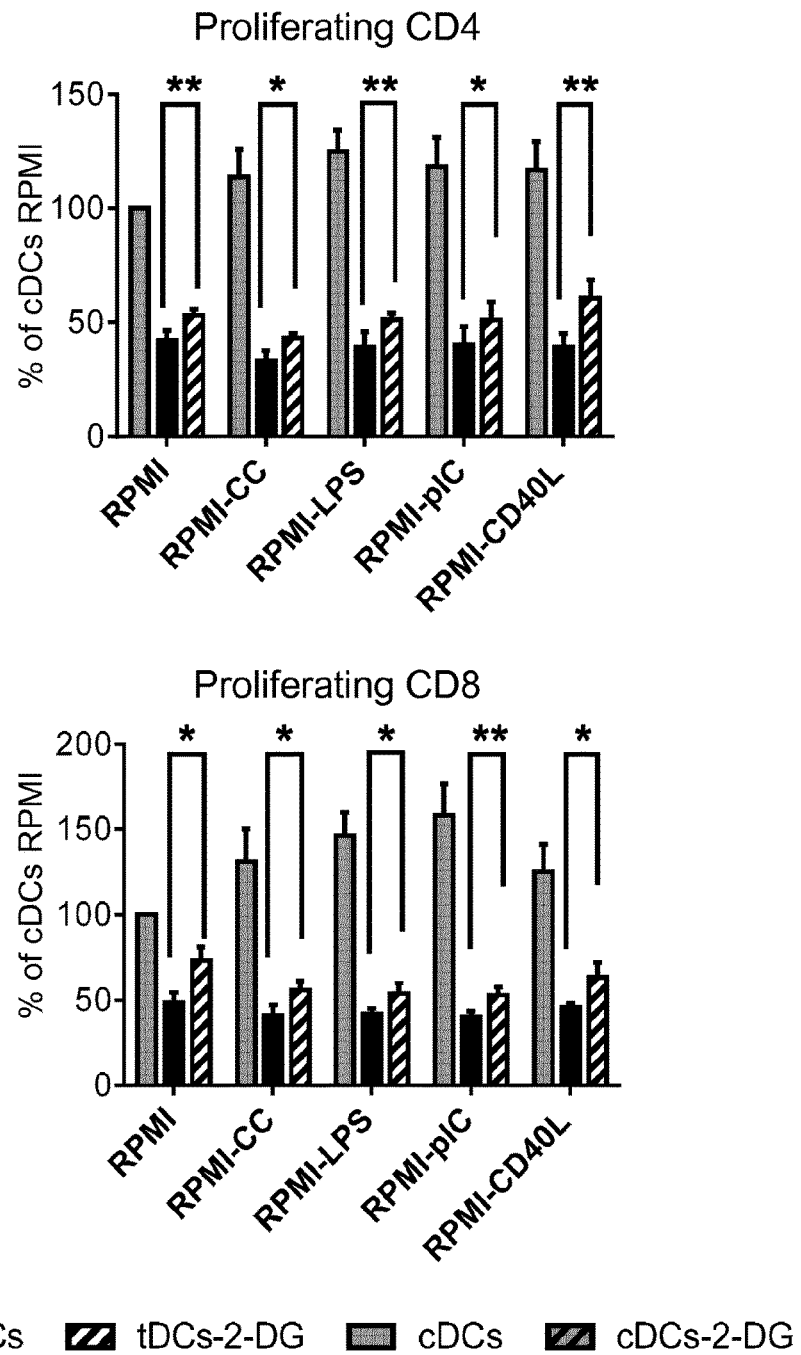

To investigate the glycolytic activity, glucose consumption and lactate production were analyzed in tDCs and cDCs supernatants as an indicator for glycolytic activity. As shown in FIG. 20A, Dex/VitD tDCs cultured in Cell Gro secreted similar levels of lactate as cDCs. However, the restimulation of tDCs led to robust accumulation of lactate in cell supernatants that was accompanied with more pronounced gradual decrease in the media glucose content when compared to cDCs. Consistent with the increased glucose consumption and lactate production, tDCs after restimulation revealed higher activity of cellular lactate dehydrogenase, an oxidoreductase enzyme that catalyses the interconversion of pyruvate and lactate, in all the conditions tested compared to cDCs. These data suggest increased glycolysis in Dex/VitD2 tDCs in contrast to cDCs. To test whether mTOR regulates enhanced glycolytic metabolism in tDCs after restimulation, blocking experiments were performed using chemical mTOR inhibitor rapamycin. Rapamycin markedly down-regulated lactate generation in Dex/VitD tDCs (FIG. 20B). Thus, restimulation of Dex/VitD tDCs was accompanied by enhanced glycolysis via mTOR activation pathway. Next, it was tested whether enhanced glycolysis regulated tolerogenic properties of tDCs after restimulation by adding 10 mM 2-deoxyglucose (2-DG) which acts as an inhibitor of glycolysis and prevents generation of lactate to the DC cultures. Addition of 2-DG to the DCs cultures significantly prevented lactate generation in Dex/VitD tDCs (FIG. 20B). Moreover, under these conditions, tDCs failed to up-regulate ILT-3 and PD-L1 molecules (FIG. 20C) and markedly decreased IL-10 production (FIG. 20D). Expression of CD86 as well as IL-12p70 production remained unaffected upon 2-DG treatment in tDCs in contrast to cDCs. On the other hand, inhibition of glycolysis in tDCs increased partially the ability to induce allogeneic CD4+ as well as CD8+ T cell proliferation (FIG. 20D). Taken together, these data show that enhanced glycolysis alters expression of inhibitory molecules, IL-10 production and allostimulatory potential of Dex/VitD tDCs after mimicking in vivo subsequent pro-inflammatory activation.

7.3 Discussion

The present analysis showed that Dex/VitD tDCs maintains tolerogenic phenotype and function in the inflammatory environment in the absence of tolerogenic factors. The data presented herein show for the first time that stability of Dex/VitD tDCs in the inflammatory environment is orchestrated by down-regulated NF-κB, modest activation of p38 MAPK and strong activation of ERK1/2, mTOR and STAT3 molecules that regulate expression of CD86, ILT-3 and PD-L1, production of IL-10 and IL-12p70 and allostimulatory potential of Dex/VitD tDCs.

Recent studies showed a stable tolerogenic phenotype of Dex and/or VitD-treated DCs in terms of maturation markers expression and stable high IL-10 production upon repeated maturation with LPS or pro-inflammatory cytokines [Unger W W, Laban S, Kleijwegt F S, van der Slik A R, Roep B O: Induction of Treg by monocyte-derived DC modulated by vitamin D3 or dexamethasone: Differential role for PD-L1. Eur J Immunol 2009; 39:3147-3159; Chamorro S, Garcia-Vallejo J J, Unger W W, Fernandes R J, Bruijns S C, Laban S, Roep B O, T Hart B A, van Kooyk Y: TLR triggering on tolerogenic dendritic cells results in TLR2 up-regulation and a reduced proinflammatory immune program. J Immunol 2009; 183:2984-2994; Harry R A, Anderson A E, Isaacs J D, Hilkens C M: Generation and characterisation of therapeutic tolerogenic dendritic cells for rheumatoid arthritis. Ann Rheum Dis 2010; 69:2042-2050]. The data presented herein showing stable low to intermediate CD86, CD83 and CD40 expression in contrast to high expression of ILT-3, TIM-3, TLR2 and PD-L1 after restimulation of tDCs corroborate and significantly extend recent findings about the stability of tDCs and indicate the preservation of anti-inflammatory phenotype of tDCs [Naranjo-Gomez M, Raich-Regue D, Onate C, Grau-Lopez L, Ramo-Tello C, Pujol-Borrell R, Martinez-Caceres E, Borras F E: Comparative study of clinical grade human tolerogenic dendritic cells. J Transl Med 2011; 9:89; Unger W W, Laban S, Kleijwegt F S, van der Slik A R, Roep B O: Induction of Treg by monocyte-derived DC modulated by vitamin D3 or dexamethasone: Differential role for PD-L1. Eur J Immunol 2009; 39:3147-3159]. ILT-3 signaling was shown to result in inhibition of NF-κB and p38 MAPK pathways in DC [Chang C C, Liu Z, Vlad G, Qin H, Qiao X, Mancini D M, Marboe C C, Cortesini R, Suciu-Foca N: Ig-like transcript 3 regulates expression of proinflammatory cytokines and migration of activated T cells. J Immunol 2009; 182:5208-5216]. TLR-2, ILT-3 and PD-L1 signaling was reported to participate in Tregs induction [Unger W W, Laban S, Kleijwegt F S, van der Slik A R, Roep B O: Induction of Treg by monocyte-derived DC modulated by vitamin D3 or dexamethasone: Differential role for PD-L1. Eur J Immunol 2009; 39:3147-3159; Sutmuller R P, den Brok M H, Kramer M, Bennink E J, Toonen L W, Kullberg B J, Joosten L A, Akira S, Netea M G, Adema G J: Toll-like receptor 2 controls expansion and function of regulatory T cells. J Clin Invest 2006; 116:485-494]. In the present study, restimulation of tDCs, especially with CC and LPS, led to up-regulation of PD-L1 and ILT-3 expression and stable capacity to induce IL-10 producing CD4+ T cells possessing suppressive capacity. Therefore, the data presented herein predict that stable expression of TLR2, ILT-3 and up-regulation of PD-L1 after restimulation of tDCs might play a role in tolerance induction.

The data presented herein demonstrated that tolerogenic DCs restimulated by inflammatory signals maintained stable cytokine profile with high IL-10 production, up-regulated TGF-β, reduced TNF-α and virtually absent IL-12. The high production of IL-10 together with low production of pro-inflammatory cytokines TNF-α and IL-12 could favor Dex/VitD2 tDCs for immunotherapy.

Consistent with the observed tolerogenic phenotype, Dex/VitD2 tDCs restimulated by inflammatory signals not only showed a reduced ability to induce T cell proliferation, but also were capable of inducing T cells with low IFN-γ and high IL-10 production, by both CD4+ and CD8+ compartments when compared to T cell responses induced by cDCs. The reduction of IFN-γ positive T cells after restimulation with concomitant stable IL-10 positive T cells might be caused by switching T cell response rather toward Th2 due to higher IL-10 production from restimulated tDCs and cDCs [Langenkamp A, Messi M, Lanzavecchia A, Sallusto F: Kinetics of dendritic cell activation: Impact on priming of Th1, Th2 and nonpolarized T cells. Nature Immunology 2000; 1:311-316].

As tDCs reported in the present study produced TGF-β, which can induce Tregs as well as Th17 cells [Xu L, Kitani A, Fuss I, Strober W: Cutting edge: Regulatory T cells induce CD4+CD25-FoxP3- T cells or are self-induced to become Th17 cells in the absence of exogenous TGF-b. J Immunol 2007; 178:6725-6729], their Th17 polarizing activity was analyzed by testing the production of IL-17 from T cells co-cultured with tDCs. It was demonstrated that Dex/VitD2 tDCs significantly reduced IL-17A production from T cells, even after restimulation with pro-inflammatory stimuli, in contrast to cDCs. As Th17 as well as IFN-γ contributes for pathogenesis of autoimmune diseases [Li C R, Mueller E E, Bradley L M: Islet antigen-specific Th17 cells can induce TNF-a-dependent autoimmune diabetes. J Immunol 2014; 192:1425-1432], the reduction of T cells that secrete IL-17A and IFN-γ might halt or reverse harmful autoimmune processes in subjects with autoimmune disease. Importantly, the low production of IFN-γ and IL-17A with concomitant increased secretion of IL-10 was observed in CD4+ Tregs generated after repetitive stimulation with Dex/VitD2 tDCs and remained similar even upon restimulation with mature DCs. Therefore, cytokine alterations of T cells after priming with Dex/VitD2 DCs cannot be easily explained as the direct result of an insufficient stimulation.

Next, the present study focused on activation pathways triggered in Dex/VitD2 tDCs upon mimicking subsequent pro-inflammatory activation. The data presented herein demonstrate stable down-regulation of NF-κB pathway in Dex/VitD2 tDCs, further documented by abrogated phosphorylation of IκB-α. In contrast to cDCs, Dex/VitD2 tDCs exhibited low nuclear translocation of NF-κB subunits p65/RelA, RelB and c-Rel that have been shown to up-regulate pro-inflammatory cytokine production [Cao S, Zhang X, Edwards J P, Mosser D M: NF-kB1 (p50) homodimers differentially regulate pro- and anti-inflammatory cytokines in macrophages. J Biol Chem 2006; 281:26041-26050]. The data presented herein are consistent with the observation that extent of nuclear expression of RelB as a p50/RelB heterodimer in DCs correlates with the degree of maturation [Scheinman R I, Gualberto A, Jewell C M, Cidlowski J A, Baldwin A S, Jr.: Characterization of mechanisms involved in transrepression of NF-kB by activated glucocorticoid receptors. Mol Cell Biol 1995; 15:943-953]. As c-Rel plays a role in IL-12 production [Grumont R, Hochrein H, O'Keeffe M, Gugasyan R, White C, Caminschi I, Cook W, Gerondakis S: C-Rel regulates interleukin 12 p70 expression in CD8(+) dendritic cells by specifically inducing p35 gene transcription. J Exp Med 2001; 194:1021-1032], down-regulated levels of c-Rel in the tDCs of the present study reflect their abrogated ability to produce IL-12 even after secondary stimulation when the tolerogenic agents are absent. High levels of p50 in nucleus of tDCs can reflect the fact that p50 homodimers repress proinflammatory cytokine production but serve as transcriptional activators of IL-10 [Cao S, Zhang X, Edwards J P, Mosser D M: NF-kB1 (p50) homodimers differentially regulate pro- and anti-inflammatory cytokines in macrophages. J Biol Chem 2006; 281: 26041-26050]. The link between high levels of p50 and high production of IL-10 in tDCs is supported by strong reduction of IL-10 production after treatment with NF-κB inhibitor Bay 11-7082 reported previously to block phosphorylation of p50 [Lee J, Rhee M H, Kim E, Cho J Y: Bay 11-7082 is a broad-spectrum inhibitor with anti-inflammatory activity against multiple targets. Mediators of Inflammation 2012; 2012:416036].

The data presented herein support the use of distinct MAPK activation pathways in tDCs vs cDCs after restimulation with inflammatory stimuli. In tDCs, activation of p38 MAPK after restimulation is lower compared to cDCs. However, the experiments with p38 MAPK inhibitor show that p38 MAPK plays an important role in IL-10 production and expression of tolerogenic molecules ILT-3 and PD-L1 in tDCs. In contrast, p38 MAPK is markedly activated in cDCs after restimulation and controls mainly IL-12 production with no significant effect on the expression of tolerogenic molecules. Next, it was shown that significant ERK1/2 phosphorylation after restimulation with all stimuli tested in tDCs but only after LPS restimulation in cDCs. This might correlate with marked up-regulation of IL-10 production in these stimulatory conditions. Blocking experiments with ERK1/2 inhibitor PD98059 confirmed the role of ERK1/2 in IL-10 production after inflammatory trigger in tDCs and support the role of ERK1/2 activation in IL-10 secretion [Saraiva M, O'Garra A: The regulation of IL-10 production by immune cells. Nat Rev Immunol 2010; 10:170-181]. Moreover, blocking of ERK1/2 activation partially restored CD86 up-regulation, prevented PD-L1 up-regulation and partially restored allostimulatory potential of tDCs. These data suggest the distinct role of p38 MAPK and ERK in tolerogenic vs pro-inflammatory maturation. Corroborating the results presented herein, p38 MAPK and ERK were shown to regulate PD-L1 expression in different DCs types [Wolfle S J, Strebovsky J, Bartz H, Sahr A, Arnold C, Kaiser C, Dalpke A H, Heeg K: PD-L1 expression on tolerogenic APCs is controlled by STAT-3. Eur J Immunol 2011; 41:413-424].

Dex/VitD2 tDCs also express high levels of IDO that remains stable after restimulation. As expression of IDO in tDCs and the ensuing production of tryptophan metabolites has been shown to induce direct suppression of effector T cell activity and concurrent expansion of Tregs [Harden J L, Egilmez N K: Indoleamine 2,3-dioxygenase and dendritic cell tolerogenicity. Immunol Invest 2012; 41:738-764; Manches O, Fernandez M V, Plumas J, Chaperot L, Bhardwaj N: Activation of the noncanonical NF-kB pathway by HIV controls a dendritic cell immunoregulatory phenotype. PNAS 2012; 109:14122-14127], stable IDO expression might support tolerogenic properties of Dex/VitD2 tDCs.

Finally, the present study newly documented that mTOR and STAT3 inhibition led to up-regulated CD86 expression, down-regulated ILT-3 and PD-L1 expression, down-regulated IL-10 production and increased ability to stimulate T cell proliferation in Dex/VitD2 tDCs after restimulation. This phenotype was not observed in control DCs in which surface expression of CD86 was down-regulated but PD-L1 and ILT-3 expression remained similar upon mTOR inhibition. The data presented herein demonstrate the novel and important anti-inflammatory role of mTOR and STAT3 in Dex/VitD2 tDCs and brings additional knowledge about the versatile role of mTOR in DC activation. Recently, the PI3K/mTOR pathway has been documented as a negative regulator of TLR signaling in human monocytes and myeloid DCs. Rapamycin-treated myeloid immune cells display a strong Th1 and Th17 polarization [Weichhart T, Costantino G, Poglitsch M, Rosner M, Zeyda M, Stuhlmeier K M, Kolbe T, Stulnig T M, Horl W H, Hengstschlager M, Muller M, Saemann M D: The TSC-mTOR signaling pathway regulates the innate inflammatory response. Immunity 2008; 29:565-577] and are capable of blocking the anti-inflammatory effects of dexamethasone [Weichhart T, Haidinger M, Katholnig K, Kopecky C, Poglitsch M, Lassnig C, Rosner M, Zlabinger G J, Hengstschlager M, Muller M, Horl W H, Saemann M D: Inhibition of mTOR blocks the anti-inflammatory effects of glucocorticoids in myeloid immune cells. Blood 2011; 117:4273-4283]. It might suggest that dexamethasone used for generation of Dex/VitD2 tDCs of the present study requires active mTOR for maintaining its anti-inflammatory effects. On the other hand, mTOR was documented to be indispensable for monocyte-derived DC survival and differentiation [Weichhart T, Costantino G, Poglitsch M, Rosner M, Zeyda M, Stuhlmeier K M, Kolbe T, Stulnig T M, Horl W H, Hengstschlager M, Muller M, Saemann M D: The TSC-mTOR signaling pathway regulates the innate inflammatory response. Immunity 2008; 29:565-577; Haidinger M, Poglitsch M, Geyeregger R, Kasturi S, Zeyda M, Zlabinger G J, Pulendran B, Horl W H, Saemann M D, Weichhart T: A versatile role of mammalian target of rapamycin in human dendritic cell function and differentiation. J Immunol 2010; 185:3919-3931; Hackstein H, Taner T, Zahorchak A F, Morelli A E, Logar A J, Gessner A, Thomson A W: Rapamycin inhibits IL-4-induced dendritic cell maturation in vitro and dendritic cell mobilization and function in vivo. Blood 2003; 101:4457-4463]. Data from the work presented herein suggest that in Dex/VitD tDCs, mTOR pathway dictate the maintenance of tolerogenic DC phenotype.

Surprisingly, the data presented herein demonstrate that enhanced glycolysis modulated via mTOR signaling pathway regulate tolerogenic phenotype and function of Dex/VitD tDCs in the inflammatory environment by modulating CD86, ILT-3 and PD-L1 expression, IL-10/IL-12 ratio and ability to stimulate T cell proliferation. The data presented herein are in a contrast to previous studies showing enhanced glycolysis and PI3/Akt/mTOR signaling pathway being indispensable for pro-inflammatory maturation and function of DCs and T cells [Krawczyk C M, Holowka T, Sun J, Blagih J, Amiel E, DeBerardinis R J, Cross J R, Jung E, Thompson C B, Jones R G, Pearce E J: Toll-like receptor-induced changes in glycolytic metabolism regulate dendritic cell activation. Blood 2010; 115:4742-4749; Locasale J W, Cantley L C: Genetic selection for enhanced serine metabolism in cancer development. Cell Cycle 2011; 10:3812-3813]. However, in line with the data presented herein, Ferreira et al. documented very recently that tolerogenic DC generated by VitD3 use the activation of glucose metabolism controlled by the PI3/Akt/mTOR signaling pathway to promote tolerogenic phenotype and function [Ferreira G B, Vanherwegen A S, Eelen G, Gutierrez A C, Van Lommel L, Marchal K, Verlinden L, Verstuyf A, Nogueira T, Georgiadou M, Schuit F, Eizirik D L, Gysemans C, Carmeliet P, Overbergh L, Mathieu C: Vitamin D3 induces tolerance in human dendritic cells by activation of intracellular metabolic pathways. Cell Reports 2015].

Taken together, the present study reports that the clinical grade Dex/VitD2 tDCs presented herein preserve their phenotypic and functional properties upon stimulation with a variety of biologically relevant inflammatory stimuli in the absence of tolerogenic factors. This study describes for the first time the regulation of key activation pathways after restimulation of tDCs in the absence of tolerogenic agents. The data presented herein show that tDCs employ distinct activation pathways such as p38 MAPK, ERK1/2, IDO, mTOR and STAT3 to maintain their tolerogenic phenotype and immunoregulatory function upon mimicking subsequent pro-inflammatory activation in contrast to cDCs characterized by strong activation of p38 MAPK and NF-κB. Distinct pattern of signaling pathways triggered by inflammatory stimuli can also serve as a feasible and robust identity test that would distinguish inflammatory and tolerogenic DCs in culture. This study on clinical grade tDCs provides a rationale for their testing in the clinical settings, such as in autoimmune diseases or transplantation.

8. EXAMPLE 3

This example demonstrates that monocyte-derived tolerogenic DCs (tDCs) generated using Dexamethasone and vitamin D2 from type 1 diabetes (T1D) patients are stable phenotypically and functionally. In addition, this example demonstrates that tDCs derived from patients with a glycated hemoglobin (Hb) A1c ("HbA1c") level of less than or equal to 60 mmol/mol Hb induce stable hyporesponsiveness of GAD-specific T cells. This example further demonstrates the feasibility of reestablishing tolerance using cryopreserved tDCs in a future clinical trial.

8.1 Materials and Methods:

Subjects:

Anticoagulated blood samples (50-60 ml, EDTA) were obtained from totally 71 children with T1D after signing informed consent form/or signing by their legal representatives (when needed). None of the enrolled patients has other co-morbidities, except co-morbidities related to T1D such as thyroiditis or celiac disease (15.5%, 18% of recruited subjects). In this study, patients with different time of disease duration and different long-term control of the disease were enrolled (Table 10). None of the subjects was recruited at the time of diagnosis, nor had ketoacidosis in the time of blood draw. In all subjects complete HLA-DQA1 and HLA-DQB1 genotyping for risk alleles was performed by polymerase chain reaction (PCR) with sequence specific primers (Table 11).

TABLE 10

Clinical data of patients enrolled in the study

| Patients (total) | Number | Female:Male | Age [years] (mean ± SD) (range) | Time since manifestaton [years] (mean ± SD) (range) | HbA1c [mmol/mol] (mean ± SD) (range) | DDI [IU/kg/day] (mean ± SD) (range) |
|---|---|---|---|---|---|---|
|  | 71 | 35:36 | 16 ± 1.8 11-19 | 7 ± 4.7 0-17 | 80.4 ± 26 38-150 | 1 ± 0.24 0.7-1.2 |

TABLE 11

Distributions of analyzed HLA alleles of enrolled patients

| HLA characteristic | No. (%) of subjects | HLA alleles |
|---|---|---|
| Hight risk | 5 (7.5%) | DQA1*05-DQB1*0201/ DQA1*03-DQB1*0302 positive |
| Standart risk | 58 (86.6%) | DQA1*05-DQB1*0201/X or DQB1*0302/X, when X is not DQB1*0602, DQB1*0301, DQB1*0603 |
| Avarage | 2 (2.9%) | a) Negative for both: DQB1*0302, DQA1*05-DQB1*0201, DQB1*0602, DQB1*0301, DQB1*0603 b) Children with genotypies DQB1*0301/0302 or DQB1*0302/0603 |
| Low risk | 0 (0%) | DQB1*0301/X or DQB1*0603/X, when X is notDQB1*0302 ani DQB1*0602 |
| Very low risk | 2 (2.9%) | DQB1*0602/X, when X is any kind of allele |

Dendritic Cell Generation:

Peripheral blood mononuclear cells (PBMC) from whole blood of patients were isolated using Ficoll-Paque (GE Healthcare) gradient centrifugation and monocytes were separated by allowing 2 h of cell adhesion in 75-cm2 culture flasks (Nunc). Then, non-adherent cells were washed out and frozen. Dendritic cells (DCs) were generated from monocytes in CellGro medium (CellGenix) containing penicillin and streptomycin (100 U/ml and 100 μg/ml, respectively; Gibco) in the presence of IL-4 (248 IU/ml, CellGenix) and GM-CSF (500 IU/ml, Gentaur) for 6 days. Fresh medium with cytokines was added on day 3. Tolerogenic dendritic cells (tolDCs) were induced by adding Dexamethasone on day 3 (1 μM, Medochemie) and Dexamethasone (1 μM) and vitamin D2 (Zemplar; 1.5 ng/ml, Abbott Laboratories) on day 6. Control DCs (cDCs) were generated without tolerogenic factors. On day 6, tolDCs and cDCs were harvested and seeded into 96-well plates (both 1×106 DCs/ml). On day 7, tolDCs and cDCs were left unpulsed or loaded with GAD-65 (65 kDa isoform of glutamate decarboxylase; 5 μg/ml, Diamyd Medical or with PPD (tuberculin purified protein derivative; 5 μg/ml, Statens Serum Institut). After 4 h, tolDCs and cDCs were finally matured with VacciGrade MPLA (2 μg/ml, Cayla-InvivoGen) for next 24 h.

On day 8, DCs were analyzed for the expression of surface markers, viability, phenotypic stability after freezing and thawing and resistance to repetitive maturation and functional tests were performed. Supernatants from DC stimulations were collected and frozen at −80° C. until analysis.

Dendritic Cell Phenotypic Stability after Freezing and Thawing:

24 h after final maturation with MPLA, $1 \times 10^6$ tolDCs and $1 \times 10^6$ cDCs were frozen in CryoStore solution (BioLife Solutions) using cell freezing container (BioCision) and stored in liquid nitrogen for 1 month. After thawing, MPLA-matured tolDCs and MPLA-matured cDCs were washed and transferred into complete RPMI 1640 (Gibco) medium containing 5% human serum (HS; Invitrogen), 1% L-glutamin (Gibco), penicillin and streptomycin (100 U/ml and 100 μg/ml, respectively, Gibco), 1% non-essential amino acids (Gibco), 1 mM sodium pyruvate (Gibco) and 50 μM beta-mercaptoethanol (Gibco). DCs were left unstimulated or they were stimulated with LPS (1 μg/ml, Sigma-Aldrich) or megaCD40L™ (1000 ng/ml, Enzo Life Sciences) for 24 h. Supernatants and cells were collected for further analysis.

Flow Cytometry Analysis:

Following fluorochrome-conjugated monoclonal antibodies (mAb) were used: anti-CD86-FITC (clone 2231 FUN-1), CD274 (PD-L1)-FITC (clone MIH1), HLA-DR-PE-Cy7 (clone L243) purchased from BD Biosciences; CD83-PerCP-Cy5.5 (clone HB15a) purchased from Beckman Coulter; CD80-FITC (clone MAB104), CD40-PerCP-eFluor710 (clone 5C3), CD54-FITC (clone RR1/1), CD184 (CXCR4)-PE (clone 12G5), CD197 (CCR7)-APC-eFluor780 (clone 3D12), CD4-PE-Cy7 (clone RPA-T4), FoxP3-AF488 (clone PCH101) purchased from eBioscience; TLR2-FITC (clone T2.1), CD183 (CXCR3)-PerCP-Cy5.5 (clone G025H7), TGFβ (LAP)-PE-Cy7 (clone TW4-2F8), CD25-PerCP-Cy5.5 (clone BC96), TIM-3-PE (clone F38-2E2), KI-67-PE (clone Ki-67), IFN-γ-PB (clone 4S.B3) purchased from BioLegend; CD14-PE-DL594 (clone MEM-15), CD11c-APC (clone BU15), CD3-AF700 (clone MEM-57), CD8-PE-Dy590 (clone MEM-31) purchased from Exbio; CD85k (IL-T3)-PE (clone 293623) purchased from R&D Systems.

Cells were stained with mAb for 30 min in PBS at 4° C., washed and analyzed by LSR Fortessa cell analyzer (BD Biosciences). Data were analyzed using FlowJo software (Tree Star). DCs were defined based on SSC and FSC position and CD11c expression; only live (DAPI negative) cells were included into analysis. DC viability was assessed with Annexin V-PE (Exbio) plus DAPI (Invitrogen) staining. T cells were defined based on SSC and FSC position and CD3, CD4 and CD8 expression. Appropriate isotype controls were included.

Before intracellular marker staining, cells were permeabilized in fixation/permeabilization buffer (eBioscience) for 30 min at 4° C., washed and then stained with mAb for 30 min in permeabilization buffer (eBioscience) at 4° C. When indicated, T cells were stimulated for maximal cytokine production with PMA (50 ng/ml, Sigma-Aldrich) plus ionomycin (1 μg/ml, Sigma-Aldrich) for 4 h in the presence of Brefeldin A (5 μg/ml, BioLegend) before intracellular cytokine staining for flow cytometry analysis.

Analysis of Cytokines in Cell Culture Supernatants:

Supernatants from DCs and cultures of T cells stimulated with DCs were collected and frozen at −80° C. until analysis. IL-10, IL-12p70, IL-6, TNF-α, IL-23, IFN-γ and IL-17A concentrations were determined using multiplex cytokine assay (MILLIPLEX™ Human Cytokine/Chemokine Kit, Merck Millipore) according to the manufacturer's instructions. Data were acquired using Luminex MAGPIX.

DCs and T Cell Cultures:

Autologous T cells were obtained from non-adherent PBMC fraction. T cells ($2\times10^5$) were stimulated with unpulsed or antigen-loaded tolDCs or cDCs ($2\times10^4$) in complete RPMI medium (containing 5% human AB serum, 1% L-glutamine, penicillin and streptomycin (100 U/ml and 100 μg/ml, respectively), 1% non-essential amino acids, 1 mM sodium pyruvate and 50 μM beta-mercaptoethanol) in 96-well, round-bottom plates (Nunc). IL-2 (20 U/ml, PeproTech) was added on day 3, 6 and 9.

T cells proliferation was determined by intracellular detection of KI-67 by flow cytometry on day 6. Cell culture supernatants were collected and frozen on day 6. Multiplex cytokine assay was used to detect cytokines in these supernatants, as described above. For intracellular flow cytometry detection of IFNγ, IL-17A on day 6, T cells were restimulated with PMA and ionomycine for 4 h in presence of brefeldin A.

Dendritic Cell Suppression Assay:

To evaluate suppressive effect of tolDCs on cDC-induced GAD-65-specific T cell cytokine secretion, $2\times10^5$ T cells were cultivated with cDCs (ratio of T cells to cDCs was 10:1) and different number of tolDCs (ratio of tolDCs to cDCs ratio was 0.25:1; 0.5:1; and 1:1) was added. Supernatants from cultures of T cells stimulated with DCs were collected, frozen at −80° C. and analyzed for secreted cytokines using multiplex cytokine assay.

Tolerance Assay to Detect Antigen-Specific T Cell Hyporesponsiveness:

To verify whether tolDCs induce antigen specific T cell hyporesponsiveness, $2\times10^5$ unlabelled T cells were stimulated with unpulsed or GAD-pulsed tolDCs or cDCs. After 7 days, T cells were harvested, stained with 3 μM CFSE and repetitively stimulated with unpulsed or GAD- or PPD-loaded cDCs (ratio of T cells to cDCs was 10:1). Number of proliferating T cells was quantified by flow cytometry on day 6. Supernatants from cultures were collected, frozen at −80° C. and later analyzed for secreted cytokines using multiplex cytokine assay (described above).

Regulatory T Cell Induction:

Naïve CD4+ T cells were purified by negative selection kit (The EasySep™ Human Naïve CD4+ T Cell Enrichment Kit, StemCell Technologies) from thawed and overnight rested autologous T cells. $2\times10^5$ naïve CD4+ T cells were stimulated with $2\times10^4$ unpulsed or GAD-loaded tolDCs or cDCs for 9 days. Phenotype of differentiated regulatory T cells was evaluated by flow cytometry. Cell culture supernatants were collected on day 9 and frozen. IL-2 (20 U/ml, PeproTech) was added on day 2, 5 and 7.

Statistical Analysis:

Results are given as mean±SEM of at least 3 samples from at least 3 independent experiments. Data were analyzed in GraphPad PRISM 6. Comparisons between two groups were performed using the paired and unpaired two-tailed Student's t-test for parametric data, and the Wilcoxon test (paired data) for nonparametric data. Probability levels for correlation were calculated using the Pearson's correlation test (correlation coefficient: r). A value of $p\leq0.05$ was considered statistically significant.

8.2 Results

Figures 1, 21A:
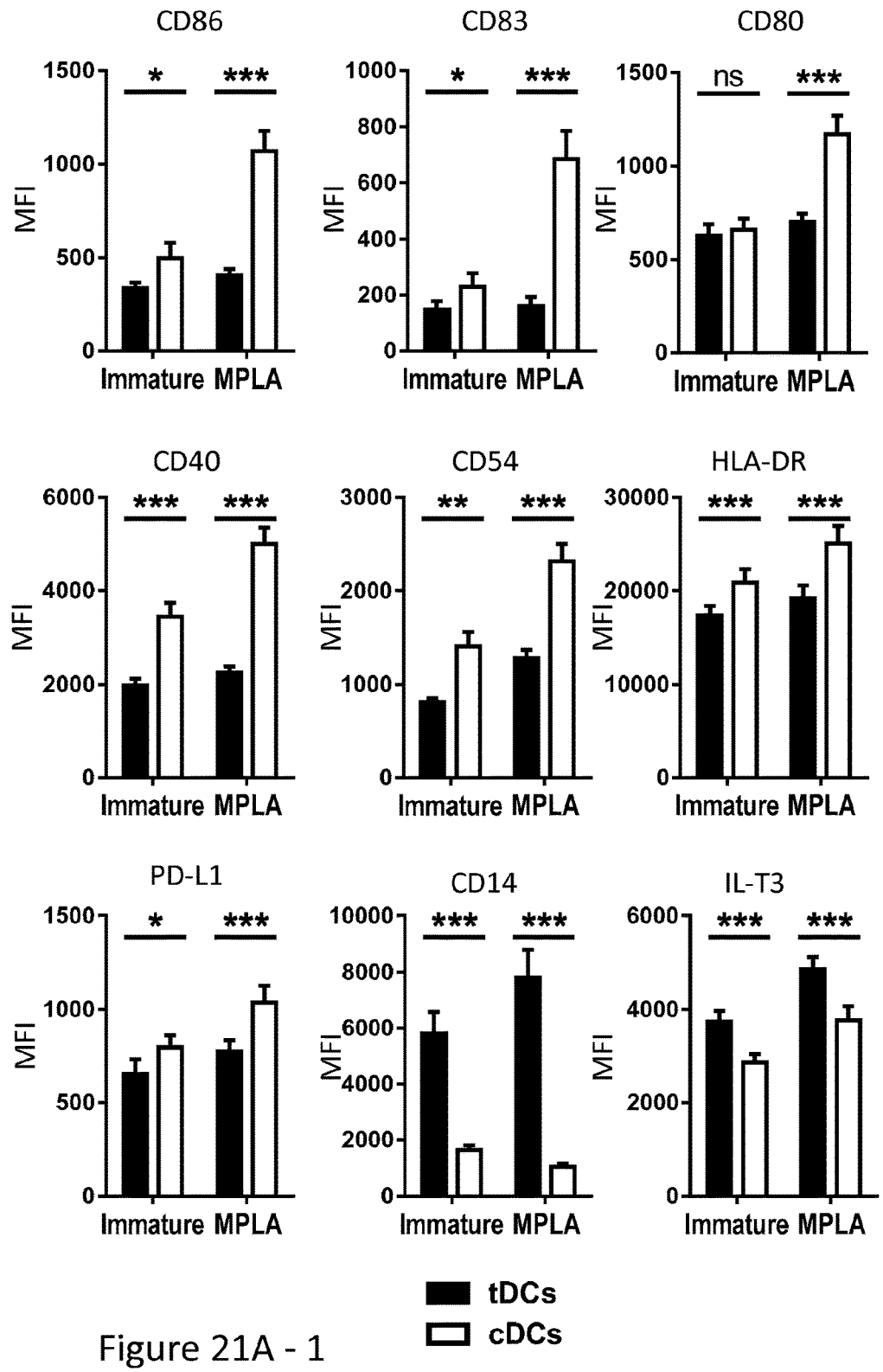
Figures 2, 21A:
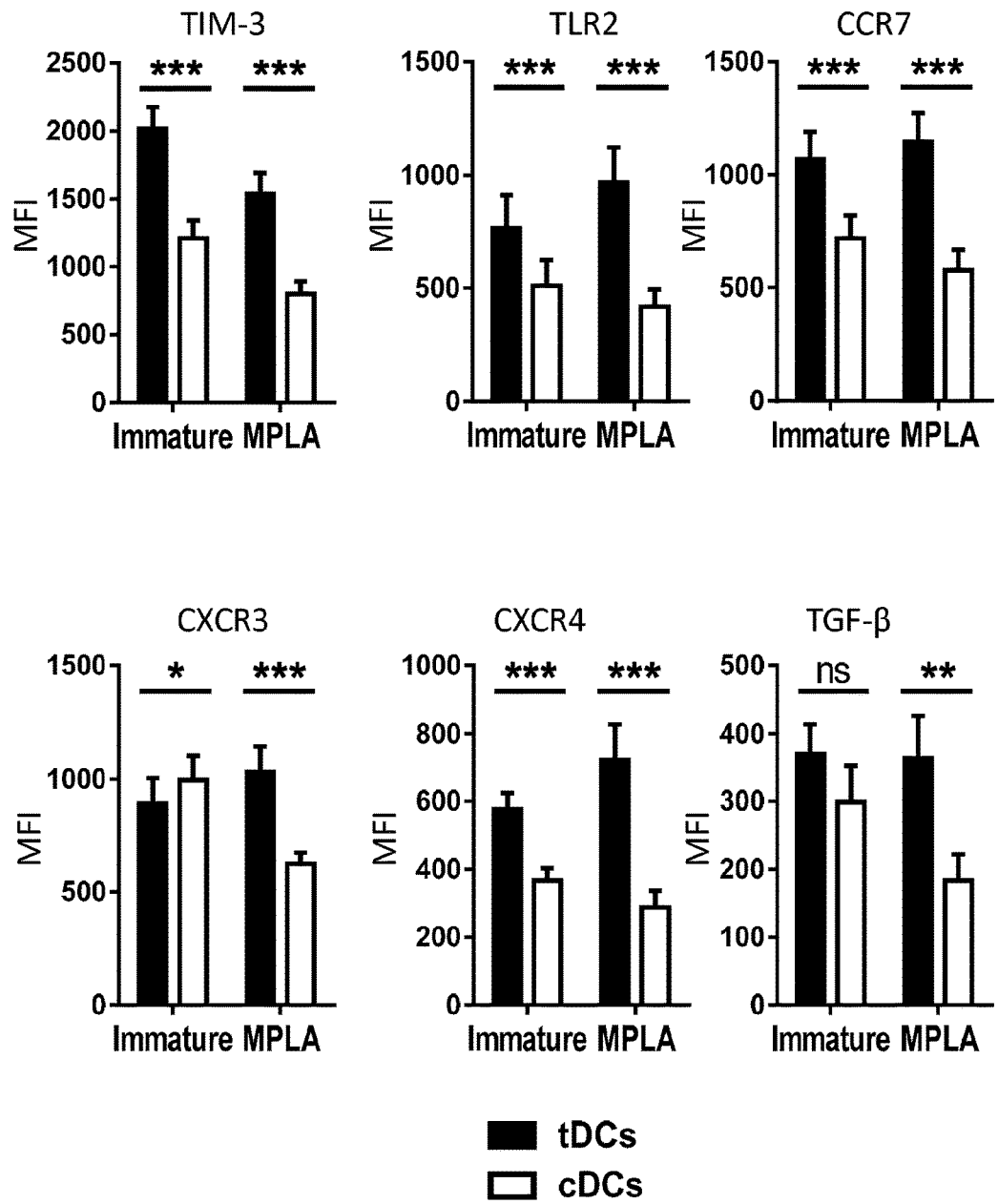
Figures 1, 21B:
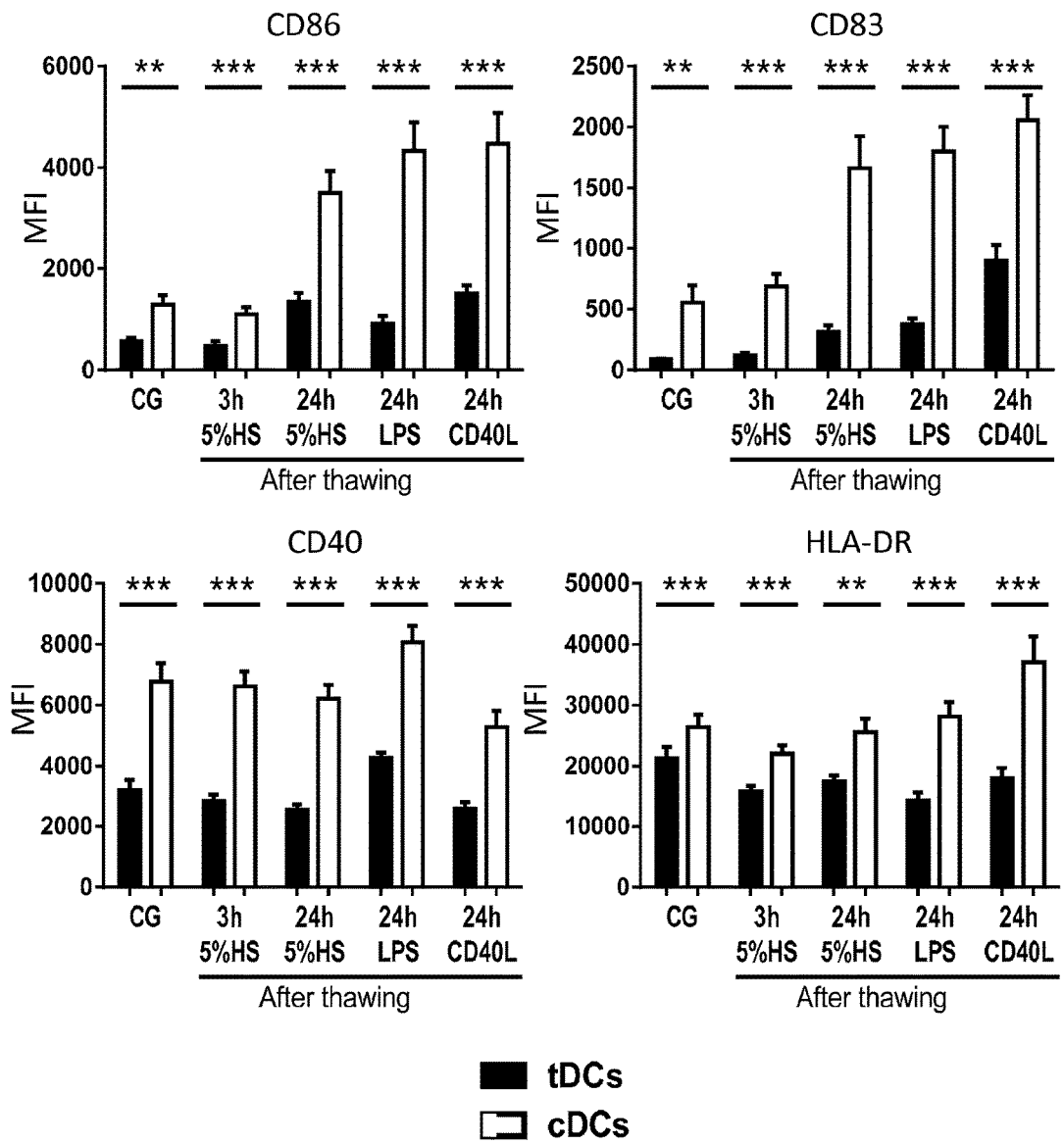
Figures 2, 21B:
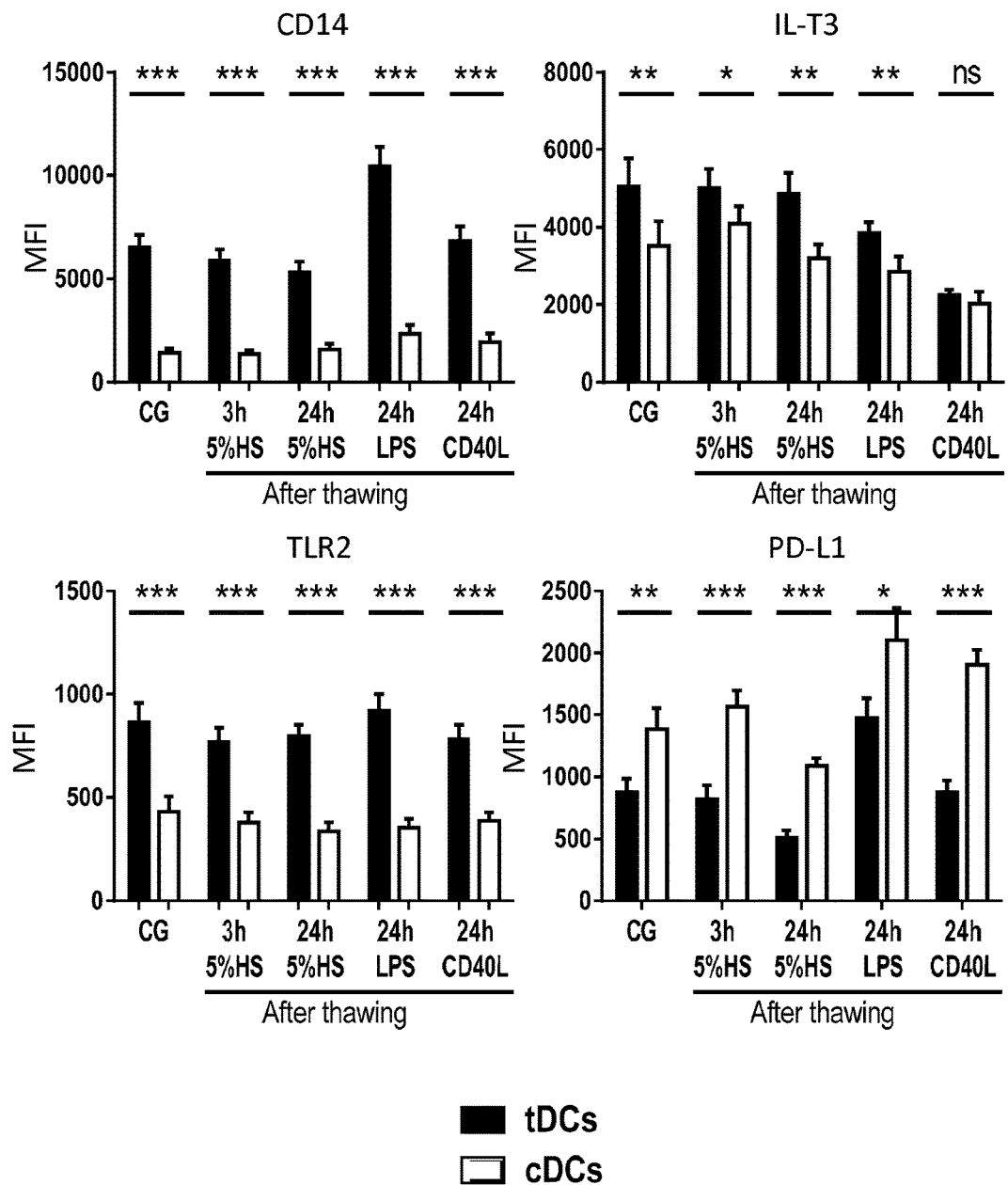

GMP-Prepared, Monocyte-Derived tolDCs from T1D Patients Display a Highly Stable Semimature Phenotype:

The phenotype and stability of tolDCs from T1D patients, established in GMP-certified CellGro medium in the presence of Dex and VitD2, in comparison with control DCs (cDCs) generated without tolerogenic factors, was initially investigated. Both types of DCs were further matured with monophosphoryl lipid A (MPLA) for 24 h. As shown in FIG. 21A (1-2) and FIG. 29 (A-C), maturation-associated markers CD80, CD83, CD86, CD54, CD40 and HLA-DR were low on tolDCs and slightly enhanced upon MPLA maturation, when compared to cDCs. In contrast, immature as well as mature tolDCs expressed significantly higher levels of surface CD14, TLR2, TGF-β and tolerogenic markers IL-T3 and TIM-3 when compared to cDCs. Expression of regulatory molecule PD-L1 was lower on tolDCs in comparison to cDCs. Furthermore, the ratio of PD-L1 expression over CD86 expression was higher in tolDCs than in cDCs (FIG. 32). This ratio can be used as a marker of tolerogenicity. Expression of chemokine receptors CCR7, necessary to enter lymphoid tissues, and CXCR3 and CXCR4 involved in migration to inflamed tissues was higher on mature tolDCs compared to mature cDCs (FIG. 21A (1-2) and FIG. 29 (A-C)). The expression at the cell surface of all these molecules was unaffected by pulsing tolDCs or cDCs with diabetogenic β cell antigen GAD (65 kDa isoform of glutamate decarboxylase) (data not shown). Although Dex and VitD2 demonstrated clear effect on DC's capability to mature, Dex and VitD2 did not affect the viability of DCs (FIG. 30A).

Figure 30B:
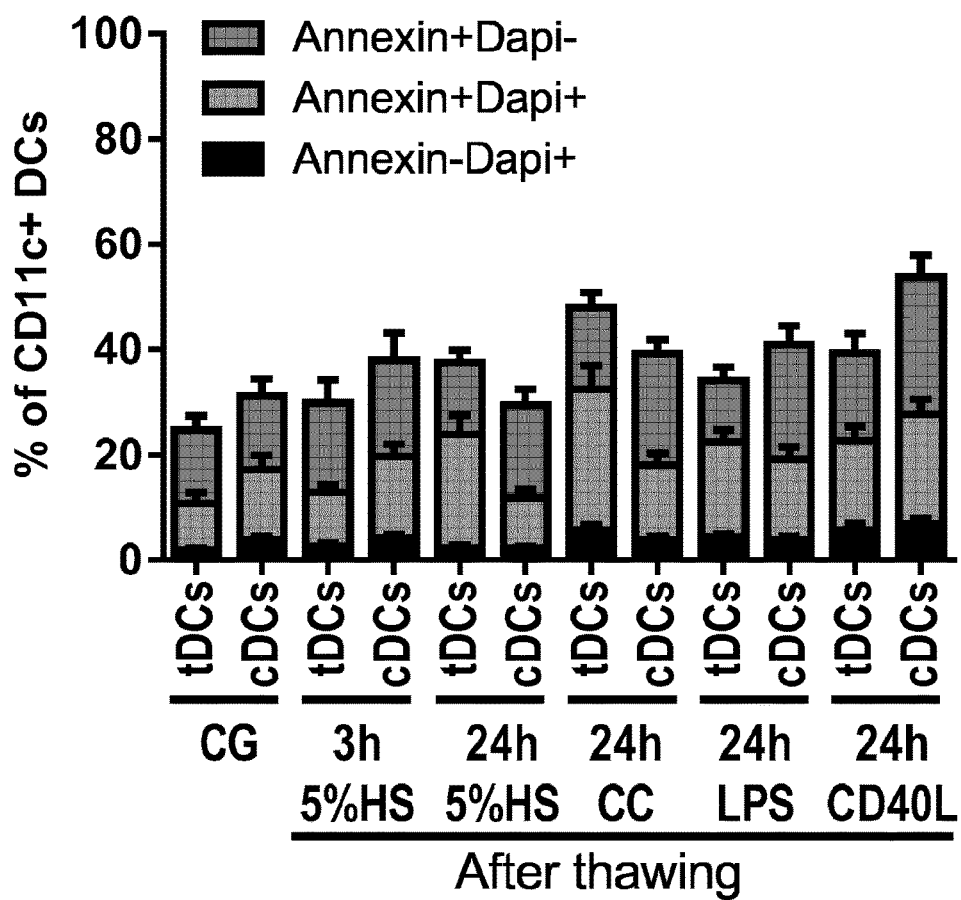

One of the key qualities of tolDCs used for immunotherapy of autoimmune disorders is the stability of their regulatory phenotype. Thus, the impact on their surface molecule expression of cryopreservation and subsequent transfer of tolDCs into proinflammatory environment was tested. MPLA-matured tolDCs or MPLA-matured cDCs were frozen and left in liquid nitrogen for at least one month. DCs were then thawed, re-cultured in RPMI supplemented with 5% HS and either left unstimulated or subsequently exposed to LPS or soluble CD40L. Neither the freezing/thawing cycle nor the subsequent restimulation reversed the tolerogenic phenotype of tolDCs. Although tolDCs moderately increased the expression of activation molecules CD86 and CD83 after cryopreservation and restimulation, their expression remained significantly lower than in equivalent cDCs. On the other hand, the expression of TLR2, CD14, and IL-T3 was maintained on tolDCs despite restimulation, except down-regulation of ILT-3 after cD40L stimulation. Moreover, tolDCs showed the potential to up-regulate PD-L1 expression after LPS stimulation (FIG. 21B (1-2)). Freezing and thawing cycle only slightly affected tolDC viability, as shown in FIG. 30B.

Tolerogenic DCs from T1D Patients Secrete More Suppressive IL-10 and Low Amounts of Pro-Inflammatory Cytokines than Control DCs:

Multiplex cytokine assay was used to determine concentrations of IL-6, TNF-α, IL-12p70, IL-23 and IL-10 in cell culture supernatants 24 h after DC maturation with MPLA. Mature tolDCs secreted significantly lower amounts of pro-inflammatory cytokines IL-6, TNF-α and IL-23 and almost undetectable levels of IL-12, compared to cDCs. In contrast, tolDCs produced higher amounts of anti-inflammatory IL-10 (FIG. 22A). Although the amounts of IL-6 and TNF-α secreted by tolDCs increased after cryopreservation and subsequent restimulation with LPS and CD40L, levels of IL-12p70 were barely detectable and IL-23 levels were very low, while the amount of IL-10 increased compared with cDCs (FIG. 22B (1-2)).

Tolerogenic DCs Induce Low Proliferation of Autoreactive T Cells Compared to cDCs:

The impact of tolDCs on the outcome of autologous T cell responses was quantified by intracellular KI-67 staining after 6 days of DC/T cell co-cultivation. DC-induced T cell antigen-specific response has been shown to depend on clinical parameters of T1D patients [Segovia-Gamboa, N., et al., Tolerogenic dendritic cells induce antigen-specific hyporesponsiveness in insulin- and glutamic acid decarboxylase 65-autoreactive T lymphocytes from type 1 diabetic patients. Clin Immunol, 2014. 154(1): p. 72-83]. Therefore, in this study, patients were divided into 2 groups based on the level of glycated hemoglobin (Hb) A1c (group 1, well compensated: HbA1c≤60 mmol/mol Hb, group 2, uncompensated: HbA1c>60 mmol/mol Hb).

Figure 23A:
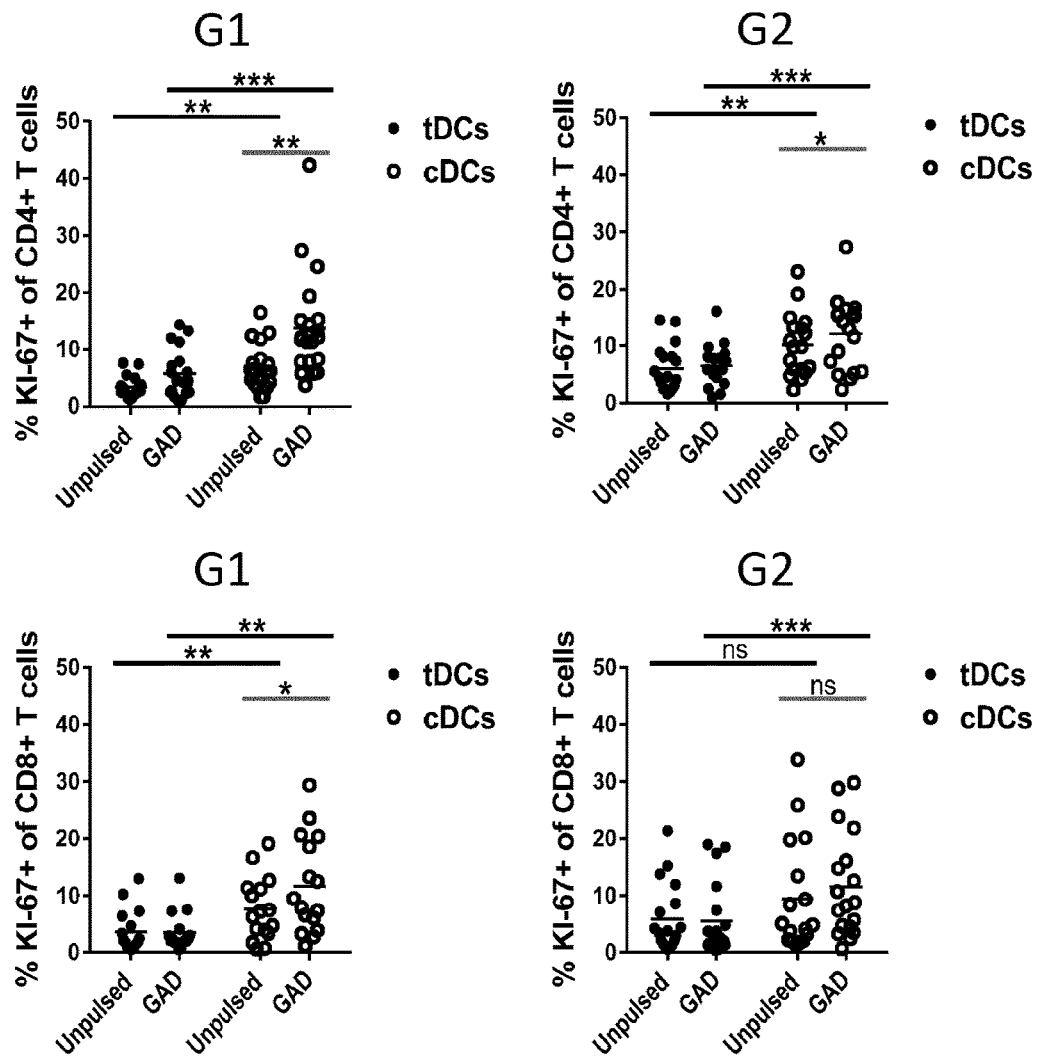

As shown in FIG. 23A, unpulsed as well as GAD-loaded tolDCs from both groups poorly induced proliferation of both CD4+ and CD8+ T cells in contrast to their cDC counterparts. The response to GAD-loaded tolDCs was similar to that of unloaded tolDCs in both groups. Investigation of antigen-specific response of T cells to GAD-loaded cDCs, however, showed the significant differences between group 1 and group 2. In group 1 of T1D patients, the significant antigen-specific proliferation of both CD4+ and CD8+ T cells against GAD-loaded cDCs in contrast to that induced by unpulsed cDCs was observed (CD4+ T cells: p=0.0023, 17 out of 20 patients; CD8+ T cells: p=0.029, 15 out of 16 patients). In contrast, the significant antigen-specific proliferation of T cells from group 2 against GAD-loaded cDCs was documented only in CD4+ but not CD8+ T cells and tended to be weaker (CD4+ T cells: p=0.041, 13 out of 18 patients; CD8+ T cells: p=0.49, 10 out of 18 patients). Moreover, the homeostatic proliferation of CD4+ T cells cultured with unpulsed cDCs was significantly higher (p<0.04) in group 2 (patients with high levels of HbA1c) compared to group 1. These data suggest that higher levels of HbA1c are connected with increased homeostatic T cell proliferation and affect, in turn, the antigen-specific proliferation of T cells.

Figure 23B:
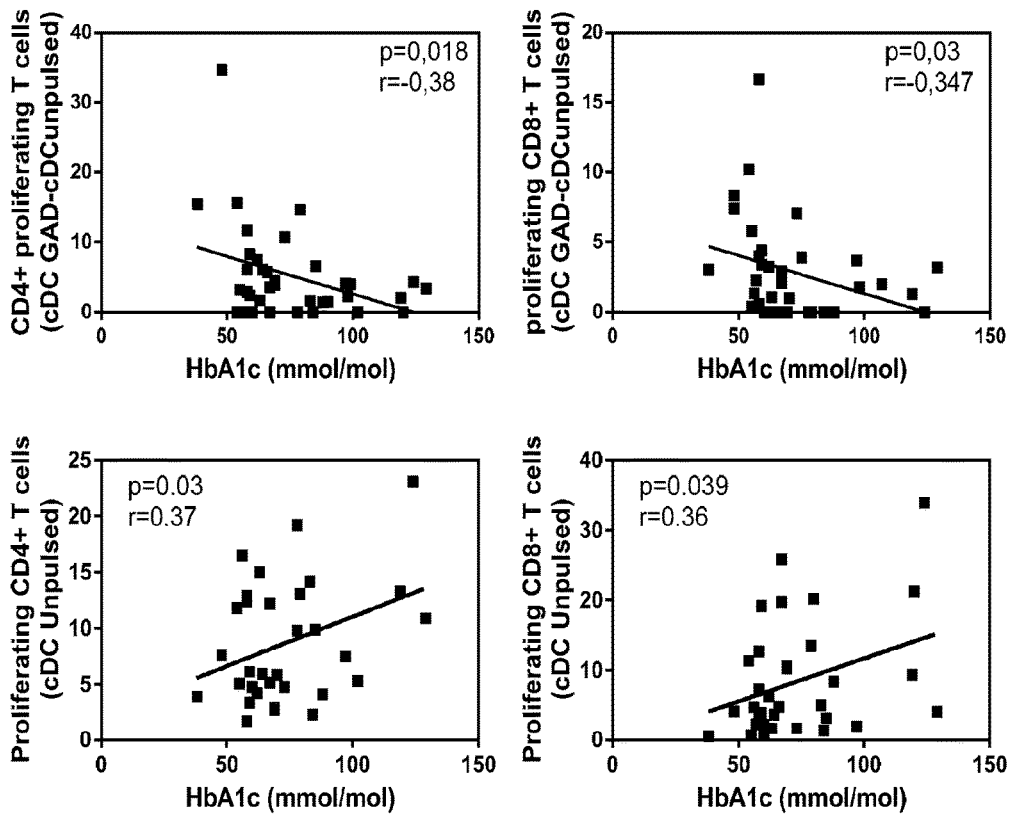

Correlation Analysis of CD4+ and CD8+ T Cell Responses and Clinical Parameters of T1D Patients:

On the basis of the different antigen-specific T cell response between T1D patients with lower and higher HbA1c levels, correlation analysis with CD4+ T cell and CD8+ T cell specific response to GAD-loaded cDCs was carried out. HbA1c level negatively correlated with T cells (CD4+ T cells: r=−0.38, p=0.018; CD8+ T cells: r=−0.347, p=0.03). T cell proliferation induced by unpulsed cDCs markedly correlated positively with HbA1c levels in both CD4+ and CD8+ T cells (CD4+ T cells: r=0.37, p=0.03; CD8+ T cells: r=0.36, p=0.039) (FIG. 23B).

Figure 23C:
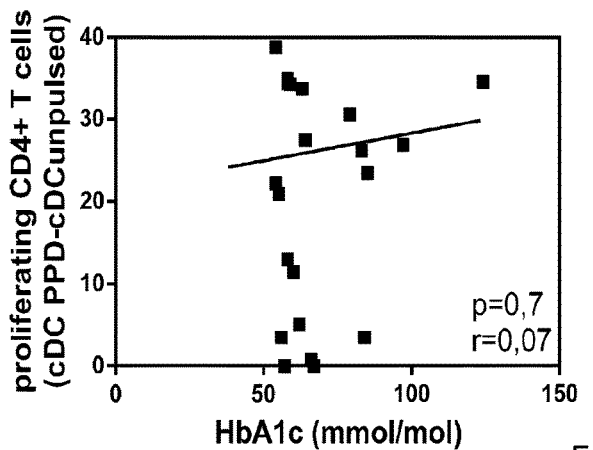

To tests, whether the lower T-cell reactivity to GAD in T1D patients with higher HbA1c levels might simply reflect a higher basal T cell proliferation or may reflect general down-regulation of T-cell reactivity against other antigens, correlation tests with the T cell responses to PPD-loaded cDC and the level of HbA1c was carried out. In this case, CD4+ T cell responses to PPD did not negatively correlate with HbA1c levels, suggesting that higher levels of HbA1c affect specifically response to GAD65 but not to other antigens (FIG. 23C).

Figures 24A, 24B:
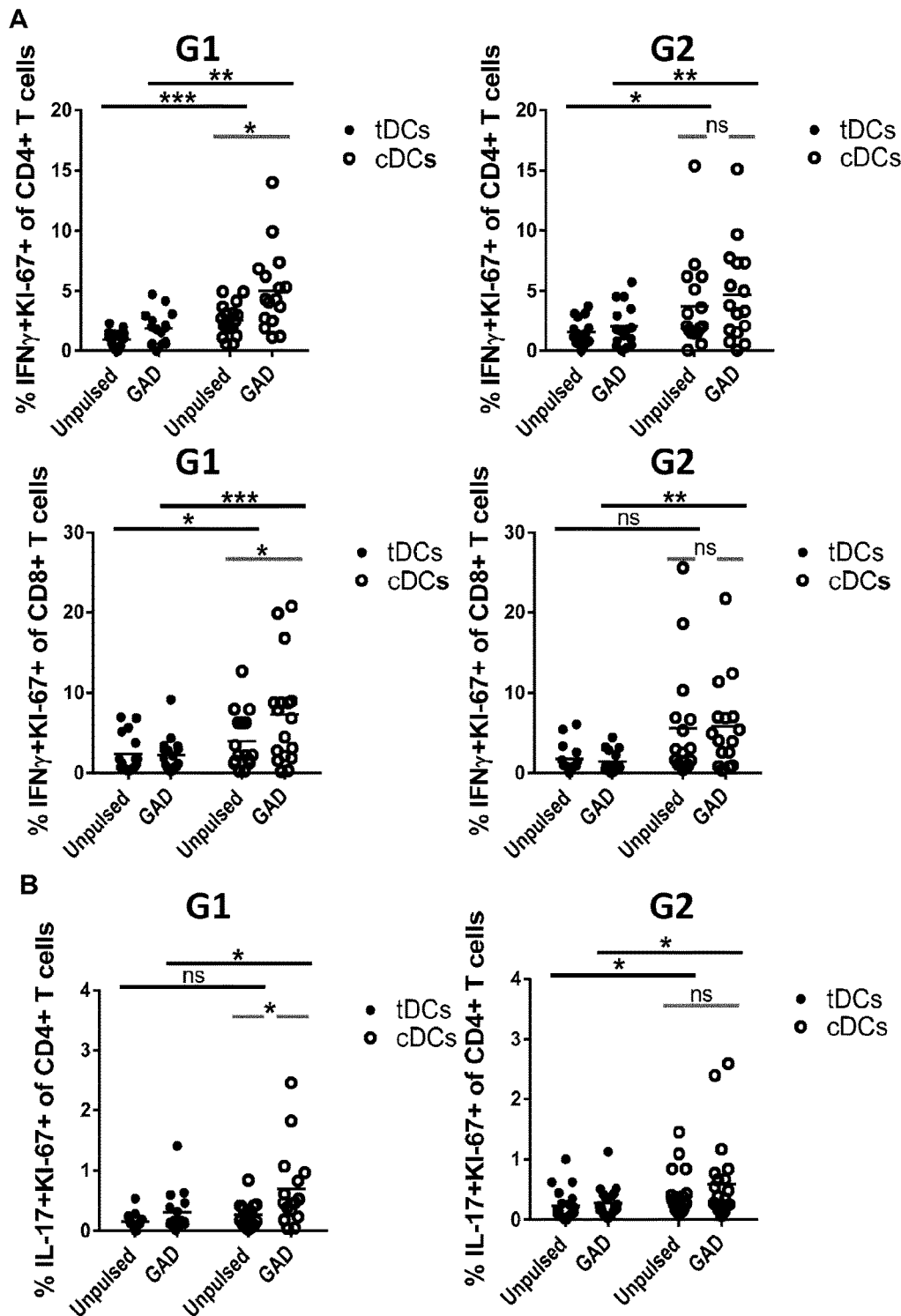

Tolerogenic DCs Poorly Induce IFN-γ and IL-17 Production by Autologous T Cells:

The induction of IFNγ- or IL-17A-producing T cells in cultures of tolDCs or cDCs with autologous T cells was measured. GAD-loaded tolDCs induced significantly lower number of INFγ-producing CD4+ and CD8+ T cells compared to GAD-loaded cDCs in both groups. However, the significant difference between number of cDC-induced IL-17A-producing CD4+ T cells and that of induced by tolDCs was significantly different only in group 1 of well-compensated patients. The percentage of IFNγ- or IL-17A-producing T cells induced by unloaded and antigen-loaded tolDCs was comparable (FIGS. 24A and 24B).

Moreover, an antigen-specific response in IFNγ production by CD4+ and CD8+ T cells against GAD-loaded cDCs was observed in group 1 but not in group 2 when compared to unpulsed cDCs (CD4+ T cells: p=0.022, 14 out of 17 patients; CD8+ T cells: p=0.02, 14 out of 17 patients and CD4+ T cells: p=0.1, 11 out of 16 patients; CD8+ T cells: p=0.86, 8 out of 16 patients, respectively) (FIG. 24A). The same results were obtained for antigen-specific response in IL-17A production, where antigen-specific IL-17A production against GAD-loaded cDCs was detected in group 1 but not in group 2, when compared to unpulsed cDCs (CD4+ T cells: p=0.012, 12 out of 16 patients and CD4+ T cells: p=0.67, 6 out of 14 patients, respectively) (FIG. 24B).

The basal level of IFNγ-producing CD4+ or IFNγ-producing CD8+ T cells induced by unpulsed cDCs was higher in group 2 compared to group 1 (CD4+ IFNγ T cells p=0.05, CD8+ IFNγ T cells p=0.05). These data indicate that high levels of HbA1c are also connected with the increased level of basal cytokine production and the lower antigen-specific activation of T cells.

Figures 24C, 24D:
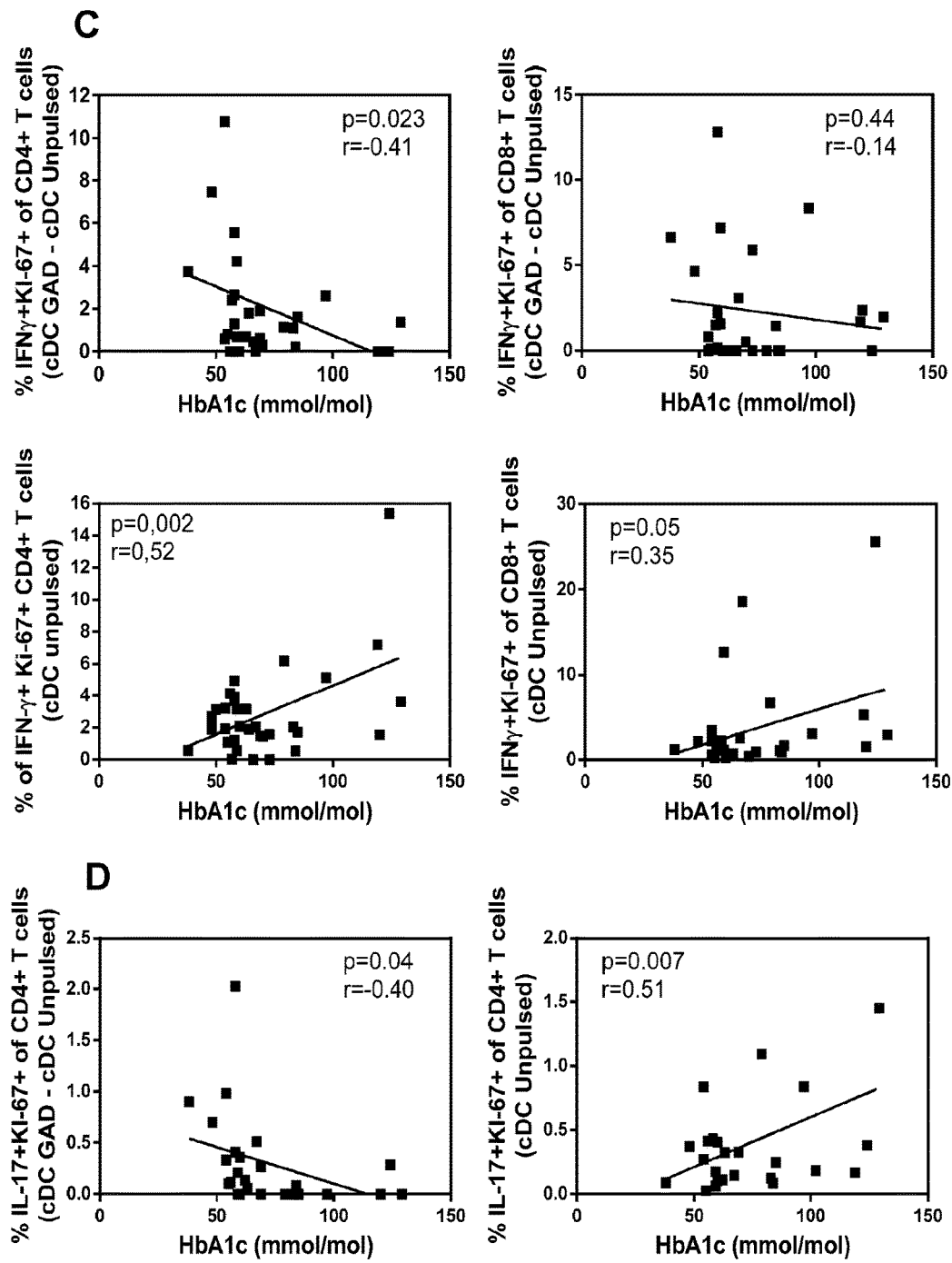

HbA1c level significantly correlated negatively with specific IFNγ or IL-17A production by CD4+ T cells against GAD-loaded cDCs (IFNγ: r=−0.41, p=0.023; IL-17A: r=−0.40, p=0.04). HbA1c level only moderately negatively correlated with specific IFNγ production by CD8+ T cells against GAD-loaded cDCs (r=−0.14, p=0.44) (FIG. 24C). Furthermore, HbA1c level strongly correlated positively with cytokine production of CD4+ as well as CD8+ T cells induced by unpulsed cDCs (CD4+ IFNγ: r=0.52, p=0.002; CD8+ IFNγ: r=0.35, p=0.05; CD4+ IL-17A: r=0.51, p=0.007) (FIGS. 24C and 24D).

Tolerogenic DCs Induce Lower Amounts of Pro-Inflammatory Cytokines in tolDC and T Cell Co-Cultures:

The amount of Th1-, Th17- and regulatory T cells-related cytokines was measured in supernatants of 6 day-cultures of T cells stimulated with cDCs or tolDCs (unpulsed or loaded with GAD65). In the presence of tolDCs prepared from G1 patients, supernatants contained significantly reduced concentration of Th1-related cytokines IFN-γ and TNF-α and Th17-related cytokine IL-17A compared to co-cultures with cDCs. The levels of IFN-γ, TNF-α and IL-17 in cultures with GAD-loaded cDCs were superior to the corresponding levels in cultures with unpulsed cDCs. The levels of IL-23 and IL-6 were lower in cultures of T cells stimulated with tolDCs but the statistical significance was reached only for IL-23 in cultures contained GAD-loaded tolDCs. In contrast, higher amounts of IL-10 were found in supernatants from T cells stimulated with GAD-loaded tolDCs in comparison to supernatants from T cells cultured with GAD-loaded cDCs (FIGS. 25A and 25B).

For G2 patients, only significant decrease in levels of IFN-γ and IL-17 in cultures with unpulsed or GAD-loaded tolDCs was detected, compared to their cDCs counterparts. Moreover, in contrast to G1 patients, the superior production of cytokines in cultures with GAD-loaded cDCs compared to unpulsed cDCs was not detected (FIGS. 25A and 25B).

Tolerogenic DCs Suppress Production of Pro-Inflammatory Cytokines Induced by Control DCs:

The previous experiments showed that tolDCs are weaker inducers of T cell activation than cDCs. In order to investigate whether tolDCs are also able to attenuate autoreactive T cell responses induced by cDCs, a suppression assay was carried out to. Different numbers of GAD-loaded tolDCs were added to T cells stimulated with GAD-loaded cDCs to reveal the tolDC suppressive potential. As shown in FIG. 26, tolDCs from both G1 and G2 up-regulated cDCs-induced IL-10 production at 1:1 and 0.5:1 ratio (tolDC/cDC), respectively. However, only tolDCs from G1 significantly reduced cDCs-induced IFN-γ and IL-17A production at 1:1 or all the ratios tested, respectively (FIG. 26). These data suggest that tolDCs from a group of T1D patients, predominantly comprised by well-compensated patients, are able to suppress T cell responses induced by cDCs.

tolDCs Induce Stable, Antigen-Specific Hyporesponsiveness in Patients with a Good Compensation of T1D:

The above described data show that tolDCs are able to induce hyporesponsiveness of GAD-reactive T cell accompanied by a down-regulation of proinflammatory cytokines and up-regulation of IL-10. To further evaluate the T cell responses promoted by tolDCs, stability and antigen-specificity of T cell hyporesponsiveness was tested. T cells recovered from primary cultures with GAD-loaded cDCs (GAD-cDCs T cells) or GAD-loaded tolDCs (GAD-tolDCs T cells) were stained with CFSE and subsequently restimulated with GAD-loaded cDCs (FIG. 27). In group of well-compensated patients (G1), GAD-cDCs T cells readily responded after restimulation with GAD-loaded cDCs in contrast to GAD-tolDCs T cells, as shown by the significantly reduced proliferation. In contrast, GAD-tolDCs T cells from G2 patients were not readily tolerized after restimulation with GAD-loaded cDCs.

Further, it was tested whether the induction of stable hyporesponsiveness induced by tolDCs was antigen-specific, that is, whether tolDCs-induced T cells maintained the ability to respond to unrelated antigen. The unrelated antigen was PPD (tuberculin purified protein derivative). T cells from T1D patients reactive to PPD recovered from primary cultures with GAD-loaded tolDCs (GAD-tolDCs T cells) were restimulated with PPD-loaded cDCs. The results showed that GAD-tolDCs T cells from G1 group of T1D patients readily responded after restimulation with PPD-loaded cDCs when compared to GAD-tolDC T cell restimulated with GAD-loaded cDCs. Overall, these data show that GAD-loaded tolDCs from the group 1 of T1D patients selectively induce stable hyporesponsiveness of GAD-specific T cells but did not impair their ability to respond to unrelated antigens such as PPD (FIG. 27).

Tolerogenic DCs Induce Differentiation of Regulatory CD4+CD25+CD127lowFoxP3+ T Proliferating Cells from Naïve CD4+ T Cells:

One of a key feature of tolerogenic DCs is their capacity to instigate regulatory T cell differentiation. This tolDC ability is crucial for the induction of the long-lasting regulation of autoimmune process ongoing in patient's body. To test the ability of tolDCs to induce Tregs, autologous naïve CD4+ T cells were isolated and stimulated with unpulsed or GAD-loaded tolDCs or GAD-loaded cDCs for 9 days. The frequency of induced regulatory T cells, characterized as CD4+KI-67+CD25+CD127low and defined by FoxP3 expression was measured (FIG. 31). GAD-loaded tolDCs were able to induce markedly higher proportion of FoxP3+ regulatory T cells from naïve CD4+ T cells than cDCs (FIG. 28A) and this tendency was more pronounced in group 1 of patients (FIG. 28B).

The embodiments described herein are intended to be merely exemplary, and those skilled in the art will recognize, or be able to ascertain using no more than routine experimentation, numerous equivalents to the specific procedures described herein. All such equivalents are considered to be within the scope of the present invention and are covered by the following claims.

All references (including patent applications, patents, and publications) cited herein are incorporated herein by reference in their entirety and for all purposes to the same extent as if each individual publication or patent or patent application was specifically and individually indicated to be incorporated by reference in its entirety for all purposes.

What is claimed:

1. A method for generating stable semi-mature tolerogenic dendritic cells, the method comprising:
   a. culturing monocytes isolated from a subject's blood in culture medium comprising GM-CSF and IL-4;
   b. after a first period of time in culture, culturing the cells from step (a) in culture medium comprising Dexamethasone, GM-CSF and IL-4;
   c. after a second period of time in culture, culturing the cells from step (b) in culture medium comprising Dexamethasone, vitamin D2, GM-CSF and IL-4 for a third period of time to generate tolerogenic dendritic cells; and
   d. after third period of time in culture, culturing the tolerogenic dendritic cells in culture medium comprising MPLA, GM-CSF and IL-4, or MPLA, GM-CSF, IL-4 and an antigen(s) associated with an autoimmune disease, graft rejection or graft-versus-host disease;
   wherein the cells from step (a) are cultured in culture medium comprising Dexamethasone, GM-CSF and IL-4 on the $3^{rd}$ day in culture, and
   wherein the cells from step (b) are cultured in culture medium comprising Dexamethasone, vitamin D2, GM-CSF and IL-4 on the $6^{th}$ day of culture, and
   wherein the tolerogenic dendritic cells are cultured in culture medium comprising MPLA, GM-CSF and IL-4, or GM-CSF, IL-4, MPLA and the antigen(s) on the $7^{th}$ day of culture.

2. The method of claim 1, wherein monocytes are isolated from a subject's blood by leukapheresis.

3. The method of claim 1, wherein the vitamin D2 is present in the culture medium at a final concentration between 0.1 and 10 nanomole per liter.

4. The method of claim 1, wherein the Dexamethasone is present in the culture medium at a final concentration between 0.5 and 3 micromole per liter.

5. The method of claim 1, wherein the MPLA is present in the culture medium at a final concentration of between 1 and 3 µg per ml.

6. The method of claim 1, wherein the tolerogenic dendritic cells are cultured in culture medium comprising MPLA or MPLA and the antigen for a certain period of time before the cells are harvested.

7. The method of claim 6, wherein the yield of tolerogenic dendritic cells in culture at the time the cells are harvested is similar to the yield of dendritic cells obtained by culturing the monocytes in culture medium comprising GM-CSF and IL-4 without Dexamethasone and vitamin D2.

8. The method of claim 6, wherein the percentage of CD11c$^+$ dendritic cells in culture at the time the cells are harvested is equivalent or superior to the yield of CD11c$^+$ dendritic cells obtained by culturing monocytes in culture medium comprising GM-CSF and IL-4 without Dexamethasone and vitamin D2.

9. The method of claim 8, wherein the percentage of CD11c$^+$ dendritic cells in culture at the time the cells are harvested is at least 20 percent.

10. The method of claim 6, wherein the expression of PD-L1 on the tolerogenic dendritic cells in culture at the time the cells are harvested is lower than the expression of PD-L1 on dendritic cells obtained by culturing monocytes in culture medium comprising GM-CSF and IL-4 without Dexamethasone and vitamin D2.

11. The method of claim 6, wherein the expression of CD14 on the tolerogenic dendritic cells in culture at the time the cells are harvested is at least 3 times higher than the expression of CD14 on dendritic cells obtained by culturing monocytes in culture medium comprising GM-CSF and IL-4 without Dexamethasone and vitamin D2.

12. The method of claim 6, wherein the expression of CD86 on the tolerogenic dendritic cells in culture at the time the cells are harvested is lower than the expression of CD86 on dendritic cells obtained by culturing monocytes in culture medium comprising GM-CSF and IL-4 without Dexamethasone and vitamin D2.

13. The method of claim 6, wherein the expression of CXCR3 on the tolerogenic dendritic cells in culture at the time the cells are harvested is higher than the expression of CXCR3 on dendritic cells obtained by culturing monocytes in culture medium comprising GM-CSF and IL-4 without Dexamethasone and vitamin D2.

14. The method of claim 6, wherein the tolerogenic dendritic cells induce a higher number of CD4$^+$CD25$^+$ FoxP3$^+$ regulatory T cells than dendritic cells obtained by culturing monocytes in culture medium comprising GM-CSF and IL-4 without Dexamethasone and vitamin D2.

15. The method of claim 6, wherein the harvested tolerogenic dendritic cells are cryopreserved.

16. The method of claim 1, wherein the tolerogenic dendritic cells are cultured in culture medium comprising MPLA or MPLA and the antigen for approximately 24 hours before the cells are harvested.

17. The method of claim 1, wherein the monocytes are from a type 1 diabetes mellitus (T1D) subject with hemoglobin (Hb) A1c (HbA1c) level of less than or equal to 60 mmol/mol Hb.

18. The method of claim 1, wherein the monocytes are from a type 1 diabetes mellitus (T1D) subject with hemoglobin (Hb) A1c (HbA1c) level of greater than 60 mmol/mol Hb.

19. The method of claim 1, wherein the antigen(s) is associated with an autoimmune disease.

20. The method of claim 19, wherein the autoimmune disease is type 1 diabetes.

21. The method of claim 19, wherein the antigen is a purified GAD65 polypeptide.

22. The method of claim 19, wherein the antigen is a purified insulin polypeptide.

23. The method of claim 19, wherein the antigens are a purified GAD65 polypeptide and a purified insulin polypeptide.

24. The method of claim 1, wherein the antigen(s) is associated with graft rejection.

25. The method of claim 1, wherein the antigen(s) is associated with graft-versus-host disease.

* * * * *